(12) United States Patent
Evans et al.

(10) Patent No.: US 12,186,211 B2
(45) Date of Patent: Jan. 7, 2025

(54) ARM PROSTHETIC DEVICE

(71) Applicant: DEKA Products Limited Partnership, Manchester, NH (US)

(72) Inventors: Christopher O. Evans, Amherst, NH (US); Keith D. Violette, Sandown, NH (US)

( * ) Notice: Subject to any disclaimer, the term of this patent is extended or adjusted under 35 U.S.C. 154(b) by 0 days.

(21) Appl. No.: 18/461,605

(22) Filed: Sep. 6, 2023

(65) Prior Publication Data
US 2024/0000587 A1 Jan. 4, 2024

Related U.S. Application Data

(60) Continuation of application No. 17/963,689, filed on Oct. 11, 2022, now Pat. No. 11,779,476, which is a
(Continued)

(51) Int. Cl.
*A61F 2/54* (2006.01)
*A61F 2/58* (2006.01)
(Continued)

(52) U.S. Cl.
CPC .................. *A61F 2/70* (2013.01); *A61F 2/54* (2013.01); *A61F 2/581* (2013.01); *A61F 2/585* (2013.01);
(Continued)

(58) Field of Classification Search
CPC .... A61F 2/70; A61F 2/54; A61F 2/581; A61F 2/585; A61F 2/74; A61F 2/582; A61F 2/586; A61F 2/78; A61F 2002/30462; A61F 2002/5001; A61F 2002/5061; A61F 2002/5083; A61F 2002/587; A61F 2002/6836; A61F 2002/6845; A61F 2002/6881; A61F 2002/701; A61F 2002/702–708; A61F 2002/7625; A61F 2002/7635; A61F 2002/764; A61F 2002/7645; A61F 2002/7665;
(Continued)

(56) References Cited

U.S. PATENT DOCUMENTS 43,590 A 7/1864 Koeller
975,029 A 11/1910 Galvin
(Continued)

FOREIGN PATENT DOCUMENTS

DE 357699 8/1922
DE 19624215 4/1997
(Continued)

OTHER PUBLICATIONS

Evolution of Microprocessor Based Control Systems in Upper Extremity Prosthetics, Lake et al., Technology and Disability IOS Press, vol. 15 (2003), pp. 63-71.
(Continued)

*Primary Examiner* — Christopher P Schwartz

(57) ABSTRACT

A system for powering a prosthetic arm is disclosed. The system includes at least one internal battery located in the prosthetic arm, at least one external battery connected to the prosthetic arm, and a master controller configured to connect either the at least one internal battery or the at least one external battery to a power bus to power the prosthetic arm.

6 Claims, 127 Drawing Sheets

Related U.S. Application Data division of application No. 16/588,236, filed on Sep. 30, 2019, now Pat. No. 11,464,655, which is a division of application No. 15/427,306, filed on Feb. 8, 2017, now Pat. No. 10,426,638, which is a continuation-in-part of application No. 15/198,929, filed on Jun. 30, 2016, which is a continuation of application No. 13/566,736, filed on Aug. 3, 2012, now Pat. No. 9,381,099, which is a continuation-in-part of application No. 13/088,063, filed on Apr. 15, 2011, now Pat. No. 8,979,943, which is a continuation-in-part of application No. 12/706,609, filed on Feb. 16, 2010, now Pat. No. 8,449,624, which is a continuation-in-part of application No. 12/027,141, filed on Feb. 6, 2008, now Pat. No. 9,114,028.

(60) Provisional application No. 62/292,611, filed on Feb. 8, 2016, provisional application No. 61/604,950, filed on Feb. 29, 2012, provisional application No. 61/551,119, filed on Oct. 25, 2011, provisional application No. 61/542,928, filed on Oct. 4, 2011, provisional application No. 61/168,786, filed on Apr. 13, 2009, provisional application No. 60/963,639, filed on Aug. 6, 2007, provisional application No. 60/899,833, filed on Feb. 6, 2007.

(51) Int. Cl.
| | | |
|---|---|---|
| *A61F 2/70* | (2006.01) | |
| *A61F 2/30* | (2006.01) | |
| *A61F 2/50* | (2006.01) | |
| *A61F 2/68* | (2006.01) | |
| *A61F 2/74* | (2006.01) | |
| *A61F 2/76* | (2006.01) | |
| *A61F 2/78* | (2006.01) | |
| *B25J 19/00* | (2006.01) | |
| *F16D 9/06* | (2006.01) | |
| *F16D 27/01* | (2006.01) | |
| *F16D 41/10* | (2006.01) | |
| *F16D 41/12* | (2006.01) | |

(52) U.S. Cl.
CPC ............. *A61F 2002/30462* (2013.01); *A61F 2002/5001* (2013.01); *A61F 2002/5061* (2013.01); *A61F 2002/5083* (2013.01); *A61F 2/582* (2013.01); *A61F 2/586* (2013.01); *A61F 2002/587* (2013.01); *A61F 2002/6836* (2013.01); *A61F 2002/6845* (2013.01); *A61F 2002/6881* (2013.01); *A61F 2002/701* (2013.01); *A61F 2002/702* (2013.01); *A61F 2002/704* (2013.01); *A61F 2002/705* (2013.01); *A61F 2002/708* (2013.01); *A61F 2/74* (2021.08); *A61F 2002/7625* (2013.01); *A61F 2002/7635* (2013.01); *A61F 2002/764* (2013.01); *A61F 2002/7645* (2013.01); *A61F 2002/7665* (2013.01); *A61F 2002/768* (2013.01); *A61F 2002/769* (2013.01); *A61F 2/78* (2013.01); *A61F 2002/7862* (2013.01); *A61F 2220/0075* (2013.01); *A61F 2250/0074* (2013.01); *A61F 2250/008* (2013.01); *B25J 19/005* (2013.01); *F16D 9/06* (2013.01); *F16D 27/01* (2013.01); *F16D 41/105* (2013.01); *F16D 41/12* (2013.01)

(58) Field of Classification Search
CPC .......... A61F 2002/768; A61F 2002/769; A61F 2002/7862; A61F 2220/0075; A61F 2220/0074; A61F 2220/008; B25J 19/005

USPC ............. 623/63–65; 294/106; 414/1, 4
See application file for complete search history.

(56) References Cited

U.S. PATENT DOCUMENTS

| | | | |
|---|---|---|---|
| 1,004,489 | A | * 9/1911 | Shackelford et al. ... A47C 4/24 297/46 |
| 1,507,682 | A | * 9/1924 | Pecorella ................ A61F 2/583 623/64 |
| 1,745,959 | A | 2/1930 | Steiner |
| 1,928,368 | A | 9/1933 | Coffey |
| 2,070,960 | A | 2/1937 | Phillips |
| 2,350,339 | A | 6/1944 | Costa |
| 2,408,880 | A | 10/1946 | Rebers |
| 2,516,791 | A | 7/1950 | Motis et al. |
| 2,535,489 | A | 12/1950 | Edwards |
| 2,847,678 | A | * 8/1958 | Opuszenski ............. A61F 2/58 623/64 |
| 3,654,855 | A | 4/1972 | Longo |
| 3,745,998 | A | 7/1973 | Rose |
| 3,763,773 | A | 10/1973 | Clay |
| 3,779,654 | A | 12/1973 | Horne |
| 3,883,900 | A | 5/1975 | Jerard et al. |
| 3,935,795 | A | 2/1976 | Hawley |
| 3,964,692 | A | 6/1976 | Pendleton |
| 3,987,498 | A | 10/1976 | Mason |
| 4,030,141 | A | 6/1977 | Graupe |
| 4,067,070 | A | 1/1978 | Seamone et al. |
| 4,068,763 | A | 1/1978 | Fletcher et al. |
| 4,155,169 | A | 5/1979 | Drake et al. |
| 4,155,769 | A | 5/1979 | Almagro |
| 4,209,860 | A | 7/1980 | Graupe |
| 4,253,449 | A | 3/1981 | Arkans et al. |
| 4,258,441 | A | 3/1981 | Bell |
| 4,291,106 | A | 9/1981 | Hooke |
| 4,413,895 | A | 11/1983 | Lee |
| 4,521,924 | A | 6/1985 | Jacobsen et al. |
| 4,604,098 | A | 8/1986 | Seamone et al. |
| 4,628,765 | A | 12/1986 | Dien et al. |
| 4,657,003 | A | 4/1987 | Wirtz |
| 4,674,351 | A | 6/1987 | Byrd |
| 4,696,377 | A | 9/1987 | Richardson et al. |
| 4,720,923 | A | 1/1988 | Quinton et al. |
| 4,743,264 | A | 5/1988 | Sherva-Parker |
| 4,792,338 | A | 12/1988 | Rennerfelt |
| 4,831,897 | A | 5/1989 | Dobbs |
| 4,840,634 | A | 6/1989 | Muller et al. |
| 4,842,608 | A | 6/1989 | Marx et al. |
| 4,896,239 | A | 1/1990 | Ghose |
| 4,903,536 | A | 2/1990 | Salisbury, Jr. et al. |
| 4,908,037 | A | 3/1990 | Ross |
| 4,946,421 | A | 8/1990 | Kerley, Jr. |
| 5,018,513 | A | 5/1991 | Charles |
| 5,088,171 | A | 2/1992 | Suzuki |
| 5,108,456 | A | 4/1992 | Coonan, III |
| 5,201,772 | A | 4/1993 | Maxwell |
| 5,263,990 | A | 11/1993 | Handal |
| 5,336,269 | A | 8/1994 | Smits |
| 5,376,128 | A | 12/1994 | Bozeman, Jr. |
| 5,405,405 | A | 4/1995 | Love |
| 5,413,611 | A | 5/1995 | Haslam, II et al. |
| 5,420,489 | A | 5/1995 | Hansen et al. |
| 5,480,454 | A | 1/1996 | Bozeman, Jr. |
| 5,501,498 | A | 3/1996 | Ulrich |
| 5,611,774 | A | 3/1997 | Postelmans |
| 5,673,367 | A | 9/1997 | Buckley |
| 5,724,714 | A | 3/1998 | Love |
| 5,793,185 | A | 8/1998 | Prelec et al. |
| 5,796,229 | A | 8/1998 | Akeel |
| 5,836,083 | A | 11/1998 | Sangwan |
| 5,888,213 | A | 3/1999 | Sears et al. |
| 5,910,720 | A | 6/1999 | Williamson et al. |
| 6,129,476 | A | 10/2000 | Berman et al. |
| 6,171,239 | B1 | 1/2001 | Humphrey |
| 6,244,644 | B1 | 6/2001 | Lovchik et al. |
| 6,276,155 | B2 | 8/2001 | Siman-Tov et al. |

(56) References Cited

U.S. PATENT DOCUMENTS

| | | |
|---|---|---|
| 6,286,225 B1 | 9/2001 | Schimmels et al. |
| 6,287,159 B1 | 9/2001 | Polakowski et al. |
| 6,301,964 B1 | 10/2001 | Fyfe et al. |
| 6,344,062 B1 | 2/2002 | Abboudi et al. |
| 6,350,211 B1 | 2/2002 | Kolmar |
| 6,361,570 B1 | 3/2002 | Gow |
| 6,379,393 B1 | 4/2002 | Mavroidis et al. |
| 6,424,886 B1 | 7/2002 | Iversen et al. |
| 6,454,513 B1 | 9/2002 | Friederichs et al. |
| 6,483,275 B1 | 11/2002 | Nebrigic et al. |
| 6,494,039 B2 | 12/2002 | Pratt et al. |
| 6,500,210 B1 | 12/2002 | Sabolich et al. |
| 6,585,774 B2 | 7/2003 | Dean, Jr. et al. |
| 6,597,965 B2 | 7/2003 | Graves et al. |
| 6,806,621 B2 | 10/2004 | Heim et al. |
| 6,876,213 B2 | 4/2005 | Beck |
| 6,896,704 B1 | 5/2005 | Higuchi et al. |
| 6,962,220 B2 | 11/2005 | Takenaka et al. |
| 6,987,374 B2 | 1/2006 | Iribe et al. |
| 7,001,434 B2 | 2/2006 | Van De Veen |
| 7,086,322 B2 | 8/2006 | Schulz |
| 7,144,430 B2 | 12/2006 | Archer et al. |
| 7,150,762 B2 | 12/2006 | Caspers |
| 7,186,270 B2 | 3/2007 | Elkins |
| 7,744,551 B2 | 6/2010 | Pick et al. |
| 7,828,857 B2 | 11/2010 | Farnsworth et al. |
| 7,837,474 B1 | 11/2010 | Nuccio-Youngs |
| 8,087,498 B2 | 1/2012 | Dupuis et al. |
| 8,257,090 B1 | 9/2012 | Nuccio-Youngs |
| 8,453,340 B2 | 6/2013 | van der Merwe et al. |
| 8,696,764 B2 | 4/2014 | Hansen et al. |
| 8,821,587 B2 | 9/2014 | Lanier et al. |
| 9,381,099 B2 | 7/2016 | Perry et al. |
| 10,426,638 B2 | 10/2019 | Evans et al. |
| 2002/0099450 A1 | 7/2002 | Dean, Jr. et al. |
| 2002/0116055 A1 | 8/2002 | Snyder |
| 2002/0143405 A1 | 10/2002 | Davalli et al. |
| 2002/0170193 A1 | 11/2002 | Townsend et al. |
| 2003/0078674 A1 | 4/2003 | Phillips |
| 2003/0120183 A1 | 6/2003 | Simmons |
| 2003/0139783 A1 | 7/2003 | Kilgore et al. |
| 2003/0149384 A1 | 8/2003 | Davis et al. |
| 2003/0181990 A1 | 9/2003 | Phillips |
| 2003/0196490 A1 | 10/2003 | Cardarelli |
| 2004/0030411 A1 | 2/2004 | Caspers |
| 2004/0049290 A1 | 3/2004 | Bedard |
| 2004/0054423 A1 | 3/2004 | Martin |
| 2004/0064286 A1 | 4/2004 | Levi et al. |
| 2004/0078091 A1 | 4/2004 | Elkins |
| 2004/0088057 A1 | 5/2004 | Bedard |
| 2005/0028392 A1 | 2/2005 | Campbell et al. |
| 2005/0066810 A1 | 3/2005 | Schulz |
| 2005/0119777 A1 | 6/2005 | Arbogast et al. |
| 2005/0156878 A1 | 7/2005 | Logue |
| 2005/0192676 A1 | 9/2005 | Sears et al. |
| 2005/0192677 A1 | 9/2005 | Ragnarsdottir et al. |
| 2005/0197717 A1 | 9/2005 | Ragnarsdottir et al. |
| 2005/0234564 A1 | 10/2005 | Fink et al. |
| 2006/0006280 A1 | 1/2006 | Wood |
| 2006/0083454 A1 | 4/2006 | Ason et al. |
| 2006/0122710 A1 | 6/2006 | Bedard |
| 2006/0167562 A1 | 7/2006 | Williams, III et al. |
| 2006/0167564 A1 | 7/2006 | Flaherty et al. |
| 2006/0187073 A1 | 8/2006 | Lin et al. |
| 2006/0189899 A1 | 8/2006 | Flaherty et al. |
| 2006/0224247 A1 | 10/2006 | Clausen et al. |
| 2006/0224249 A1 | 10/2006 | Winfrey |
| 2006/0282175 A1 | 12/2006 | Haines et al. |
| 2007/0011919 A1 | 1/2007 | Case, Jr. |
| 2007/0021841 A1 | 1/2007 | Al-Temen et al. |
| 2007/0040449 A1 | 2/2007 | Spurlin et al. |
| 2007/0055383 A1 | 3/2007 | King |
| 2007/0093786 A1 | 4/2007 | Goldsmith et al. |
| 2007/0186429 A1 | 8/2007 | Bonnet et al. |
| 2007/0191965 A1 | 8/2007 | Colvin et al. |
| 2007/0198098 A1 | 8/2007 | Roston et al. |
| 2007/0250179 A1 | 10/2007 | Latour |
| 2007/0282228 A1 | 12/2007 | Einav et al. |
| 2008/0009771 A1 | 1/2008 | Perry et al. |
| 2008/0045932 A1 | 2/2008 | Beau et al. |
| 2008/0215162 A1 | 9/2008 | Farnsworth et al. |
| 2008/0243266 A1 | 10/2008 | Haynes et al. |
| 2008/0246433 A1 | 10/2008 | Kim et al. |
| 2008/0252552 A1 | 10/2008 | Goebel et al. |
| 2008/0288088 A1 | 11/2008 | Langenfeld et al. |
| 2008/0312753 A1 | 12/2008 | Puchhammer |
| 2009/0000136 A1 | 1/2009 | Crampton |
| 2009/0038421 A1 | 2/2009 | Wilson et al. |
| 2009/0264799 A1 | 10/2009 | Bonutti et al. |
| 2009/0265570 A1 | 10/2009 | Chen |
| 2009/0271000 A1 | 10/2009 | Altobelli et al. |
| 2009/0306594 A1 | 12/2009 | Pang et al. |
| 2010/0036455 A1 | 2/2010 | Sanders et al. |
| 2010/0081974 A1 | 4/2010 | Vess |
| 2010/0086836 A1 | 4/2010 | Dai |
| 2010/0113994 A1 | 5/2010 | Ingimundarson et al. |
| 2010/0301799 A1 | 12/2010 | Lin et al. |
| 2011/0098828 A1 | 4/2011 | Balboni et al. |
| 2011/0247321 A1 | 10/2011 | Streeter et al. |
| 2011/0257765 A1 | 10/2011 | Evans et al. |
| 2011/0316471 A1 | 12/2011 | Yang et al. |
| 2012/0123558 A1 | 5/2012 | Gill |
| 2012/0210590 A1 | 8/2012 | Ferrari |
| 2013/0053736 A1 | 2/2013 | Konishi |

FOREIGN PATENT DOCUMENTS

| | | |
|---|---|---|
| EP | 1159940 | 12/2001 |
| EP | 1675212 | 6/2006 |
| EP | 1837129 | 9/2007 |
| EP | 1916561 | 4/2008 |
| EP | 2112740 | 10/2009 |
| EP | 2133662 | 12/2009 |
| FR | 2877227 | 5/2006 |
| WO | 2004096502 | 11/2004 |
| WO | 2005087583 | 9/2005 |
| WO | 2006069264 | 6/2006 |
| WO | 2008044207 | 4/2008 |
| WO | 2008098059 | 8/2008 |
| WO | 2010033098 | 3/2010 |
| WO | 2010120403 | 10/2010 |
| WO | 2010120404 | 10/2010 |
| WO | 2011036473 | 3/2011 |

OTHER PUBLICATIONS

Examination Report from corresponding European Appln. No. 10714392.7 dated Oct. 25, 2012 (4 pages).
Graupe, "Control of an Artificial Upper Limb in Three Degrees of Freedom," Bulletin of Prosthetics Research, Fall 1975, pp. 25-39.
International Partial Search Report dated Aug. 29, 2013, received in International Patent Application No. PCT/US2013/039081, 6 pgs.
International Partial Search Report dated May 10, 2012, received in International Patent Application No. PCT/US2011/041339, 8 pgs.
International Preliminary Report on Patentability for International Application No. PCT/US2008/053183 dated Aug. 11, 2009.
International Preliminary Report on Patentability for International Application No. PCT/US2008/053187 dated Aug. 11, 2009.
International Preliminary Report on Patentability for International Application No. PCT/US2008/053191 dated Aug. 11, 2009.
International Search Report and Written Opinion dated Mar. 14, 2013, received in International patent application PCT/US2012/049586, 16 pgs.
International Search Report and Written Opinion dated Oct. 29, 2013, received in International Patent Application Serial No. PCT/US2013/039081, 15 pgs.
International Search Report and Written Opinion dated Jul. 6, 2012, received in International Patent Application No. PCT/US2011/041339, 19 pgs.
International Search Report and Written Opinion from corresponding International Appln. No. PCT/US2009/069491 dated May 20, 10 (13 pages).

(56) References Cited

OTHER PUBLICATIONS

International Search Report and Written Opinion from corresponding International Appln. No. PCT/US2011/031797 dated Jun. 15, 2012 (14 pages).
International Search Report and Written Opinion from corresponding International Appln. No. PCT/US2013/039081 dated Aug. 20, 2013 (15 pages).
International Search Report and Written Opinion from related International Application No. PCT/US2010/024316 dated Jun. 11, 2010 (14 pages).
International Search Report for International Application No. PCT/US08/53187 dated Sep. 24, 2008.
International Search Report for International Application No. PCT/US08/53191 dated Jul. 31, 2008.
International Search Report for International Application No. PCT/US2008/053183 dated Jun. 17, 2008.
International Search Report from corresponding International Appln. No. PCT/US2010/024326 dated Dec. 13, 2010 (7 pages).
International Search Report from corresponding International Appln. No. PCT/US2010/024334 dated Dec. 16, 2010 (6 pages).
Jacobsen et al., "Development of the Utah Artificial Arm", IEEE Transactions on Biomedical Engineering, vol. BME-29, No. 4, Apr. 1982, pp. 249-269.
Karoui MS et al., "Study and Design of a Loop Antenna for Application of Medical Telemetry" Industrial Technology, 2004, IEEE ICIT '04, IEEE International Conference on Hammamet, Tunsia, vol. 3, Dec. 8, 04, pp. 1589-1595.
Lake, et al., Evolution of Microprocessor Based Control Systems in Upper Extremity Prosthetics, Technology and Disability IOS Press, vol. 15 (2003), pp. 63-71 (6 pages).
Merriam Webster Online Dictionary, Definition of "prosthesis" accessed May 7, 2010.
Partial International Search Report from corresponding international appln. No. PCT/US2011/031797 dated Dec. 8, 2011 (4 pages).
Partial International Search Report from corresponding International Appln. No. PCT/US2011/041339 dated May 10, 2012 (6 pages).
Partial International Search Report from corresponding international appln. No. PCT/US2011/041343 dated Nov. 24, 2011 (6 pages).
Partial International Search Report from corresponding international appln. No. PCT/US2011/041345 dated Mar. 5, 2012 (22 pages).
Partial International Search Report from corresponding international appln. No. PCT/US2013/039081 dated Aug. 29, 2013 (6 pages).
Partial International Search Results from related International Application No. PCT/US2010/024326 dated Jul. 21, 2010 (6 pages).
Partial International Search Results from related International Application No. PCT/US2010/024334 dated Jul. 21, 2010 (5 pages).
Poulton et al., "Experience with the Intelligent Hybrid Arm Systems" from "MEC '02 TH Next Generation," Proceedings of the 2002 MyoElectric Controls/Powered Prosthetics Symposium Fredericton, New Brunswick, Canada, Aug. 21-23, 2002, Copyright University of New Brunswick, pp. 1-4.
Preliminary Report on Patentability from corresponding International Appln. No. PCT/US2011/031797 dated Oct. 9, 2012 (8 pages).
Quick Guide #3, C-Leg Patient Training Overview, Otto Bock, 2006, Training Pamphlet, pp. 1-4.
Search Report from corresponding European Appln. No. 08729167.0 dated Feb. 6, 2012 (6 pages).
Search Report from European Appln. No. 08729171.2 dated Aug. 29, 11 (7 Pages).
Search Report from European Appln. No. 08729175.3 dated Aug. 29, 11 (5 Pages).
U.S. Appl. No. 12/026,971 on "Dynamic Support Apparatus" filed Feb. 6, 2008.
U.S. Appl. No. 12/027,116 on "Method and Apparatus for Control of a Prosthetic" filed Feb. 6, 2008.
U.S. Appl. No. 12/706,340 on Dynamic Support Apparatus and System filed Feb. 16, 2010.
U.S. Appl. No. 12/706,471 on System, Method and Apparatus for Orientation Control filed Feb. 16, 2010.
U.S. Appl. No. 12/706,575 on System, Method and Apparatus for Control of a Prosthetic Device filed Feb. 16, 2010.
U.S. Appl. No. 12/706,609 on Arm Prosthetic Device filed Feb. 16, 2010.
U.S. Appl. No. 13/088,035 on Dynamic Support Apparatus and System filed Apr. 15, 2011.
U.S. Appl. No. 13/088,063 on Arm Prosthetic Device filed Apr. 15, 2011.
U.S. Appl. No. 13/088,085 on System, Method and Apparatus for Control of a Prosthetic Device filed Apr. 15, 2011.
U.S. Appl. No. 13/323,094 entitled "Dynamic Support Apparatus and System" filed Dec. 12, 2011 (35 pages).
Wikipedia article on medical devices, obtained on Dec. 31, 2018 (8 pages).
Yekeh Ket al., "Wireless Communications for Body Implanted Medical Device" Microwave Conference, 2007, Asia-Pacific, IEEE, Piscataway, NJ, Dec. 11, 2007, pp. 1-4.
Zaghloul et al., "Hybrid Reflector-Array Antenna Concept," Antennas and Propagation Society International Symposium 2006 IEEE, Jul. 9-14, 2006, Virginia Polytechnic Institute and State University, Blacksburg, pp. 4311-4314, Conference Publications.
U.S. Appl. No. 12/027,141.

\* cited by examiner

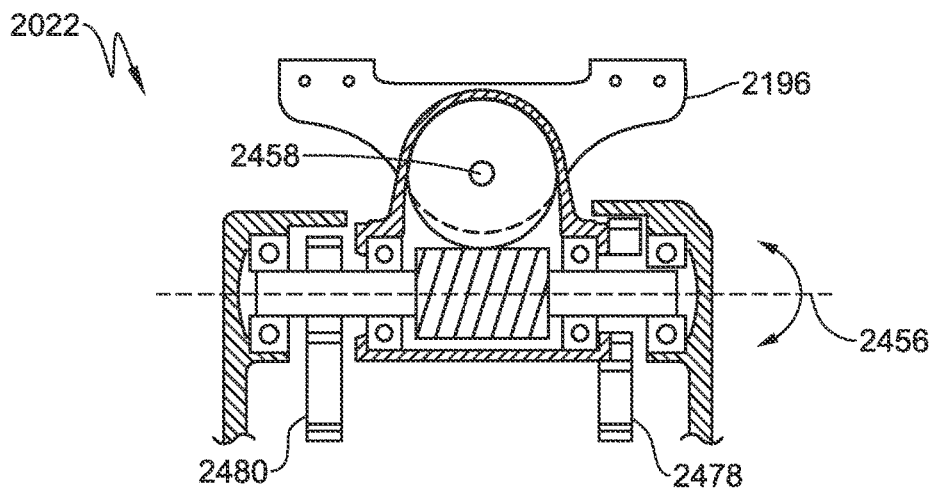
FIG. 56
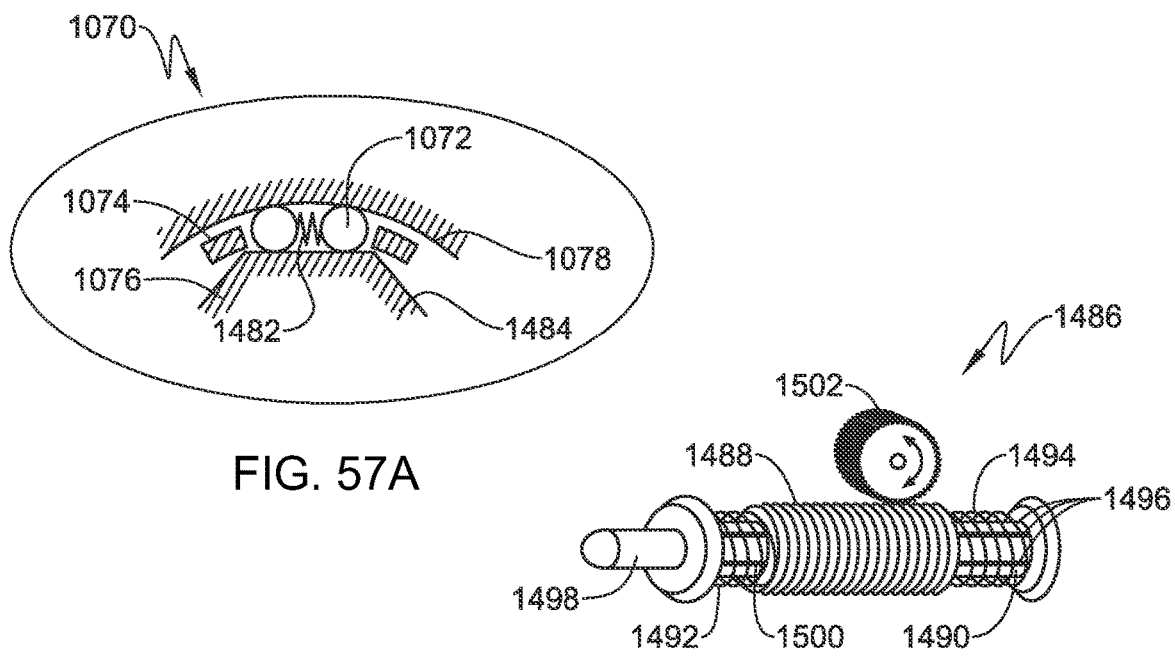
FIG. 57A
FIG. 59
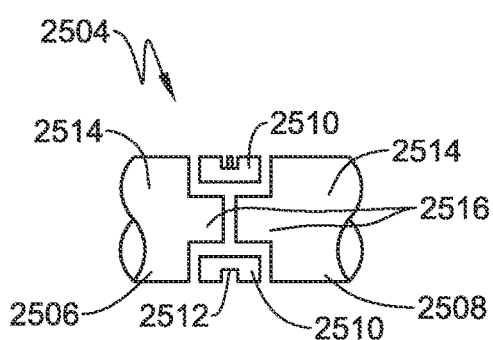
FIG. 60A
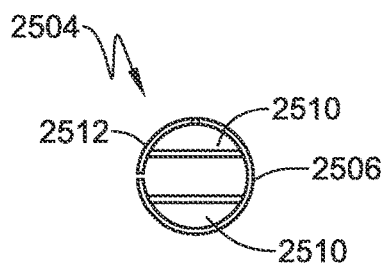
FIG. 60B

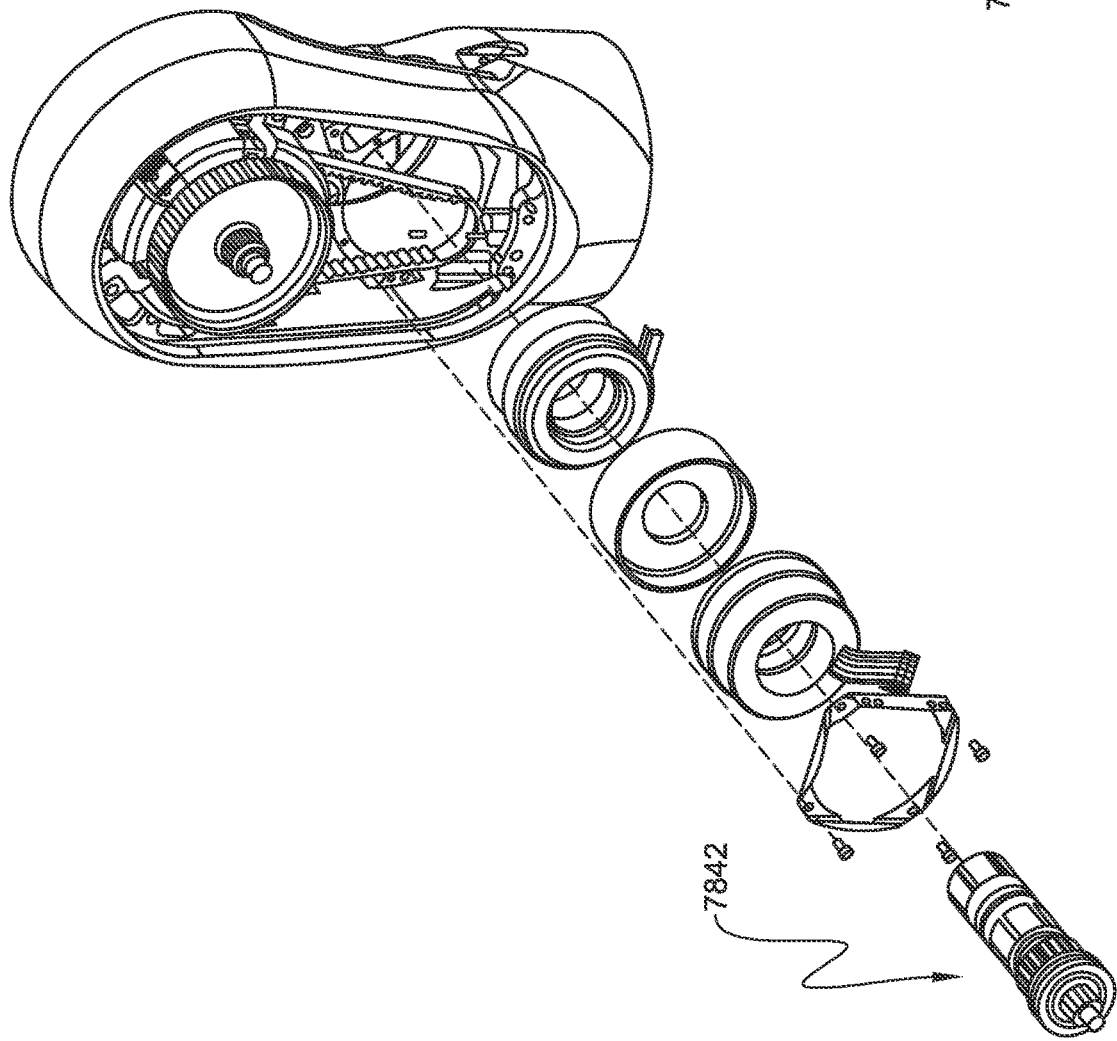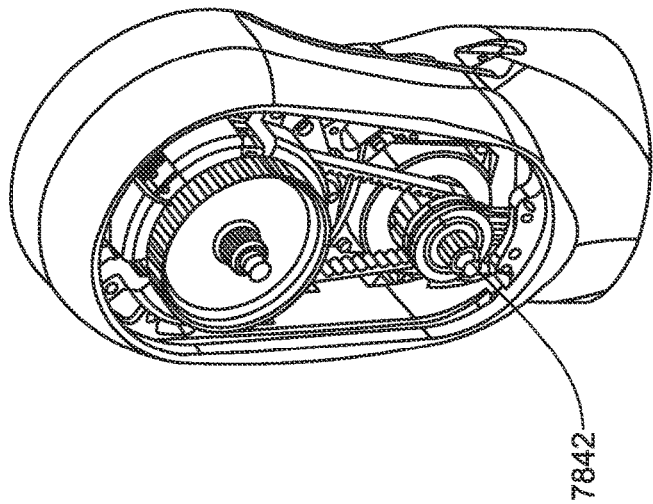

SECTION B-B

SECTION B-B

SECTION C-C

ARM PROSTHETIC DEVICE

CROSS-REFERENCE TO RELATED APPLICATIONS

This application is a Continuation of U.S. patent application Ser. No. 17/963,689, filed Oct. 11, 2022, entitled "Arm Prosthetic Device", which is a Divisional of Ser. No. 16/588,236, filed Sep. 30, 2019, entitled Arm Prosthetic Device, now U.S. Pat. No. 11,464,655, issued Oct. 11, 2022, which is a Divisional of U.S. patent application Ser. No. 15/427,306, filed Feb. 8, 2017, entitled Arm Prosthetic Device, now U.S. Pat. No. 10,426,638, issued Oct. 1, 2019, which claims the benefit of U.S. Provisional Application Ser. No. 62/292,611, filed Feb. 8, 2016, entitled Arm Prosthetic Device, each of which are hereby incorporated by reference herein in its entirety.

U.S. patent application Ser. No. 15/427,306, filed Feb. 8, 2017 is a Continuation-in-Part of U.S. patent application Ser. No. 15/198,929, filed Jun. 30, 2016, entitled Arm Prosthetic Device, which is a Continuation of U.S. patent application Ser. No. 13/566,736, filed Aug. 3, 2012, entitled Arm Prosthetic Device, now U.S. Pat. No. 9,381,099, issued Jul. 5, 2016, which is a Continuation-In-Part of U.S. patent application Ser. No. 13/088,063, filed Apr. 15, 2011, entitled Arm Prosthetic Device, now U.S. Pat. No. 8,979,943 issued Mar. 17, 2015, which is also a Continuation-In-Part of U.S. patent application Ser. No. 12/706,609, filed Feb. 16, 2010, entitled Arm Prosthetic Device, now U.S. Pat. No. 8,449,624, issued May 28, 2013, which claims the benefit of U.S. Provisional Patent Application Ser. No. 61/168,786, filed Apr. 13, 2009, entitled Arm Prosthetic Device, and is a Continuation-In-Part of U.S. patent application Ser. No. 12/027,141, filed Feb. 6, 2008, entitled Arm Prosthetic Device, now U.S. Pat. No. 9,114,028, issued Aug. 25, 2015, which claims the benefit of U.S. Provisional Patent Application Ser. No. 60/899,833, filed Feb. 6, 2007, entitled Arm Prosthetic Device, and U.S. Provisional Patent Application Ser. No. 60/963,639, filed Aug. 6, 2007, entitled Arm Prosthetic Device, each of which is hereby incorporated by reference herein in its entirety.

U.S. application Ser. No. 13/566,736, filed Aug. 3, 2012, entitled Arm Prosthetic Device, now U.S. Pat. No. 9,381,099, issued Jul. 5, 2016 also claims the benefit of U.S. Provisional Patent Application Ser. No. 61/542,928, filed Oct. 4, 2011, entitled Arm Prosthetic Device, U.S. Provisional Patent Application Ser. No. 61/551,119, filed Oct. 25, 2011, entitled Arm Prosthetic Device, and U.S. Provisional Patent Application Ser. No. 61/604,950, filed Feb. 29, 2012, entitled Arm Prosthetic Device, each of which are also hereby incorporated by reference herein in their entirety.

STATEMENT OF GOVERNMENT INTEREST

This invention was made with Government support under Contract Number W911 NF-09-C-0035 awarded by the U.S. Army RDECOM ACQ CTR. The Government has certain rights in the invention.

TECHNICAL FIELD

The present development relates to mechanical and medical devices and, more particularly, to prosthetic devices. More particularly, the development utilizes mechanical structure and user or motor stimuli to operate a prosthesis similarly to a human limb.

BACKGROUND INFORMATION

Existing prosthetic arms have limited movement for the user. Further, there are limited options for those patients who have lost their entire arm, shoulder to hand. Also, hand portions of existing prosthetic arms give the user, in many instances, one degree of movement. These known prosthetic devices provide limited capability with respect to, amongst other things, finer tasks.

Accordingly, there is a need for a prosthetic arm that replaces an arm from shoulder to hand and that has increased degrees of freedom. There is also a need for a prosthetic hand that moves in a realistic manner.

SUMMARY

In accordance with one aspect of the present invention, a system for powering a device is disclosed. The system includes at least one internal battery located in a device, at least one external battery connected to the device, and a master controller configured to connect either the at least one internal battery or the at least one external battery to a power bus to power the device.

Some embodiments of this aspect of the present invention include one or more of the following, wherein the system further includes wherein the at least one external battery further includes a keying feature. Wherein the system further includes a battery charger for charging the at least one external battery.

Wherein the battery charger is configured to accommodate at least two external batteries. Wherein the system includes at least two external batteries. Wherein the external batteries include built-in circuits for measuring state-of-charge. Wherein the system further includes a holster configured to accept and secure the at least one external battery. Wherein the holster further includes a power button. Wherein the at least one external battery powers the device. Wherein the at least one internal battery is rechargeable. Wherein the at least one external battery is rechargeable. Wherein the system further includes at least one AC adapter. Wherein the AC adapter charges the internal battery. Wherein the master controller is configured to recharge the internal battery using the at least one external battery. Wherein the system further includes wherein the master controller is configured to determine the capacity of the at least one internal battery, and when the capacity of the at least one internal battery is below a threshold, and determine whether to charge the internal battery using an AC adapter or from the at least one external battery. Wherein the master is controller is configured to determine when to switch from receiving power from the internal battery to receiving power from the at least one external battery. Wherein the master controller is configured to determine the capacity of the internal battery, and when the capacity of the internal battery is below a threshold, determining whether to charge the internal battery using an AC adapter or from the at least one external battery. Wherein the master controller is configured to determine the external battery has been disconnected from a holster, and switch to use the internal battery to power the bus. Wherein the master controller is configured to
    determine if an external battery is connected to the system, and if an external battery is connected to the system, connecting the external battery to the power bus, and disconnecting the internal battery from the power bus. Wherein the master controller is configured to determine the external battery remaining capacity is below a predetermined threshold, and command the internal battery to switch to power the bus. Wherein the master controller is configured to power the device using a first external battery, disconnect the first external battery from the device, connect an internal battery to a power bus to power the device, connecting an AC adapter to the device, charging the internal battery using the AC adapter, disconnecting the AC adapter from the device, connecting the first external battery to the device, and charging the internal battery using the first external battery. Wherein the master controller is configured to power the device using a first external battery, disconnect the first external battery from the device, connect an internal battery to a power bus to power the device, connect an AC adapter to the device, and charge the internal battery using the AC adapter. Wherein the master controller is configured to power the device using a first external battery, disconnect the first external battery from the device, connect an internal battery to a power bus to power the device, connect a second external battery to the device, disconnect the internal battery from the power bus, and connect the second external battery to the power bus. Wherein the master controller is configured to power the device using a first external battery, determine that the first external battery is disconnected from the device, and turn the internal interface circuit on to power the device using an internal battery.

Wherein the master controller is configured to monitor the capacity of an internal battery, determine the capacity of an external battery, determine whether the internal battery capacity is less than a predetermined threshold, and if the internal battery capacity is less than a predetermined threshold, and the external battery capacity if above a predetermined threshold, charging the internal battery using the external battery. Wherein the master controller is configured to determine if an external battery is connected to the device, if not, the master controller allowing the internal battery to power the bus, if an external battery is connected to the device, determine the capacity of the external battery, if the capacity exceeds a predetermined threshold, disconnecting the internal battery from powering the bus, and connect the external battery to power the bus. Wherein the master controller is configured to determine if an external battery is connected to the device, if not, the master controller allowing the internal battery to power the bus, if an external battery is connected to the device, disconnect the internal battery from powering the bus and connect the external battery to power the bus.

In accordance with one aspect of the present invention, a method for powering a device is disclosed. The method includes determining the total capacity of the installed batteries in a device; and if the total capacity is below a predetermined threshold, then alerting a user that the total capacity is below a threshold.

In accordance with one aspect of the present invention, a method for powering a device is disclosed. The method includes determining if an external battery is connected to the device, if not, the master controller allowing the internal battery to power the bus, if an external battery is connected to the device, disconnecting the internal battery from powering the bus, and connecting the external battery to power the bus.

In accordance with one aspect of the present invention, a method for powering a device is disclosed. The method includes determining if an external battery is connected to the device, if not, the master controller allowing the internal battery to power the bus, if an external battery is connected to the device, determining the capacity of the external battery, if the capacity exceeds a predetermined threshold, disconnecting the internal battery from powering the bus, and connecting the external battery to power the bus.

In accordance with one aspect of the present invention, a method for powering a device is disclosed. The method includes monitoring the capacity of an internal battery, determining the capacity of an external battery, determining whether the internal battery capacity is less than a predetermined threshold, and if the internal battery capacity is less than a predetermined threshold, and the external battery capacity if above a predetermined threshold, charging the internal battery using the external battery.

In accordance with one aspect of the present invention, a method for powering a device is disclosed. The method includes determining an external battery has been disconnected from a holster, and the microcontroller switching to use an internal battery of the device to power the bus.

In accordance with one aspect of the present invention, a method for powering a device is disclosed. The method includes powering the device using a first external battery, determining that the first external battery is disconnected from the device, and turning the internal interface circuit on to power the device using an internal battery.

In accordance with one aspect of the present invention, a method for powering a device is disclosed. The method includes powering the device using a first external battery, disconnecting the first external battery from the device, connecting an internal battery to a power bus to power the device, connecting a second external battery to the device, disconnecting the internal battery from the power bus, and connecting the second external battery to the power bus.

In accordance with one aspect of the present invention, a method for powering a device is disclosed. The method includes powering the device using a first external battery, disconnecting the first external battery from the device, connecting an internal battery to a power bus to power the device, connecting an AC adapter to the device, and charging the internal battery using the AC adapter.

In accordance with one aspect of the present invention, a method for powering a device is disclosed. The method includes powering the device using a first external battery, disconnecting the first external battery from the device, connecting an internal battery to a power bus to power the device, connecting an AC adapter to the device, charging the internal battery using the AC adapter, disconnecting the AC adapter from the device, connecting the first external battery to the device; and charging the internal battery using the first external battery.

According to some aspects of the present invention, a battery system is disclosed. The system includes at least one electronic device having a housing, at least one rechargeable internal battery located inside the electronic device housing, and at least one external battery located outside the electronic device housing, wherein the at least one external battery charges the at least one internal battery.

It is one aspect of the present device to provide a prosthetic device that will allow the user improved range of motion, improved tactile capabilities, increased comfort for the user, and decreased reliance on manual positioning of the prosthesis.

According to some aspects of the present invention, a compound motion assembly for providing a two-axis compound motion through a pre-determined path includes an input member and an output member moveably coupled to the input member. Actuation of the compound motion assembly generates movement of the output member relative to the input member along a compound motion path having motion about at least two axes. In some embodiments, the compound motion assembly includes a drive arrangement for controlling movement of the output member relative to the input member. In these embodiments, the rate of motion about each axis may vary as the drive arrangement is actuated at a constant rate.

According to some embodiments, the output member may be moveably coupled to the input member through at least a first joint having a first axis and a second joint having a second axis, the first and second joints being connected in series. The compound motion assembly may include a path member that is fixedly coupled to the input member and has a fixed path profile formed therein defining the compound motion path. A follower member may be coupled to the output member and engaging the fixed path profile of the path member such that pivotal movement of the output member relative to the input member about both the first axis and the second axis is generated as the follower member moves along the pre-determined path. In some embodiments, the drive arrangement may drive the compound motion assembly through one of the first or second joints to cause movement of the output member.

According to some aspects of the present invention, a prosthetic limb segment has a housing with an input interface and an output interface that are moveable with respect to one another and a motorized drive for effecting movement of at least one of the output interface or the input interface. The prosthetic limb segment also includes a controller disposed within the housing for controlling the motorized drive and also for communicating with and controlling at least a second motorized drive of at least a second prosthetic limb segment.

According to some embodiments, the prosthetic limb segment may include a user interface integrally formed in the housing and in communication with the controller. The user interface may include a status indicator for displaying information from the controller. In some embodiments, the status indicator may have one or more LEDs for displaying information from the controller. In some embodiments, at least a portion of the LEDs are arranged in an array. In some embodiments, the user interface includes at least one input member for providing a signal to the controller. The user interface may include a protective cover, which may be flexible and may include at least a portion that is translucent to allow light from an LED disposed beneath the protective cover therethrough.

According to some aspects of the present invention, a safety mechanism for a prosthetic device having at least one motorized drive and a controller for controlling the motorized drive is provided. The safety mechanism includes an actuator electrically coupled in parallel with the controller between the motorized drive and a power source so that actuation of the actuator supplies power to the motorized drive bypassing the controller and actuates the motorized drive until it reaches a safe position.

According to some embodiments, the safety mechanism may include an actuator that has at least two switches coupled to actuate simultaneously and electrically coupled in parallel so that actuation of only one switch of the at least two switches is sufficient to actuate the motorize drive, thereby providing redundancy. In some embodiments, the actuator is electrically coupled in parallel with the controller between the power source and a plurality of motorized drives such that actuation of the actuator supplies power to the plurality of motorized drives and actuates each motorized drive until it reaches a safe position.

The same compliance method is applied to the MRP drive, allowing it to store elastic energy.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 56 is a cross-sectional view of another embodiment of a wrist flexion assembly according to the present invention;

FIG. 57A is a partial cross-sectional view of another embodiment of the non-backdriving clutch of FIG. 12;

FIG. 59 is a perspective view of a compliance assembly according to an embodiment of the present invention;

FIG. 60A is a side view of a breakaway mechanism according to an embodiment of the present invention;

FIG. 60B is a front cross-sectional view of the breakaway mechanism of FIG. 60A;

FIGS. 101A, 101B, 101C and 101D are various views of the brake mechanism according to one embodiment;

FIGS. 102A, 102B, 102C, 102D and 102E are various views of the abductor potentiometer sensor system according to one embodiment;

FIGS. 103A, 103B and 103C are various views of the wrist rotator sensor according to one embodiment;

FIGS. 104A and 104B are various views of the wrist according to one embodiments, including a wrist position sensor;

FIG. 105 is one embodiments of a battery interface;

FIG. 106 shows one embodiment of an external battery and one embodiment of a holster;

FIG. 107 shows one embodiment of a charger and one embodiment of two external batteries;

FIG. 108 is a diagram of one embodiment of the battery system;

FIG. 109 is a diagram of one embodiment of the internal battery interface;

FIG. 110 is a diagram of one embodiment of the internal battery interface;

FIG. 111 is a diagram of one embodiment of the external battery interface;

FIG. 112 is a diagram of one embodiment of the external battery interface;

FIG. 113 is a diagram of one embodiment of the external battery and internal battery system;

Figure 115A:
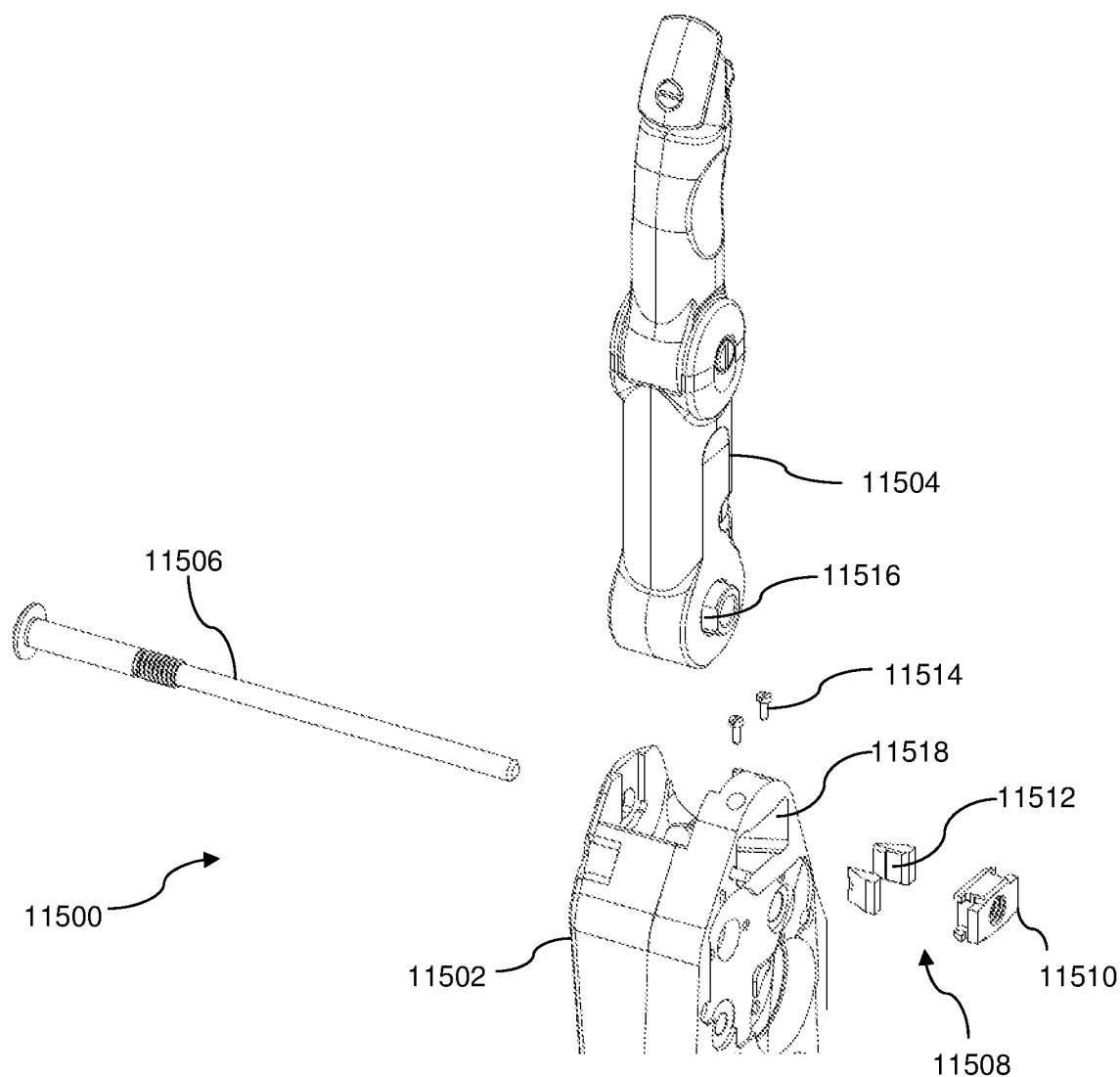
Figure 115B:
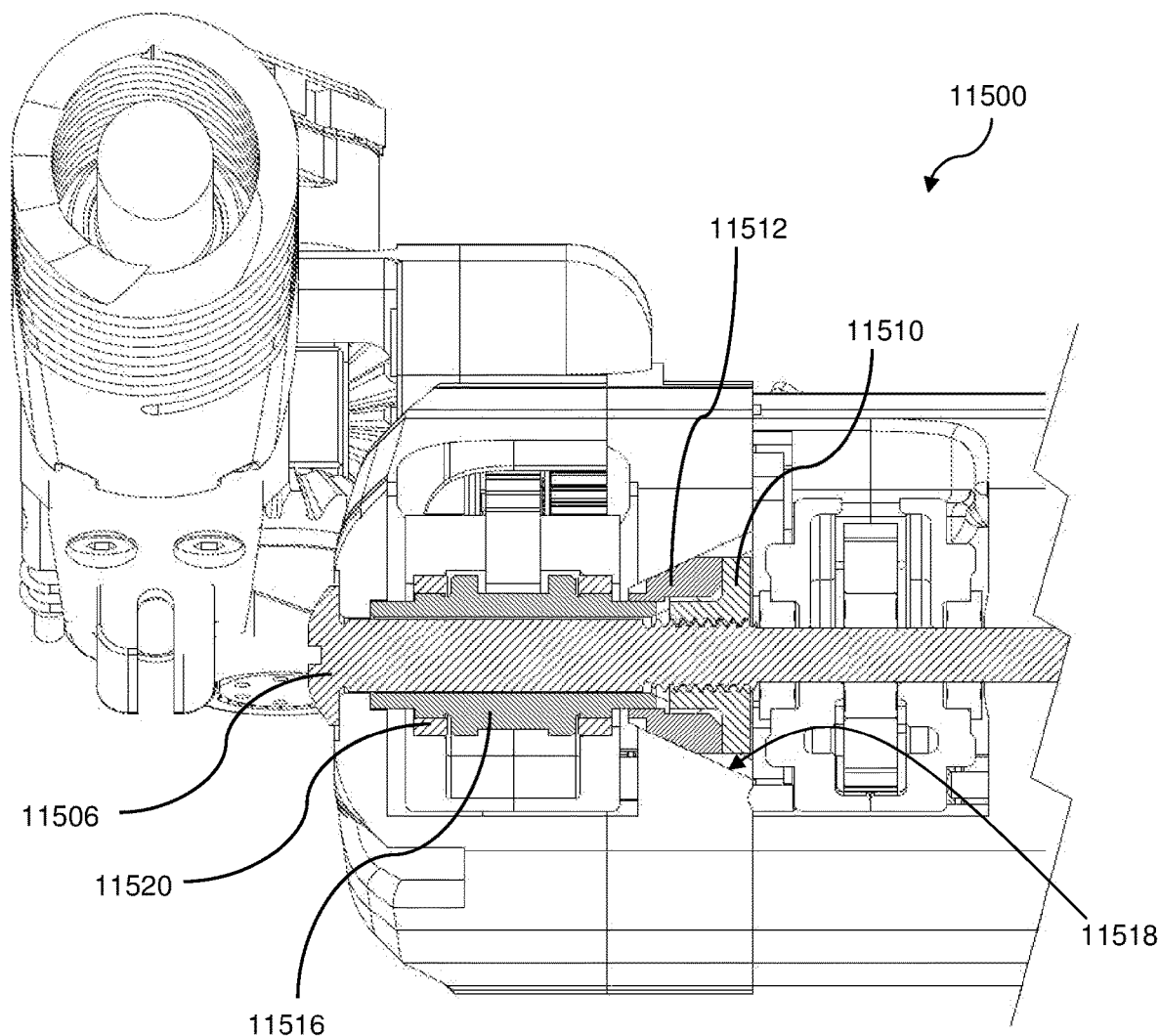
Figure 116A:
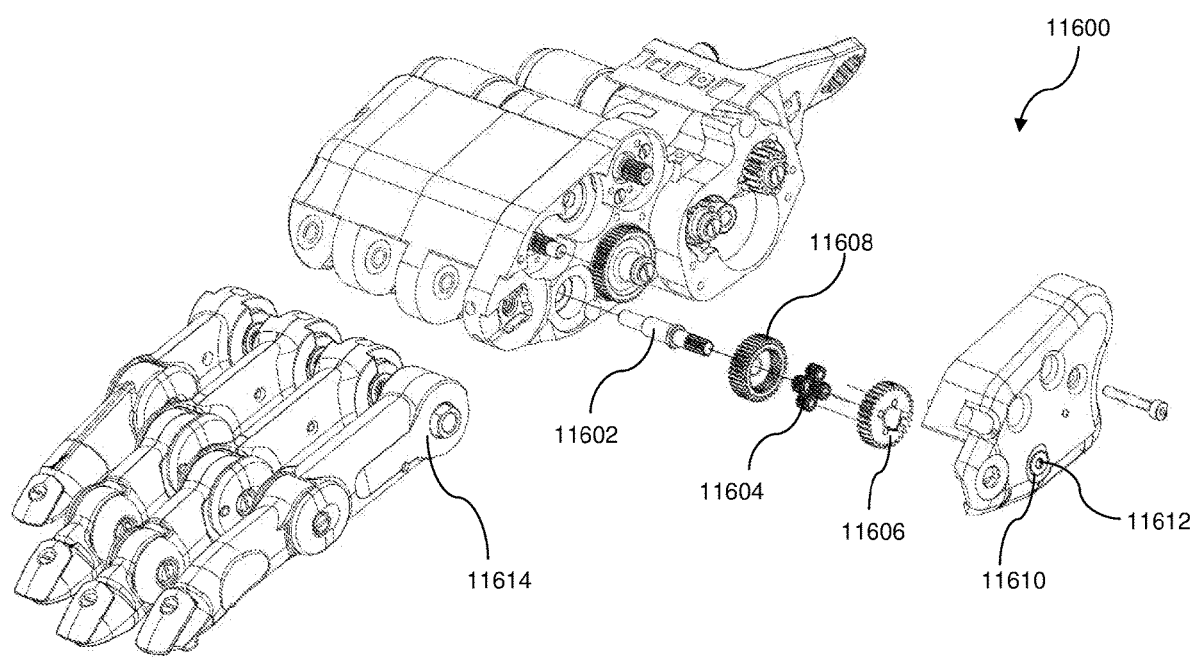
Figure 116B:
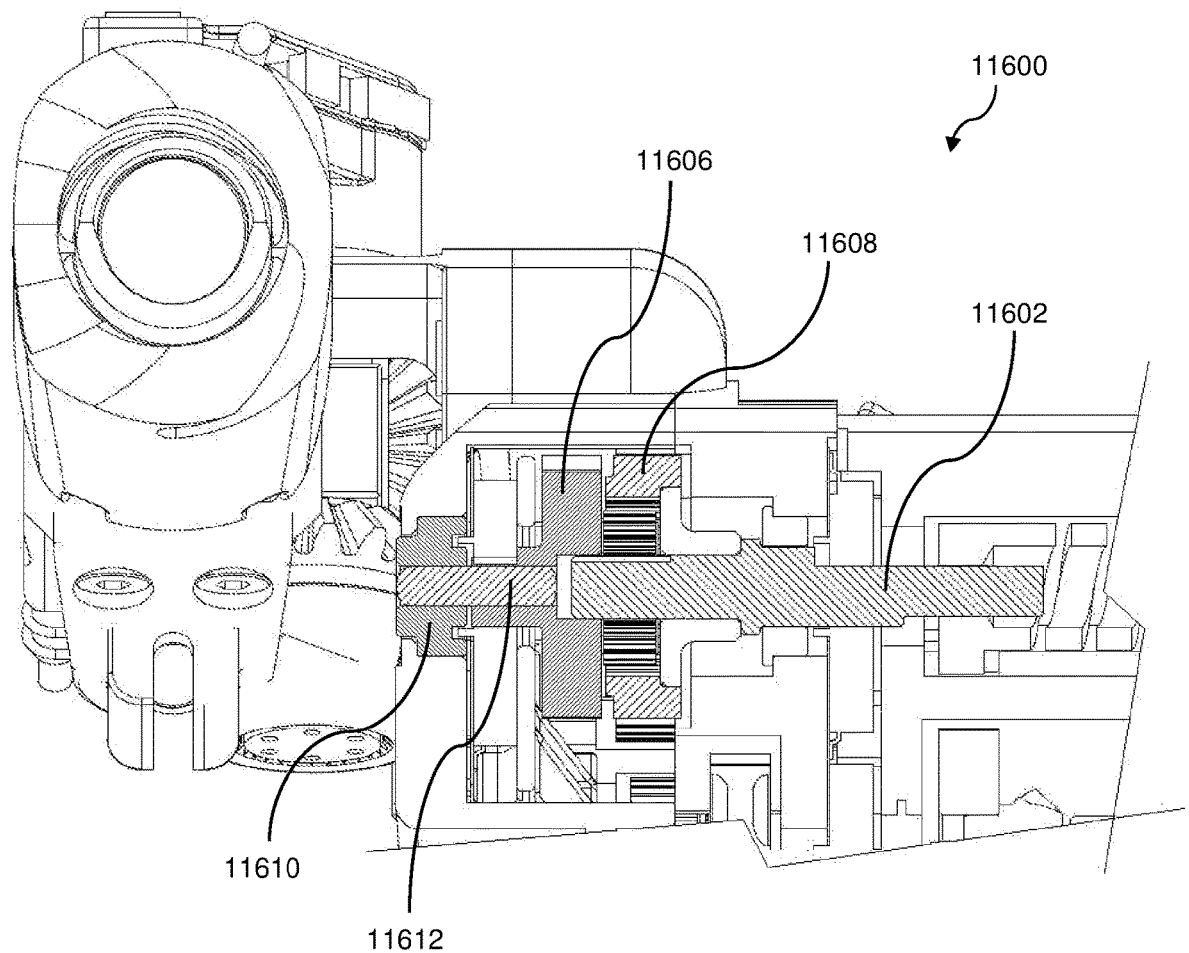

FIGS. 114A, 114B, 114C, 114D, 114E and 114F are various views of the caliper braking system according to one embodiment;

FIGS. 115A and 115B are various views of the index pivot system according to one embodiment; and FIGS. 116A and 116B are various views of one embodiment of a hand including an embodiment of a compliance assembly.

DETAILED DESCRIPTION OF VARIOUS EMBODIMENTS

Figure 1:
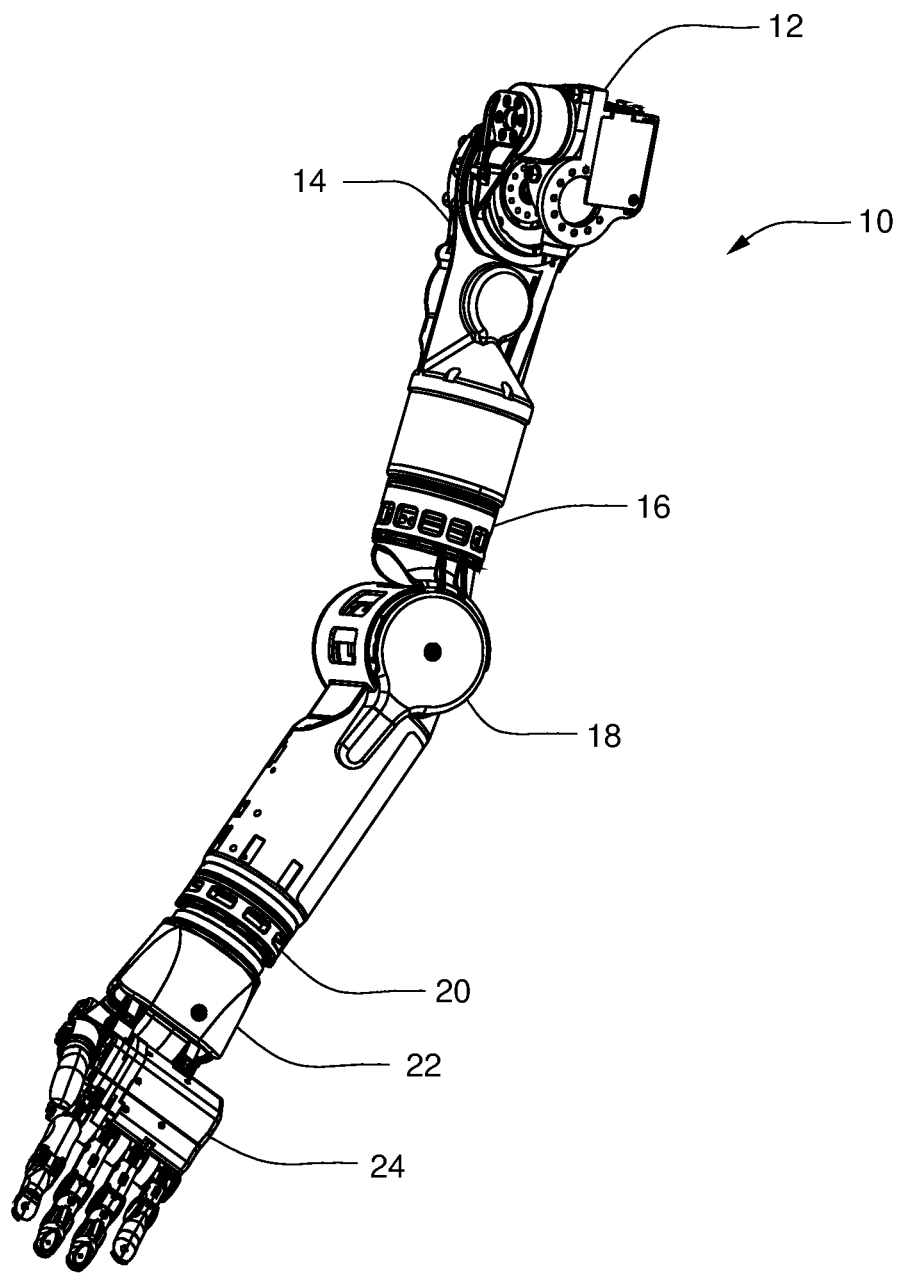
FIG. 1 is a perspective view of one embodiment of a prosthetic arm apparatus according to the present invention.
Figure 2:
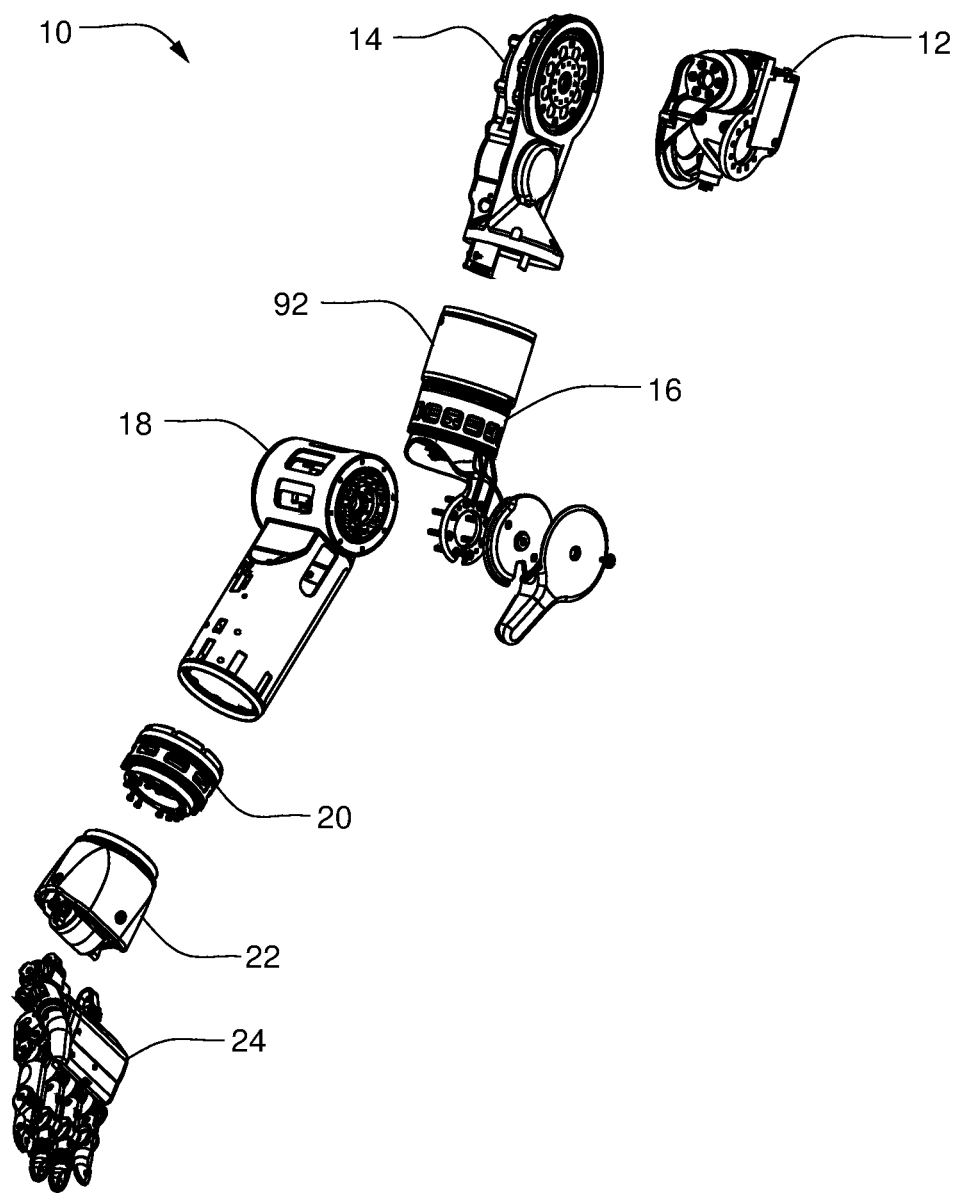
FIG. 2 is an exploded view of the prosthetic arm apparatus of FIG. 1.

Referring to FIGS. 1 and 2, a prosthetic arm apparatus 10 for attachment to a shoulder of a shoulder disarticulated amputee includes a plurality of segments, including a shoulder abductor 12, a shoulder flexion assembly 14, a humeral rotator 16, an elbow flexion assembly 18, a wrist rotator 20, a wrist flexion assembly 22, and a hand assembly 24. The prosthetic arm apparatus 10, in the exemplary embodiment, has the dimensions and weight of a female arm of a fiftieth percentile, so that many different users may comfortably use the prosthetic arm apparatus 10. As should be understood by those skilled in the art, the prosthetic arm apparatus 10 may be constructed to larger or smaller dimensions if desired.

The prosthetic arm apparatus 10 may be controlled by a control system (not shown), such as the various control systems described in U.S. patent application Ser. No. 12/027,116, filed Feb. 6, 2008, U.S. patent application Ser. No. 12/706,575, filed Feb. 16, 2010, U.S. patent application Ser. No. 12/706,471, filed Feb. 16, 2010, and the U.S. patent application entitled SYSTEM, METHOD AND APPARATUS FOR CONTROL OF A PROSTHETIC DEVICE, filed on the same day as the present application and assigned to the same assignee, each of which is hereby incorporated by reference in its entirety.

Figure 3:
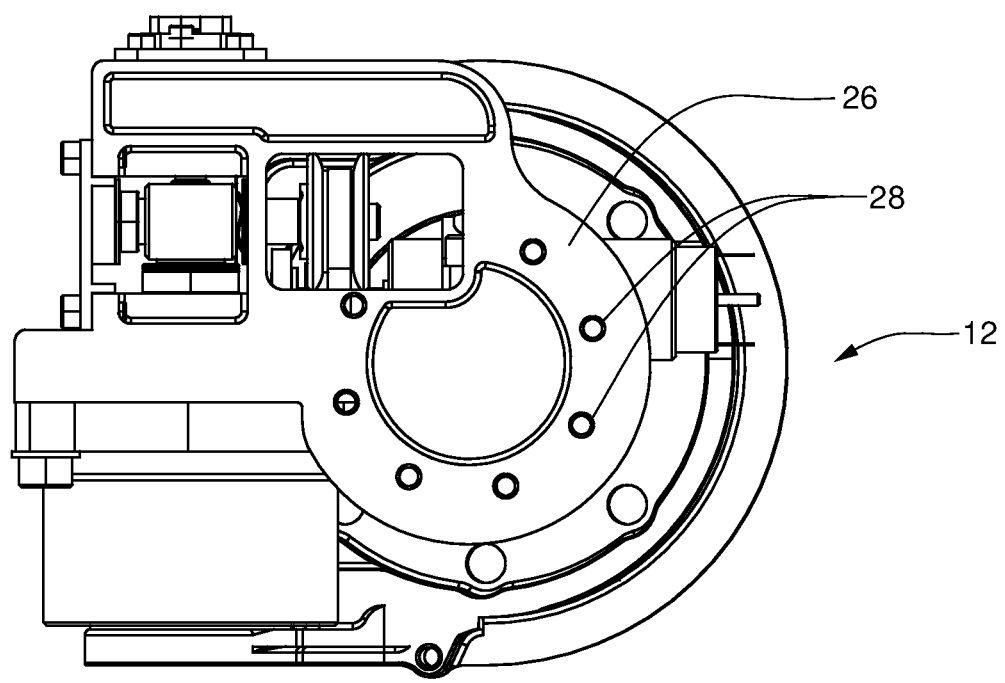
FIG. 3 is a rear view of a shoulder abductor of the prosthetic arm apparatus of FIG. 1 according to the present invention.

Referring to FIG. 3, one embodiment of the shoulder abductor 12 is shown. The shoulder abductor 12 includes a harness mount 26 for connecting the prosthetic arm apparatus 10, shown in FIG. 1, to a support apparatus, as the various prosthetic supports described in U.S. patent application Ser. No. 12/026,971, filed Feb. 6, 2008, U.S. patent application Ser. No. 12/706,340, filed Feb. 16, 2010, and the U.S. patent application entitled DYNAMIC SUPPORT APPARATUS AND SYSTEM, filed on the same day as the present application and assigned to the same assignee, each of which is hereby incorporated by reference in its entirety. The harness mount 26 has harness interface holes 28 that may be used to attach the abductor 12 to a prosthetic harness (not shown) or other system for supporting the prosthetic arm apparatus 10. In the exemplary embodiment, the harness or prosthetic support apparatus may also be one disclosed in co-pending U.S. patent application Ser. No. 12/026,971, by Altobelli, et al., entitled Dynamic Support Apparatus filed on Feb. 6, 2008, which is hereby incorporated by reference in its entirety.

Figure 4:
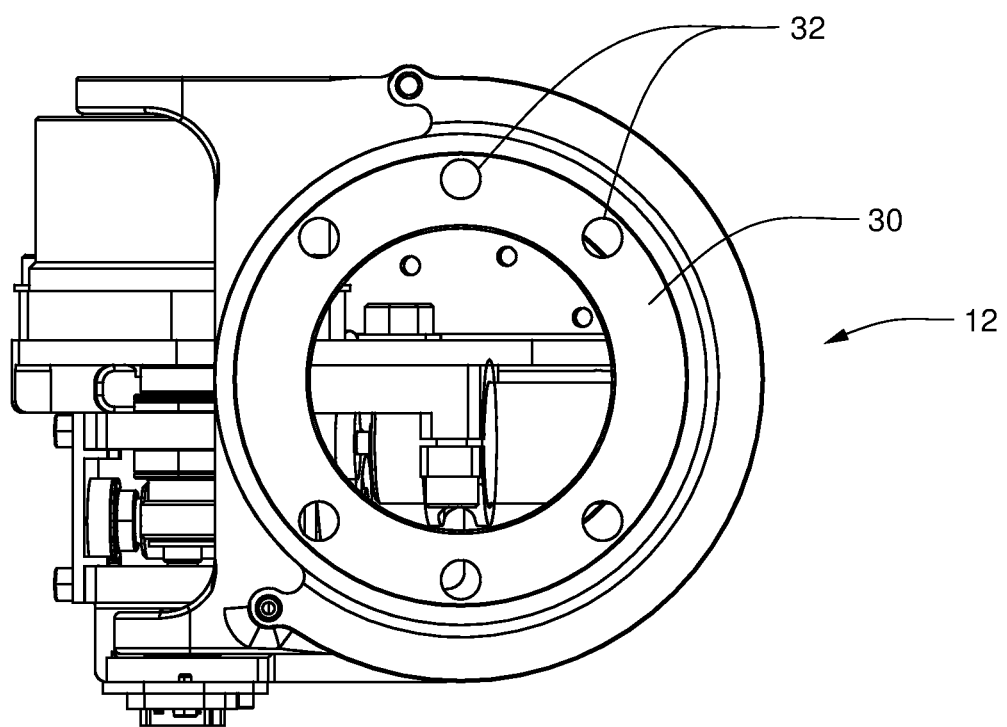
FIG. 4 is a front view of the shoulder abductor of FIG. 3.

Referring to FIG. 4, the shoulder abductor 12 also has a shoulder flexion assembly mount 30, shown according to one embodiment. The shoulder flexion assembly mount 30 interfaces with the shoulder flexion assembly 14 to mount the shoulder flexion assembly 14 onto the shoulder abductor 12. In one embodiment, the flexion assembly mount 30 has interface holes 32 to facilitate connection of the shoulder flexion assembly 14 by attachment means such as bolts.

Figure 5:
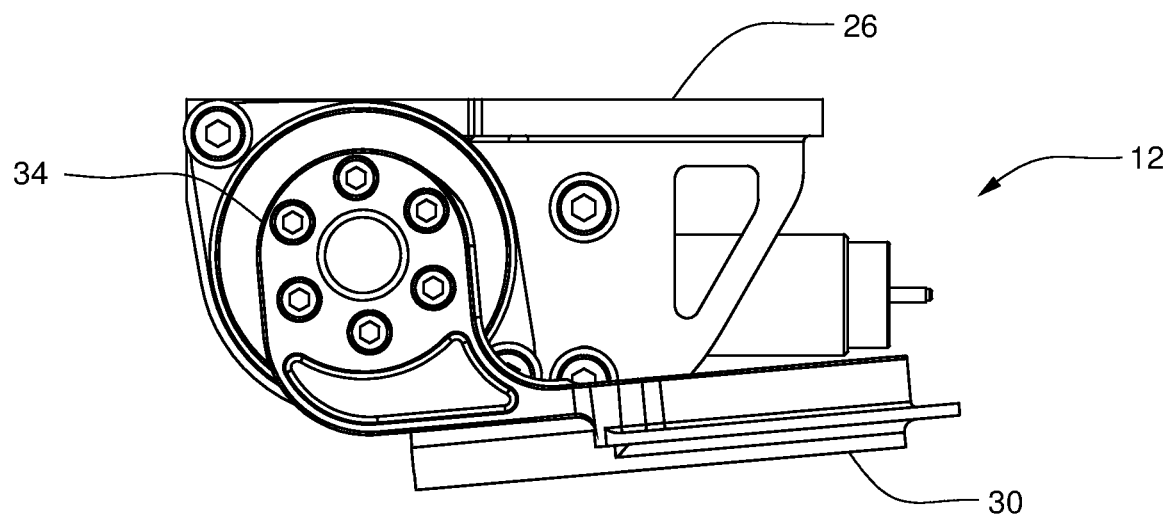
FIG. 5 is a side view of the shoulder abductor of FIG. 3.

Referring to FIG. 5, the shoulder abductor 12 further includes an abductor joint 34, shown according to one embodiment. The abductor joint 34 is used to pivot the shoulder flexion assembly mount 30 away from the harness mount 26 and back toward the harness mount 26.

Figure 6:
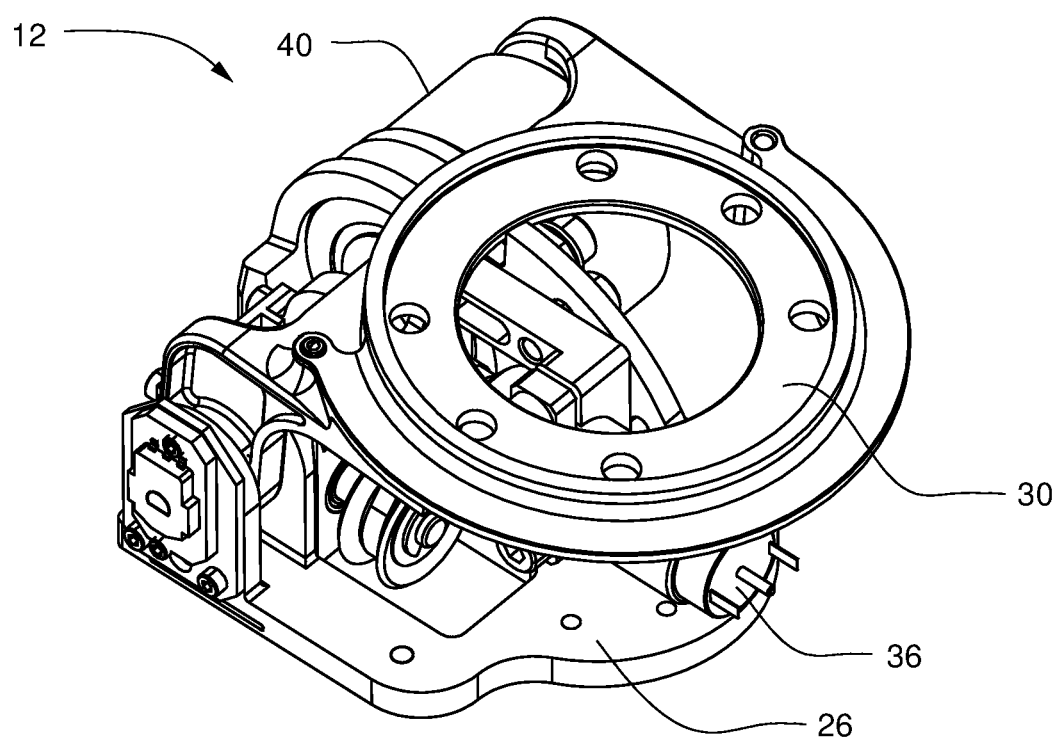
FIG. 6 is a perspective view of the shoulder abductor of FIG. 3.
Figure 7:
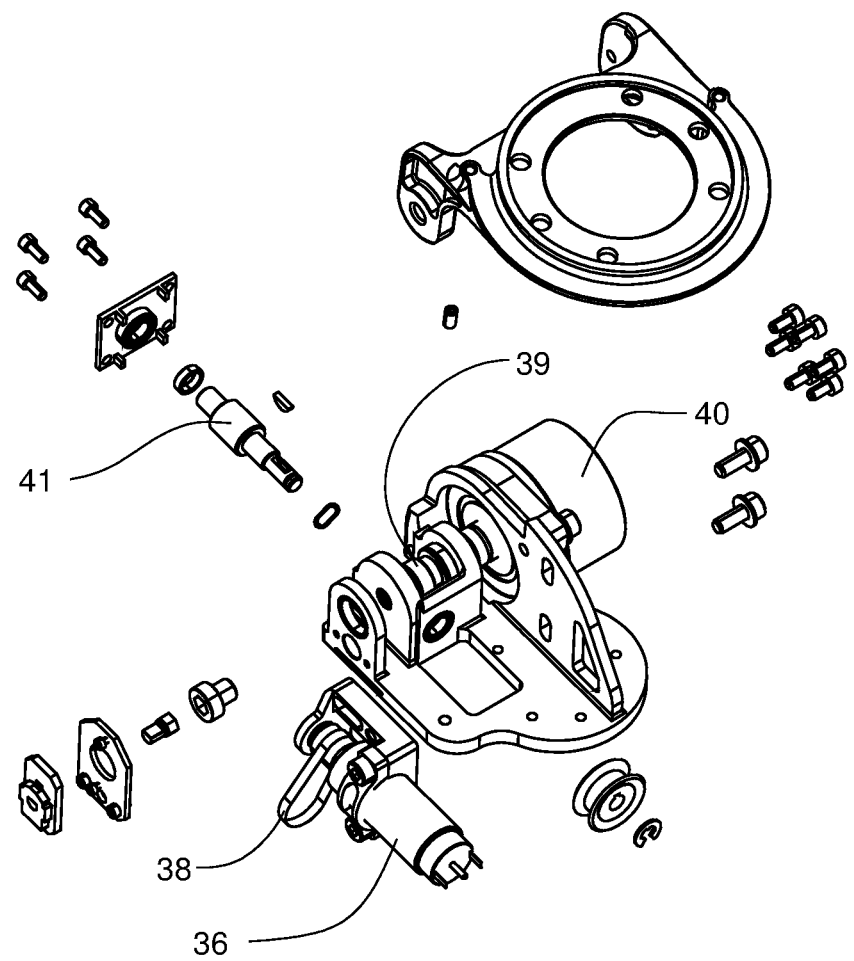
FIG. 7 is an exploded perspective view of the shoulder abductor of FIG. 6.

Referring to FIGS. 6 and 7, the shoulder abductor 12 includes an abductor motor 36 to control the pivotal movement of the abductor joint 34, shown in FIG. 5, both the shoulder abductor 12 and abductor motor 36 shown according to one embodiment. In this embodiment, the abductor motor 36 is a brushed DC motor controlling the pivotal movement through an abductor belt 38 connected to a worm drive 41 driving a worm wheel 39 connected to an abductor harmonic drive gearing system 40.

Figure 8:
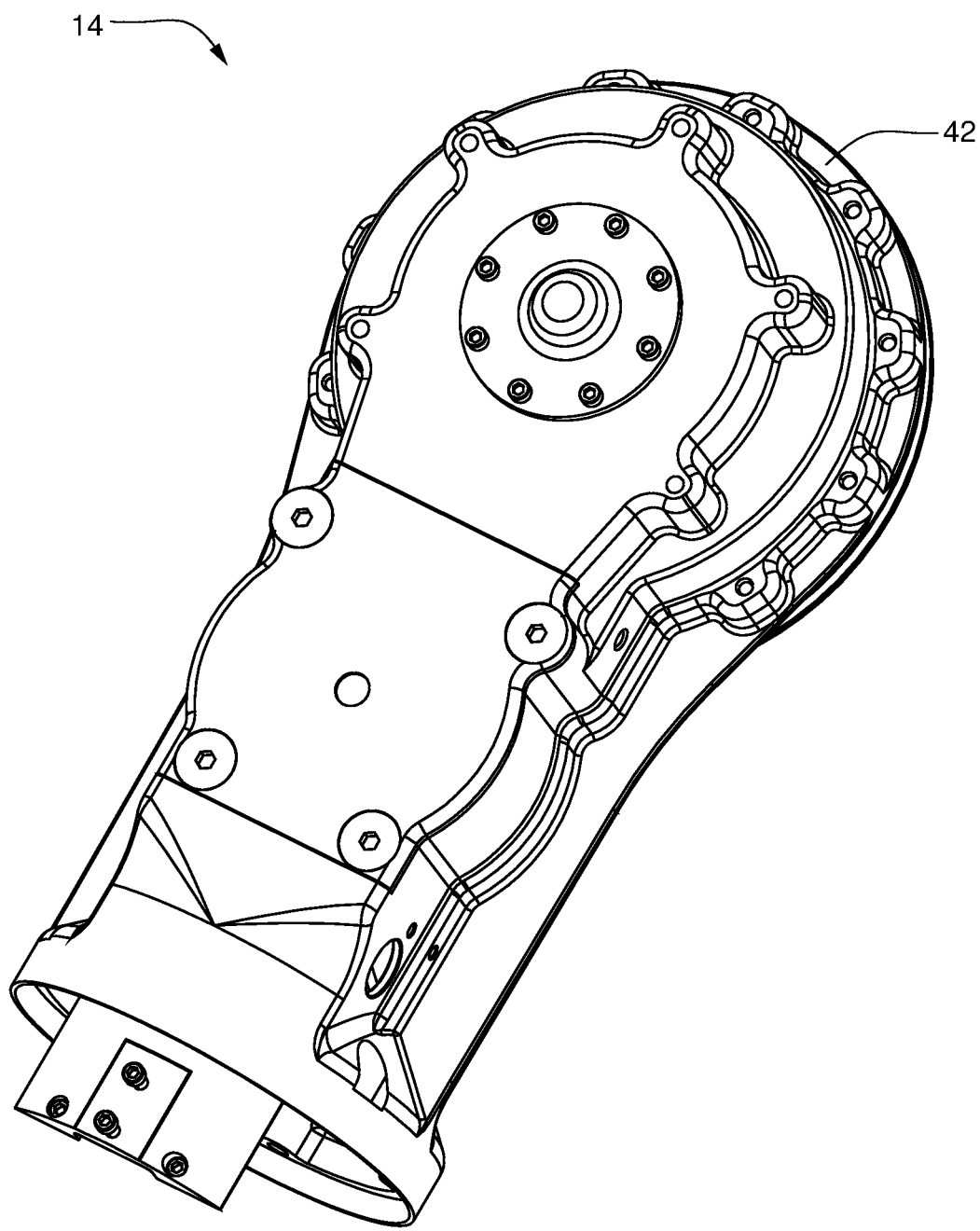
FIG. 8 is a perspective view of a shoulder flexion assembly of the prosthetic arm apparatus of FIG. 1 according to the present invention.
Figure 9:
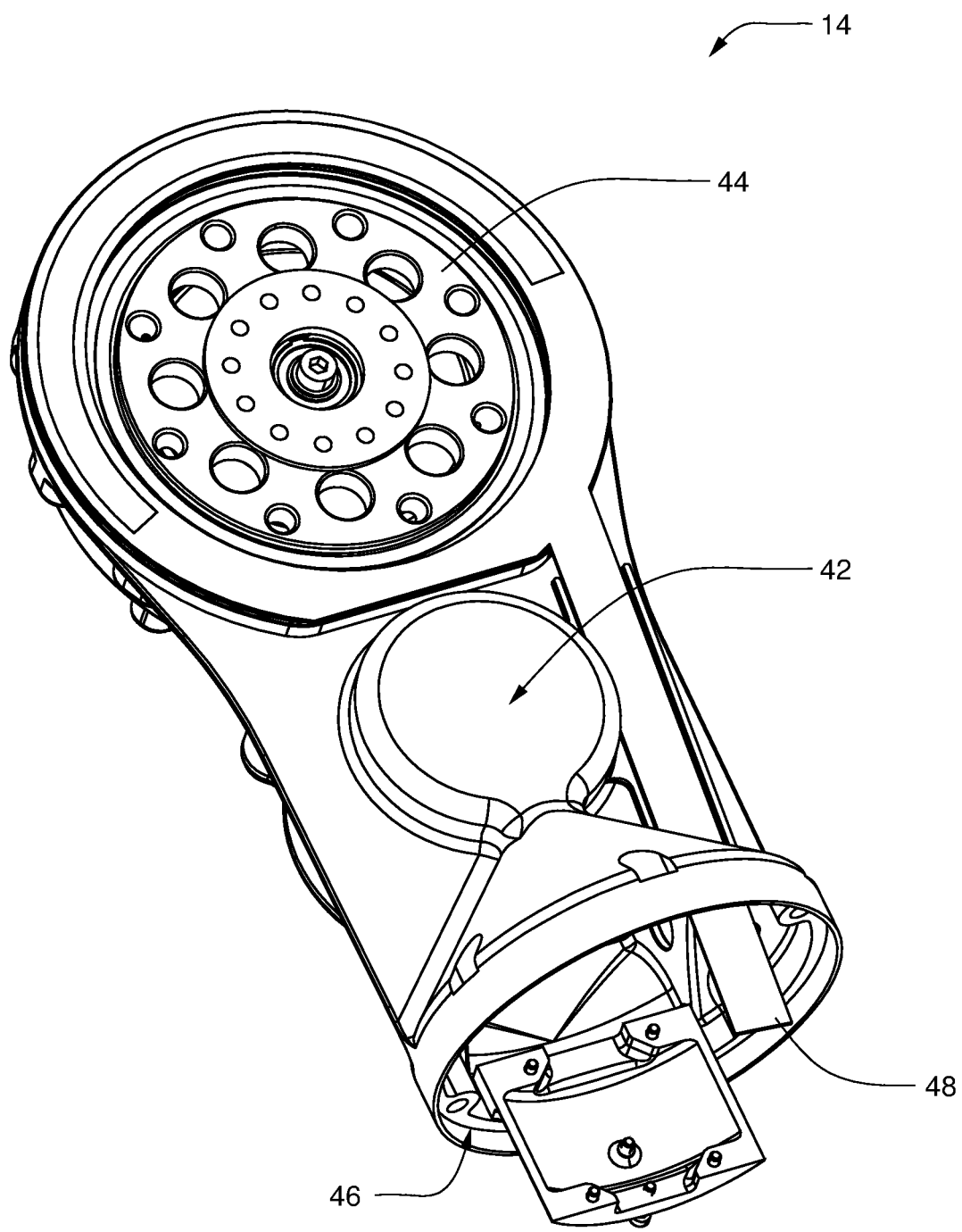
FIG. 9 is a reverse perspective view of the shoulder flexion assembly of FIG. 8.

Referring to FIGS. 8 and 9, the shoulder flexion assembly 14, in one embodiment, has a main shoulder housing 42, with an abductor interface 44 for connecting the shoulder flexion assembly 14 to the shoulder abductor 12. The shoulder flexion assembly 14 also has a humeral interface 46 for connecting the humeral rotator 16 to the shoulder flexion assembly 14.

Figure 10:
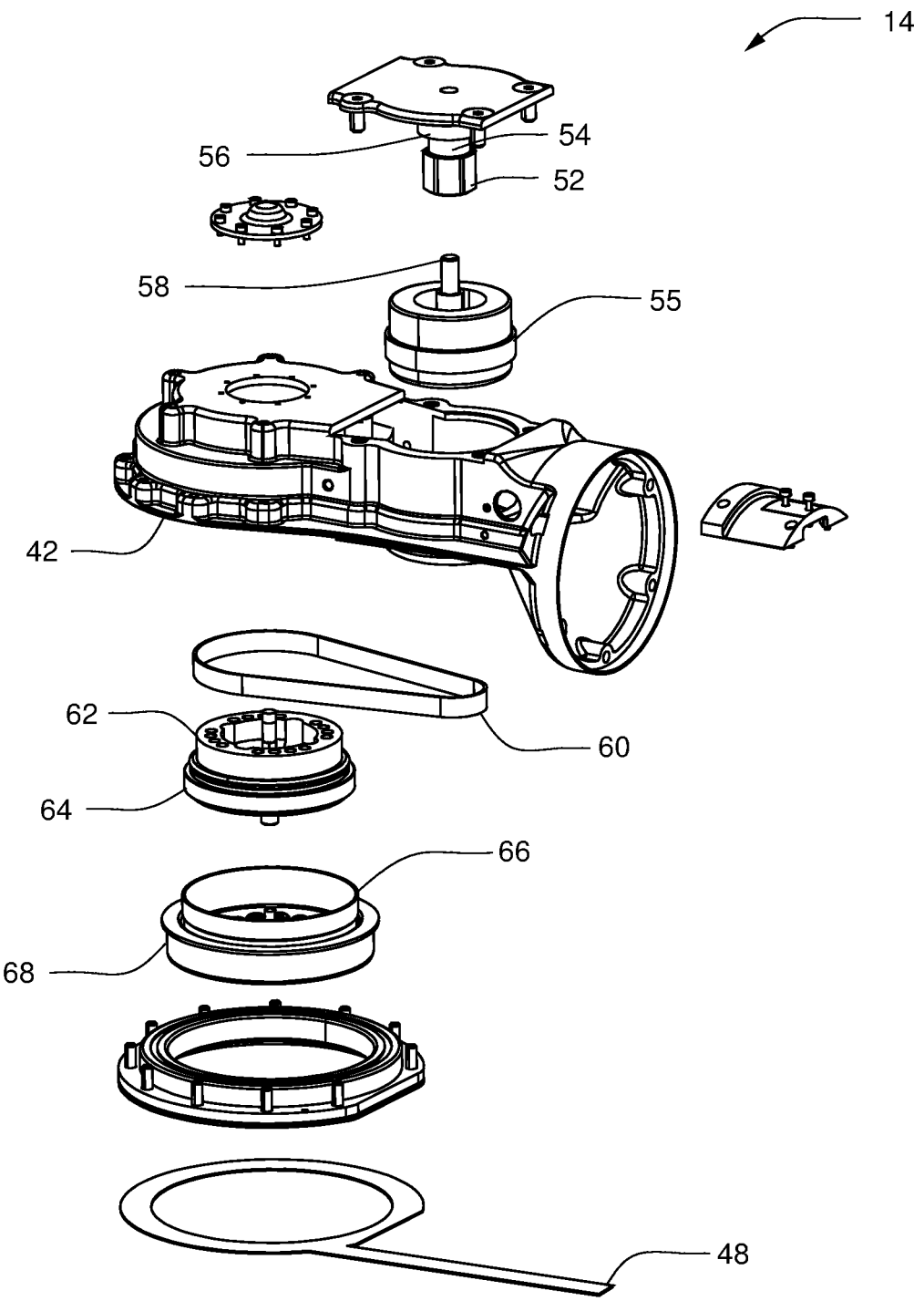
FIG. 10 is an exploded perspective view of the shoulder flexion assembly of FIG. 8.
Figure 11:
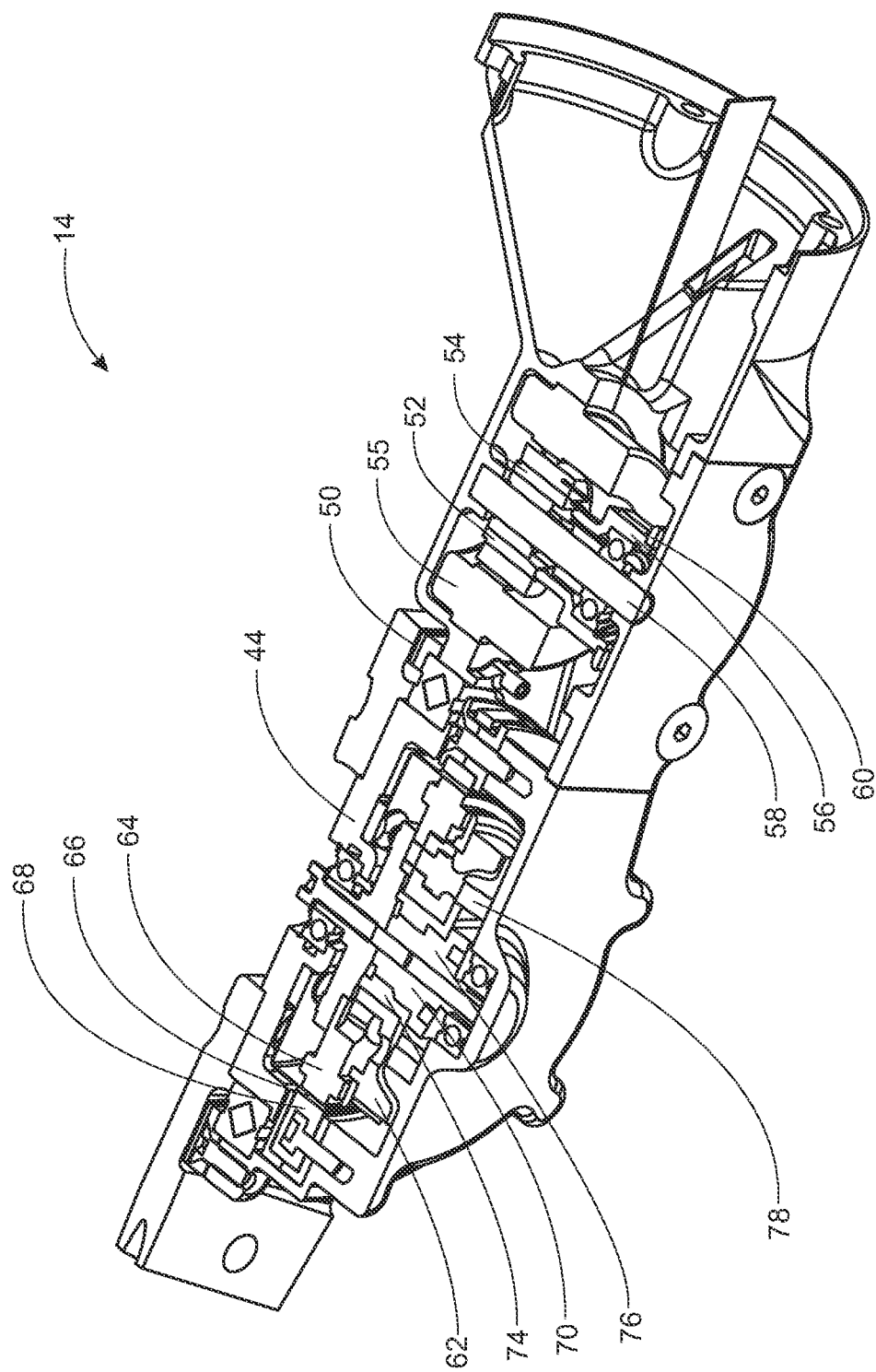
FIG. 11 is a cross-sectional perspective view of the shoulder flexion assembly of FIG. 8.

Referring to FIGS. 10 and 11, in one embodiment, shoulder flexion motor magnets 52 are disposed around a shaft 58 of a shoulder flexion motor rotor 54. In this embodiment, a shoulder flexion motor armature 55 drives the shoulder flexion motor rotor 54, which in turn drives a shoulder flexion motor pulley 56 around a motor shaft 58. The shoulder flexion motor pulley 56 supports a shoulder flexion belt 60, which is linked between the shoulder flexion motor pulley 56 and a shoulder flexion belt-driven pulley 62. The shoulder flexion belt-driven pulley 62 drives a shoulder flexion harmonic drive gearing system wave generator 64. A shoulder flexion harmonic drive gearing system flexspline 66 rotates against the shoulder flexion harmonic drive gearing system wave generator 64 and a shoulder flexion harmonic drive gearing system circular spline 68, resulting in reduced speed for the joint movement. The shoulder flexion harmonic drive gearing system flexspline 66 is connected to the abductor interface 44, and is thus able to rotate the shoulder flexion assembly 14 in reference to the abductor interface.

Referring to FIG. 11, in one embodiment, a non-backdriving clutch 70 is disposed inside the main shoulder housing 42. The non-backdriving clutch 70 allows the prosthetic arm 10 to hold position by locking when the prosthetic arm 10 is not moving.

Figure 12:
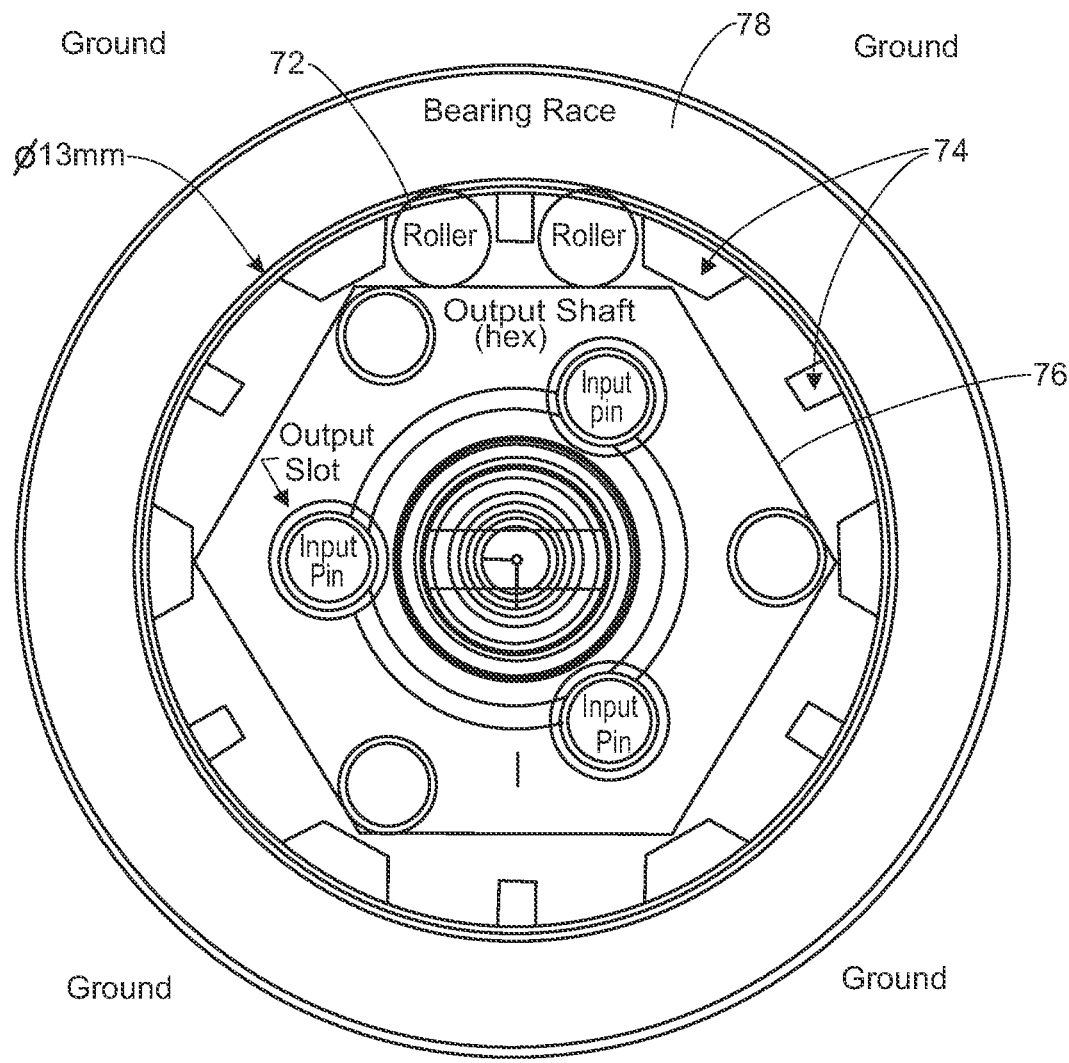
FIG. 12 is a top view of a non-backdriving clutch according to the present invention.

Referring to FIG. 11 and FIG. 12, in one embodiment, roller bearings 72 line the interface between an input cage 74 and an output hex 76. When a force is applied to the shoulder abductor interface 44, the output hex 76 locks against the bearing race 78 and the roller bearings 72. This prevents the shoulder flexion assembly 14 from moving due to force applied to its output, shoulder abductor interface 44. Upon the exertion of a necessary amount of input force through the clutch input cage 74, the output hex 76 disengages and allows the shoulder flexion assembly 14 to move. The clutch input cage 74 and the output hex 76 are both constrained by a clutch race 78. It should be understood by those skilled in the art, that other mechanisms could be used to prevent backdriving of the prosthetic arm 10, such as a clutch that locks in one direction or a solenoid with brakes that engage when the solenoid is powered. Additionally, although described in connection with the shoulder flexion assembly 14, it should be understood by those skilled in the art that the non-backdriving clutch 70 may be included in other prosthetic joints described herein.

Figure 13:
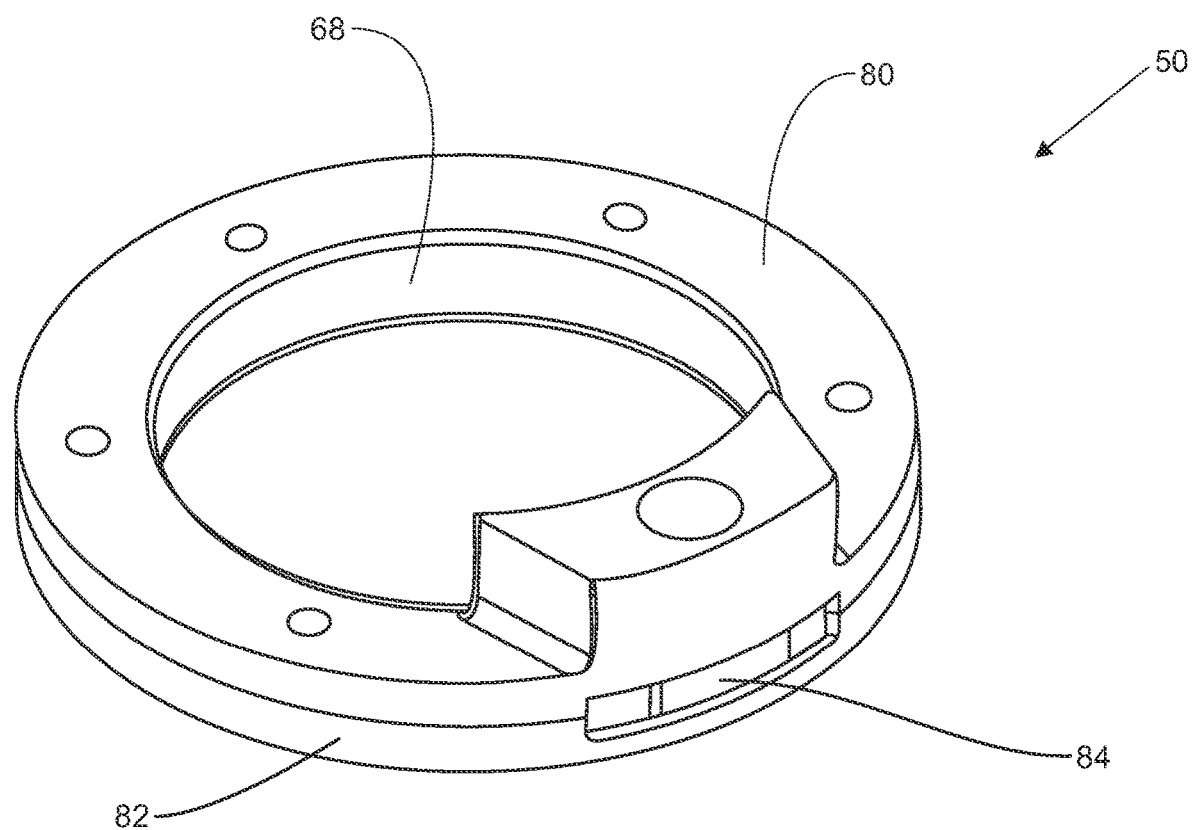
FIG. 13 is a perspective view of a fully assembled compliance subassembly of the shoulder flexion assembly of FIG. 8.

Referring to FIG. 13, in one embodiment, a compliance subassembly 50, shown in FIG. 11, includes a compliance reactor 80 positioned on top of the shoulder flexion harmonic drive gearing system circular spline 68, shown in FIG. 10, and held in place by the clamp 82. The compliance reactor 80 measures the amount of displacement in the compliance subassembly 50 in relation to the position of a compliance sensor magnet 84.

Figure 14:
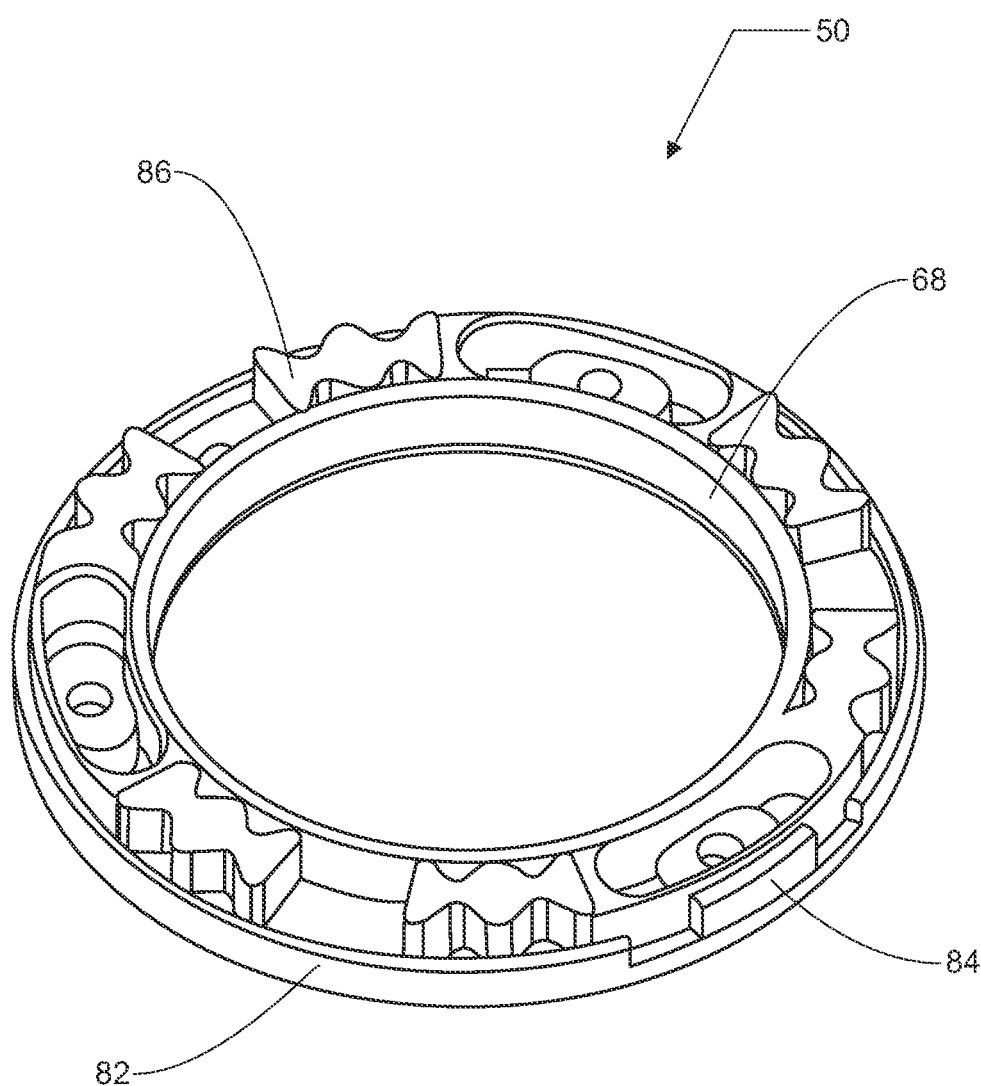
FIG. 14 is a perspective view of the bottom portion of the compliance subassembly of FIG. 13.

Referring to FIG. 14, in one embodiment, the interior of compliance subassembly 50 includes series elastic elements 86. The shoulder flexion harmonic drive gearing system circular spline 68 defines the interior of the compliance subassembly 50 and is formed to accommodate the placement of the series elastic elements 86 around an outer diameter 87 of the shoulder flexion harmonic drive gearing system circular spline 68. The series elastic elements 86 are confined by the shoulder flexion harmonic drive gearing system circular spline 68 and the clamp 82.

Figure 15:
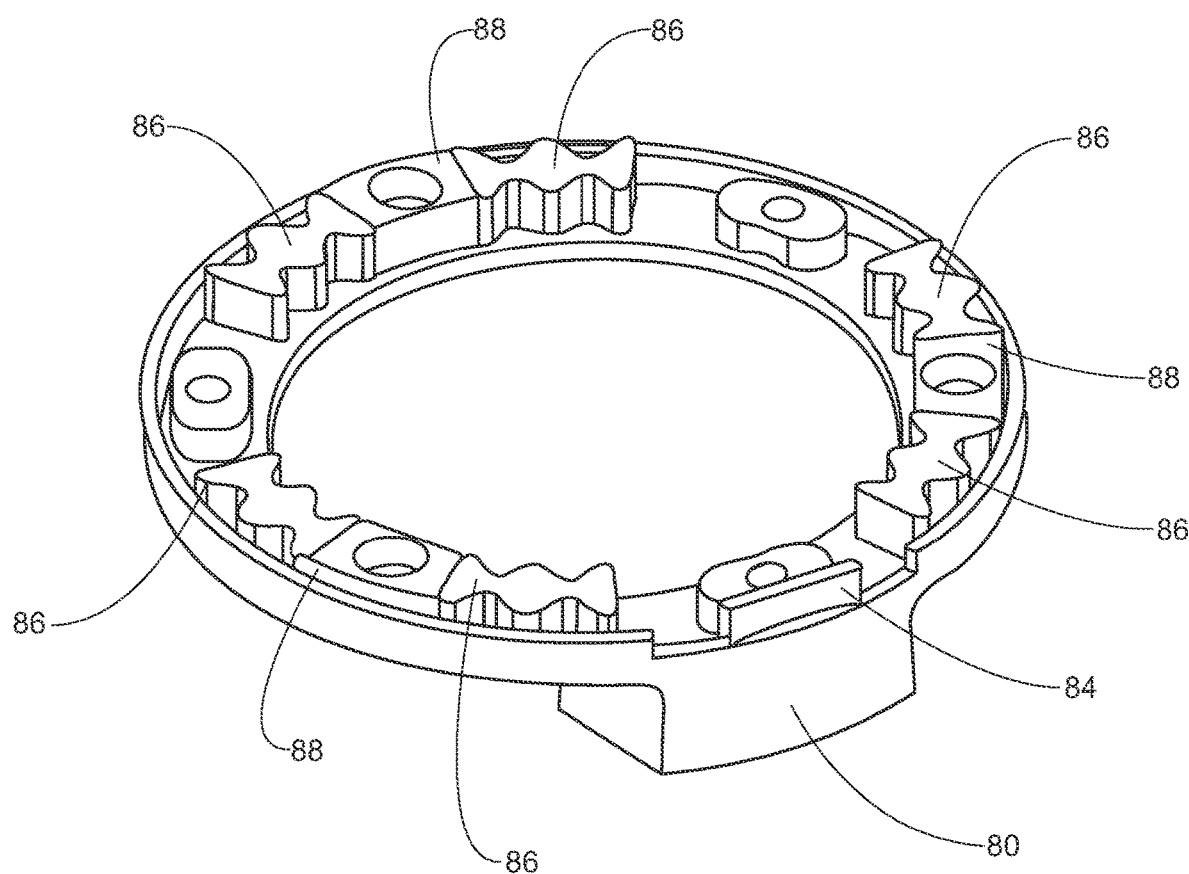
FIG. 15 is a perspective view of the top portion of the compliance subassembly of FIG. 13.

Referring to FIG. 15, the placement of the compliance reactor 80 in relation to the series elastic elements 86 and reactor elements 88 is shown. In this embodiment, three reactor elements 88 are positioned around the compliance reactor 80, equidistant to each other. One series elastic element 86 is placed on either side of each reactor element 88. When the shoulder flexion assembly 14 is subjected to unexpected force, such as a sudden jolt or impact, the compliance reactor 80 and reactor elements 88 displace from their rest positions and compress against the series elastic elements 86. In that way, the compliance subassembly 50 attenuates the shock being transferred to the rest of the shoulder flexion assembly 14. The compliance reactor 80 may also measure the amount of displacement and compliance by measuring the movement of the compliance reactor 80 in relation to the stationary position of the compliance sensor magnet 84.

Figure 16:
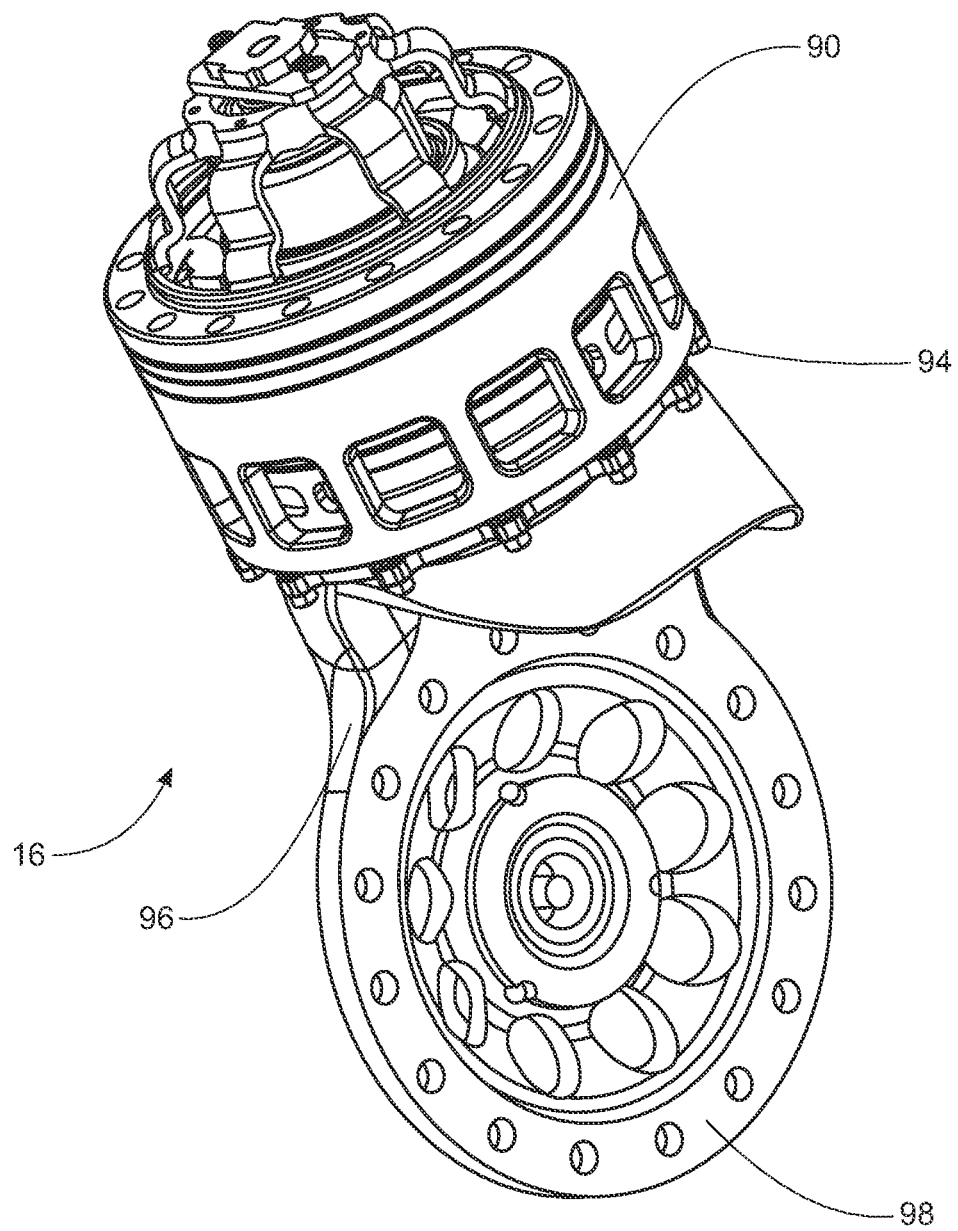
FIG. 16 is a perspective view of a humeral rotator of the prosthetic arm apparatus of FIG. 1 according to the present invention.

Referring to FIG. 16, one embodiment of the humeral rotator 16 is shown. The humeral rotator 16 includes an outer bearing carrier 90 attached to the first control housing 92, shown in FIG. 2. The first control housing 92, shown in FIG. 2, is used to connect the humeral rotator 16 to the shoulder flexion assembly 14. The inner rotational elements of the humeral rotator are held in place by a clamp 94, which is fastened to the outer bearing carrier 90. A humeral mount 96 passes through the clamp 94 and includes an elbow interface 98 for attaching the elbow flexion assembly 18 to the humeral rotator 16.

Figure 17:
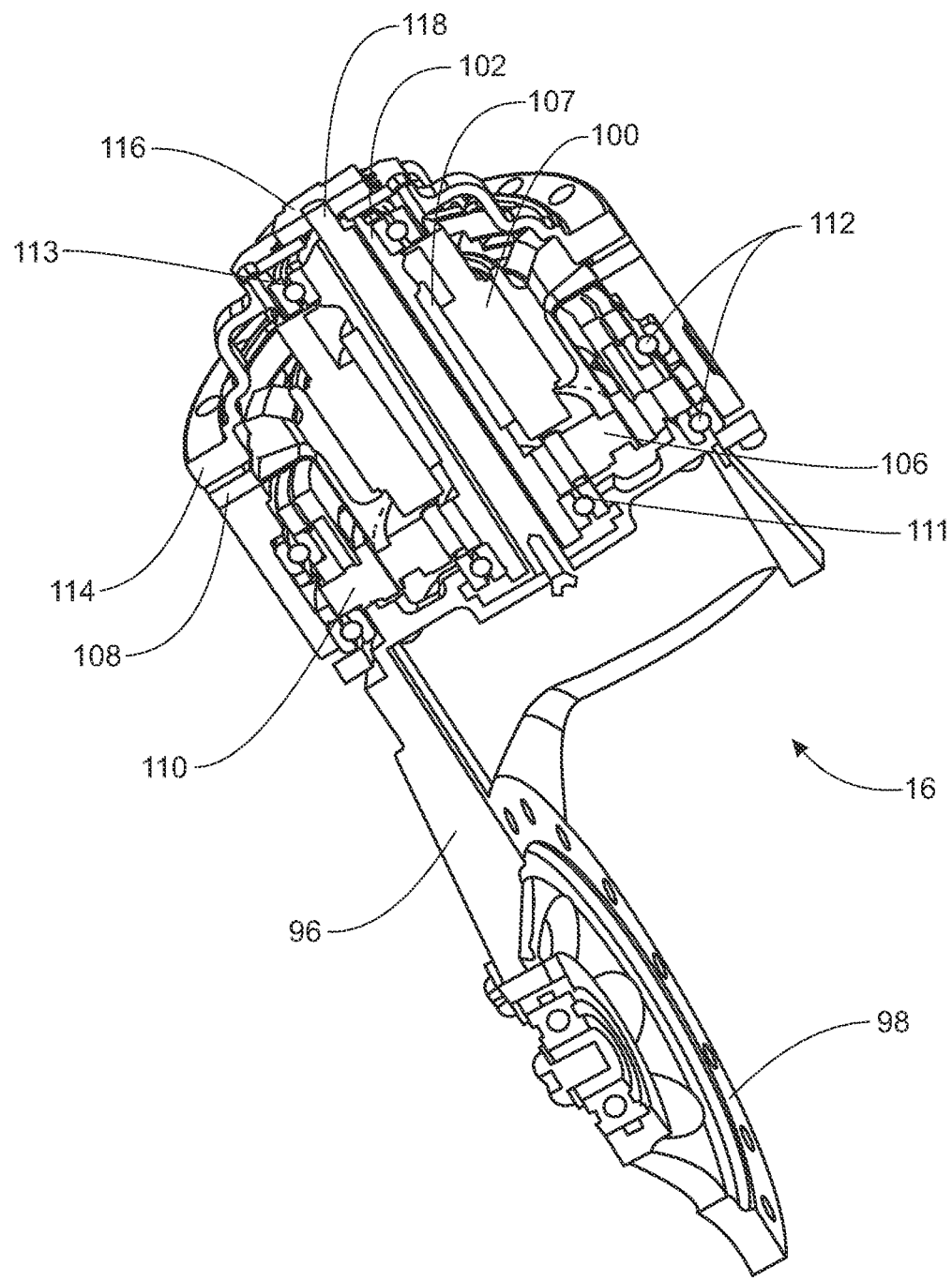
FIG. 17 is a cross-sectional perspective view of the humeral rotator of FIG. 16.

FIG. 17 shows a cross-sectional view of the humeral rotator 16. A humeral motor armature 100 drives a humeral motor rotor 102 having humeral magnets 104 disposed on its surface. The lower portion of the motor rotor 102 engages a humeral harmonic drive gearing system wave generator 106. A humeral harmonic drive gearing system flexspline 108 rotates with the humeral harmonic drive gearing system wave generator 106 against the humeral harmonic drive gearing system circular spline 110, resulting in a speed of rotation reduction as the humeral harmonic drive gearing system flexspline 108 causes the humeral mount 96 to move. Bearings 111 and 113 support the humeral motor rotor 102. Bearings 112 support the harmonic drive gearing system components 106, 108, 110. A bearing support 114 caps the outer bearing carrier 90 between the outer bearing carrier 90 and the first control housing 92, shown in FIGS. 16 and 2, respectively.

Still referring to FIG. 17, the one embodiment, a humeral potentiometer 116 of the humeral rotator 16, measures the rotational displacement of a humeral potentiometer shaft 118 that rotates proportionately to the humeral mount 96.

Figure 18:
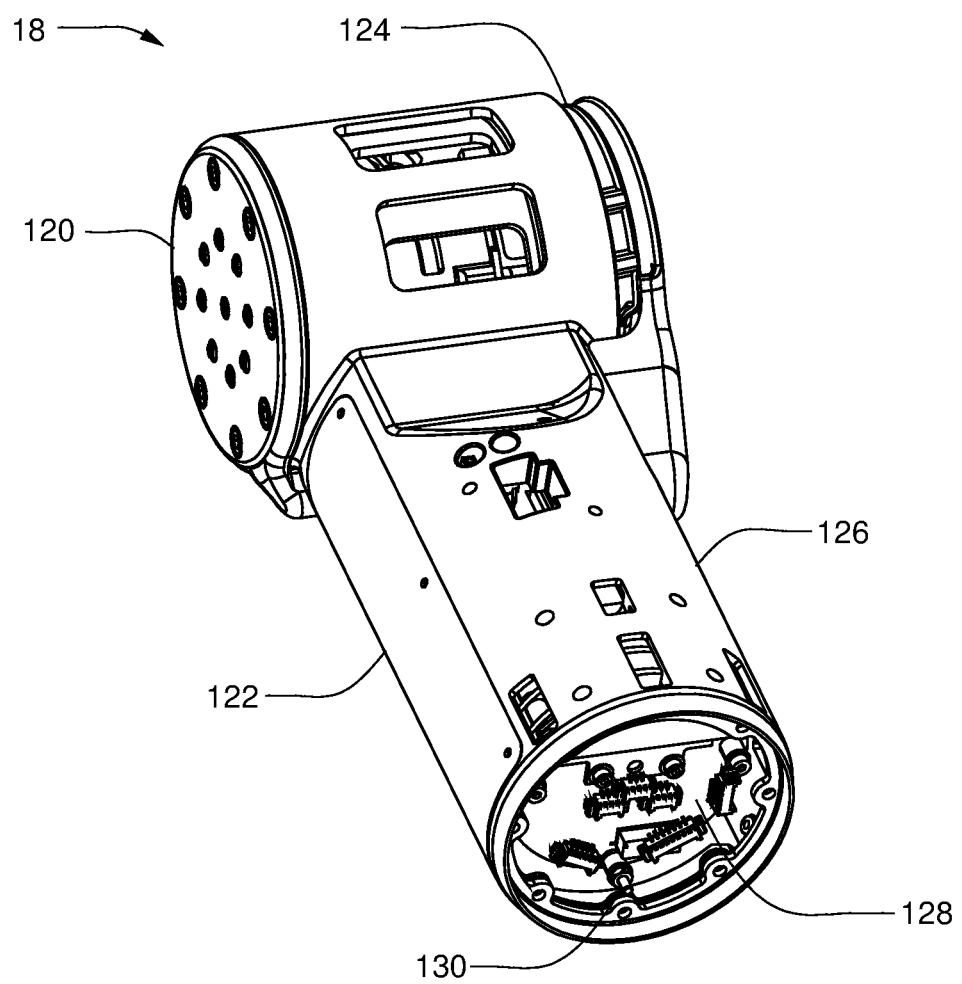
FIG. 18 is a perspective view of an elbow flexion assembly of the prosthetic arm apparatus of FIG. 1 according to the present invention.

Referring to FIG. 18, the elbow flexion assembly 18 includes an elbow joint 120 and a radial mount 122. The elbow joint 120 includes a slot 124 into which the elbow interface 98 of the humeral rotator is inserted to facilitate connection of the elbow flexion assembly 18 to the humeral rotator 16. The radial mount 122 provides a second electronics housing 126, in which an ACM stack 128 is located. "ACM" as used herein refers to Arm Control Module. The radial mount 122 includes a wrist interface 130, for attachment of the wrist rotator 20.

In some embodiments, the ACM stack 128 may be integrated into the wrist rotator 20, as will be discussed in greater detail below. Integrating the ACM stack 128 into the wrist rotator may be advantageous since the wrist rotator 20 is likely to be present in prosthetic arms for essentially all types of amputees, whereas the elbow flexion assembly 18 may not be present, such as in a prosthetic arm for a transradial amputee.

Figure 19:
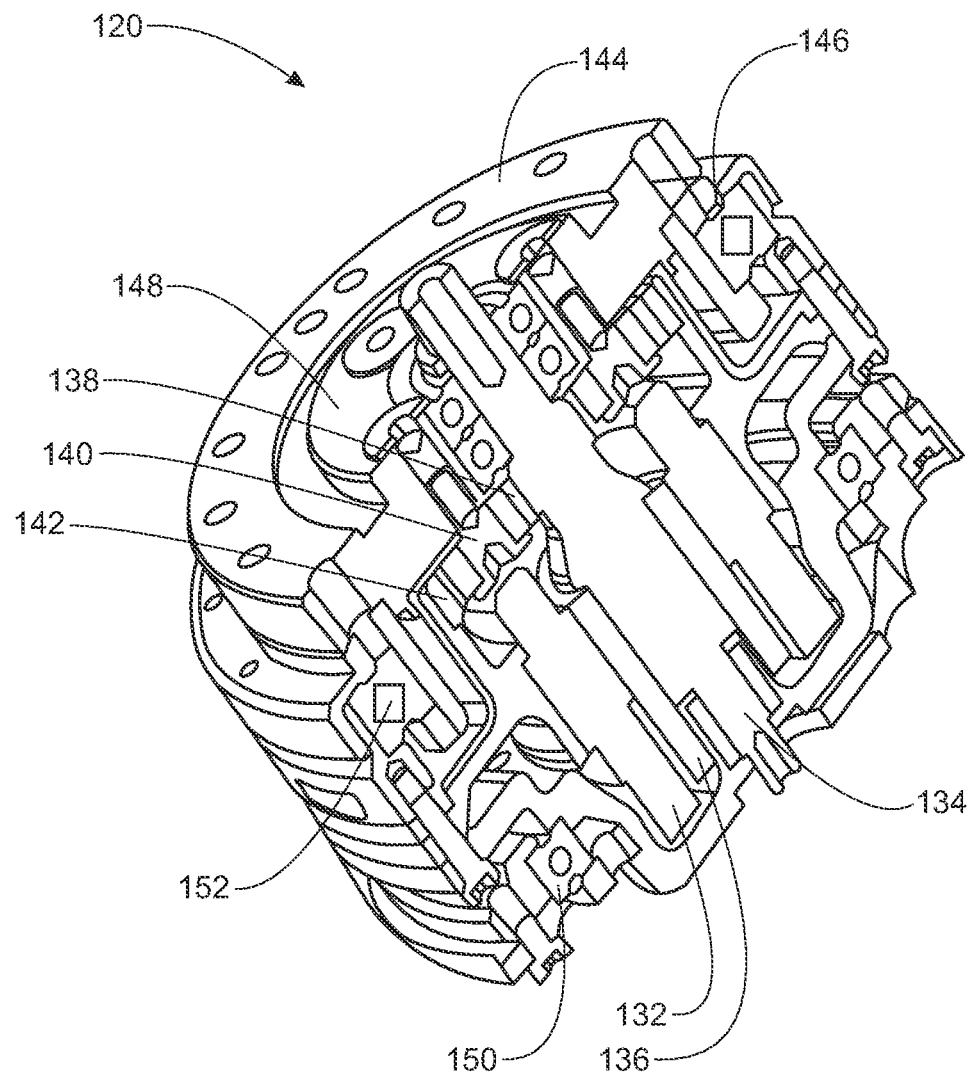
FIG. 19 is a cross-sectional perspective view of one embodiment of the elbow flexion 15 assembly shown without the radial mount.

Referring to FIG. 19, the elbow joint 120 includes an elbow motor armature 132 that drives an elbow motor rotor 134. Elbow magnets 136 are disposed at one end of the motor rotor 134, and the opposing end of the motor rotor 134 has a sun gear 138. As the motor armature 132 drives the sun gear 138, the sun gear 138 in turn drives four planetary gears 140 positioned equidistant from each other around the sun gear 138. The four planetary gears 140 in turn react against a ring gear 142, giving the elbow flexion assembly 18 a first stage of speed reduction through an elbow harmonic drive gearing system wave generator 148 which also acts as the planet carrier. The elbow harmonic drive gearing system wave generator 148 powers the elbow harmonic drive gearing system flexspline 146, which drives against the elbow harmonic drive gearing system circular spline 144, giving the elbow flexion assembly 18 a second stage of reduction. The elbow harmonic drive gearing system flexspline 146 then drives the motion of the elbow flexion assembly 18. Bearings 150 and crossed roller bearings 152 support the outer perimeter of the elbow flexion assembly 18. Although described with both a planetary gear system and an elbow harmonic drive gearing system, the elbow flexion assembly 18 could be controlled solely by a harmonic drive gearing system by changing the gear reduction ratio.

In various embodiments, it may be desirable to avoid having to perform additional measurement by using the measurement in the compliance process. One example includes, in various embodiments, where the planetary gears may be used for compliance and measurement of load.

Figure 20:
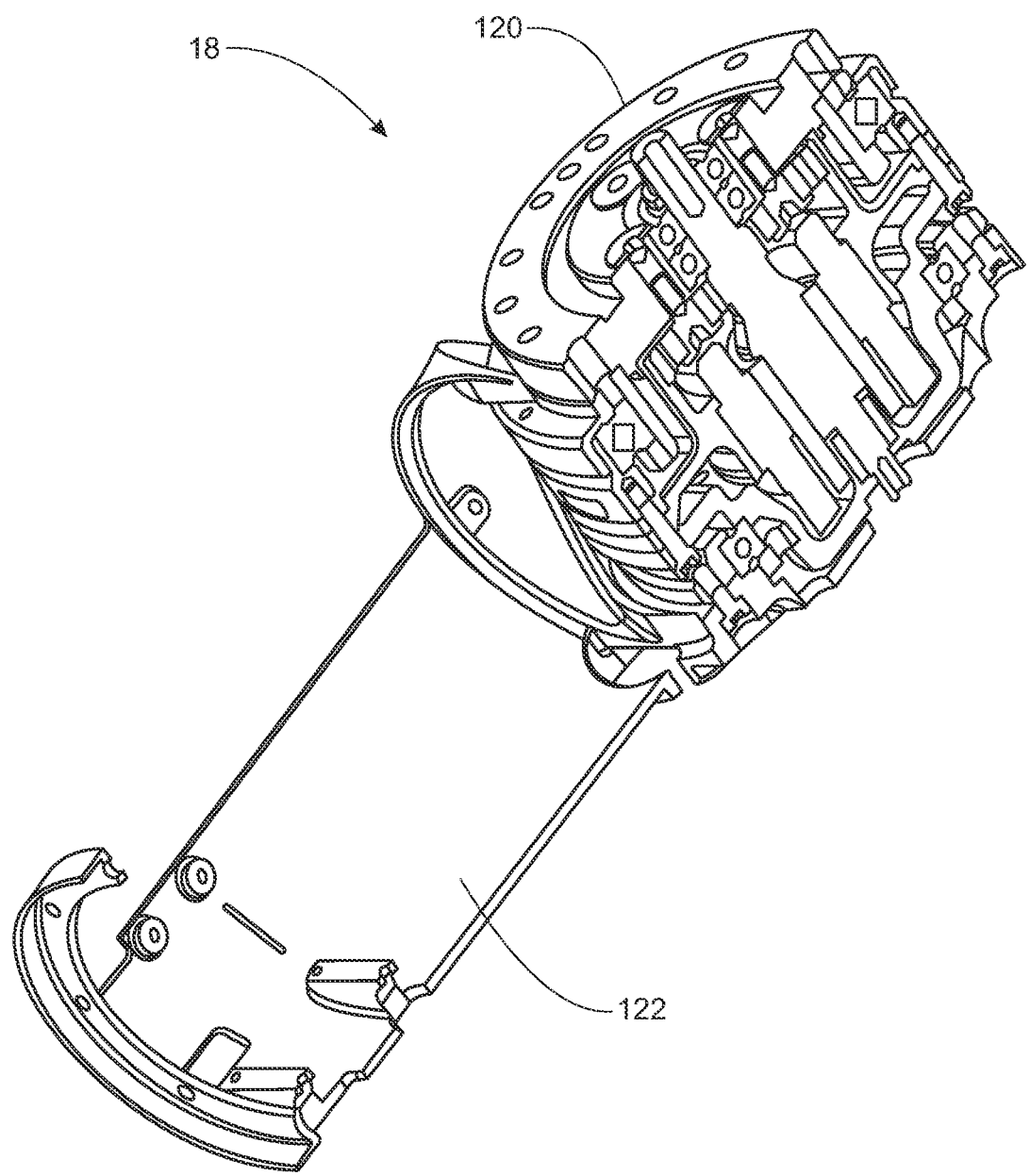
FIG. 20 is a cross-sectional perspective view of the elbow flexion assembly shown with the radial mount.

Referring to FIG. 20, in the embodiment shown, the radial mount 122 is structurally fixed to the elbow joint 120, such that when the elbow joint is actuated, the radial mount 122 moves.

Figure 21A:
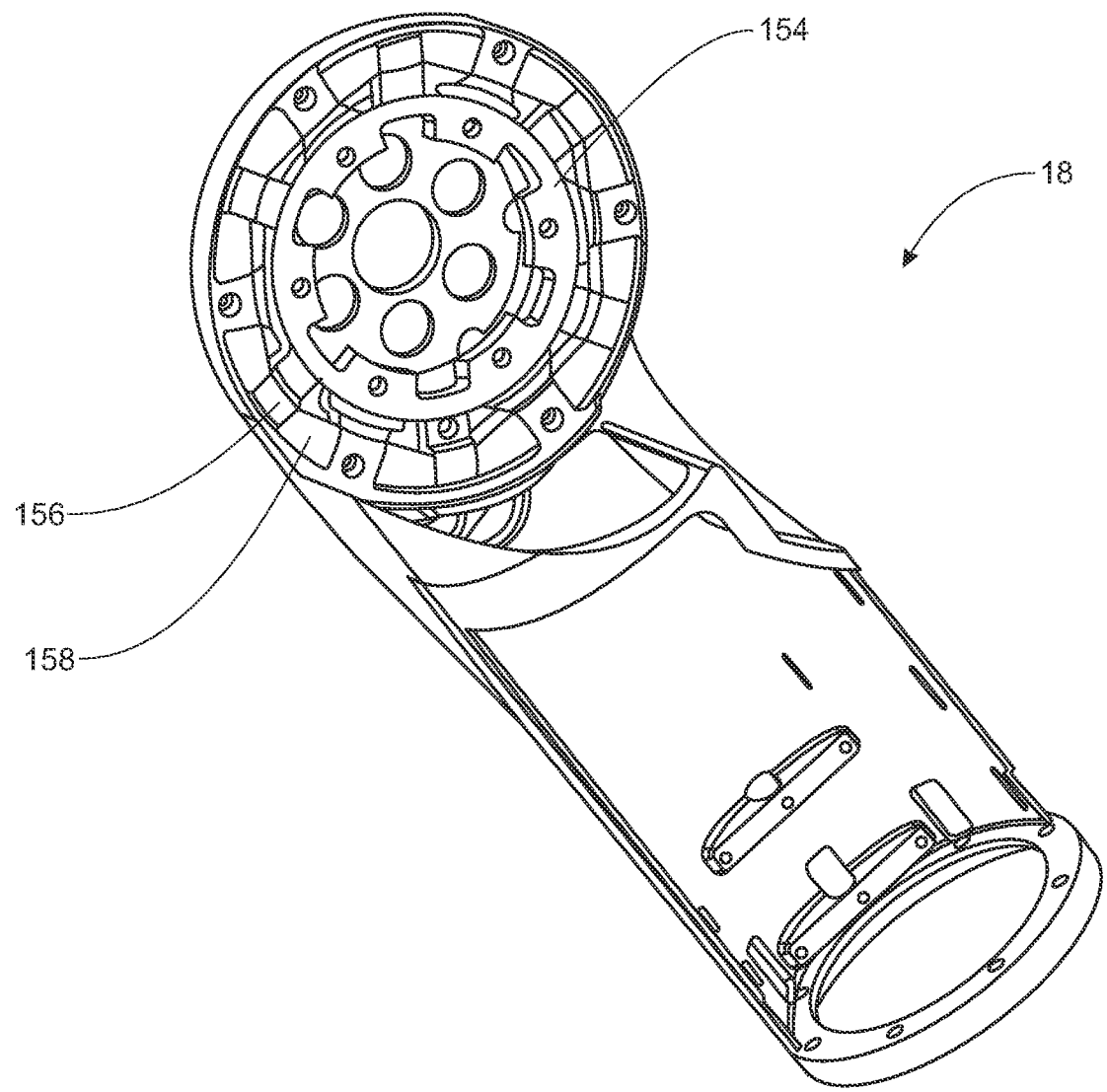
FIG. 21A is a perspective view showing the compliance subassembly of the elbow flexion assembly of FIG. 19.

Referring to FIG. 21A, an elbow compliance subassembly 154 is incorporated into the elbow flexion assembly 18. A plurality of arms 156 extends from the center portion of the elbow compliance subassembly 154. Each arm 156 has an elbow series elastic element 158 disposed on either side of the am 156. Similar to the shoulder flexion assembly 14, if the elbow flexion assembly 18 is subject to a torque, the elbow compliance subassembly 154, with its series elastic elements 158, is capable of absorbing the shock attenuating the torque magnitude through the rest of the elbow flexion assembly 18.

Figure 21B:
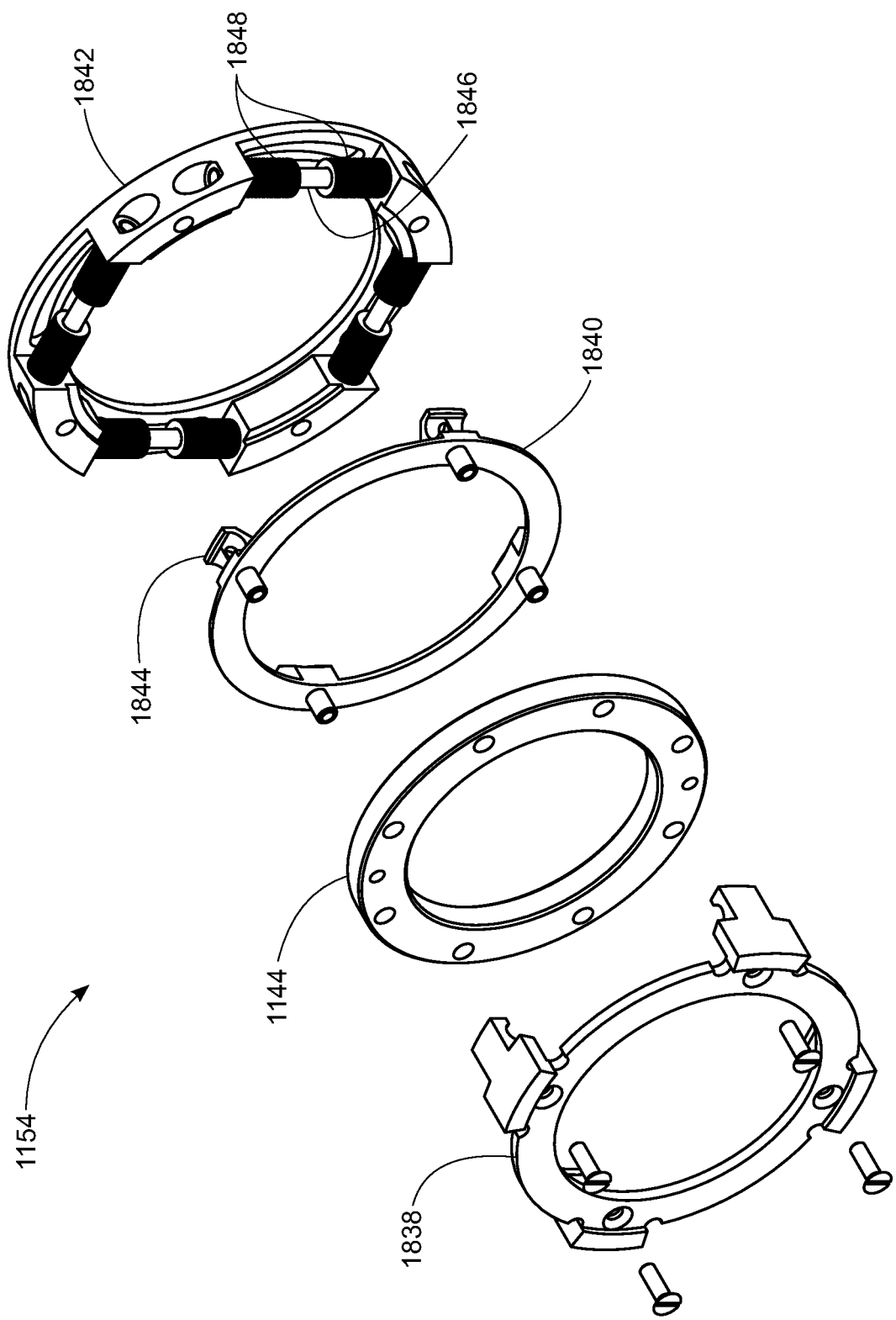
FIG. 21B is an exploded perspective view of a compliance subassembly according to another embodiment of the present invention.

Referring to FIG. 21B, wherein like numerals represent like elements, in some embodiments, the elbow compliance assembly 1154 may include a carrier having a magnet (not shown) disposed thereon and having a carrier top 1838 and a carrier bottom 1840 that connect to one another to surround the elbow harmonic drive gearing system circular spline 1144 and that interface with a compliance grounding member 1842. The carrier top 1838 and carrier bottom 1840 to restrict movement of the elbow harmonic drive gearing system circular spline 1144, thereby allowing the circular spline 1144 to operate substantially as discussed above to drive the elbow flexion assembly 18, shown in FIG. 18. The carrier bottom 1840 includes clips 1844 located around its periphery that slidably engage corresponding compliance shafts 1846 of the compliance grounding member 1842 to connect the carrier to the compliance grounding member 1842. Each clip 1844 is positioned on a compliance shaft 1846 between two compliance springs 1848 that inhibit sliding movement of the clips 1844 relative to the shafts 1846. The compliance springs 1848 are preferably formed from metal and, in some embodiments, each spring 1848 may include a plurality of stacked spring washers. In operation, as the elbow harmonic drive becomes loaded, the clips 1844 of the carrier slide on the compliance shafts 1846 and load the compliance springs 1848, which deflect in proportion to the load. A sensor (not shown) measures the displacement of the magnet (not shown), thereby providing a measurement of the torque carried by the elbow harmonic drive and, therefore, the elbow flexion assembly 18, shown in FIG. 18. The elbow compliance assembly 1154 advantageously provides improved compliance measurements due to its metal springs 1848 as compared to elastomeric spring designs, which have greater hysteresis. Additionally, the carrier of the elbow compliance assembly 1154 advantageously allows the circular spline 1144 to be mounted without any modifications that may reduce its load capacity.

Figure 22:
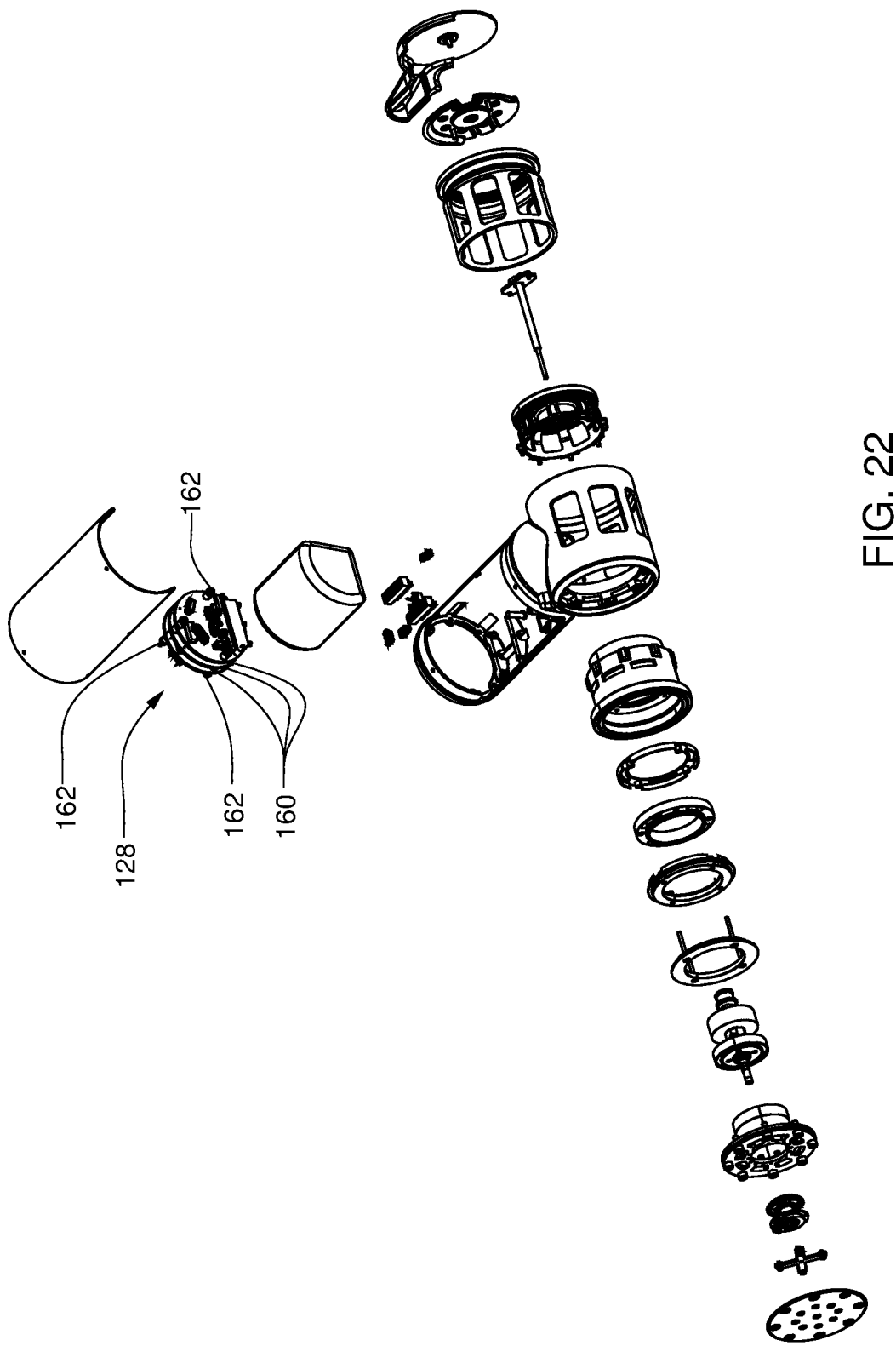
FIG. 22 is an exploded perspective view of the elbow flexion assembly of FIG. 18.

Referring to FIG. 22, the ACM stack 128, includes circuit boards 160 connected to one another by structural standoffs 162. The structural standoffs 162 are constructed of a conductive material, so that electrical power may be passed through the circuit boards 160. The structural standoffs allow power to be supplied to each circuit board 160 without conventional power connections.

Figure 23:
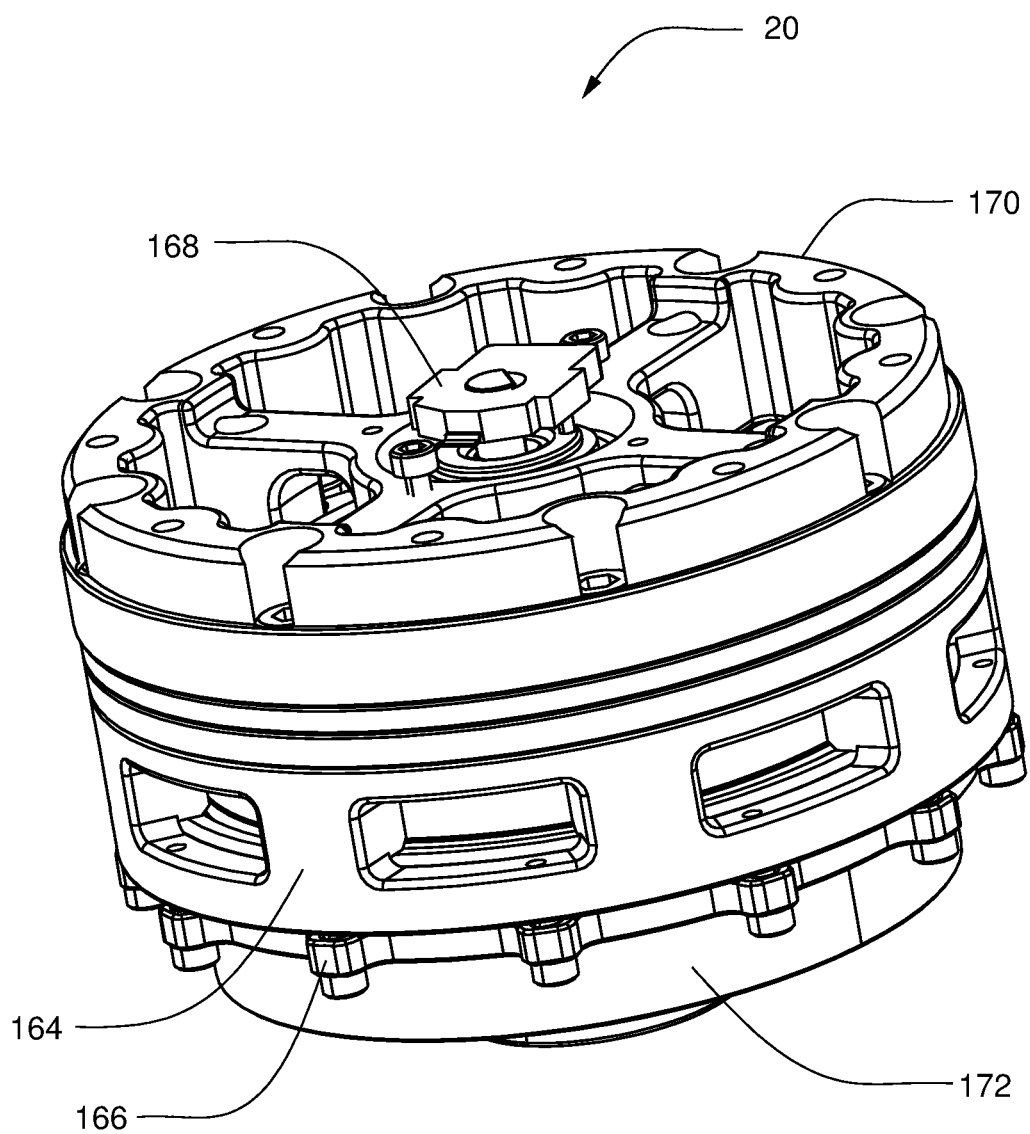
FIG. 23 is a perspective view of a wrist rotator of the prosthetic arm apparatus of FIG. 1 according to the present invention.

Referring to FIG. 23, the wrist rotator 20 includes a wrist outer bearing carrier 164, a wrist clamp 166, a wrist potentiometer 168, an elbow interface 170, and a wrist flexion assembly interface 172.

Figure 24:
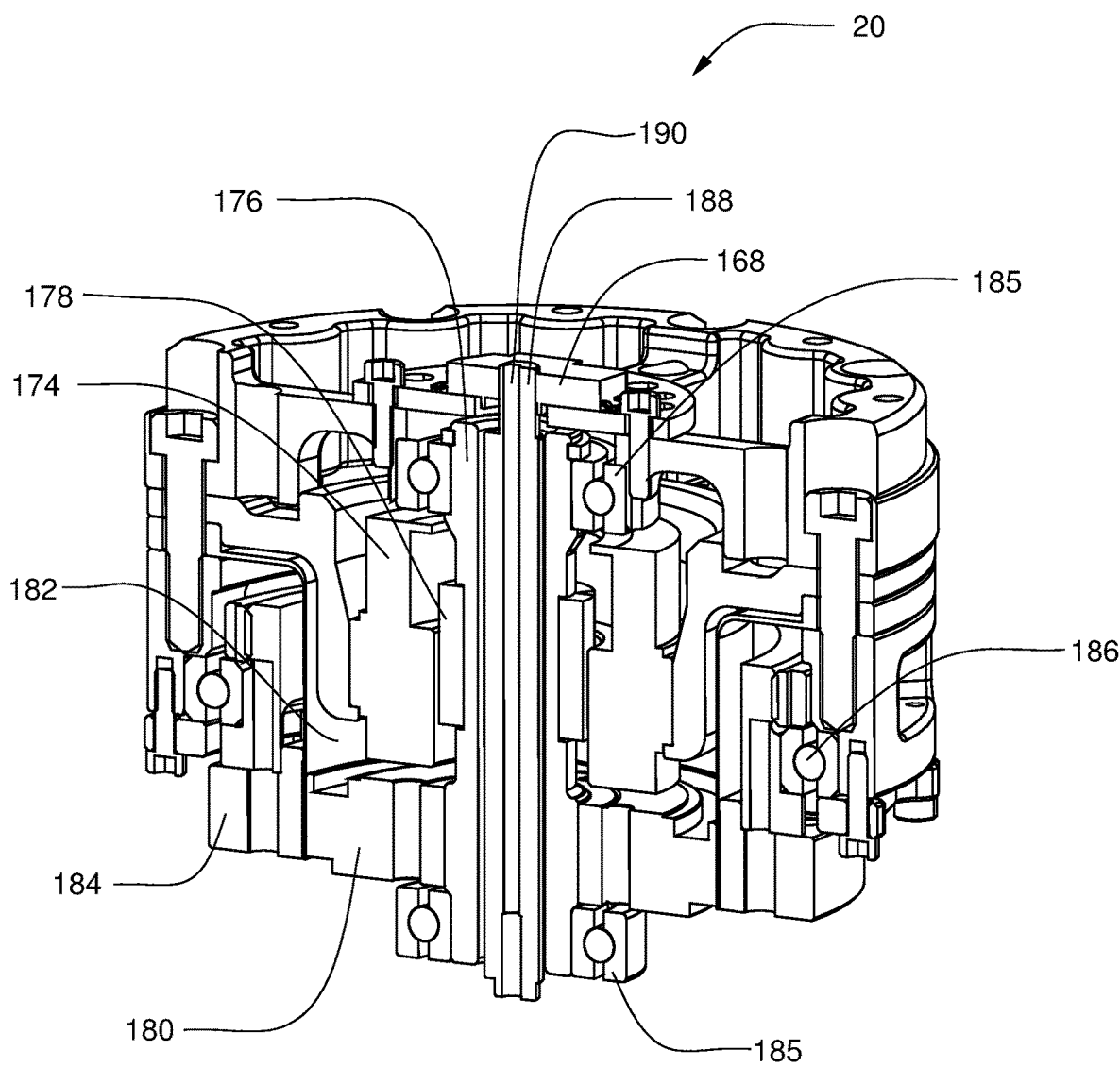
FIG. 24 is a cross-sectional perspective view of the wrist rotator of FIG. 23.

Referring to FIG. 24, movement of the wrist rotator 20 is controlled by a harmonic drive gearing system similar to that described for the humeral rotator. A wrist rotator motor armature 174 drives a wrist rotator motor rotor 176 having wrist rotator magnets 178 disposed to its surface. The lower portion of the wrist rotator motor rotor 176 integrates a wrist rotator harmonic drive gearing system wave generator 180. A wrist rotator harmonic drive gearing system flexspline 182 rotates with the wrist rotator harmonic drive gearing system wave generator 180 against a wrist rotator harmonic drive gearing system circular spline 184, resulting in reduction in the speed of rotation as the wrist rotator harmonic drive gearing system flexspline 182 causes the wrist flexion assembly interface 172 to move with respect to the rest of the wrist rotator 20. Bearings 185 support the wrist rotator motor rotor 176. Bearings 186 support the harmonic drive gearing system components 180, 182, and 184.

Still referring to FIG. 24, the wrist potentiometer 168 of the wrist rotator 20 is disposed at one end of a wrist shaft 188 and measures the rotational displacement thereof. The wrist shaft 188 may be tubular, having an electronics channel 190 for passing electronic power and controls through the wrist rotator 20.

Figure 25:
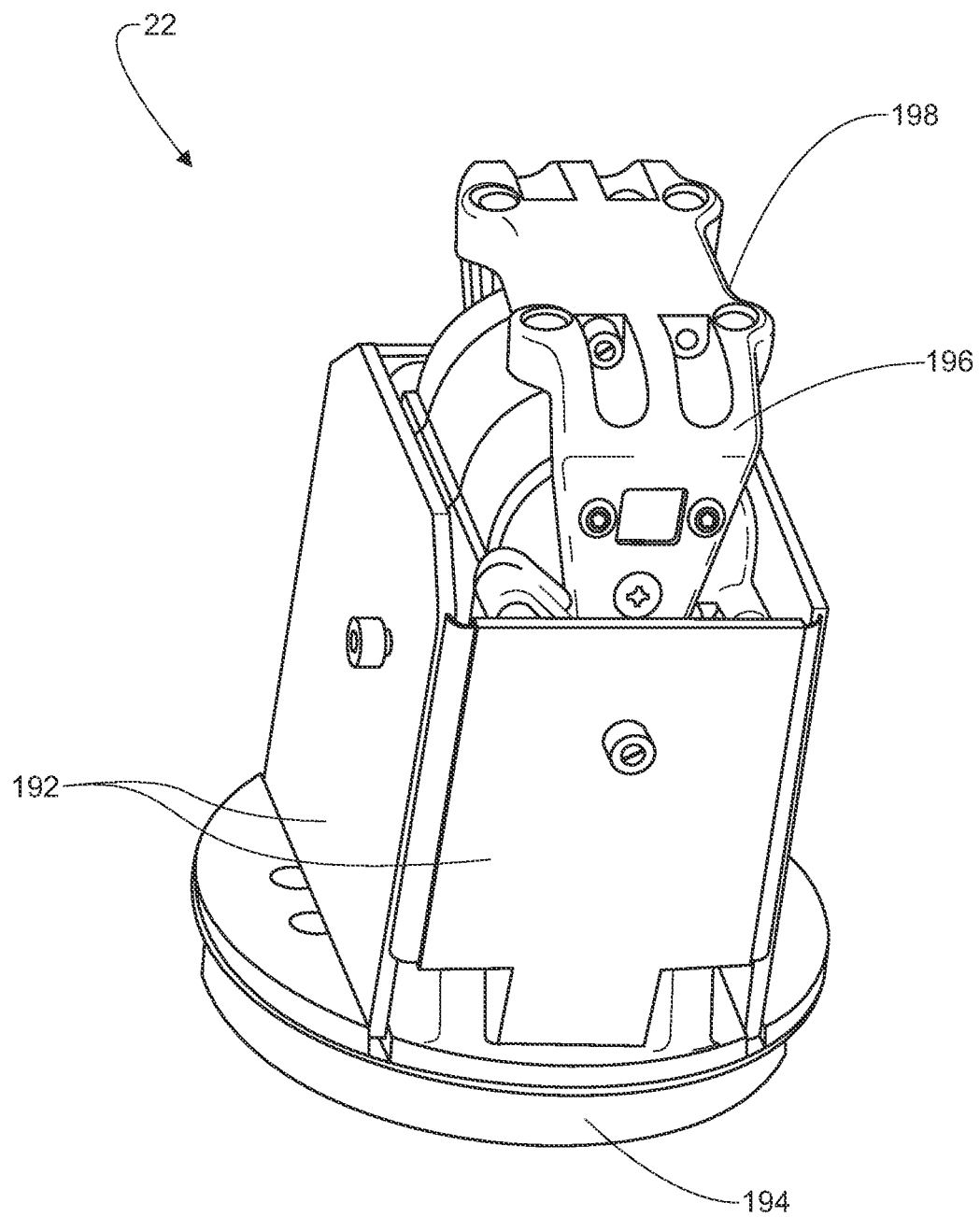
FIG. 25 is a perspective view of a wrist flexion assembly and a hand control module of the prosthetic arm apparatus of FIG. 1 according to the present invention.
Figure 26:
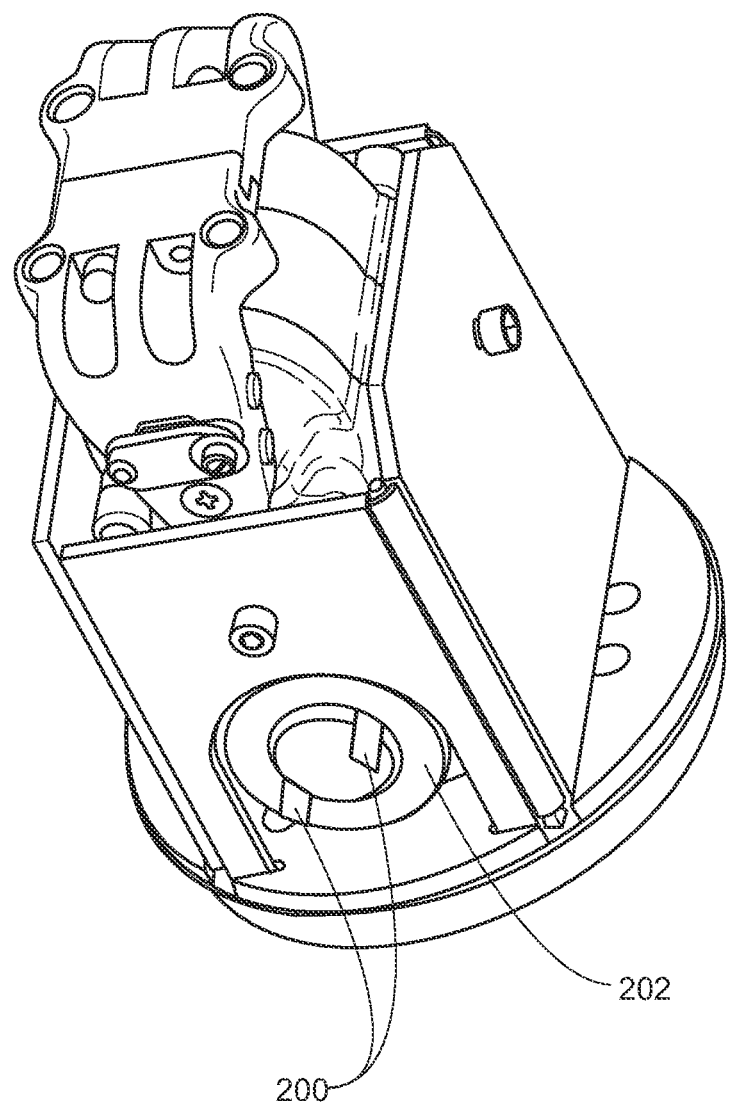
FIG. 26 is a rear perspective view of the wrist flexion assembly and hand control module of FIG. 25.

Referring to FIG. 25, the wrist flexion assembly 22 includes hand control module circuit boards 192, an input support structure 194, an output arm 196, and a hand interface 198. The input support structure 194 connects the wrist rotator 20 with the wrist flexion assembly 22. The output arm 196 has positive and negative flexion, such that the output arm 196 is able to move in two opposite directions in reference to the support structure 194. The hand interface 198 allows the hand assembly 24 to be connected to the wrist flexion assembly 22. Referring to FIG. 26, the wrist flexion assembly 22, has wrist electrical connections 200 for supplying power to a wrist flexion motor 202.

Figure 27:
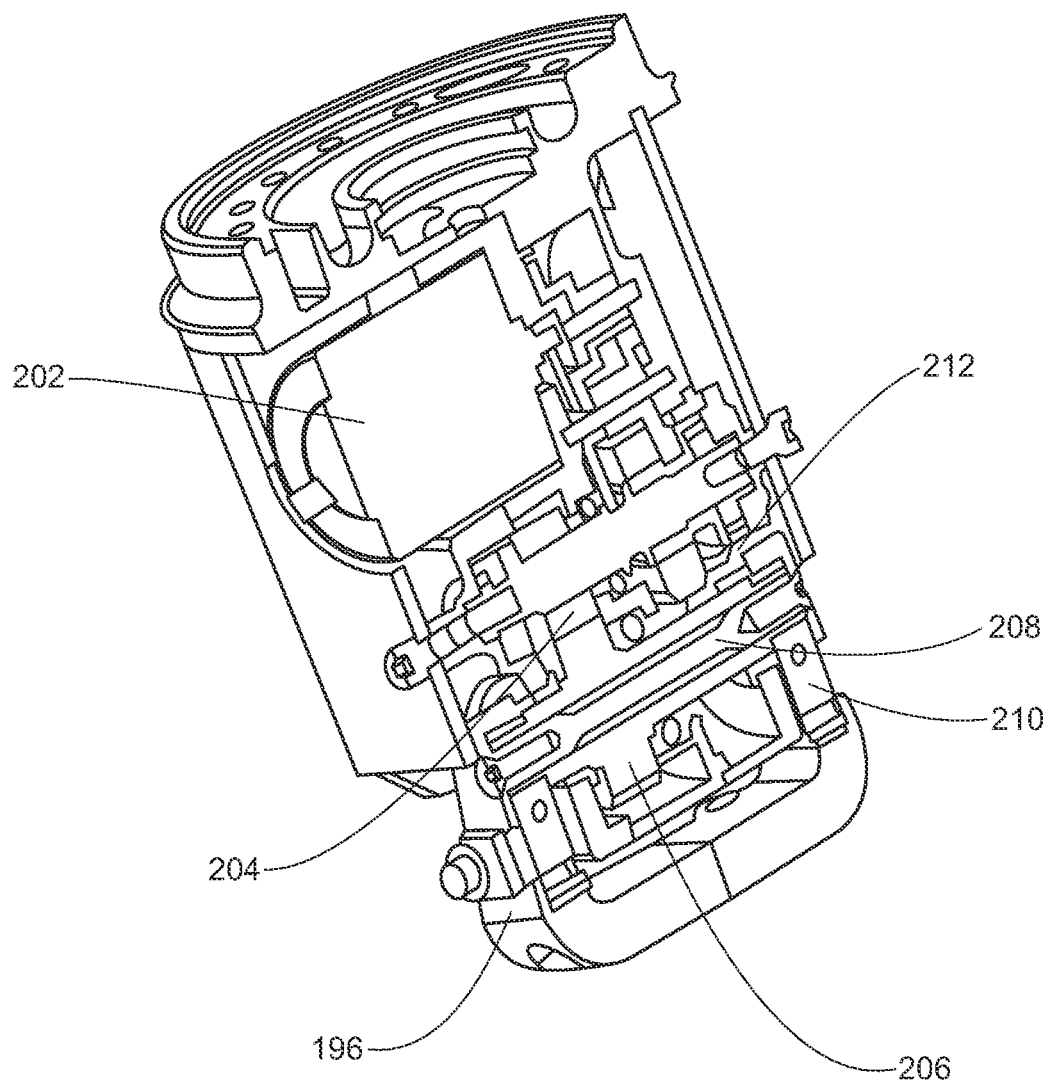
FIG. 27 is a cross-sectional perspective view of the wrist flexion assembly and hand control module of FIG. 25.

Referring to FIG. 27, in the embodiment shown, the wrist flexion motor 202 drives a wrist flexion output gear 204, which in turn drives a wrist flexion final stage-driven gear 206. A wrist flexion pivot axle 208 of the output arm 196 is axially disposed inside an opening defined by the interior of the wrist flexion final stage-driven gear 206. Wrist flexion series elastic elements 210 are disposed in the interior of the output arm 196. Movement of the wrist flexion final stage-driven gear 206 facilitates the positive and negative motion of the output arm 196. A non-backdriving clutch 212 is disposed at one end of the wrist flexion output gear 204.

Figure 28:
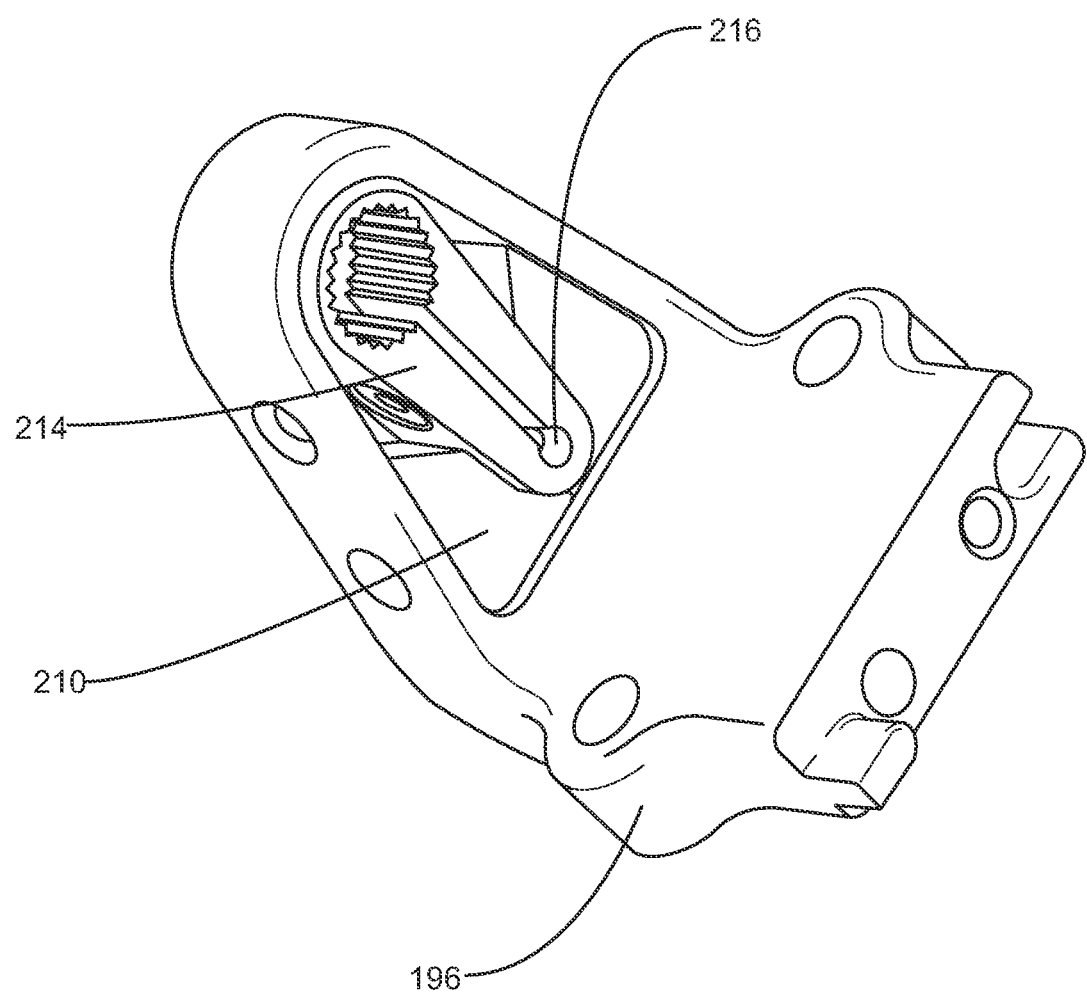
FIG. 28 is a perspective view of a wrist assembly output arm of FIG. 25.

Referring to FIG. 28, the output arm 196 has a wrist flexion drive arm 214, which is driven by the wrist flexion final stage-driven gear 206. The end of the wrist flexion drive arm 214 accommodates a wrist flexion compliance sensor magnet 216. The wrist flexion series elastic elements 210 are disposed on either side of the wrist flexion drive arm 214, and the wrist flexion series elastic elements 210 and the drive arm 214 are substantially enclosed within the output arm 196. Similar to the elbow flexion assembly 18 and the shoulder flexion assembly 14, if the wrist flexion assembly 22 is subjected to a force, the wrist flexion drive arm 214 compresses the wrist flexion series elastic elements 210 and attenuates the force or impact through the rest of the wrist flexion assembly 22.

Figure 29:
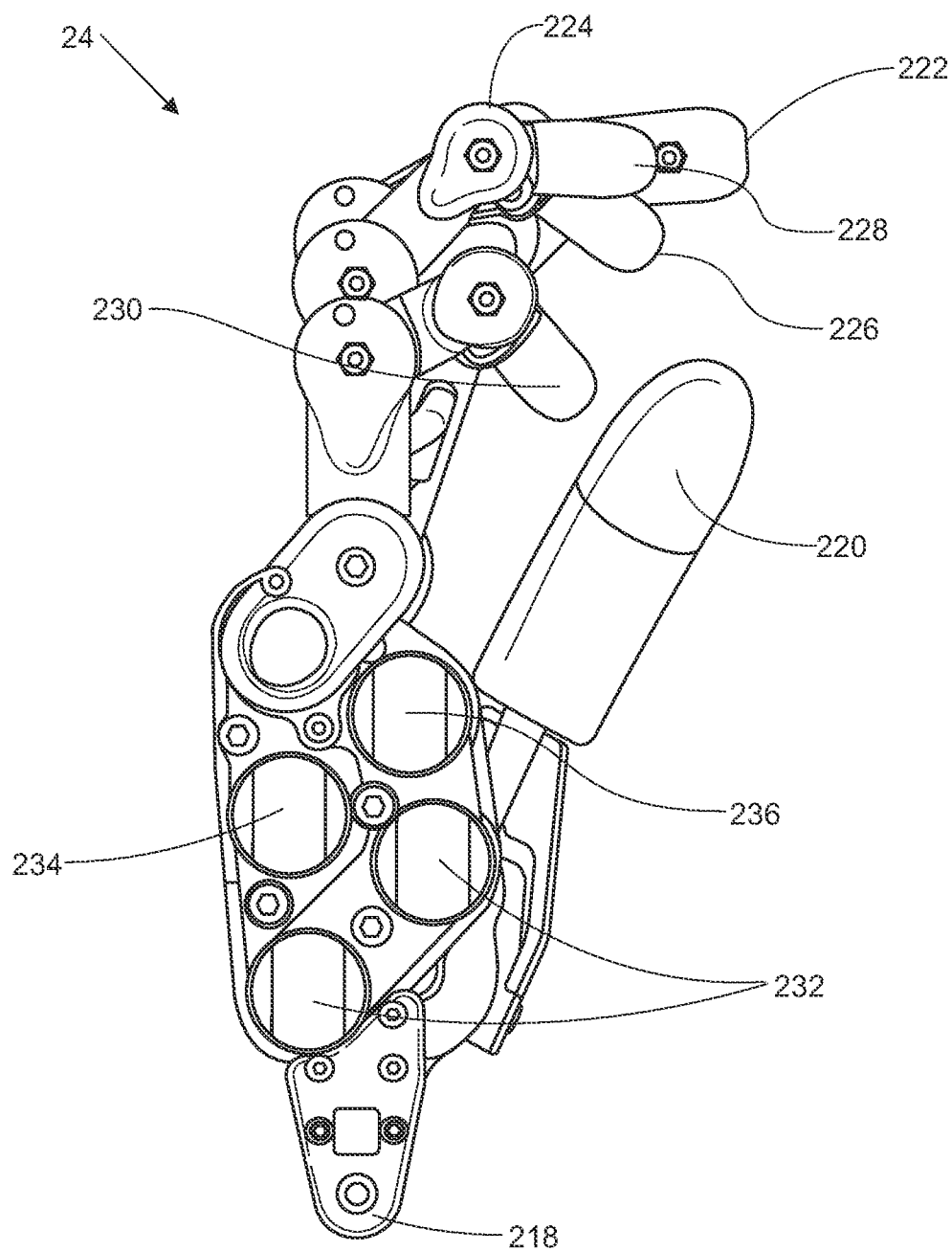
FIG. 29 is a side view of a hand assembly of the prosthetic arm apparatus of FIG. 1 according to one embodiment.
Figure 30:
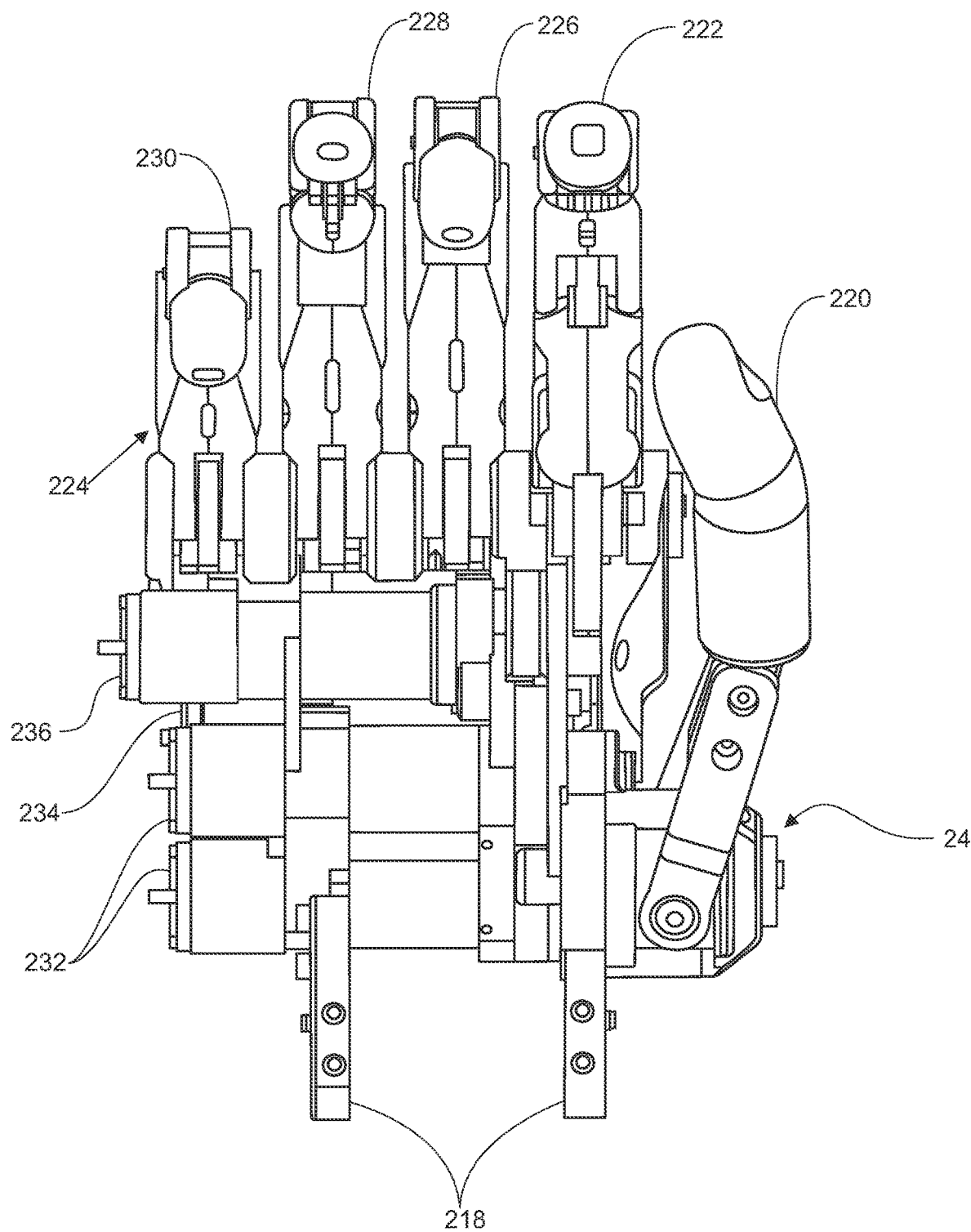
FIG. 30 is a front view of one embodiment of the hand assembly of FIG. 29.

The following is a description of one embodiment of the hand assembly. Other embodiments of the hand assembly are described and shown elsewhere in this specification. Referring to FIGS. 29 and 30 the hand assembly 24 includes a hand support 218 for providing an interface for connecting the hand assembly 24 to the wrist flexion output arm 196. The hand assembly 24 also includes a thumb structure 220, an index finger structure 222, and an MRP structure 224 replicating a middle finger 226, a ring finger 228, and a pinky finger 230. In various embodiments, the thumb structure 220 may be driven by two thumb drives 232 that feed into a single differential, giving the thumb structure 220 two degrees of freedom of movement. The index finger structure 222 may be driven by a single index drive 234 and the MRP structure 224 may be driven by a single MRP drive 236 that feeds a double differential. The MRP approach allows for an indeterminate versus determinate linkage.

Figure 31:
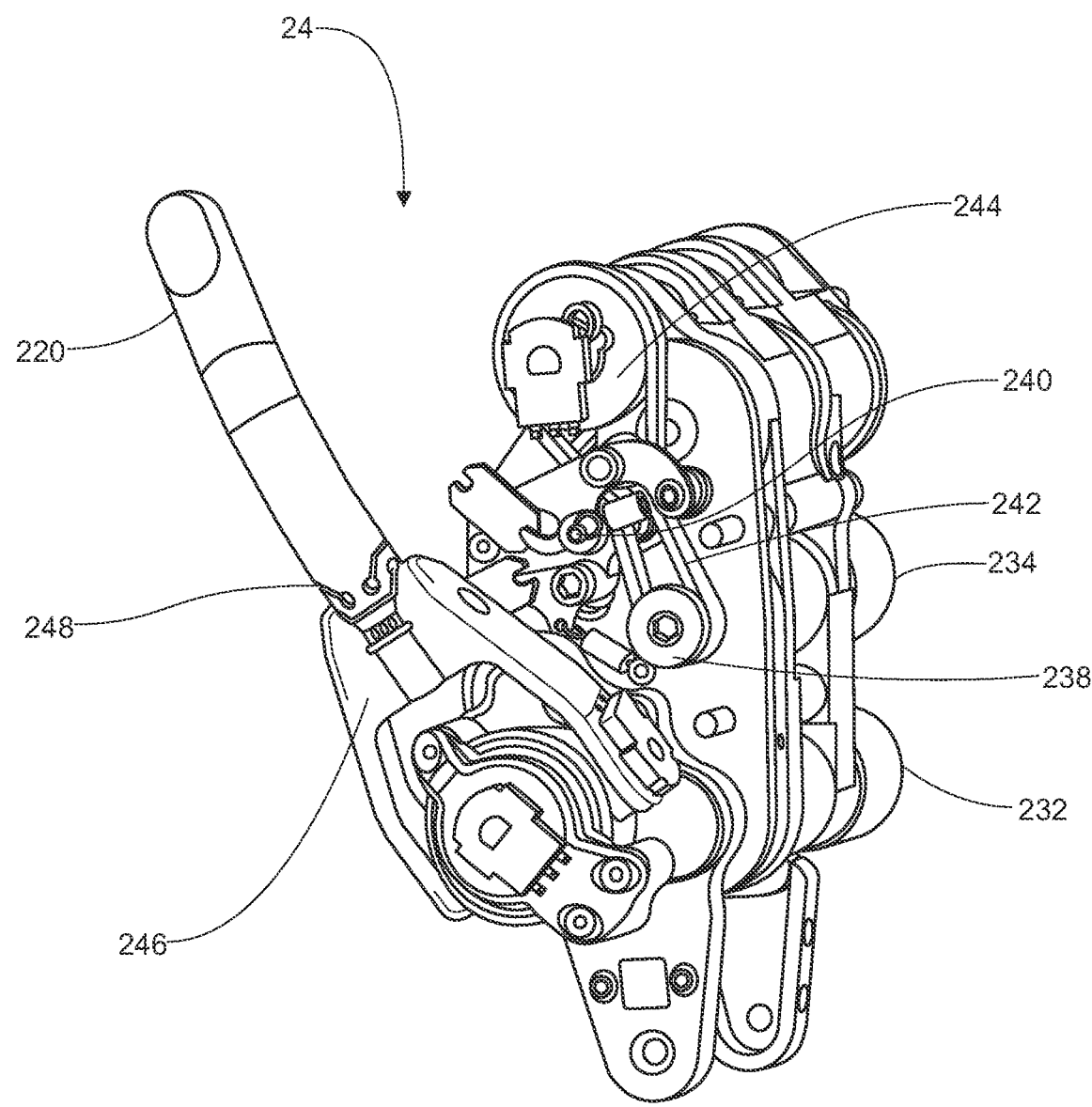
FIG. 31 is a perspective view of one embodiment of the hand assembly of FIG. 29 showing an index finger tensioner assembly.

Referring to FIG. 31, the index finger structure 222 (not shown) is driven by the index drive 234 through an index drive pulley 238, an index tensioner 240, an index tension belt 242, and an index finger pulley 244. The index drive pulley 238 is stage driven and transfers the torque to the index tension belt 242, which in turn rotates the index finger pulley 244, causing the index finger structure 222 to move. As the index tension belt 242 transfers the torque, one side of the index tension belt 242 tightens and the other side loosens, depending on which direction the index drive pulley 238 is rotated. The index tensioner 240 is located between the index drive pulley 238 and the index finger pulley 244 and the index tensioner 240 displaces in relation to the change in load to maintain the tension of the index tension belt 242. The index tensioner 240 has one side grounded and the other side capable of displacement upon the application of a load. The index tensioner 240 may instead ground the moveable side of the index tensioner 240 with a spring.

Figure 38:
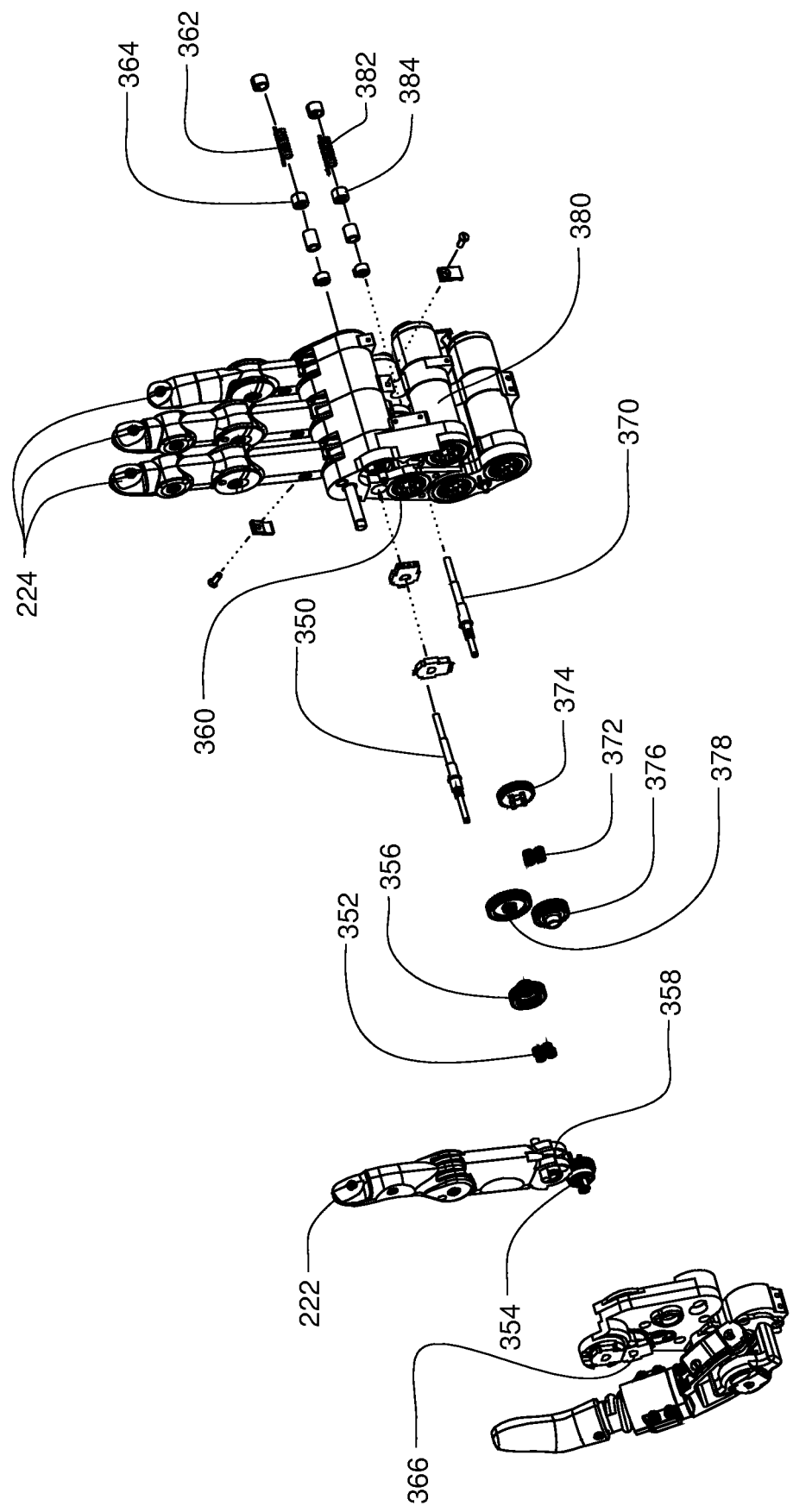
FIG. 38 is an exploded view of a portion of the hand showing another embodiment of the index and MRP fingers drives.
Figure 39:
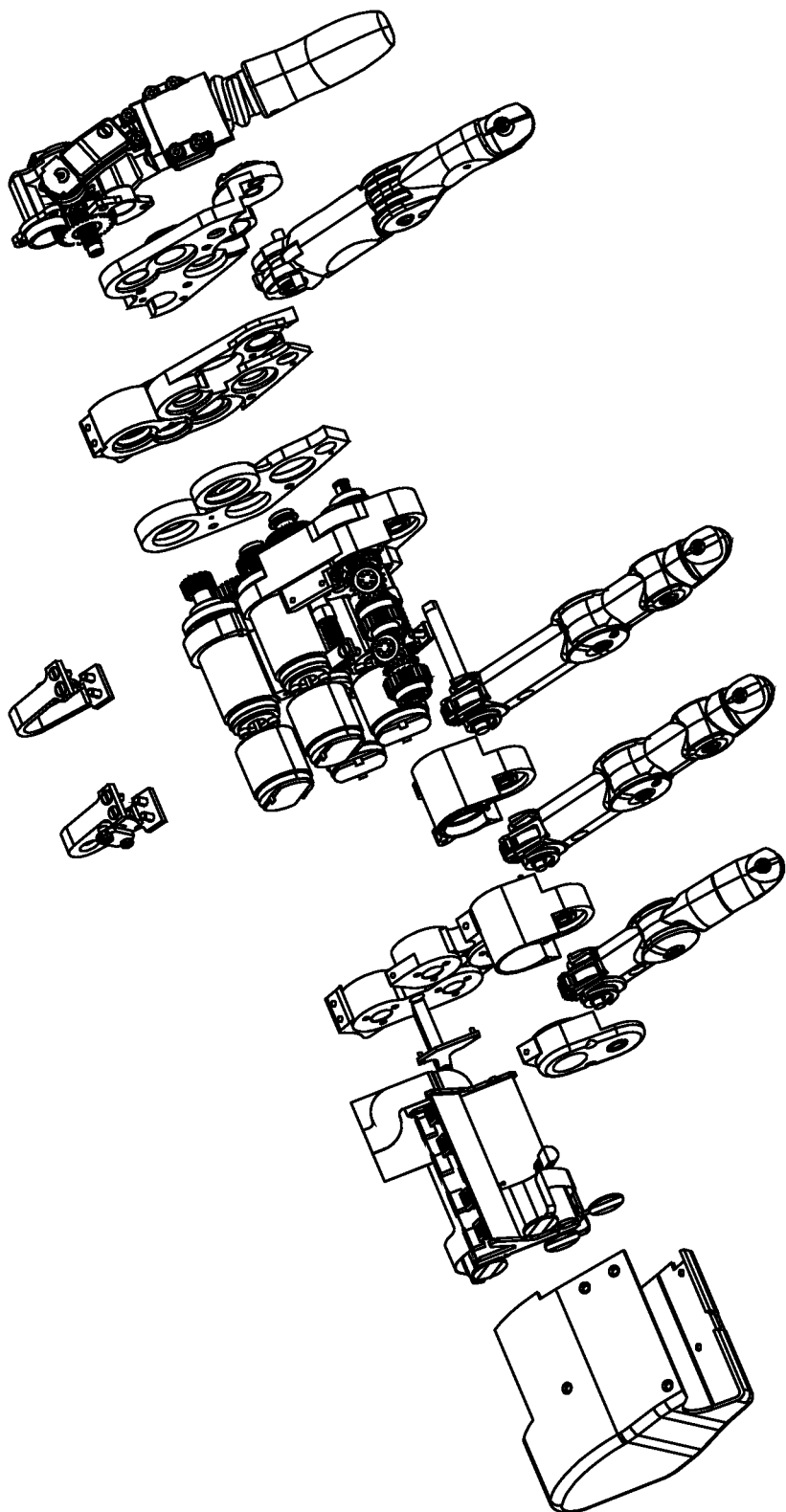
FIG. 39 is an exploded view of another embodiment of the hand.

Referring to FIG. 38, in another embodiment, the index finger structure 222 is driven through an index sun shaft 350, a set of index planets 352, an index planet carrier 354, an index ring gear 356, and an index drive gear 358. The index drive 360 drives the index ring gear 356, turning the index planets 352, the turning of which causes the index planet carrier 354 to rotate. The index drive gear 358 is driven by the external teeth of the index planet carrier 354, causing the index structure 222 to move. Any torque transmitted by the index planet carrier 354 will react against the index sun shaft 350 causing it to rotationally displace the index spring 362 through the index spring mount 364. This rotational displacement, sensed by an index potentiometer 366 can be used to infer the load on the index finger structure 222. This rotational displacement may be used to store elastic energy and to provide the index finger structure 222 with a measure of compliance that may aid in gripping and with load absorption.

Referring to FIG. 31, the thumb structure 220 is mounted on a thumb support 246, which is driven by the two thumb differential drives 232. The thumb structure 220 has flexural cuts 248 at its base allowing the compliant thumb structure 220 to move when a load is applied to it. This compliance in the thumb structure 220 may aid in gripping and with load absorption, which may prevent the hand assembly 24 from damaging objects (not shown) by closing around them too quickly and forcefully.

Figure 32:
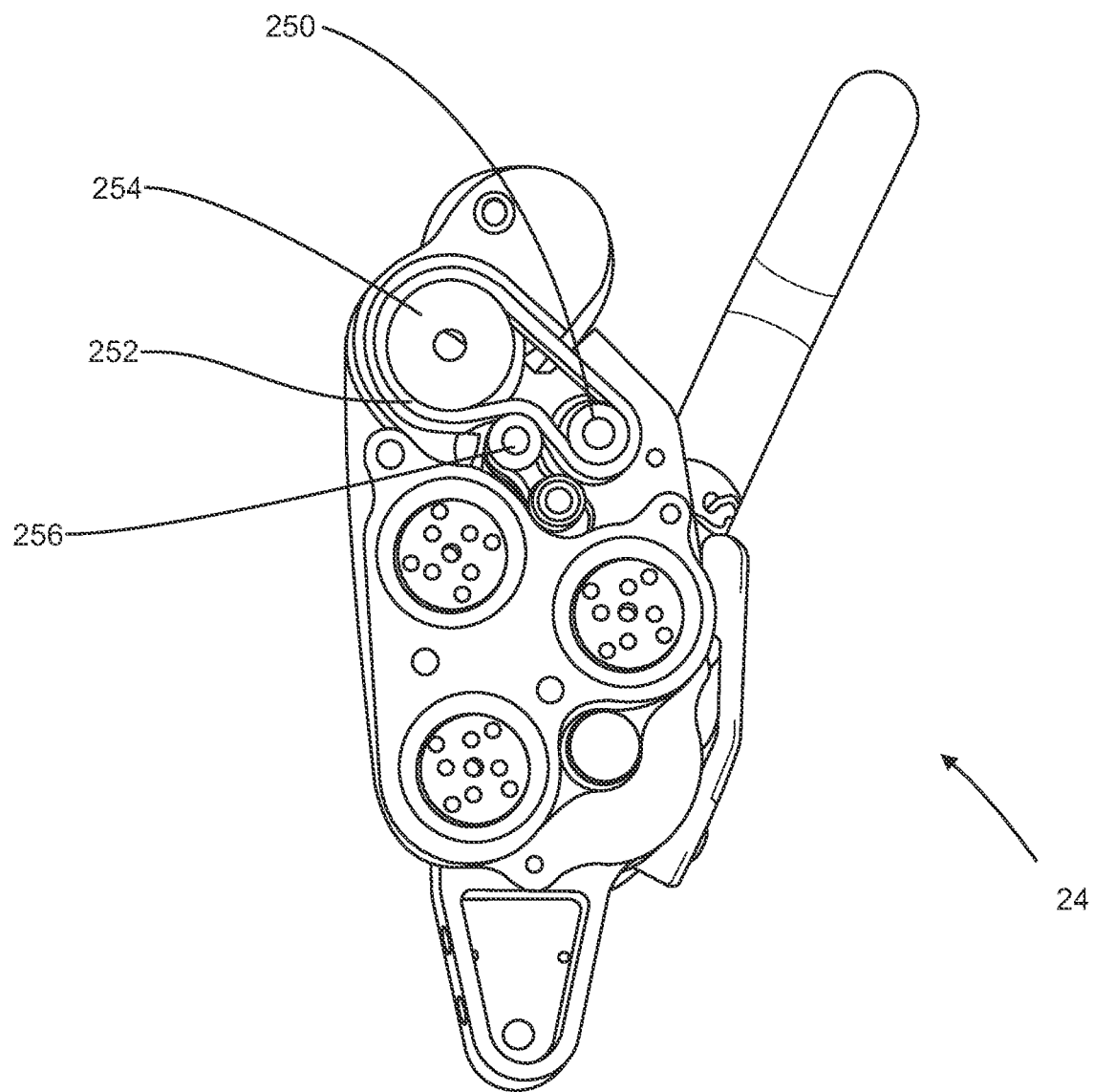
FIG. 32 is a cross-sectional view of one embodiment of the hand assembly of FIG. 29 showing an MRP tensioner assembly.

Referring to FIG. 32, the hand assembly 24 includes an MRP drive pulley 250 driven by the MRP drive 236. The MRP drive pulley 250 is connected through an MRP tension belt 252 to the MRP pulley 254, enabling movement of the MRP structure 224. The MRP drive pulley 250 is stage driven and transfers the load to the MRP tension belt 252, which in turn rotates the linked MRP structure 224 via the MRP pulley 254. As the MRP tension belt 252 transfers torque, one side of the MRP tension belt 252 tightens as the other side loosens. An MRP tensioner 256 located at one side of the MRP tension belt 252 displaces in relation to the change in load to maintain the tension of the MRP tension belt 252. This also provides the MRP structure 224 with compliance to aid in gripping and with load absorption, which may prevent the hand assembly 24 from damaging objects (not shown) by closing around the objects (not shown) too quickly and forcefully.

Referring to FIG. 38, in another embodiment, the MRP finger structures 224 are driven through an MRP sun shaft 370, a set of MRP planets 372, an MRP planet carrier 374, an MRP ring gear 376, and an MRP drive gear 378. The MRP drive 380 drives the MRP ring gear 376, turning the MRP planets 372, the turning of which causes the MRP planet carrier 374 to rotate. The MRP drive gear 378 is driven by the external teeth of the MRP planet carrier 374, causing the MRP structures 224 to move. Any torque transmitted by the MRP planet carrier 374 will react against the MRP sun shaft 370 causing it to rotationally displace the MRP spring 382 through the MRP spring mount 384. This rotational displacement can be used to store elastic energy.

Figure 33:
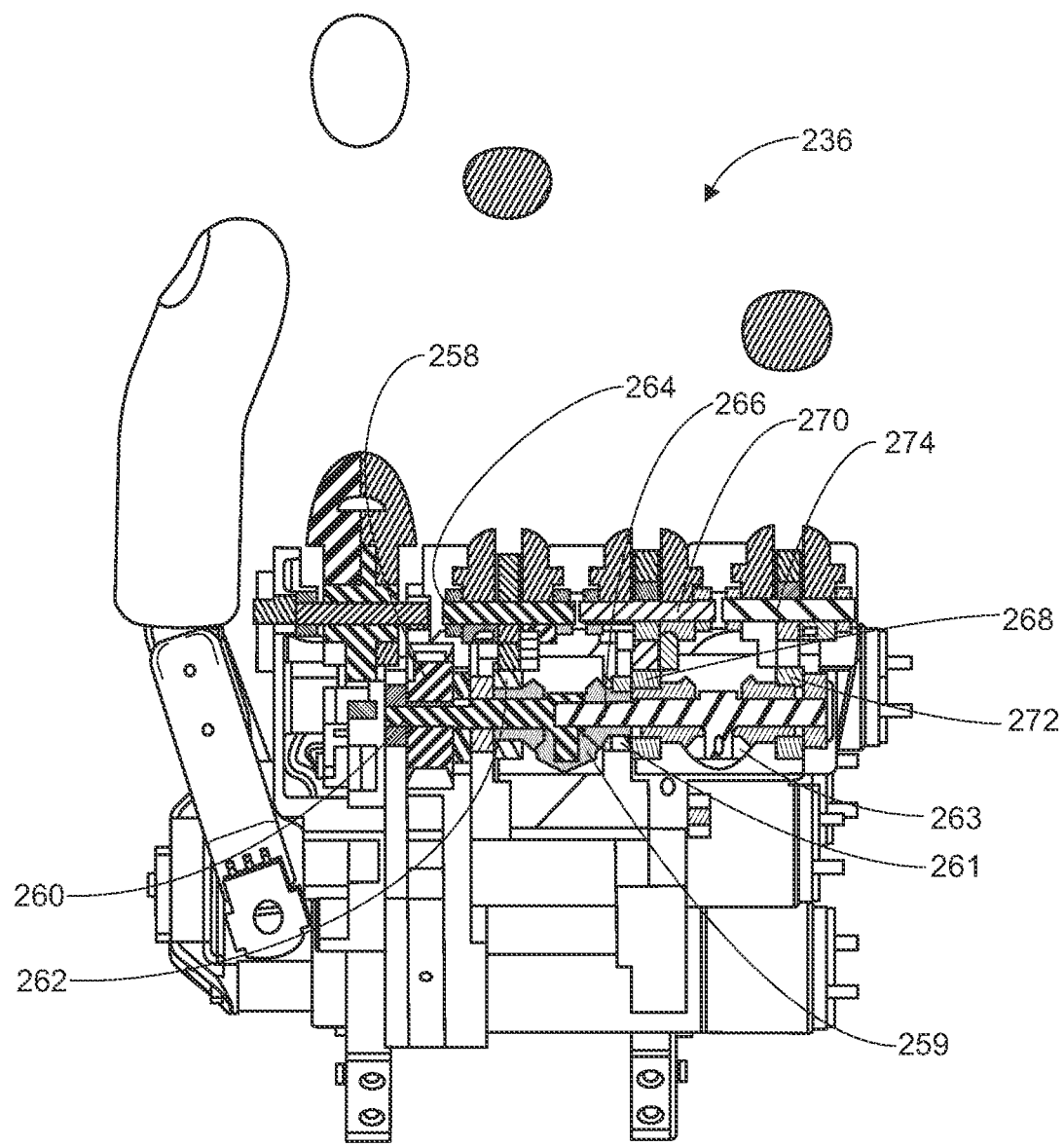
FIG. 33 is a front cross-sectional view of one embodiment of the MRP differential drive of FIG. 30.

Referring to FIG. 33 the MRP differential drive 236 includes a main MRP drive gear 258. The MRP drive gear 258 drives a first MRP input axle 260. The first MRP input axle 260 drives a first differential idler gear 259 which optionally drives a middle spur gear 262 or a differential interface gear 261. The middle spur gear 262 drives a middle pivot axle 264. The middle finger 226 is mounted on the middle pivot axle 264 and is thus actuated by the MRP differential drive 236. The differential interface gear 261 drives a second MRP input axle 266. The second MRP input axle 266 drives a second differential idler gear 263 which optionally drives a ring spur gear 268 or a pinky spur gear 272. The ring spur gear 268 drives a ring pivot axle 270. The ring finger 228 is mounted on the ring pivot axle 270 and is thus actuated by the MRP differential drive 236. The pinky spur gear 272 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 260 and the second input axle 266 allows independent movement for the under-actuated finger gear system of the MRP structures 224.

Figure 41:
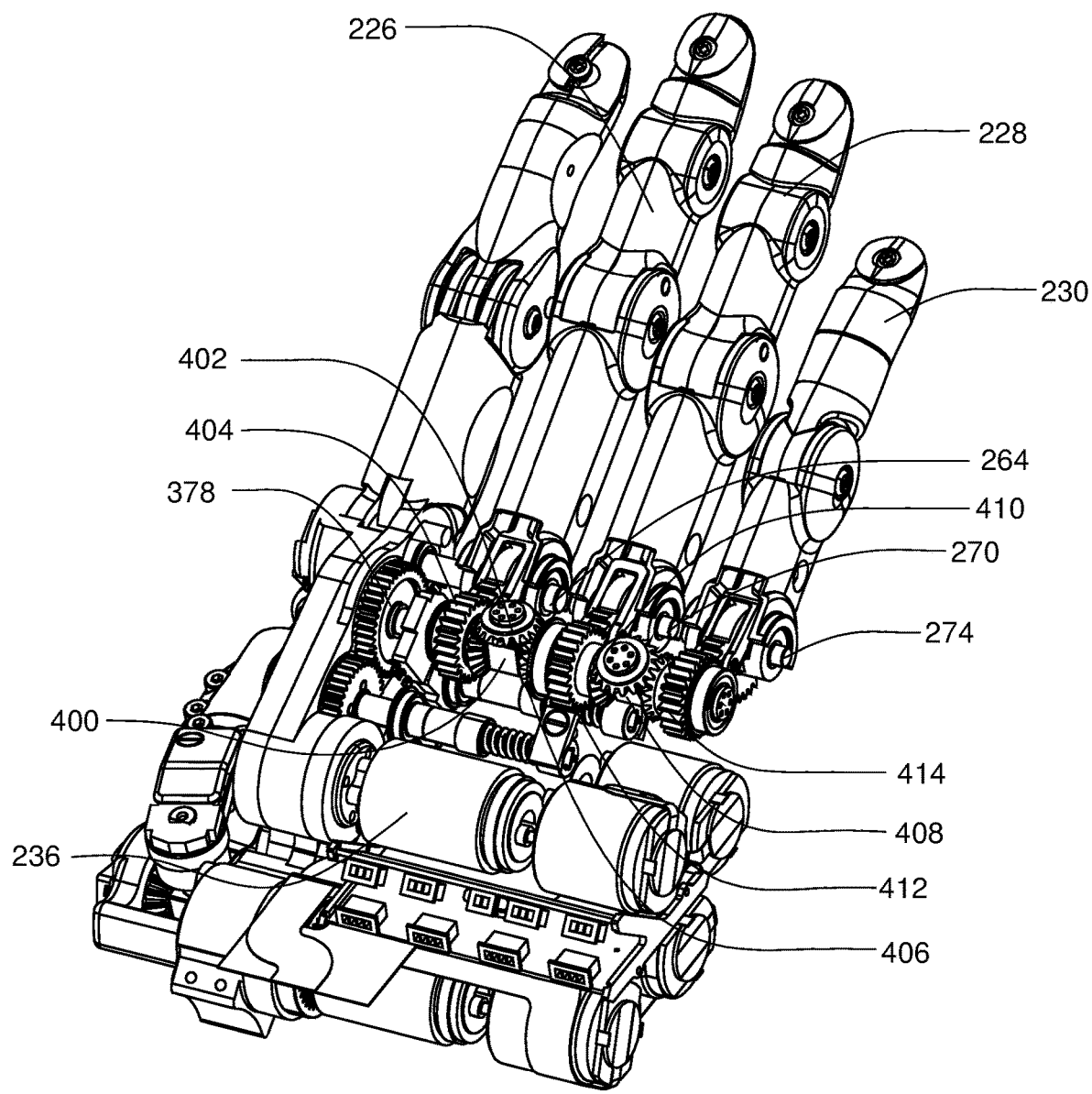
FIG. 41 is a perspective cutaway view of the hand.

Referring to FIG. 41, in another embodiment of the hand, the MRP differential drive 236 includes an MRP drive gear 378 which drives a double differential allowing the MRP fingers to conformably wrap around an object. The MRP drive gear 378 drives a first MRP input axle 400. The first input axle 400 drives a first differential idler gear 402 which optionally drives a middle spur gear 404 or a differential interface gear 406. The middle spur gear 404 drives a middle pivot axle 264. The middle finger 226 is mounted on the middle pivot axle 264 and is thus actuated by the MRP drive 236. The differential interface gear 406 drives a second MRP input axle 408. The second MRP input axle 408 drives a second differential idler gear 410 which optionally drives a ring spur gear 412 or a pinky spur gear 414. The ring spur gear 412 drives a ring pivot axle 270. The ring finger 228 is mounted on the ring pivot axle 270 and is thus actuated by the MRP drive 236. The pinky spur gear 414 drives a pinky pivot axle 274. The pinky finger 230 is mounted on the pinky pivot axle 274 and is thus actuated by the MRP drive 236. While the MRP drive 236 drives the middle finger 226, the ring finger 228 and the pinky finger 230, the gear configuration of the first input axle 400 and the second input axle 408 allows independent movement for the under-actuated finger gear system of the MRP structures 224.

Figure 34:
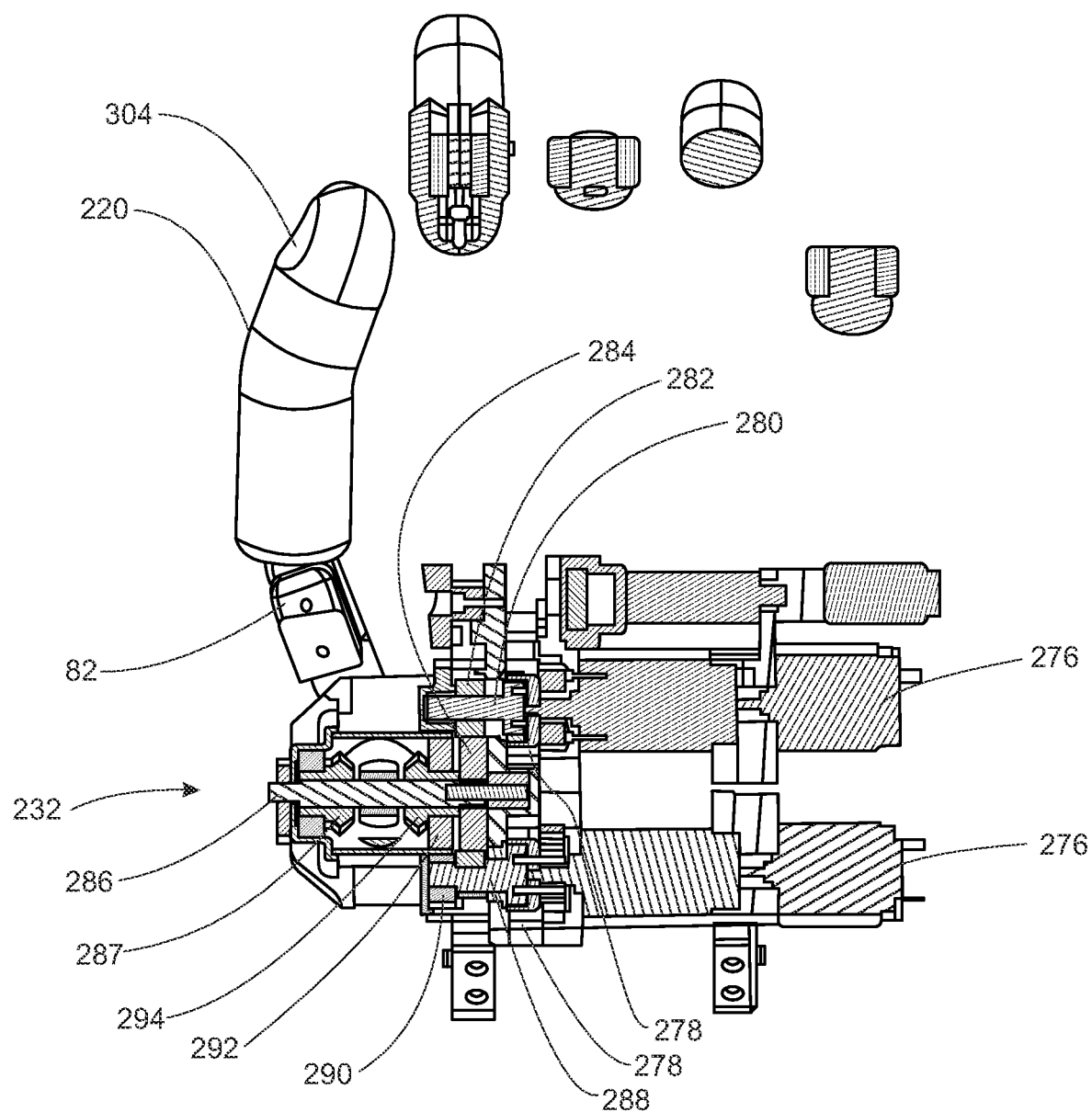
FIG. 34 is a front cross-sectional view of one embodiment of thumb differential drives of FIG. 30.

Referring to FIG. 34 the thumb differential drives 232 control the movement of the thumb structure 220 and are driven by thumb actuators 276. The thumb actuators 276 have nonbackdriving thumb clutches 278 to prevent output loads from reaching and backdriving the thumb actuators. One thumb actuator 276 drives a first thumb output drive 280 and a first thumb output gear 282. The first thumb output gear 282 in turn drives a first thumb transfer gear 284, which drives a fixed differential shaft 286. The fixed differential shaft 286 drives one thumb differential bevel gear 287. The second thumb actuator 276 drives a second thumb output drive 288 and a second thumb output gear 290. The second thumb output gear 290 drives a second thumb transfer gear 292, which drives a thumb differential bevel gear 294. The two thumb differential bevel gears 287 and 294 operate the thumb structure 220 in its two degrees of motion.

The thumb structure 220, the index finger structure 222, and MRP structure 224 in one embodiment are covered in silicone, which provides additional friction and aids in gripping objects. In some embodiments, the entire hand assembly 24 may also be covered in silicone to provide additional grip for holding objects. In other embodiments, the silicone material may be replaced by other compliant materials.

The hand assembly 24 is advantageous because the thumb structure 220, index finger structure 222 and MRP structure 224 provide various degrees of freedom that allow the formation of various grasps or grips. Additionally, the different drives for each of the thumb structure 220, index finger structure 222 and MRP structure 224 provide various beneficial characteristics to the hand assembly 24. For instance, the thumb structure 220 moves relatively slow, but with greater force than the index finger structure 222 and MRP structure 224. The index finger structure 222 moves quickly, but with less force and is non-backdrivable. This combination of thumb structure movement and index finger structure movement allow the quick formation of strong hand grips. Additionally, the combination allows for a smaller index finger actuator, which reduces size and weight of the hand assembly 24. Additionally, the index finger structure 222 and MRP structure 224 move similar to human fingers, which makes them look more natural and makes them more intuitive for the user to control. The MRP structure 224 provides only bulk control for gripping objects, without providing for individual finger manipulation, since fine control is not necessary for the MRP structure 224. Additionally, the MRP structure 224 advantageously moves each finger of the MRP structure 224 with a single actuator, eliminating excessive bulk in the hand assembly 24. Like the index finger structure, the MRP structure 224 moves quickly with low force but is also non-backdrivable. Additionally, the fingers of the MRP structure 224 are highly flexible, allowing them to grip objects of varying size and shape. The MRP structure 224 functionality allows the user to grasp an object with the MRP structure 224 and thumb structure 220, while allowing the user to move the index finger structure 222 separately, for example, to activate a button on the object.

The various parts of the prosthetic arm apparatus 10 are, in some embodiments, constructed from plastic or magnesium. However, where more strength and/or other material properties are desired, the parts may be made of aluminum, titanium or steel. In other embodiments, the various parts of the prosthetic arm may be constructed of other metals or plastics, depending on the desired characteristics, including strength, weight, compliance or other similar performance characteristics of the various parts.

Figure 35:
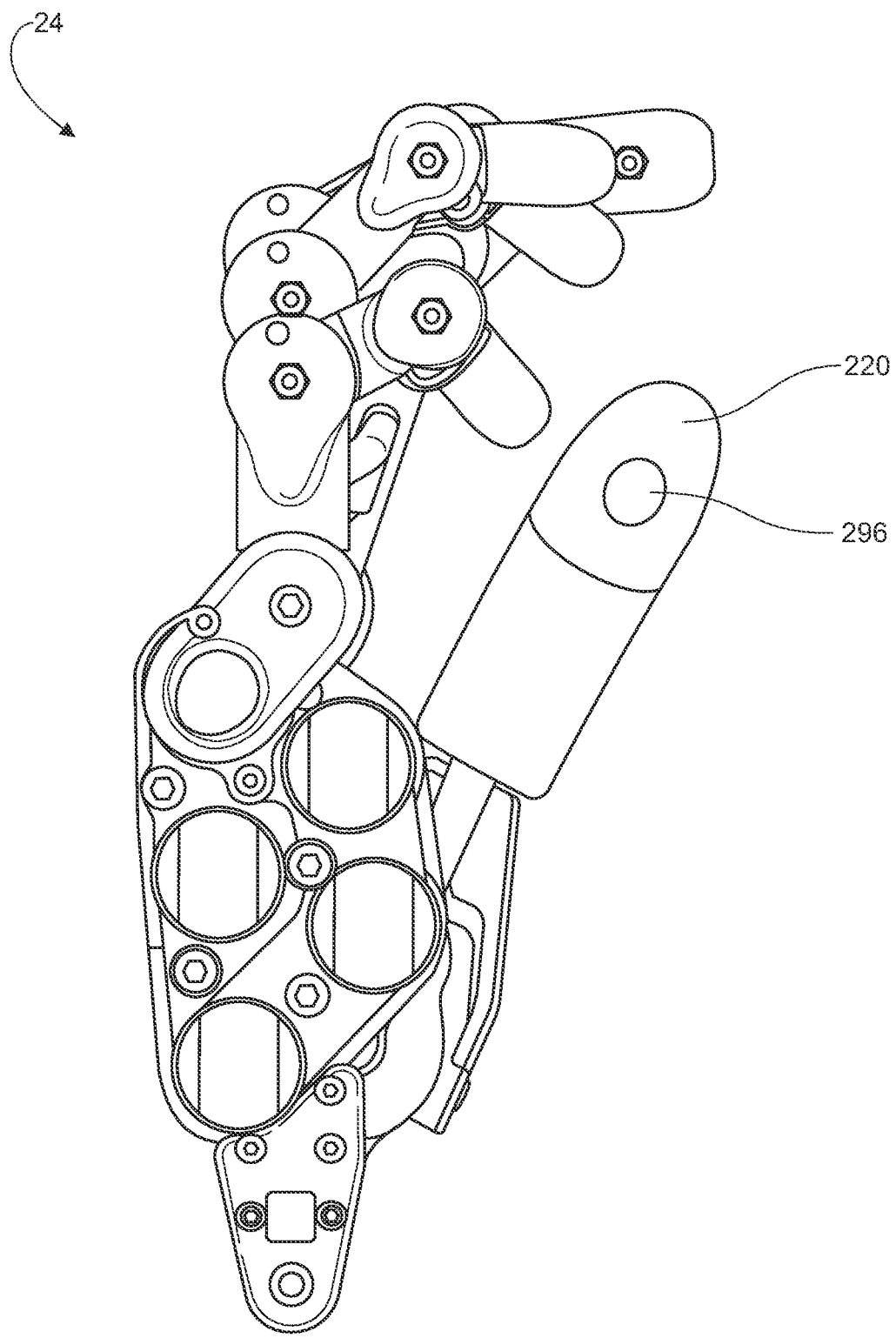
FIG. 35 is a side view of one embodiment of the hand assembly of FIG. 30 showing a tactile feedback sensor according to the present invention.
Figure 36:
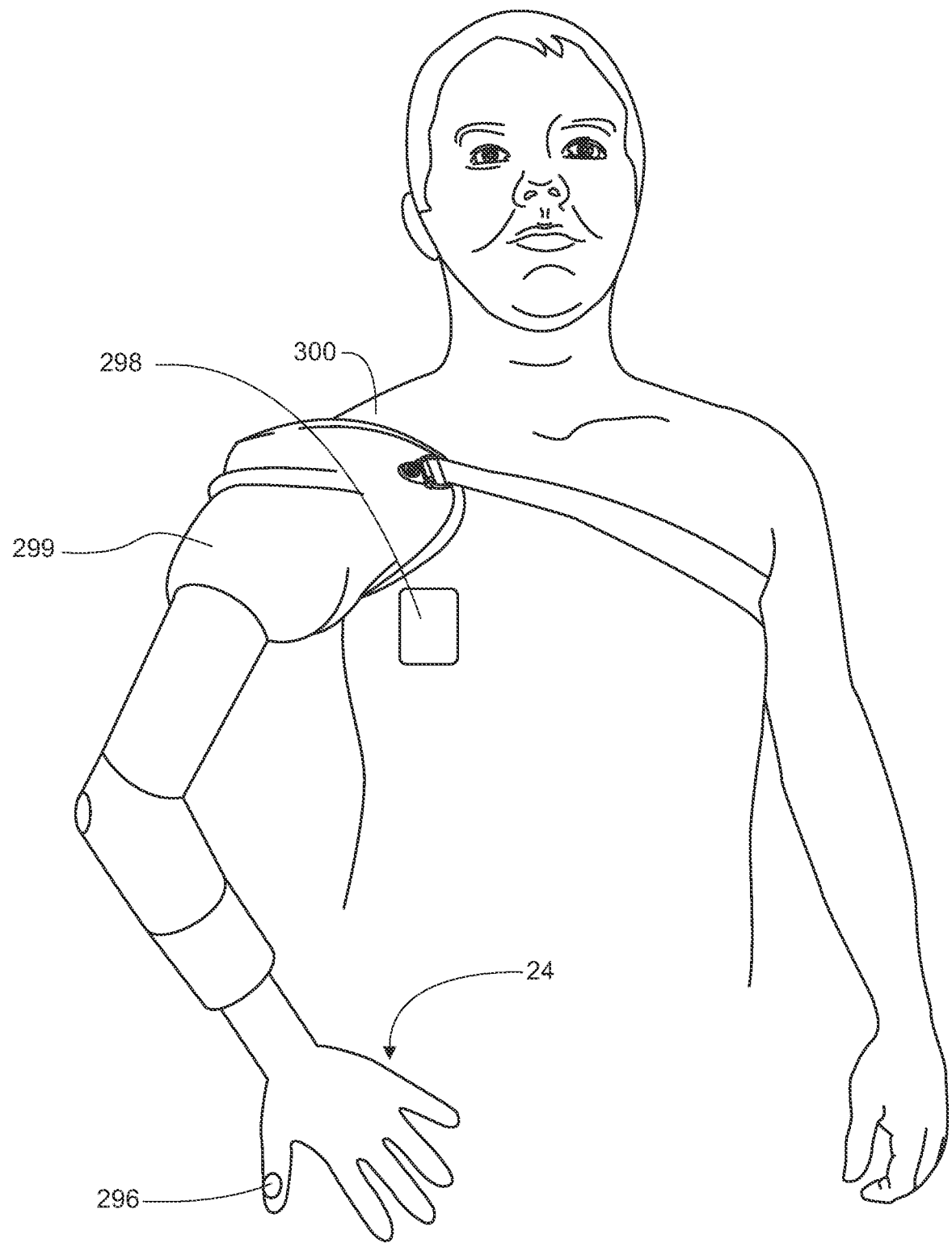
FIG. 36 is a perspective view of one embodiment of the tactile feedback sensor and a feedback actuator of the prosthetic arm apparatus of FIG. 1.
Figure 37:
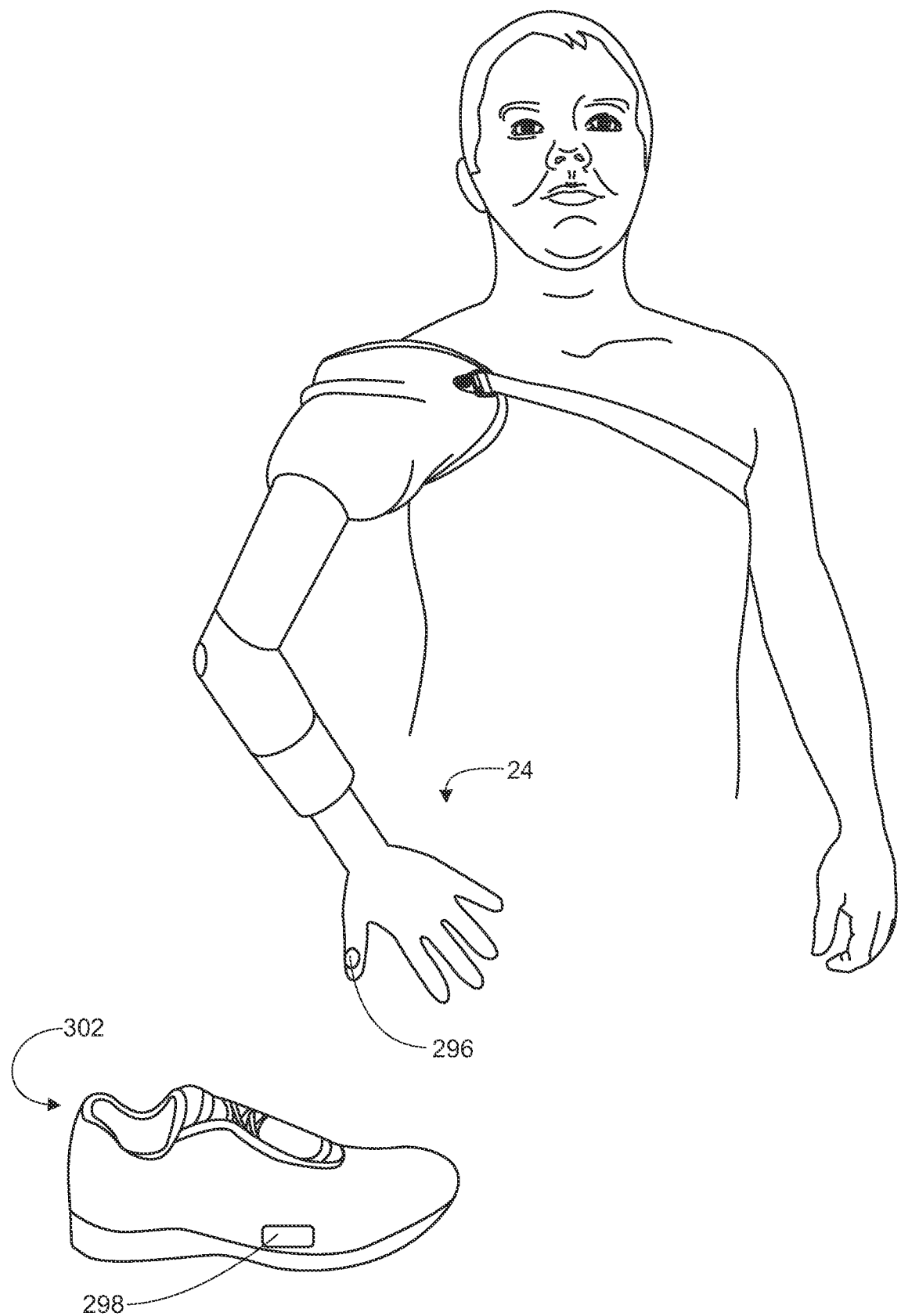
FIG. 37 is a perspective view of another embodiment of the tactile feedback sensor and feedback actuator of the prosthetic arm apparatus of FIG. 1 according to the present invention.

Referring to FIG. 35, a tactile feedback sensor 296 may be positioned on the inner side of the thumb structure 220. The tactile feedback sensor 296 may be a pressure sensor, force sensor, a displacement sensor, or other similar sensor capable of providing the user with feedback. Referring to FIG. 36, the tactile feedback sensor 296 is operatively connected to a feedback actuator 298. The tactile feedback sensor 296 may be connected to the feedback actuator 298 by either wires or wirelessly. In operation, as the user grips an object with the hand assembly 24, feedback sensor 296 reads the displacement of or the force exerted on the thumb structure 220. That reading is then sent to the feedback actuator 298, which gives the user tactile feedback that indicates the strength of the grip. Feedback actuator 298 may be placed on the chest of the user, located on a prosthetic support apparatus 299 in an area of tactile communication with the user, or in any other location capable of receiving tactile feedback, such as on a user's residuum 300. Referring to FIG. 37, the feedback actuator 298 may be located on a foot controller 302 that is used to control hand assembly 24.

Feedback actuator 298 may be a vibration motor, such as any vibration motor known in the art, placed against the skin of the user. As the user grips an object, feedback actuator 298 begins vibrating, notifying the user how strong the object is being gripped. As the force on or displacement of the tactile feedback sensor 296 changes, frequency and/or amplitude of vibration may also change, notifying the amputee of a changing grip. For example, if a vibrating actuator 298 is placed at the chest of the user as in FIG. 36, the user will feel the vibration at his chest.

The feedback actuator 298 may also be placed wherever the controller for the hand assembly 24 is located. For example, if a foot controller 302 controls the hand assembly 24, the feedback actuator 298 may be incorporated into the foot controller 302. The user will then receive tactile feedback of the strength of the prosthetic grip at the same location where the controller is located.

The actuator 298 may also be a pressure actuator that applies pressure against the user's skin. For example, the actuator 298 may have a rod that increases pressure against the amputee's skin as the hand assembly 24 increases its grip on an object.

Although described with a single tactile feedback sensor 296, additional tactile feedback sensors may be placed at other locations on the hand assembly 24. For example, additional tactile feedback sensors 296 may be placed on the index finger structure 222, the MRP structures 224, on the palm of the hand assembly 24, or on any combination of these positions or any other location. Each tactile feedback sensor 296 would then be operatively connected to an associated feedback actuator 298. Multiple tactile feedback sensors 296 and actuators 298 would provide more sophisticated tactile feedback of the strength of the grip, improving the control of the hand assembly 24.

In some embodiments, the tactile feedback sensor 296 may indicate a change in pressure or force, rather than an absolute pressure or force. For example, if the force detected by the tactile feedback sensor 296 is constant, the feedback actuator 298 does not actuate, but if that pressure or force increases or decreases, the actuator 298 would actuate to indicate the change in pressure or force. Additionally, although described in terms of grip strength, the tactile feedback sensors 296 and actuators 298 may provide a variety of other feedback in including temperature, an operational mode of the prosthetic arm 10, surface finish of a object, slip of an object within the hand assembly 24 or the like.

In operation, the prosthetic arm apparatus is able to move substantially similar to a human arm. Referring to FIGS. 29 and 30, starting with the hand assembly 24, the thumb structure 220, index finger structure 222, and MRP structure 224 are each driven independent of the others, and therefore, each may be actuated without actuating the other two structures. Both of the thumb actuators 276 control motion of the thumb structure 220 in a direction toward or away from the center of the palm of the hand assembly 24, as shown in FIG. 34, through the miter gear 294 and in a direction toward or away from the side of the palm of the hand assembly 24, as shown in FIG. 34, through the lateral rotation shaft, depending upon the direction and speed of rotation of each thumb actuator 276. Thus, the thumb actuators 276, shown in FIG. 34, provide the thumb structure 220 with two degrees of freedom in the thumb structure's movement. Coupling the two thumb actuators 276 through the differential described above to provide the two degrees of freedom to the thumb structure 220 is advantageous over providing a single degree of freedom with each actuator 276 because the torque of each actuator 276 through the differential is used for movement in both degrees of freedom, which effectively doubles the torque of the thumb in each direction as compared to single actuators. Specifically, the index finger structure 222 may be actuated toward or away from the palm of the hand assembly 24, wherein the movement path is similar to that of a human index finger while making or releasing a fist. The middle finger 226, ring finger 228, and pinky finger 230 of the MRP structure 224 are actuated by the MRP differential drive 236. Additionally, the middle finger 226, ring finger 228, and pinky finger 230 are actuated toward or away from the palm of the hand assembly 24, similar to the index finger structure 222. However, the middle finger 226, ring finger 228, and pinky finger 230 are each geared separately, such that the rate of movement of each is different, simulating human finger movement and making the hand assembly 24 more similar to a human hand than conventional prior art prosthetic devices.

Referring to FIG. 1, the hand assembly 24 is mounted on the wrist flexion assembly 22 via the hand interface 198, as shown in FIG. 25. Referring to FIG. 25, as the output arm 196 of the wrist flexion assembly 22 is actuated, the hand assembly 24 is also caused to move. The output arm 196 of the wrist flexion assembly 22 may be actuated pivotally about wrist flexion pivot axle 208, as shown in FIG. 27, moving the hand interface 198 to the left or right, and thus pivoting the hand assembly 24 in relation to the input support structure 192.

Referring back to FIG. 1, the wrist flexion assembly 22 is attached to the wrist rotator 20 via wrist flexion assembly interface 172, shown in FIG. 23. Referring to FIGS. 23 and 24, when actuated, the wrist flexion assembly interface 172 is rotated about wrist shaft 188 in relation to 10 the wrist outer bearing carrier 164. Therefore, the wrist flexion assembly 22, and attached hand assembly 24 are also caused to rotate in reference to the wrist outer bearing carrier 164 by actuation of the wrist rotator 20. Therefore, the wrist rotator 20 allows the prosthetic arm apparatus 10 to move in rotation similar to a human wrist joint.

Referring back to FIG. 1, the wrist rotator 20 is attached to the elbow flexion assembly 18 via the wrist interface 130, shown in FIG. 18. Referring to FIG. 20, when the elbow flexion assembly 18 is actuated, the radial mount 122 is rotated about the axis of motor rotor 134. The wrist rotator 20, wrist flexion assembly 22, and hand assembly 24 are thus also caused to rotate about the axis of motor rotor 134 because they are attached at the wrist interface to the radial mount 122. Therefore, the elbow flexion joint 18 allows the prosthetic arm apparatus 10 to move similar to flexion extension of a human elbow joint.

Referring back to FIG. 1, the elbow flexion assembly 18 is attached to the humeral rotator 16 via the humeral mount 96, shown in FIG. 16. Referring to FIG. 16, actuation of the humeral rotator 16 causes the humeral mount 96 to rotate in relation to the outer bearing carrier 90 of the humeral rotator 16. Since the elbow flexion assembly 18, wrist rotator 20, wrist flexion 25 assembly 22, and hand assembly 24 are attached to the humeral mount 96, they are also caused to rotate in relation to the outer bearing carrier 90. This allows the prosthetic arm apparatus 10 to rotate to perform an arm wrestling motion.

Referring back to FIG. 1, the humeral rotator 16 is attached to the shoulder flexion assembly 14 through the humeral interface 46, shown in FIG. 9. Referring to FIG. 9, actuation of the shoulder flexion assembly 14 causes the main shoulder housing 42 to pivot about the center of the abductor interface 44. Since the humeral rotator 16, elbow flexion assembly 18, wrist rotator 20, wrist flexion assembly 22, and hand assembly 24 are attached to the main housing 42, they are also caused to rotate in relation to the abductor interface 44. Therefore, the shoulder flexion assembly 14 allows the prosthetic arm apparatus 10 to move along the torso simulating running motion.

Referring to FIG. 1, the shoulder flexion joint 14 is attached to the shoulder abductor 12 through the shoulder flexion assembly mount 30, shown in FIG. 5. Referring to FIG. 5, the shoulder abductor 12 is attached to a harness that is worn by the user via harness mount 26. When the shoulder abductor 12 is actuated in a positive direction, the shoulder flexion assembly mount 30 pivots away from the harness mount 26, and the user. Similarly, by actuating the shoulder abductor in a negative direction, the shoulder flexion assembly mount 30 is pivoted toward the harness mount 26 and the user. Since the shoulder flexion assembly 14, humeral rotator 16, elbow flexion assembly 18, wrist rotator 20, wrist flexion assembly 22, and hand assembly 24 are attached to shoulder abductor 12 at the flexion assembly mount 30, they are also caused to pivot with the shoulder flexion assembly mount 30.

One characteristic of the prosthetic arm apparatus described herein is that it provides the user with substantially the same movement capabilities and degrees of freedom of a human arm, including two degrees of freedom in shoulder functionality. Additionally, the modularity of each segment of the prosthetic arm apparatus 10 provides a significant advantage over conventional prosthetic devices. In particular, since each segment of the plurality of segments operates independently of each other segment of the plurality of segments, fewer segments may be used for less severe amputees. For example, a transhumeral amputee may have full shoulder functionality in the residuum, in which case the shoulder abductor 12 and shoulder flexion assembly 14 segments would be omitted from the prosthetic arm apparatus 10. The resulting prosthetic arm apparatus 10 would include the humeral rotator 16, the elbow flexion assembly 18, the wrist rotator 20, the wrist flexion assembly 22, and the hand assembly 24, wherein the humeral rotator 16 would be attached to the prosthetic harness. In some cases, the residuum of the transhumeral amputee may even have humeral rotation, in which case the prosthetic arm apparatus 10 may be further simplified to include only the elbow flexion assembly 18, the wrist rotator 20, the wrist flexion assembly 22 and the hand assembly 24, with the elbow flexion assembly 22 being attached to the prosthetic support apparatus. Similarly, for a transradial amputee, the prosthetic arm apparatus 10 may include only the wrist rotator 20, wrist flexion assembly 22 and the hand assembly 24, with the wrist rotator 20 being attached to the prosthetic support apparatus. Additionally, in some embodiments, the prosthetic arm apparatus 10 may be further simplified to include only the wrist flexion assembly 22 and the hand assembly 24 when the transradial amputee has wrist rotation in their residuum. In these embodiments, the wrist flexion assembly 22 may be attached to the prosthetic support apparatus. Thus, the modularity of each segment of the prosthetic arm apparatus 10 advantageously allows for customization of different prosthetic arm configurations for various users based on the differing degrees of amputation of each user.

A further advantage of the present invention is the use of non-backdriving clutches to preclude movement of the segments due to forces exerted on the prosthetic arm apparatus 10 when not in motion. These non-backdriving clutches may be particularly beneficial when the segments of the prosthetic arm apparatus 10 have different strength capacities so that the clutches for specific segments of the prosthetic arm apparatus 10 may lock those segments while other stronger segments are actuated to lift heavy objects. For instance, the non-backdriving clutch in the shoulder flexion assembly 14 may be used to lock out shoulder movement while the elbow flexion assembly 18 is actuated to lift a heavy object. The non-backdriving clutches may also advantageously conserve power since the non-backdriving clutches prevent motion without using power. Thus, the power to specific segments of the prosthetic arm apparatus 10 may be shut off, on a segment-by-segment basis, when not in use, since the non-backdriving clutches in those segments are locking out motion. Additionally, the non-backdriving clutches may also save power by allowing power to the entire prosthetic arm apparatus 10 to turned off whenever the arm is not in motion while maintaining the prosthetic arm apparatus 10 in a locked position.

An additional characteristic of the apparatus is that the hand assembly includes independently moving fingers and is capable of completing fine tasks such as pinching, grasping non-uniform objects, and lifting small objects off flat surfaces. Also, the tactile feedback sensor provides the user with feedback, during use of the prosthetic arm apparatus, such as the force of a grip. The apparatus also includes a cosmesis covering on the finger structures, which will be discussed in greater detail below, providing, amongst other things, grip for grasping objects. The rigid fingernail 304, shown in FIG. 34, which may be included on any of the finger structures, provides a backstop for the finger cover to enhance gripping capability. The rigid fingernail 304 also enhances gripping capability by anchoring the finger cover to the finger and allows the user to lift small objects from a surface with the prosthetic arm apparatus 10.

Figure 42A:
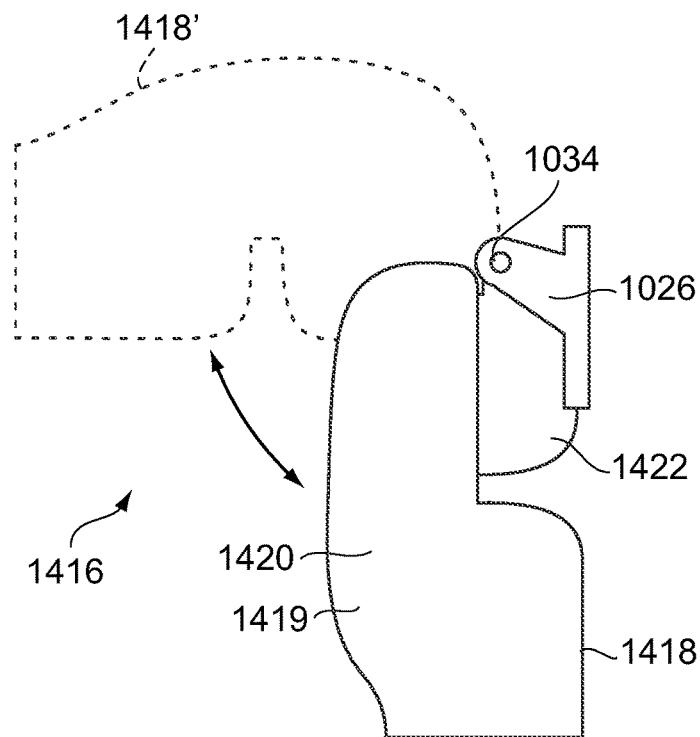
FIG. 42A shows an embodiment of an integrated shoulder unit according to an embodiment of the present invention.

Referring to FIG. 42A, wherein like numerals represent like elements, in some embodiments, the shoulder abductor 12 and the shoulder flexion assembly 14 shown in FIG. 2, may be integrated as a single shoulder unit 1416, providing both degrees of freedom provided by the shoulder abductor 12 and shoulder flexion assembly 14 of FIG. 2. The single shoulder unit 1416 includes a shoulder housing 1418 pivotally connected to the harness mount 1026, which allows the shoulder unit 1416 to be connected to a prosthetic harness (not shown) as discussed above. In some embodiments, the shoulder housing 1418 has a smooth outer surface 1419 to shape the shoulder unit 1416 to be similar to a human arm. The shoulder housing 1418 is divided into a flexor portion 1420 and an abductor portion 1422, which are movable relative to one another. The flexor portion 1420 of the shoulder housing 1418 includes the humeral interface 1046 for connecting the humeral rotator 16, shown in FIGS. 1 and 2, to the shoulder unit 1416. The abductor portion 1422 of the shoulder housing 1418 is pivotally connected to the harness mount 1026, which allows the shoulder unit 1416 to interface with a prosthetic harness (not shown) as discussed above.

Figure 42B:
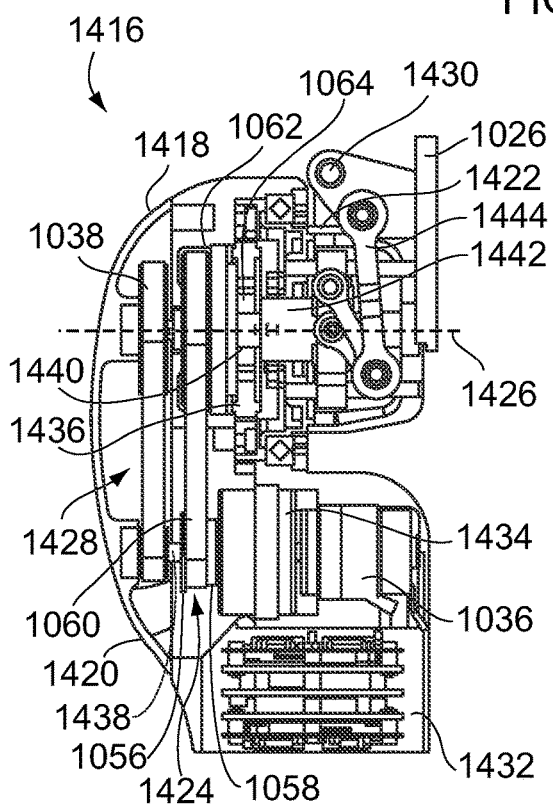
FIG. 42B is a partial cutaway view of the integrated shoulder unit of FIG. 42A in an inactuated state.
Figure 42C:
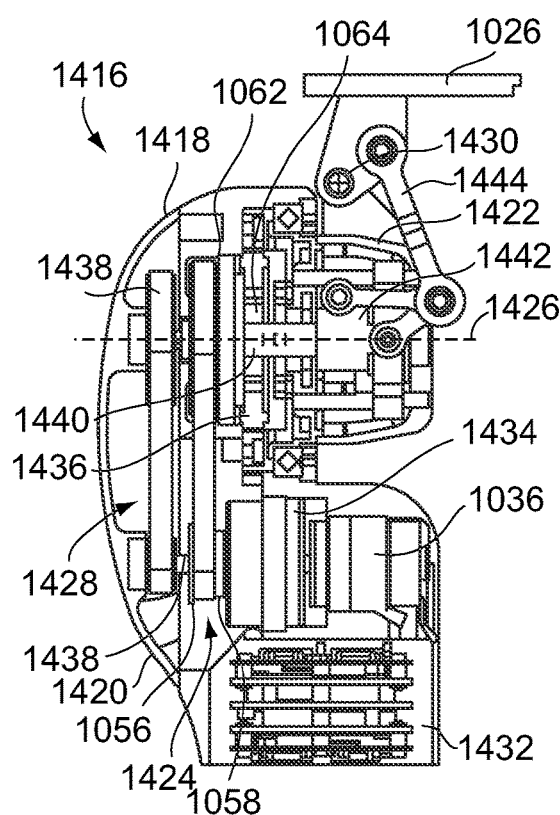
FIG. 42C is a partial cutaway view of the integrated shoulder unit of FIG. 42A in an actuated state.

Referring to FIGS. 42B and 42C, within the housing 1418 is a shoulder flexion drive 1424 for causing flexion motion of the flexor portion 1420 about a shoulder flexion axis 1426 and an abduction drive 1428 for causing abduction motion of the shoulder housing 1418 about an abduction axis 1430. Additionally, the housing also defines an electronics compartment 1432 for housing control systems and circuits for the integrated shoulder unit 1416.

The shoulder flexion drive 1424, in one embodiment, includes a shoulder flexion motor 1434 having motor shaft 1058 for driving the shoulder flexion motor pulley 1056. The shoulder flexion motor pulley 1056 drives the shoulder flexion belt 1060, which, in turn, drives the shoulder flexion belt-driven pulley 1062. The shoulder flexion belt-driven pulley 1062 drives the wave generator 1064 of a shoulder flexion harmonic drive gearing system 1436, the output of which is fixedly interfaced with the abductor portion 1422. Thus, as power is transmitted through the shoulder flexion drive 1424 from the shoulder flexion motor 1434 to the output of the harmonic drive gearing system 1436, the flexor portion 1420 rotates relative to the abductor portion 1422 about the shoulder flexion axis 1426. In some embodiments, the motor shaft 1058 and the wave generator 1064 are both hollow shafts to allow passage of an abductor motor shaft 1438 and an abductor screw shaft 1440, respectively, as will be discussed in greater detail below.

In the exemplary embodiment, the abduction drive 1428 includes the abductor motor 1036 for driving the abductor motor shaft 1438. The abductor motor shaft 1438 is configured to drive the abductor belt 1038 about its distal end. The abductor belt 1038, in turn, drives the abductor screw shaft 1440, which has an abductor nut 1442 threadedly coupled thereto. The abductor nut 1442 is connected to the harness mount 1026 through a linkage 1444, which is, in some embodiments, a four bar linkage. As power is transmitted through the abductor drive 1426 from the abductor motor 1036 to the abductor screw shaft 1440, the screw shaft 1440 rotates. The rotation of the screw shaft 1440 causes the abductor nut 1442 to displace axially along the screw shaft 1440, which causes pivotal motion of the shoulder housing 1418 through the linkage 1444 about the abduction axis 1430.

Referring to FIG. 42A, the relative movement between the flexor portion 1420 and the abductor portion 1422 provides the shoulder unit 1416 with a first degree of freedom similar to that of the shoulder flexion joint 14 of FIG. 2. The abductor portion 1422 of the shoulder housing 1418 is pivotally connected to the harness mount 1026 at the abductor joint 1034, providing the shoulder unit with the second degree of freedom by allowing the shoulder housing 1418 to pivot relative to the harness mount 1026 in a similar manner to that discussed above in connection with the shoulder abductor 12 of FIG. 2. Referring to FIGS. 42B and 42C, the integrated shoulder unit 1416 locates the shoulder flexion axis 1426 and the abduction axis 1430 relatively close to one another as compared to separate shoulder flexion and shoulder abduction assemblies, which provides for more intuitive motion that more closely simulates the movement of a human shoulder.

The shoulder flexion drive 1424 and the abduction drive 1428 discussed above include coaxial motors and coaxial shafts to minimize the size of the single shoulder unit 1416 and to reduce the weight thereof. Thus, these exemplary single shoulder unit 1416 is beneficial because its weight relative to the separate shoulder abductor 12 and shoulder flexion assembly 14, shown in FIG. 2. Additionally, the single shoulder unit 1416 provides more narrow housing 1418, which allows a more natural anatomical position of the shoulder for a broader range of users and may reduce bumping with the user's residuum during use. This embodiment has an additional benefit of decreasing the weight of the prosthetic. Additionally, as seen in FIGS. 42B and 42C, both the abduction motor 1036 and the shoulder flexion motor 1434 may be located in the vicinity of the electronics compartment 1432, so the electronics for both the shoulder flexion drive 1424 and the abduction drive 1428 may be located in the same place, which eliminates any need to route wiring through the shoulder unit 1416. This is advantageous since running wires across joints is a failure mode in which the wires may crimp and break when moved. Thus, the shoulder unit 1416 eliminates this failure mode by eliminating wires running across the joints that could cause failure of the prosthetic arm 1010.

Figure 43:
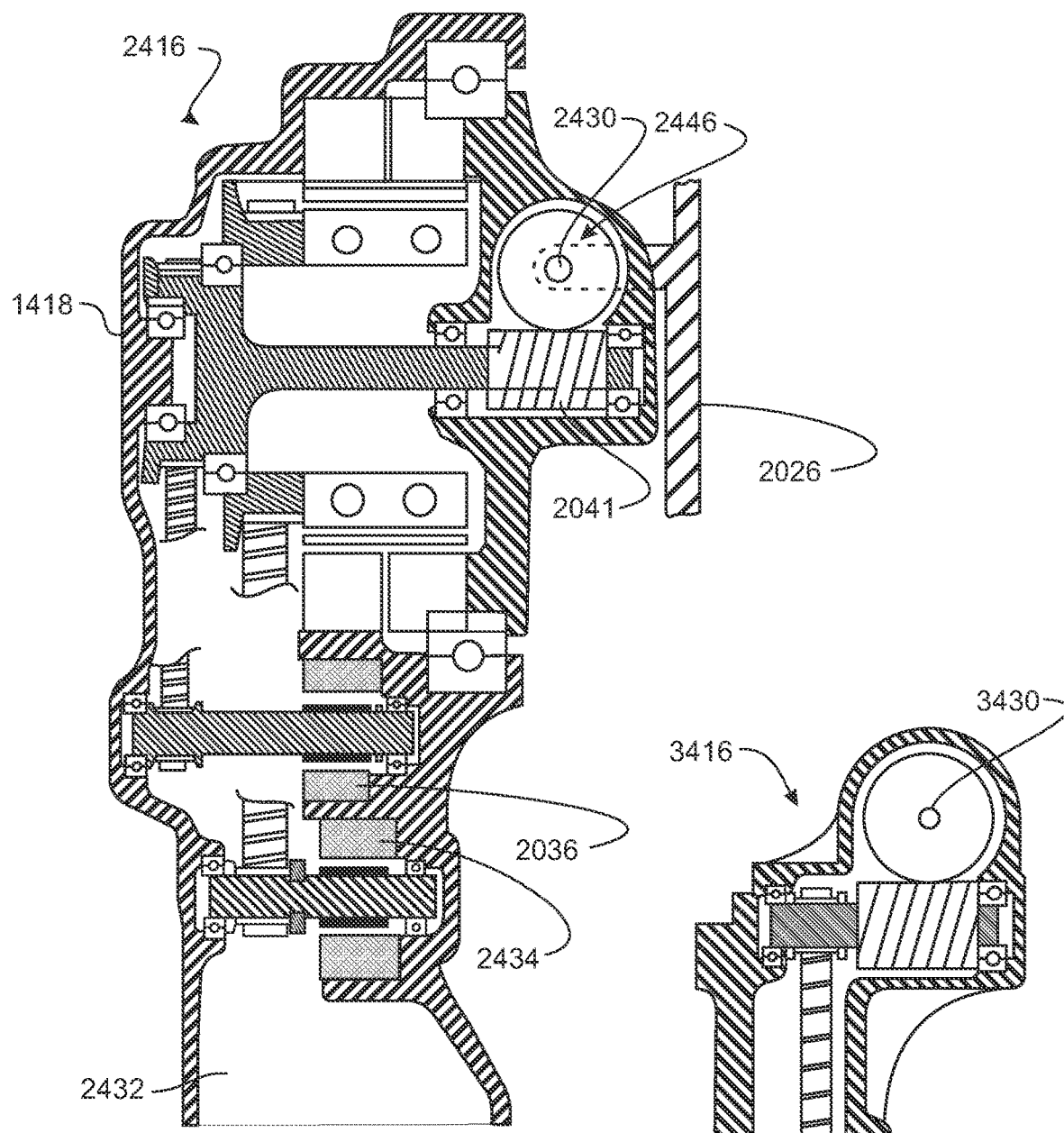
FIG. 43 is a cross sectional view of another embodiment of an integrated shoulder unit according to the present invention.

Although the shoulder flexion drive 1424 and the abduction drive 1428 have been shown in an exemplary configuration, it should be understood by those skilled in the art that other drive configurations may also be used to drive the single shoulder unit 1416 about the shoulder flexion axis 1426 and the abduction axis 1430. For instance, referring to FIG. 43, the shoulder flexion motor 2434 and the abduction motor 2036 of the single shoulder unit 2416 do not need to be coaxial and they may still each be located within the housing 2418 in the vicinity of the electronics compartment 2432. Additionally, rather than driving the linkage 1444, shown in FIG. 42B, the worm drive 2041 may instead threadably engage an abduction gear 2446 coupled to the harness mount 2026 to generate pivotal movement about the abduction axis 2430.

Figure 44:
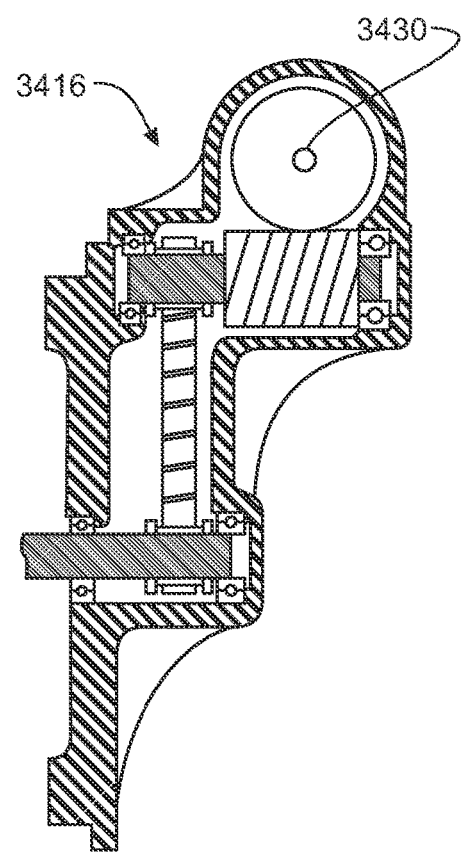
FIG. 44 is a cross sectional view of another embodiment of the integrated shoulder unit of FIG. 43.

Additionally, referring now to FIG. 44, in various embodiments, the integrated shoulder unit 3416 may shift the abduction output to change the location of the harness mount (not shown) to improve mounting location and/or to allow for ninety degrees (90°) of abduction about the abduction axis 3430 without bumping with the residuum (not shown). For example, the location of the abduction output may be changed by extending the abduction drive 3428 with one or more additional shafts, gears, and/or belts.

Figure 45:
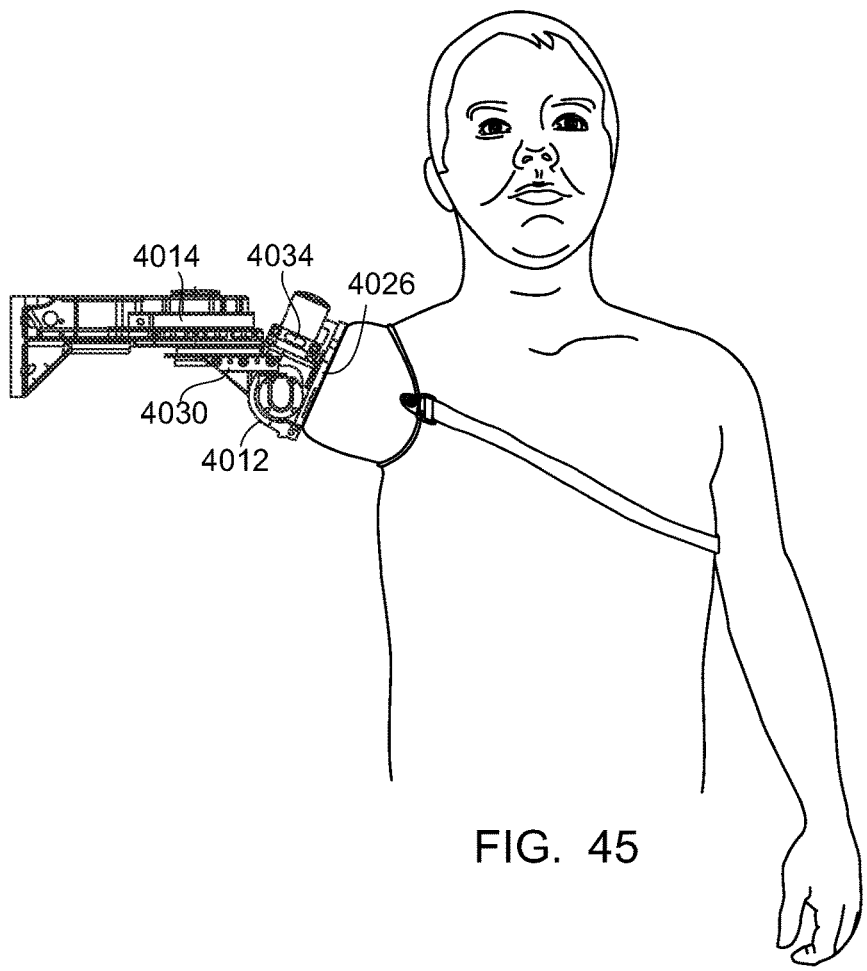
FIG. 45 is a top view of a shoulder abductor and shoulder flexion assembly according to another embodiment of the present invention.
Figure 46:
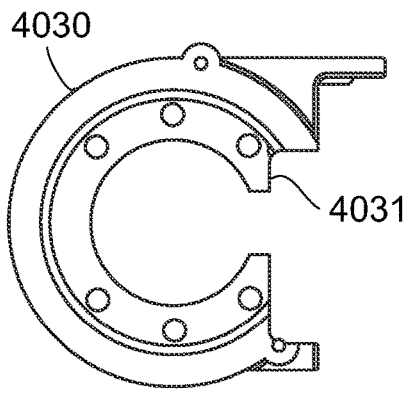
FIG. 46 is a side plane view of shoulder flexion assembly mount of the shoulder abductor of FIG. 45.

Referring to FIG. 45, the flexion assembly mount 4030 may also be shifted away from the harness mount 4026 in the non-integrated shoulder abductor 4012. Referring to FIG. 46, the flexion assembly mount 4030 may also include an accommodating slot 4031 adapted to accommodate portions of the abductor joint 4034, shown in FIG. 45. Referring back to FIG. 45, the shifted flexion assembly mount 4030 allows the user to orient the shoulder abductor 4012 on the prosthetic support apparatus (not shown) in different orientations while still allowing a range of motion of the shoulder abductor 4012 of at least approximately ninety degrees (90°). This may be particularly advantageous since the mounting orientation of the shoulder abductor 4012 may vary from user to user, which may limit the range of abduction motion with the non-shifted flexion assembly mount 30, shown in FIG. 6. Additionally, in some embodiments, the shifted flexion assembly mount 4030 may house a flex sensor plunger for detecting flexion motion of the shoulder flexion assembly 4014.

Figure 47A:
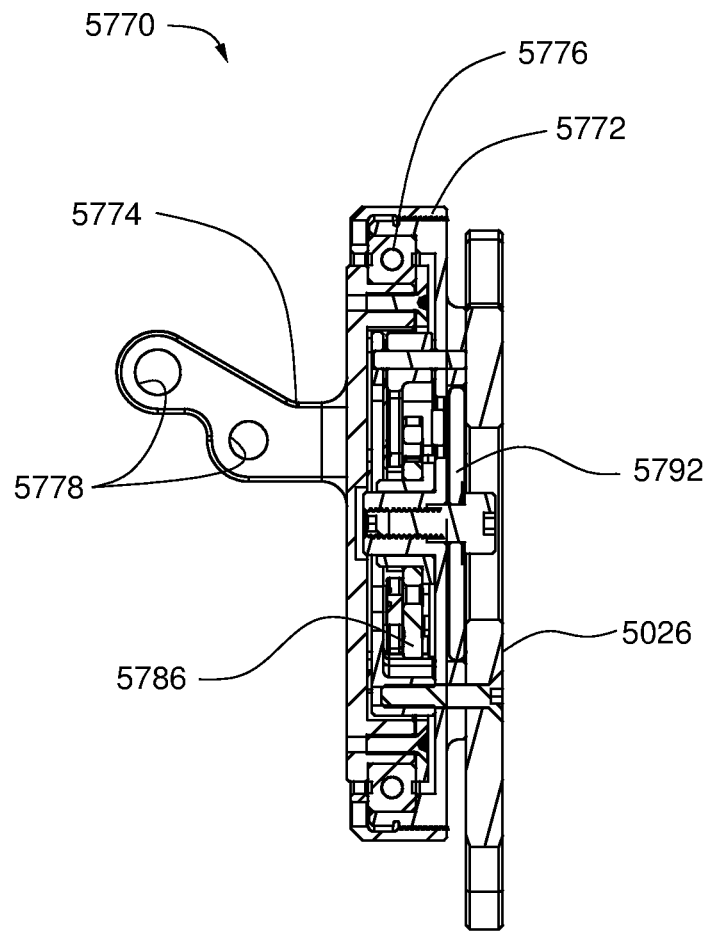
FIG. 47A is a side cross-sectional view of an embodiment of a shoulder free swing system according to the present invention.

Referring to FIG. 47A, in some embodiments of the present invention, the prosthetic arm apparatus 10, shown in FIG. 1, may include a shoulder free swing system 5770 including a housing 5772 having a harness mount 5026 fixedly secured thereto for attaching to a prosthetic harness. The shoulder free swing system 5770 also includes an arm interface 5774 rotatably secured within the housing 5772 inside a bearing 5776. The arm interface 5774 includes mounting holes 5778 for connecting the shoulder free swing system 5770 to the shoulder unit 1416, shown in FIG. 42B, through the abduction axis 1430 and the linkage 1444, each shown in FIG. 42B.

Figure 47B:
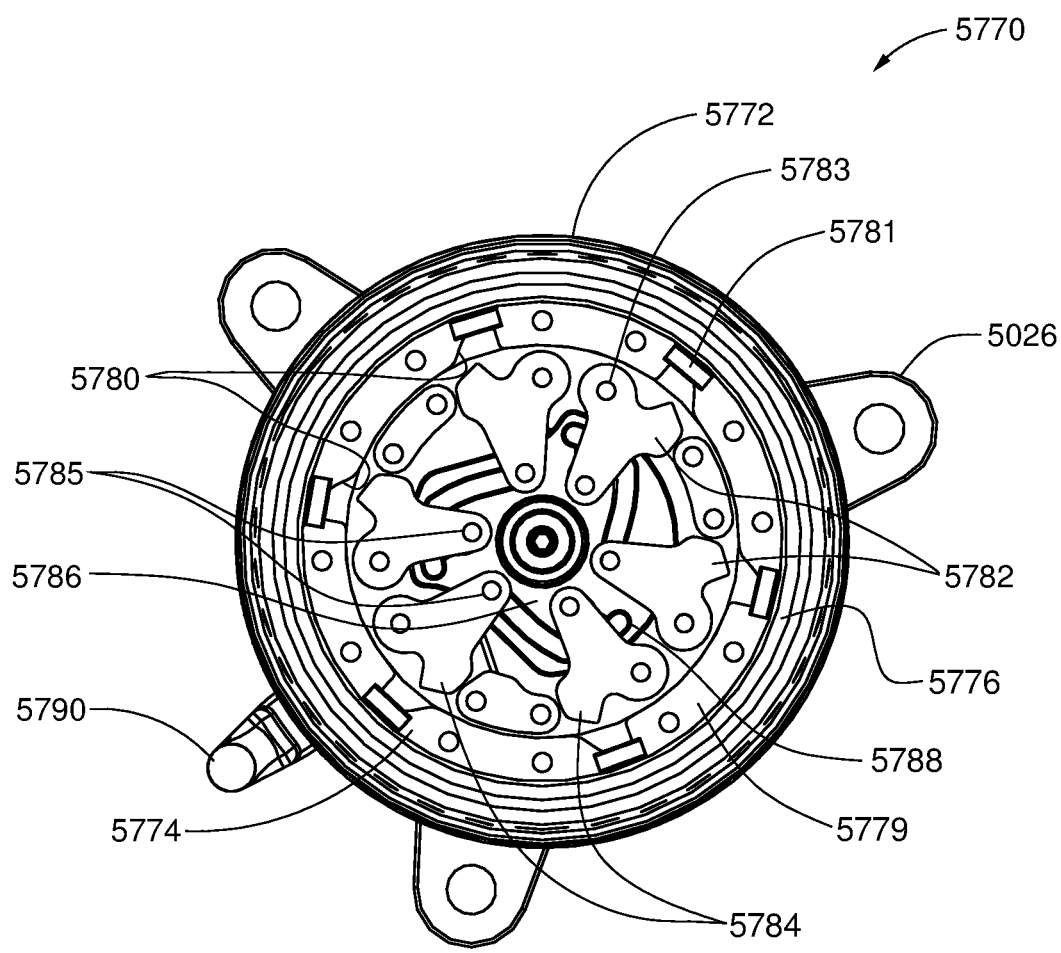
FIG. 47B is a front cross-sectional view of the shoulder free swing system of FIG. 47A when disengaged.
Figure 47C:
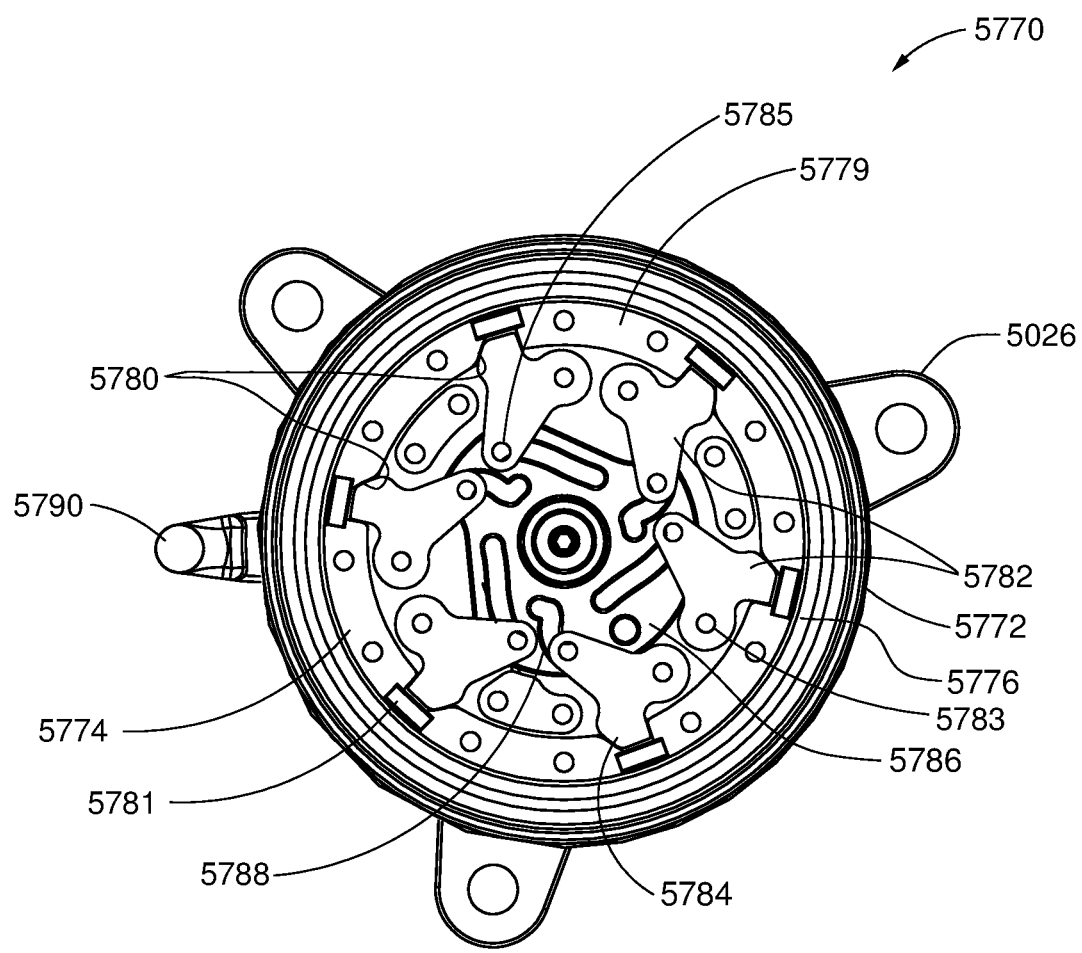
FIG. 47C is a front cross-sectional view of the shoulder free swing system of FIG. 47C when engaged.

Referring to FIGS. 47B and 47C, within the housing 5772, the arm interface 5774 includes a substantially circular portion 5779 that, at its outer circumference, engages the bearing 5776. The substantially circular portion 5779 includes a plurality of locking ramps 5780 formed therein about its inner circumference and may also include one or more magnets 5781 disposed at the outer portion of the locking ramps 5780. Within the substantially circular portion 5779, the shoulder free swing system 5770 includes a plurality of locking plates 5782, each of which has a rotation pin 5783 secured to the housing 5772 about which the locking plate 5782 may pivot. The locking plates 5782 include locking teeth 5784 configured to engage the locking ramps 5780 of the arm interface 5774. The locking plates 5782 also include cam followers 5785 for engaging a cam plate 5786 through cam paths 5788. The cam plate 5786 is connected to a handle 5790 through an actuation plate 5792, shown in FIG. 47A. The handle 5790 extends out of the housing 5772, thereby allowing for user actuation thereof.

In operation, when the locking teeth 5784 of the locking plates 5792 are disengaged from the locking ramps 5780 of the arm interface 5774, as shown in FIG. 47B, the arm interface 5774 is able to freely rotate with respect to the harness mount 5026, with its substantially circular portion 5779 rotating within the bearing 5776. However, when the user moves the handle 5790 from the position shown in FIG. 47B to the position shown in FIG. 47C, the actuation plate 5792 rotates, which in turn rotates the cam plate 5786 and causes the locking plates 5782 to rotate until the locking teeth 5784 engage the locking ramps 5780 of the arm interface 5774. The one or more magnets 5781 may advantageously aid in the engagement by drawing the locking teeth 5784 into the locking ramps 5780 and by eliminating backlash. Once the locking teeth 5784 are engaged in the locking ramps 5780, the arm interface 5774 is no longer able to freely move with respect to the harness mount 5026, unless the handle 5790 is returned to the position shown in FIG. 47B. Thus, when the locking teeth 5784 are engaged, the user may operate the prosthetic arm apparatus 10, shown in FIG. 1, in substantially the same manner as discussed above.

The slopes of the locking teeth 5784, the locking ramps 5780 and the cam paths 5788 may advantageously be designed such that the locking teeth 5784 will automatically become disengaged the from the locking ramps 5780 if a torque being transmitted through the shoulder free swing system 5770 is exceeds a maximum release torque. For example, in some embodiments the locking teeth 5784 may disengage the locking ramps 5780 if the torque being transmitted through the free swing system 5770 exceeds fifty Newton meters. Thus, the shoulder free swing system 5770 advantageously prevents excessive loading from being transmitted through the prosthetic device without permanently damaging any components of the prosthetic arm apparatus 10, shown in FIG. 1.

Figure 48A:
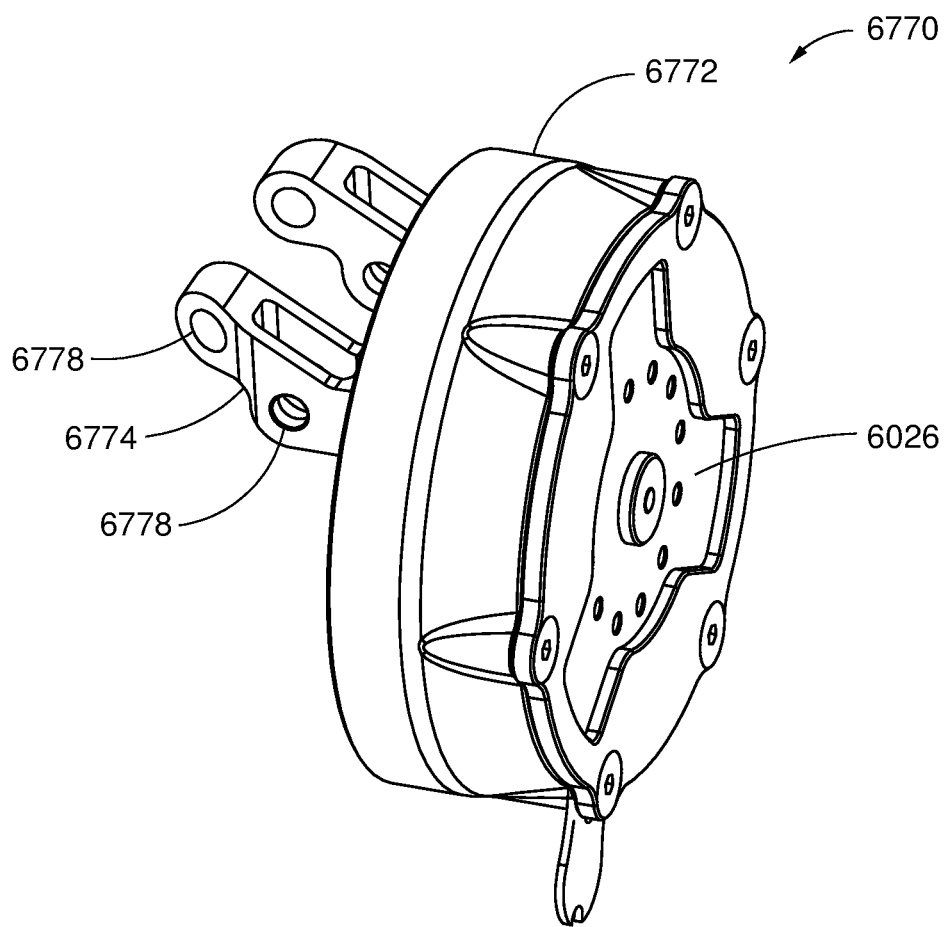
FIG. 48A is a side perspective view of a shoulder free swing system according to another embodiment of the present invention.

Referring to FIG. 48A, another embodiment of a shoulder free swing system 6770 is shown. The shoulder free swing system 6770 includes a housing 6772 having a harness mount 6026 fixedly secured thereto for attaching to a prosthetic harness. The shoulder free swing system 6770 also includes an arm interface 6774 rotatably secured within the housing 6772. The arm interface 6774 includes mounting holes 6778 for connecting the shoulder free swing system 6770 to the shoulder unit 1416, shown in FIG. 42B, through the abduction axis 1430 and the linkage 1444, each shown in FIG. 42B.

Figure 48B:
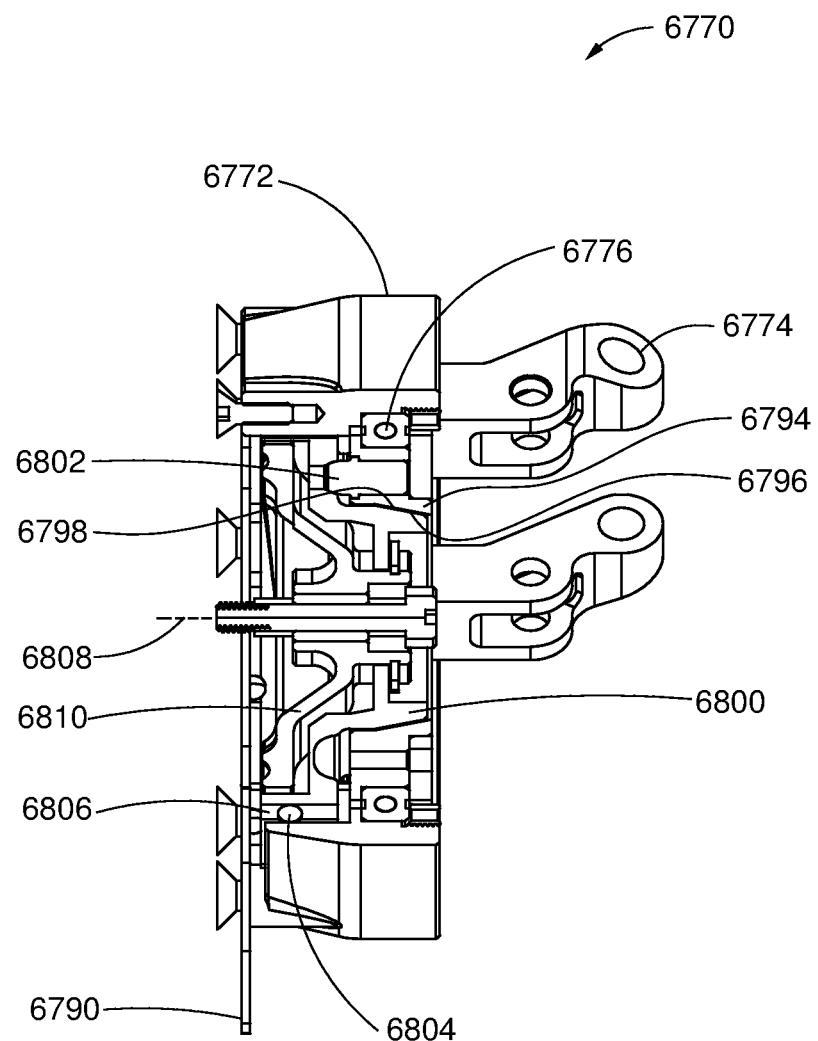
FIG. 48B is a side cross-sectional view of the shoulder free swing system of FIG. 48A.

Referring to FIG. 48B, a portion 6794 of the arm interface 6774 is rotatably secured in the housing 6772 within bearing 6776. The portion 6794 has a tapered surface 6796 at its inner circumference that contacts a corresponding tapered surface 6798 of a friction plate 6800, thereby forming a tapered frictional interface between the arm interface 6774 and the friction plate 6800. Two or more breakaway locks 6802 are loaded between the arm interface 6774 and the friction plate 6800, each breakaway lock 6802 having a spring (not shown) that tends to separate the friction plate 6800 from the arm interface 6774. The friction plate 6800 includes ball bearings 6804 located within grooves 6806 at its circumference that allow linear motion along an axis 6808, but resist rotation due to an applied torque. The breakaway locks 6802 and the geometry of the tapered surfaces 6796 and 6798 are configured so that the friction plate 6800 and the portion 6794 of the arm interface 6774 separate at a desired applied torque, for example, fifty Newton meters, thereby allowing the arm interface 6774 to slowly rotate while engaging the friction plate 6800 at the tapered surface 6798 to lower the prosthetic arm apparatus 10, shown in FIG. 1, until it loses its potential energy. To manually engage and/or disengage the free swing system 6770 The handle 6790 may be rotated to move a ramp 6810 linearly inward or outward along axis 6808, thereby reengaging or disengaging, respectively, the breakaway locks 6802 and, therefore, the free swing system 6770.

Figure 49:
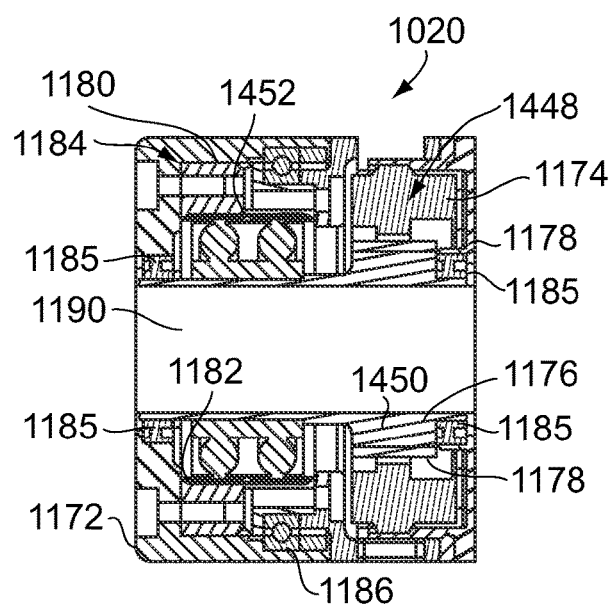
FIG. 49 is a cross-sectional view of one embodiment of a rotator according to the present invention.
Figure 50:
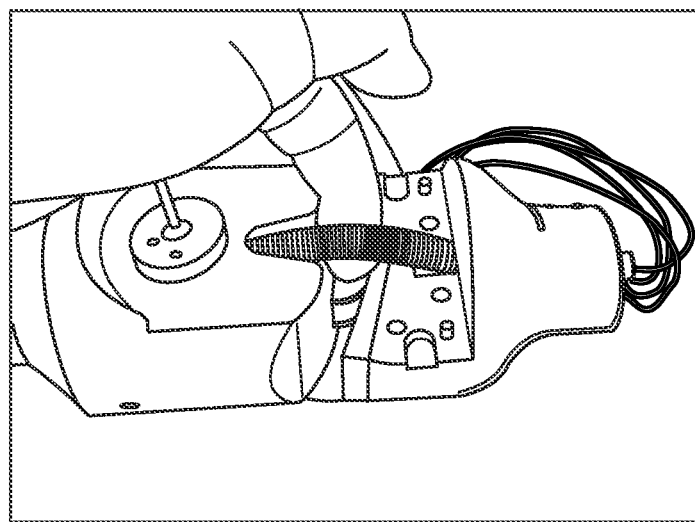
FIG. 50 is a side view of one embodiment of a flexion assembly according to the present invention.
Figure 51:
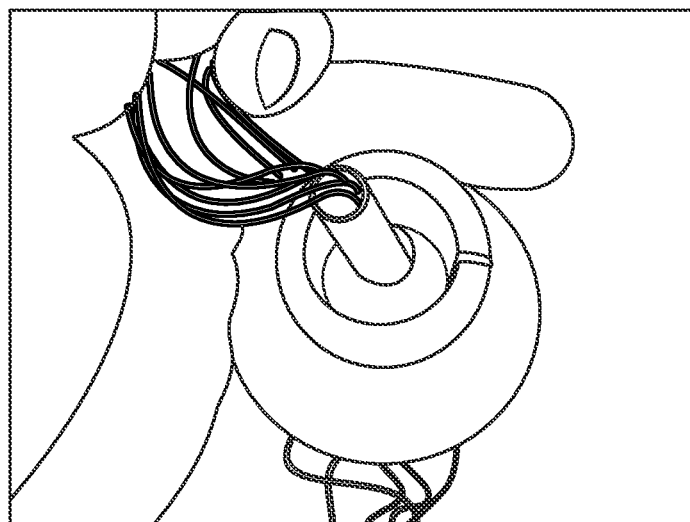
FIG. 51 is a front view of the flexion assembly of FIG. 50.

Referring now to FIG. 49, another embodiment of the wrist rotator 1020 is shown for providing improved electronic wiring capability to the prosthetic device. Although shown as the wrist rotator 1020, it should be understood by those skilled in the art that a similar configuration may be used for other rotating joints, such as the humeral rotator 16, shown in FIG. 1. In this embodiment of the wrist rotator 1020, the wrist rotator motor 1448, including the wrist rotator motor armature 1174 and a driven portion 1450 of the wrist rotator motor rotor 1176 having wrist rotator magnets 1178 disposed thereon, and the wrist harmonic drive gearing system 1452, including the wrist rotator harmonic drive gearing system wave generator 1180, the wrist rotator harmonic drive gearing system flexspline 1182 and the wrist rotator harmonic drive gearing system circular spline 1184, are separated into coaxial side-by-side units with the wrist rotator motor 1448 being proximate to the elbow interface 1170 and the harmonic drive gearing system 1452 being proximate to the wrist flexion assembly interface 1172. By arranging the wrist rotator motor 1448 and the wrist harmonic drive gearing system 1452 in the side-by-side configuration, the electronics channel 1190 passing through the center of the wrist rotator rotor 1176 may be formed large enough to allow electronic wiring to be run internally through the center of the wrist rotator 1020. Referring to FIGS. 50 and 51, the wiring through the prosthetic arm 10, shown in FIG. 1, in some embodiments, may run through one or more extension springs 1454, in particular around the flexion joints, such as the elbow flexion assembly 18 and the wrist flexion assembly 22, shown in FIG. 1, where internal wiring is difficult or impractical.

Routing the wiring through the center of the wrist rotator 1020 eliminates the need for external wiring, thereby minimizing any flexing movement experienced by the wiring, which can cause wire pinching, abrasions and failure. The internal wiring also eliminates the possibility that external wiring will become caught on something and break. Routing the wiring through the one or more extension springs 1454 where internal wiring is not practical, possible or desired allows for controlled loading of the external wiring and protects the wiring from pinching to reduce wire failure.

Figure 52:
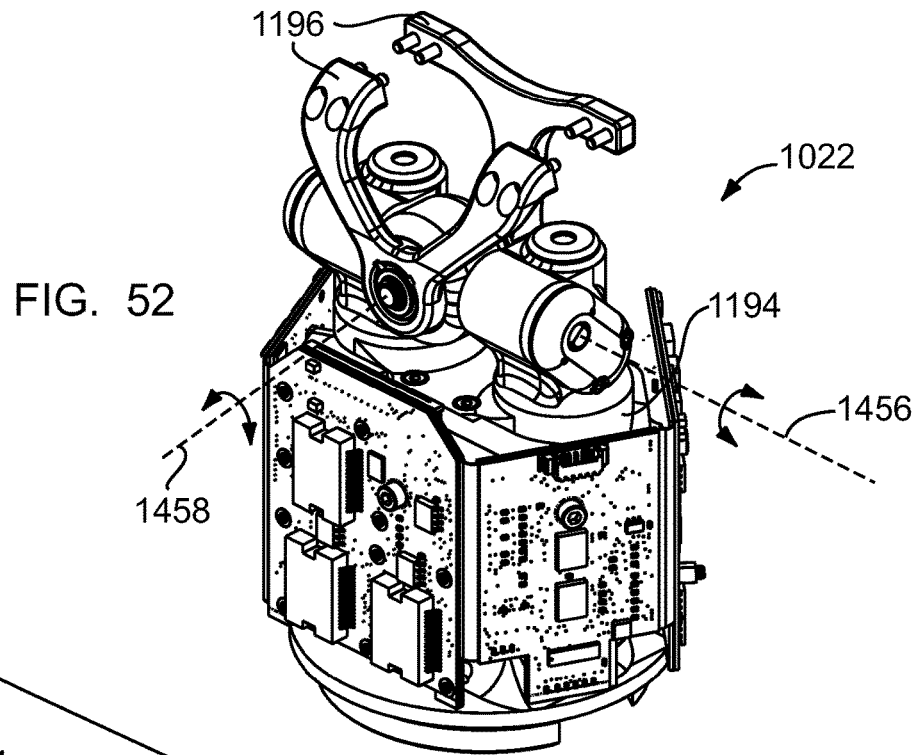
FIG. 52 is a perspective view of another embodiment of a wrist flexion assembly according to the present invention.

Referring to FIG. 52, in another embodiment of the wrist flexion assembly 1022, the output arm 1196 is able to move in flexion relative to the input support structure 1194 about a flexion axis 1456 and to move in ulnar-radial deviation relative to the input support structure 1194 about a deviation axis 1458. Thus, when the hand assembly 24, shown in FIG. 1, is attached to the output arm 1196 of the wrist flexion assembly 1022, the hand assembly 24, shown in FIG. 1, is able to move in both flexion and ulnar-radial deviation.

Figure 53:
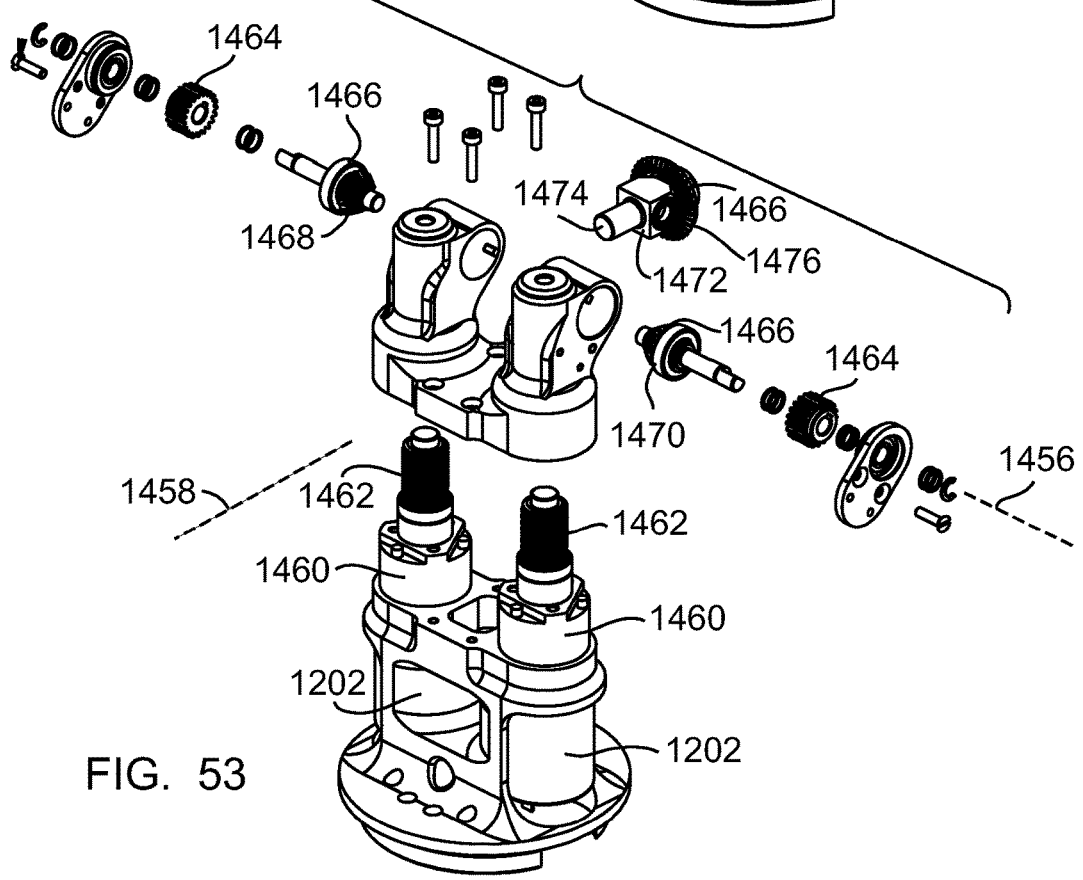
FIG. 53 is a partially exploded perspective view of the wrist flexion assembly of FIG. 52.

Referring to FIG. 53, the wrist flexion assembly 1022 includes two wrist motors 1202, for controlling the flexion and ulnar-radial deviation of the output arm 1196, shown in FIG. 52. Each wrist motor 1202 drives an input geartrain 1460, which, in turn, drives a wrist worm gear 1462. Each worm gear 1462 drives an input gear 1464 of a wrist differential 1466. The wrist differential 1466 includes a first bevel gears 1468 and a second bevel gear 1470 that are rotatable about the flexion axis 1456. The first bevel gear 1468 and the second bevel gear 1470 may be driven by one of the input gears 1464. The wrist differential 1466 also includes a differential body 1472 rotatably attached about the flexion axis 1456 between the first and second bevel gears 1468 and 1470. An ulnar-radial axle 1474 extends from one side of the differential body 1472 along the ulnar-radial axis 1458 and a third bevel gear 1476 extends from the differential body 1472 on the opposite side thereof. The third bevel gear 1476 is rotatable about the ulnar-radial axis 1458 and meshes with and is driven by the first bevel gear 1468 and the second bevel gear 1470.

Figure 54:
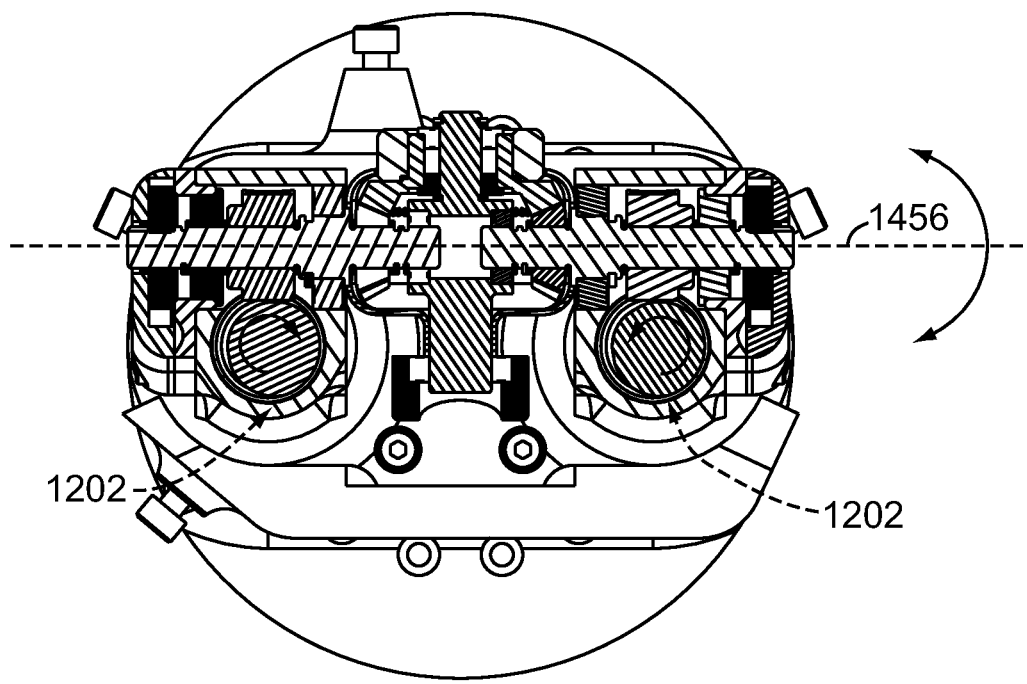
FIG. 54 is a top cross-sectional view of the wrist flexion assembly of FIG. 52.
Figure 55:
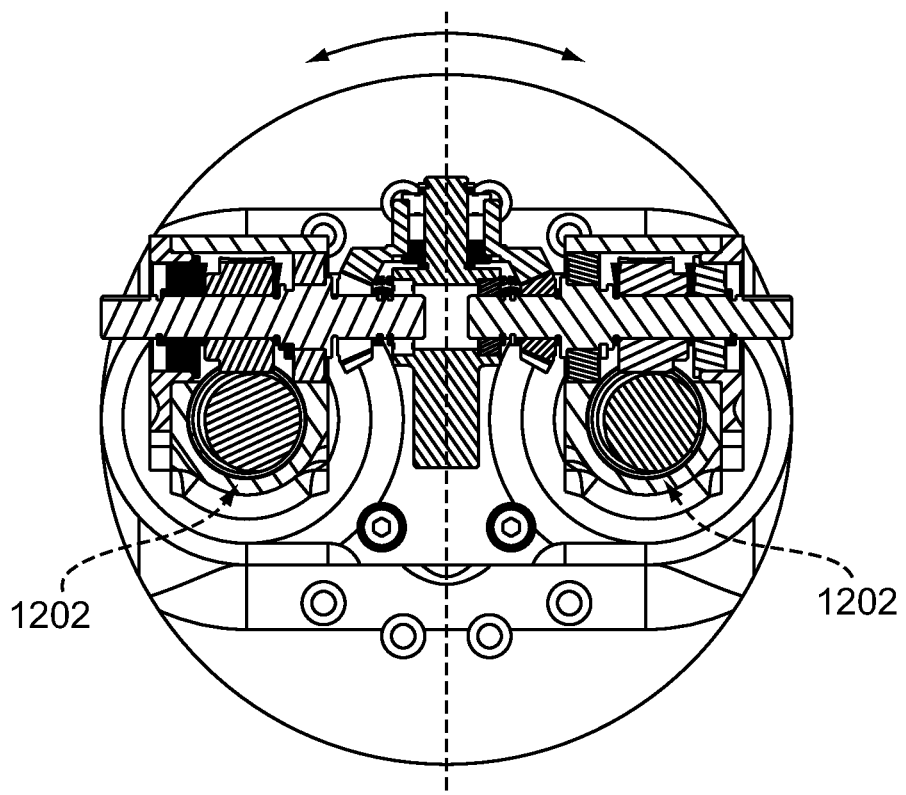
FIG. 55 is a top cross-sectional view of the wrist flexion assembly of FIG. 52.

In operation, the user is able to actuate wrist flexion, wrist ulnar-radial deviation and combinations thereof by actuating the motors 1202 in various ways. For example, referring to FIG. 54, if the motors 1202 are driven at the same speed in opposite directions, i.e. one is driven clockwise and the other counterclockwise, the output arm 1196, shown in FIG. 52 will move in flexion in one direction about the flexion axis 1456. If the direction of each motor is reversed, i.e. from spinning clockwise to counterclockwise and vice versa, the output arm 1196, shown in FIG. 52, will flex in the opposite direction. Similarly, referring to FIG. 55, if the motors 1202 are driven at the same speed in the same direction, i.e. both are driven clockwise, the output arm 1196, shown in FIG. 52, will move in ulnar-radial deviation in one direction about the deviation axis 1458. If the direction of each motor is reversed, i.e. from spinning clockwise to counterclockwise, the output arm 1196, shown in FIG. 52, will move in ulnar-radial deviation in the opposite direction about the deviation axis 1458. In addition to varying the direction of rotation of the motors 1202, varying the speed of one motor 1202 relative to the other will result in a combination of flexion and ulnar-radial deviation. Accordingly, in this embodiment, wrist flexion and ulnar-radial deviation may both be controlled simply by varying the direction and speed of the motors 1202.

Although the wrist flexion assembly 1022 is described as having a differential drive 1466 for imparting wrist flexion and wrist ulnar-radial deviation movement to the output arm 1196, it should be understood by those skilled in the art that other drives may be used to achieve similar capabilities. For instance, referring to FIG. 56, the wrist flexion assembly 2022 may include a separate wrist flexion geartrain 2478 for imparting flexion motion to the output arm 2196 about the flexion axis 2456 and a separate ulnar-radial geartrain 2480 for imparting ulnar-radial deviation to the output arm 2196 about the deviation axis 2458.

Figure 76:
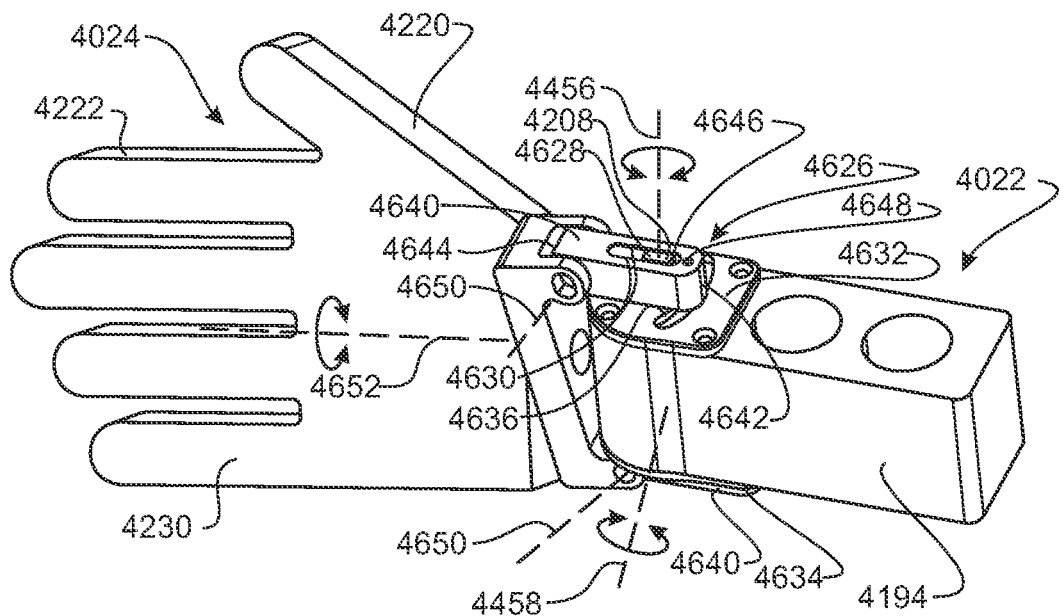
FIG. 76 is a perspective view of a wrist flexion assembly according to another embodiment of the present invention.
Figure 77:
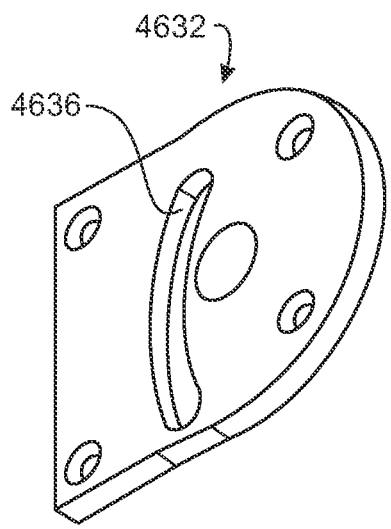
FIG. 77 is a perspective view of a first cam bearing of the wrist flexion assembly of FIG. 76.
Figure 78:
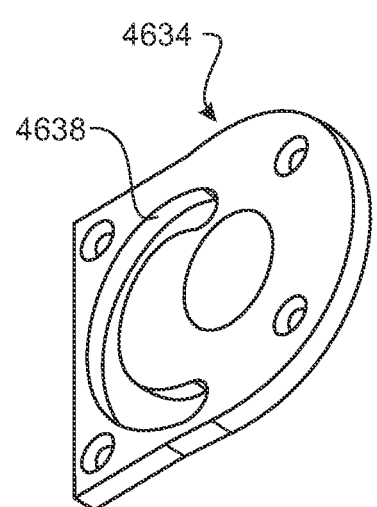
FIG. 78 is a perspective view of a second cam bearing of the wrist flexion assembly of FIG. 76.

Referring to FIG. 76, in another embodiment of the present invention, a wrist flexion assembly 4022 is provided for imparting a combination of both flexion about the flexion axis 4456 and ulnar-radial deviation about the deviation axis 4458 to the hand assembly 4024 in a single movement. The wrist flexion assembly 4022 includes the input support structure 4194 adapted to be connected to the wrist rotator 20, shown in FIG. 1, in the same manner as discussed above. The wrist support structure 4194 includes a hand interface 4626 proximate to the hand assembly 4024 for attaching the hand assembly 4024 to the wrist support structure 4194. The wrist support structure 4194 houses a wrist motor 202, shown in FIG. 26, which drives the wrist pivot axle 4208 in rotary motion about the wrist flexion axis 4456 through an appropriate gear train (not shown). The wrist pivot axle includes flattened end portions 4628 at each end thereof, extending outwardly from the wrist support structure 4194 and into the hand interface 4626. Each flattened end portion 4628 has two substantially parallel planar surface 4630 extending parallel to the wrist flexion axis 4456. The hand interface 4626 includes a first cam bearing 4632 fixedly secured to the wrist support structure 4194 about the flattened end portion 4628 of the wrist pivot axle 4208 proximate to the thumb structure 4220 of the hand assembly 4024. The hand interface also includes a second cam bearing 4634 fixedly secured to the wrist support structure 4194 about the flattened end portion 4628 of the wrist pivot axle 4208 proximate to the pinky finger 4230 of the hand assembly 4024. Referring to FIG. 77, the first cam bearing 4632 includes a first cam profile 4636 formed therein. Referring to FIG. 78, the second cam bearing 4634 includes a second cam profile 4638 formed therein. Referring back to FIG. 76, the hand interface 4626 also includes first and second slider blocks 4640 coupling the hand assembly 4024 to the wrist flexion assembly 4022. The first and second slider blocks 4640 each have a proximate end 4642 at the hand interface 4626 and a distal end 4644 near the hand assembly 4024. Each of the first and second slider blocks 4640 has a slot 4646 formed therein that slidably receives one of the flattened end portions 4628 of the wrist pivot axle 4208. The first and second slider blocks 4640 include cam followers 4648 at their proximate ends 4642 that are received within the first cam profile 4636 of the first cam bearing 4632 and the second cam profile 4638, shown in FIG. 78, of the second cam bearing 4634. The first and second slider blocks 4640 are pivotally coupled to the hand assembly 4024 at their distal ends 4644 about pivot axes 4650.

In this embodiment, the hand assembly 4024 may be angled away from the flexion axis 4456 about a wrist rotation axis 4652 to reduce the motion that the first cam profile 4636 and the second cam profile 4638 need to produce to achieve the desired combined flexion and ulnar-radial deviation movement of the hand assembly 4024. In some embodiments, the hand assembly 4024 is angled approximately thirty degrees clockwise (30° clockwise) assuming left hand user perspective from the flexion axis 4456.

Figure 79A:
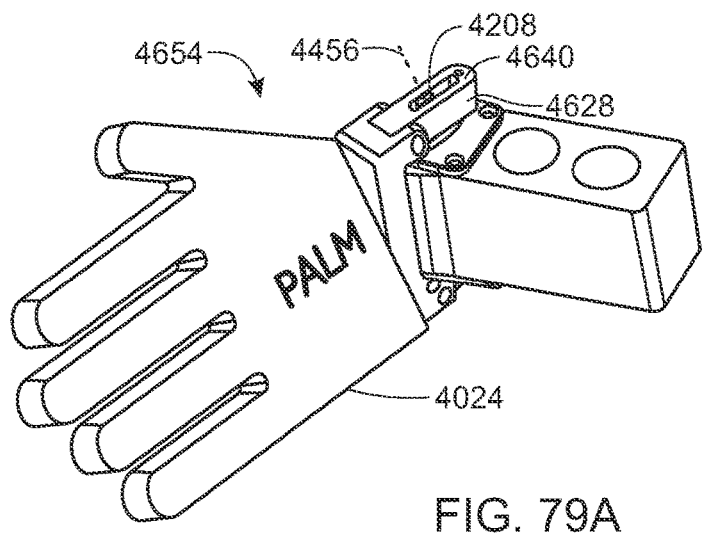
FIG. 79A is a perspective view of the wrist flexion assembly of FIG. 76 in a first position.
Figure 79B:
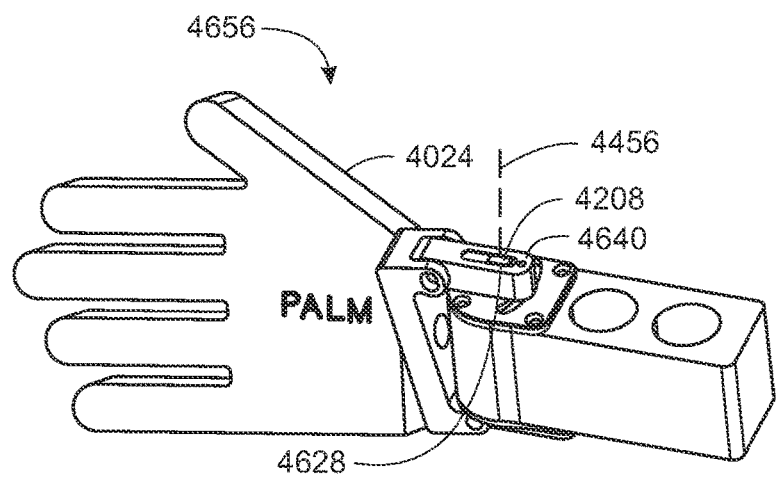
FIG. 79B is a perspective view of the wrist flexion assembly of FIG. 76 in a second position.
Figure 79C:
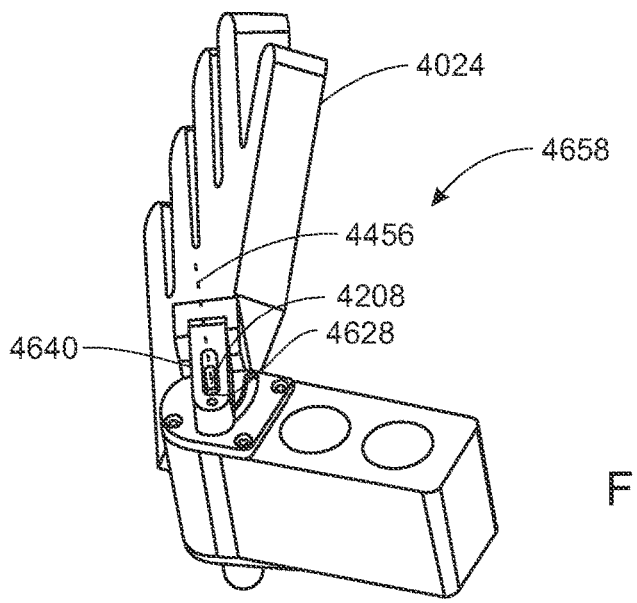
FIG. 79C is a perspective view of the wrist flexion assembly of FIG. 76 in a third position.

Referring to FIGS. 79A-79C, in operation, the wrist motor 202, shown in FIG. 26, drives the wrist pivot axle 4208 in rotation movement about the flexion axis 4456, which provides the hand assembly 4024 with flexion movement. Additionally, the sliding engagement between the flattened end portions 4628 of the wrist pivot axle 4208 and the first and second slider blocks 4640 causes the first and second slider blocks 4640 to pivot about the flexion axis 4456 as the wrist pivot axle 4208 rotates. As the first and second slider blocks 4640 pivot, the cam followers 4648, shown in FIG. 76, follow the first cam profile 4636, shown in FIG. 77, and the second cam profile 4638, shown in FIG. 78, which causes the first and second slider blocks 4640 to slide relative to the wrist pivot axle 4208. This sliding motion of each of the first and second slider blocks 4640 causes the hand assembly 4024 to pivot about the pivot axes 4650, shown in FIG. 76, which results in the ulnar-radial deviation movement of the hand assembly 4024. Thus, as the wrist motor drives the wrist pivot axle 4208, the hand assembly 4024 moves from a first position 4654, shown in FIG. 79A, in which the hand is fully flexed and deviated in the ulnar direction, to a second position 4656, shown in FIG. 79B, which is a neutral position with respect to flexion movement but includes some degree of ulnar deviation. Then, the hand assembly 4024 continues to move until it reaches a third position 4658, shown in FIG. 79C, in which the hand assembly 4024 is fully extended about the flexion axis 4456 and is also fully deviated in the radial direction.

Figure 80:
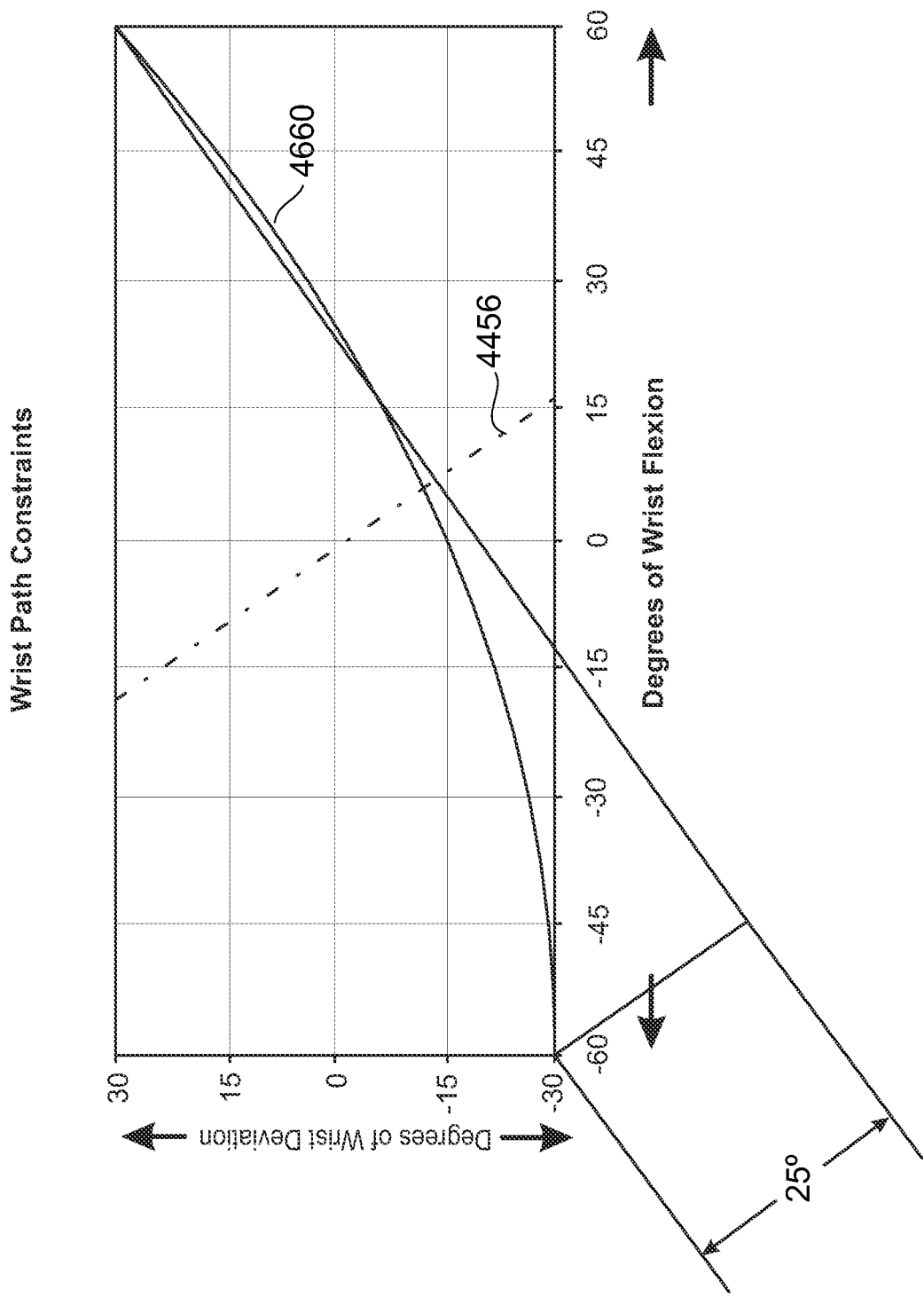
FIG. 80 is a line graph of a fixed movement path of the wrist flexion assembly of FIG. 76.

Referring to FIG. 80, the first cam profile 4636, shown in FIG. 77, and the second cam profile 4638, shown in FIG. 78, provide for movement of the hand assembly 4024, shown in FIG. 76, along a constrained flexion-deviation movement path 4660 that includes components of both flexion motion and ulnar-radial deviation motion. The constrained flexion-deviation movement path 4660 is advantageous because the user only needs to think about controlling a single degree of freedom, unlike the embodiments discussed above that provide independent wrist flexion movement and ulnar-deviation movement. Additionally, the constrained flexion-deviation movement path 4660 is beneficial because it provides for full flexion movement and also provides for nearly full ulnar deviation without requiring full wrist flexion. Thus, functionality is particularly beneficial when users use the prosthetic arm apparatus 10, shown in FIG. 1, to pick up an object (not shown) from overhead. The constrained flexion-deviation movement path 4660 also advantageously allows for approximately twenty-four degrees (24°) of flexion movement without significant ulnar deviation, which allows the user to move an object, such as a spoon, in flexion motion without spilling its contents. This range of flexion movement with minimal ulnar deviation provided by the constrained flexion-deviation movement path 4660 may also be beneficial to compensate for offset in situations where the prosthetic arm apparatus 10, shown in FIG. 1, is mounted at an offset, for example, to avoid the user's residuum. Additionally, since the hand assembly 4024, shown in FIG. 76, is angled in the neutral second position 4656, shown in FIG. 79B, pinching of the thumb structure 4220, shown in FIG. 76, and index finger structure 4222, shown in FIG. 76, are more in line with the wrist rotation axis 4652, which makes various tasks easier for the user, such as turning a door knob, turning a key or the like. Thus, the constrained flexion-deviation movement path 4660, or other similar paths, provided by the wrist flexion assembly 4022, shown in FIG. 76, provides a variety of advantages over conventional prosthetic devices.

Additionally, in some embodiments, the flexion axis 4456, shown in FIG. 76, may be shifted from its neutral position to provide various benefits. For example, the flexion axis 4456, shown in FIG. 76, is shifted approximately thirty degrees (30°) from its neutral position. This shift provides a prosthetic hand attached to the wrist flexion assembly 4022, shown in FIG. 76, with a more natural appearance and may aid in positioning the hand for various tasks, such as turning a door knob, turning a key or the like.

Although described in terms of constrained flexion-deviation movement path 4660, shown in FIG. 80, it should be understood by those skilled in the art that the first cam profile 4636, shown in FIG. 77, and the second cam profile, shown in FIG. 78, may be formed in various configurations to achieve a variety of different constrained movement paths. Additionally, although the constrained flexion-deviation movement path 4660 has been described in connection with the wrist flexion assembly 4022, the constrained flexion-deviation movement path 4660 may also be commanded using the flexion assembly 1022, shown in FIG. 52, by programming the prosthetic controller to actuate the motors 1202, shown in FIG. 53, to move the prosthetic hand assembly 24 along the same constrained flexion-deviation path 4660.

Figure 81:
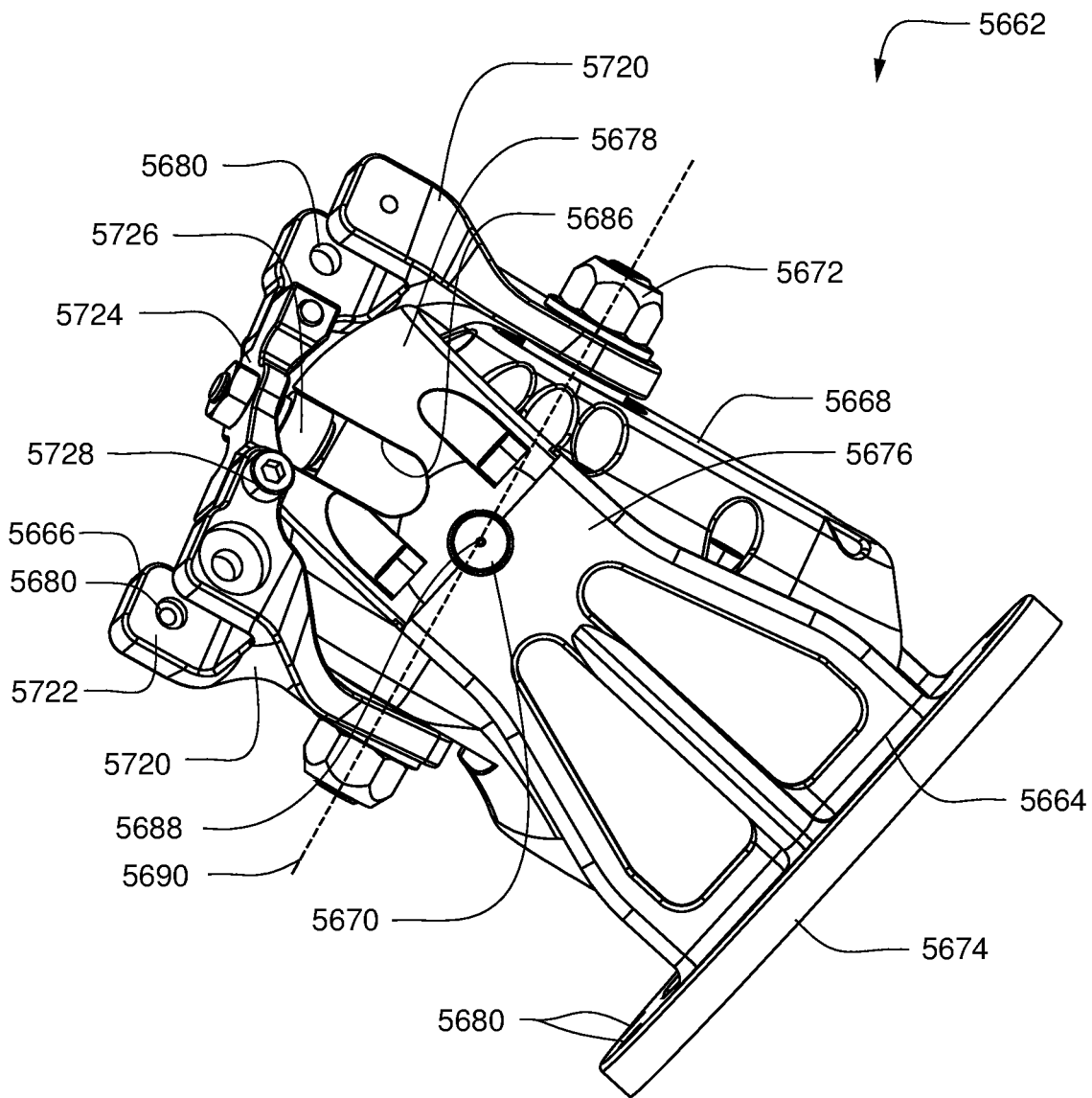
FIG. 81 is a side perspective view of a compound motion assembly according to an embodiment of the present invention.

Referring to FIG. 81, in some embodiments, a compound motion assembly 5662 may be provided to impart two-axis motion to the various segments discussed herein. The compound motion assembly 5662 includes an input member 5664, an output member 5666 and an intermediate member 5668. The input member 5664 is movably coupled to the intermediate member 5668 through a first joint 5670 and the output member 5666 is movably coupled to the intermediate member 5668 through a second joint 5672 such that the first joint 5670 and the second joint 5672 are arranged in series between the input member 5664 and the output member 5666 with the intermediate member arranged therebetween.

The input member 5664 includes an input interface 5674 at one end thereof, two support posts 5676 extending outwardly from the input interface to the first joint 5670 and a path member 5678 secured to the support posts 5676 at the first joint 5670. The input interface 5674 has bolt holes 5680 or similar connection means to allow the input member 5664 to be secured to an adjacent segment of the prosthetic device 10, shown in FIG. 1, at the input interface 5674. The support posts 5676 are spaced apart from one another at a sufficient distance to accommodate the intermediate member 5668 therebetween, as will be discussed in greater detail below. The path member 5678 forms an arch extending over the intermediate member 5668 and connecting one of the support posts 5676 to the other support post 5676.

Figure 82:
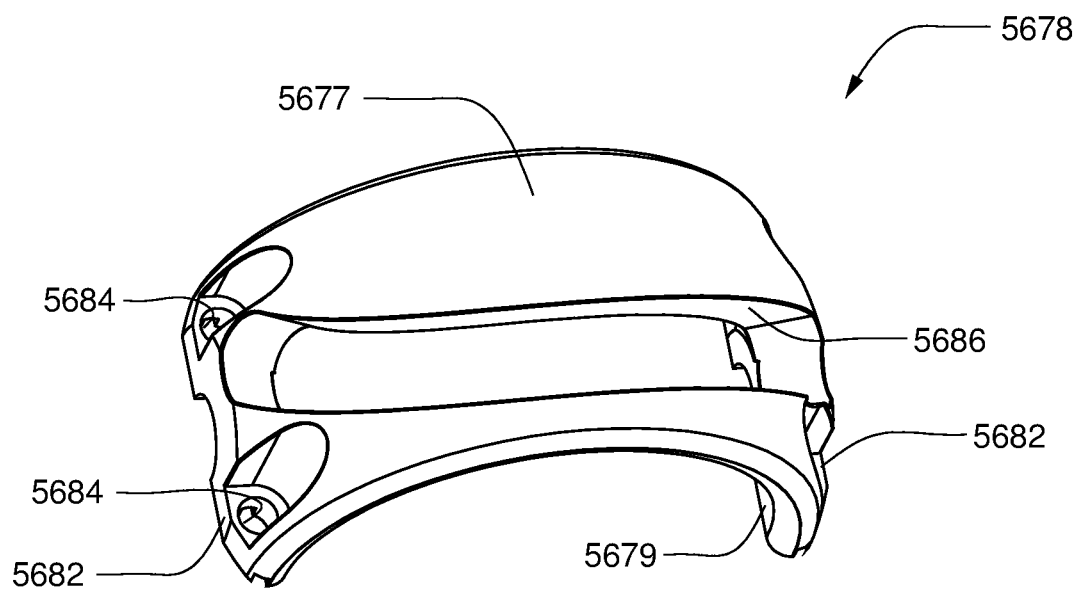
FIG. 82 is a top perspective view of an embodiment of a fixed path member of the compound motion assembly of FIG. 81.
Figure 83:
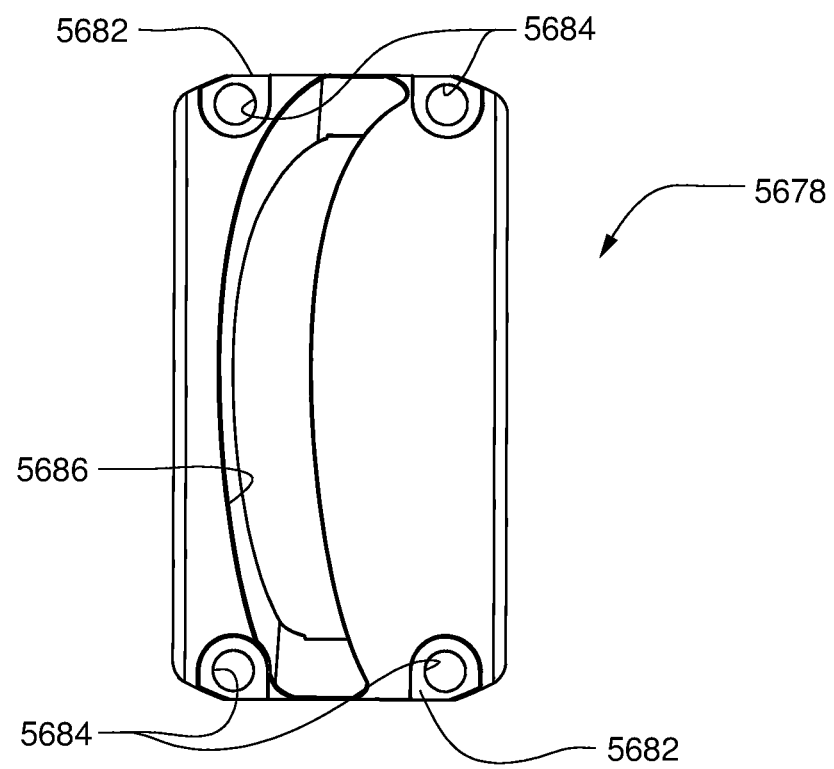
FIG. 83 is a top view of the fixed path member of FIG. 82.

Referring to FIGS. 82 and 83, the path member 5678 includes an outer surface 5677 and an inner surface 5679 that are both substantially spherically shaped to ensure clearance between the path member 5678 and the output member 5666 and the path member 5678 and the intermediate member 5668, respectively. The path member 5678 also includes a base portion 5682 at each end thereof for interfacing with the support posts 5676, shown in FIG. 81. Each base portion 5682 includes mounting holes 5684 for fastening the path member 5678 to the support posts 5676, shown in FIG. 81. The path member 5678 has a fixed path profile 5686 formed therethrough and extending along at least a portion of the arch of the path member 5678 between the two base portions 5682. The fixed path profile 5686 has a curvature that is selected to define the compound motion of the output member 5666 relative to the input member 5664, as will be discussed in greater detail below. The fixed path profile 5686 may be asymmetrical, as shown, or may instead be symmetrical depending upon the desired compound motion.

Referring back to FIG. 81, as discussed above, the path member 5678 is preferably a separate element fixedly secured to the support posts 5676 so that the path member 5678 may advantageously be removed and replaced as will be discussed below. However, those skilled in the art should understand that the path member 5678 may instead be integrally formed as part of the input member 5664.

Figure 84:
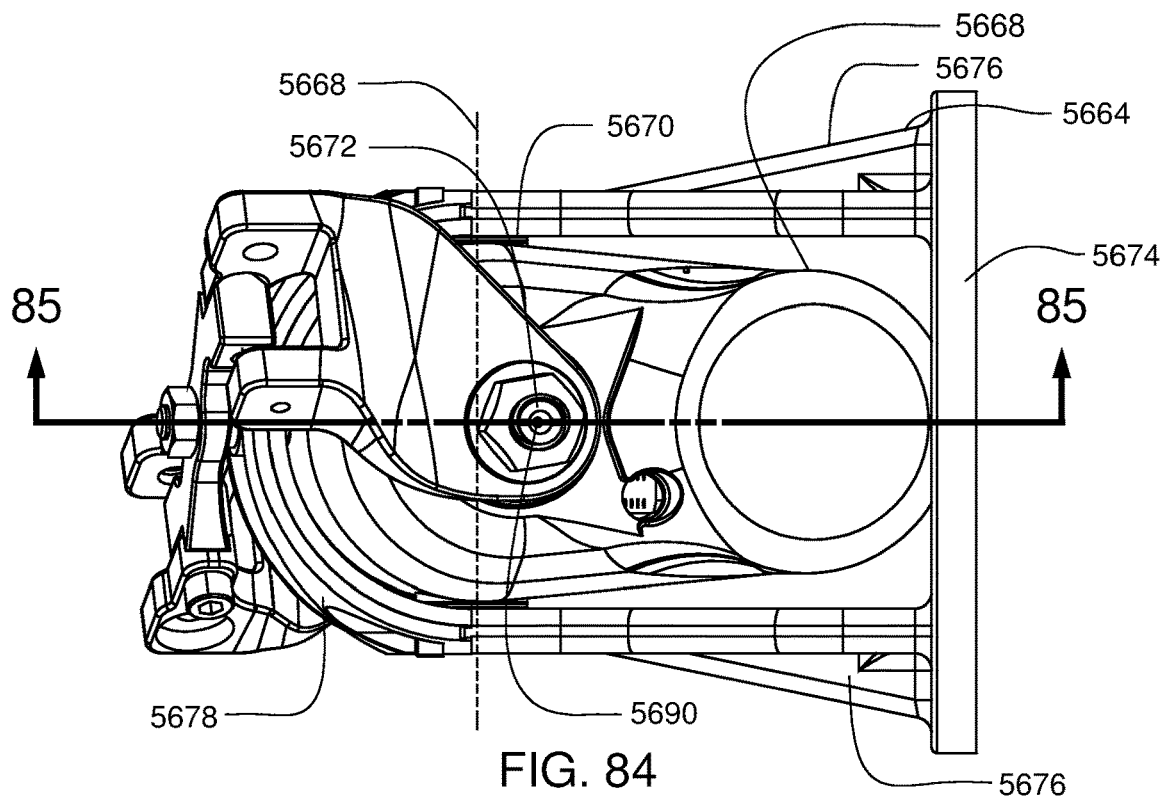
FIG. 84 is a side view of the compound motion assembly of FIG. 81.

Referring to FIGS. 81 and 84, the intermediate member 5668 of the compound motion assembly 5662 is pivotally coupled to the input member 5664 at the first joint 5670, such that the intermediate member 5668 pivots about a first axis 5688 of the first joint 5670. The intermediate member is suspended between the support posts 5676 and between the input interface 5674 and the path member 5678 by the first joint 5670 to ensure clearance as the intermediate member 5668 pivots. The intermediate member 5668 is coupled to the output member 5666 at the second joint 5672 such that the output member is able to pivot about a second axis 5690 defined by the second joint 5672. In some embodiments, the first joint 5670 and the second joint 5672 are arranged relative to one another such that the first axis 5688 and the second axis 5690 are substantially coplanar, while in other embodiments, the first axis 5688 and the second axis 5690 may not be substantially coplanar. The intermediate member 5668 may have a spherical shape at the end proximate the path member 5678 to ensure clearance between the intermediate member 5668 and the path member 5678.

Figure 85:
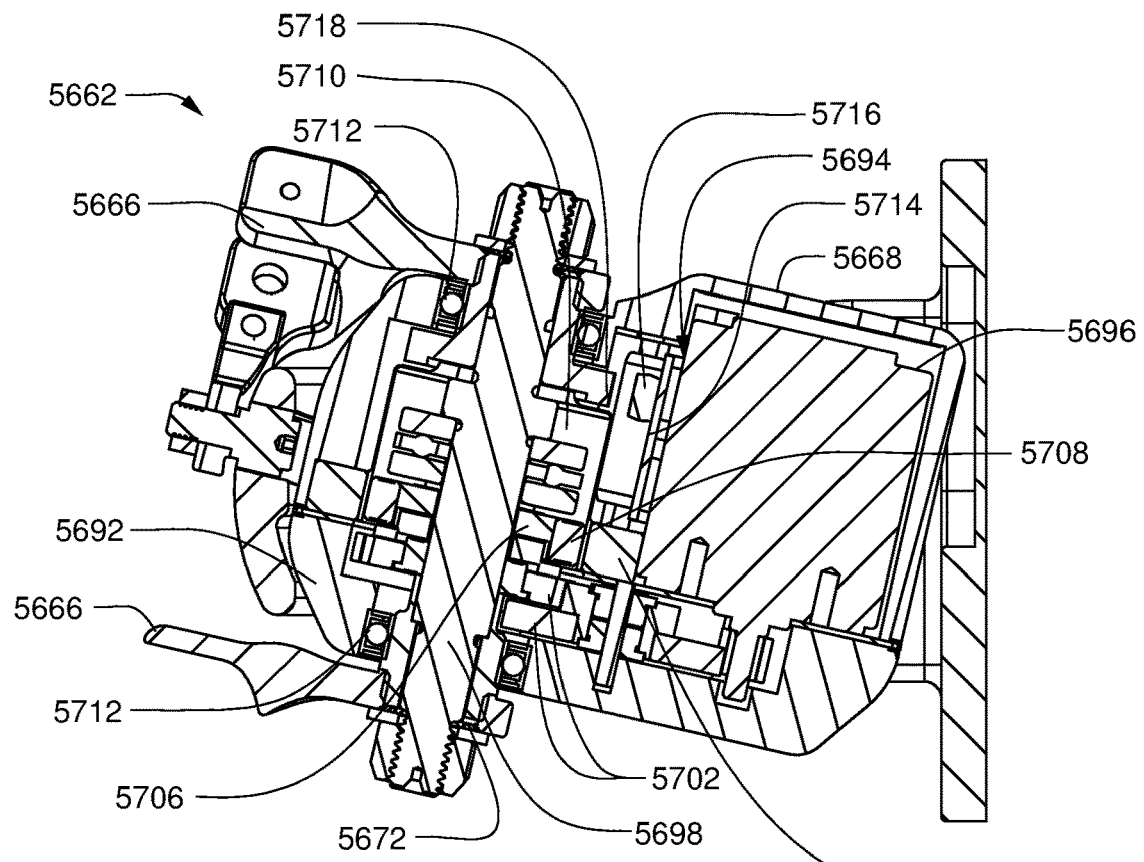
FIG. 85 is a cross sectional view of the compound motion assembly of FIG. 84.
Figure 86:
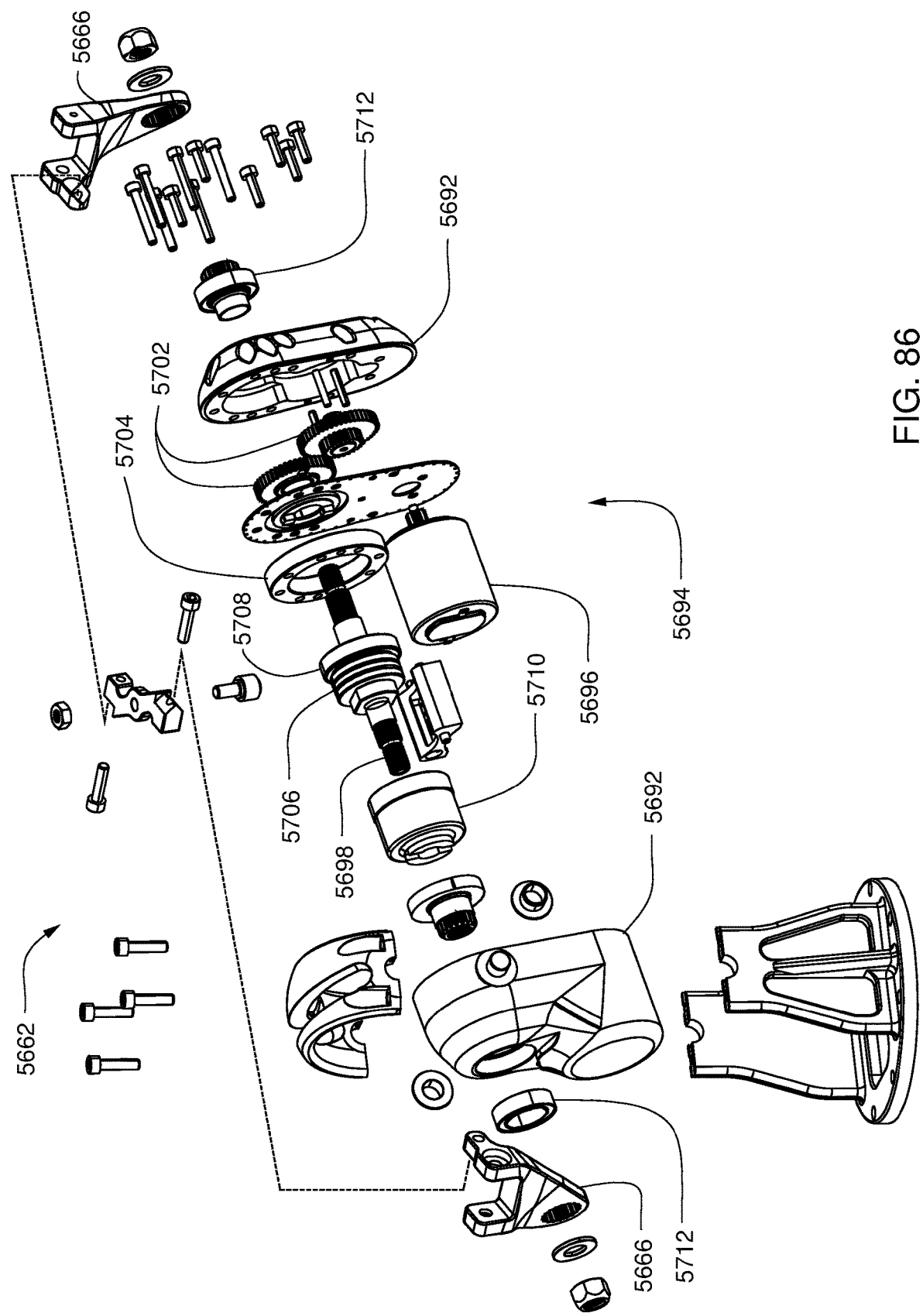
FIG. 86 is an exploded perspective view of the compound motion assembly of FIG. 84.

Referring to FIGS. 85 and 86, in some embodiments, the intermediate member 5668 may include a housing 5692 enclosing a drive arrangement 5694 for actuating the compound motion assembly 5662. The drive arrangement 5694 includes a motor 5696 coupled to an output shaft 5698 through a gear train, which may include one or more reduction gears 5702, a strain wave gearing system having a circular spline 5704, a wave generator 5706, a wave generator bearing 5708 and a flex spline 5710 or any other similar gearing system for transmitting torque from the motor 5696 to the output shaft 5698. The output shaft 5698 extends outwardly through both sides of the housing 5692 and is rotatable supported therein by bearings 5712. Each end of the output shaft 5698 is secured to the output member 5666 to form the second joint 5672, shown in FIG. 85, with the second axis 5690 being the axis of rotation of the output shaft 5698. Securing the output shaft 5698 at each end to the output member 5666 provides increased torque to the output member 5666 when the drive arrangement 5694 is actuated. However, in some embodiments, the output member 5666 may only be secured to the output shaft 5698 at one end thereof, thereby simplifying the drive arrangement 5694. In these embodiments, the other end of the output shaft 5698 may support the output member 5666 rotatably thereon.

Referring to FIG. 85, power to the motor 5696 is preferably supplied through a circuit board 5714 secured within housing 5692. The circuit board 5714 may include a shaft position sensor 5716 disposed thereon for monitoring movement of the output shaft 5698. For instance, the shaft position sensor 5716 may be an optical sensor having an infrared emitter and receiver that transmits infrared light at a reflective cam surface 5718 fixed to the output shaft 5698 and receives the reflected light signal, thereby enabling position detection. The circuit board 5714 may also include a temperature sensor (not shown) for monitoring the temperature of the motor 5696 to ensure safe operation. The circuit board 5714 may be connected to an external controller (not shown) for supplying power and control to the motor 5696 and for receiving and processing position signals from the shaft position sensor 5716 and the temperature sensor (not shown). In some embodiments, a single cable (not shown) may be used to connect the circuit board 5714 to the controller (not shown). This single cable (not shown) may reduce cable flex as the compound motion assembly 5662 actuates, thereby reducing cable failure, which may result in possible damage to the compound motion assembly 5662 or any components connected thereto. Preferably, the controller (not shown) shorts the motor 5696 when the compound motion assembly 5662 is not being actuated to prevent back-driving of the compound motion assembly 5662, which may also result in possible damage to the compound motion assembly 5662 or any components connected thereto.

Figure 67:
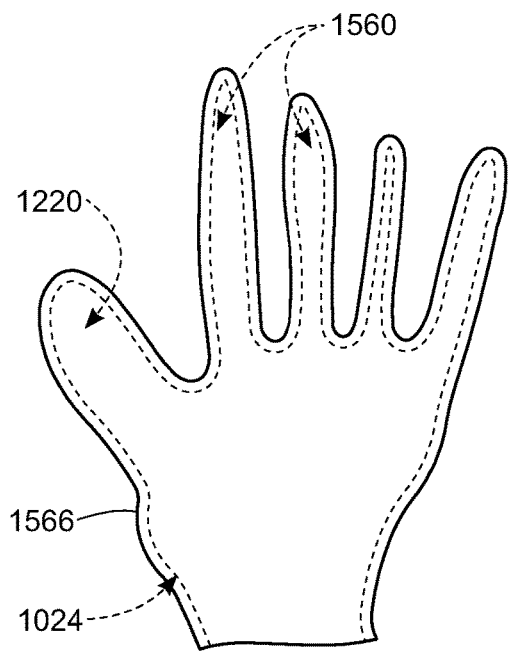
FIG. 67 is a front view of a hand assembly cosmesis according to an embodiment of the present invention.

Referring back to FIG. 81, the output member 5666 includes two output arms 5720, each secured to one end of the output shaft 5698, shown in FIG. 85, and extending outwardly past the path member 5678 to an output interface 5722. The two output arms 5720 are connected by a follower member 5724 having an extension 5726 that is accommodated within the fixed path profile 5686 of the path member 5678. The extension 5726 may be, for example, a cam bearing for slidably engaging the fixed path profile 5686, as will be discussed below. Preferably, the follower member 5724 is removably coupled to the output arms 5720 by bolts 5728 or the like. The output interface 5722 includes bolt holes 5680 or similar connection means to allow the output member 5666 to be secured to an adjacent segment of the prosthetic device 10, shown in FIG. 1, at the output interface 5722. For example, referring to FIG. 87, the compound motion assembly 5662 may be implemented as a prosthetic wrist having the hand assembly 24 mounted to the output interface 5722. Preferably, when implemented as a prosthetic wrist, the cosmesis 1566, shown in FIGS. 67 and 69, would also extend over the compound motion assembly 5662 to protect the moving components of the compound motion assembly 5662 from contamination due to dirt of the like.

Referring to FIGS. 88A-88F, in operation, as the motor 5696, shown in FIG. 85, is actuated, the output shaft 5698, shown in FIG. 85, turns causing pivotal movement of the output member 5666 at the second joint 5672 about the second axis 5690. As the output member 5666 pivots at the second joint 5672, the extension 5726 of the output member 5666 slides within the fixed path profile 5686. As the extension 5726 slides within the fixed path profile 5686, the curvature of the fixed path profile 5686 moves the extension 5726 laterally causing pivotal movement of the intermediate member 5668 relative to the input member 5664 at the first joint 5670. This pivotal movement also results in pivotal movement of the output member 5666 about the first axis 5688 of the first joint 5670 since the output member 5666 is attached to the intermediate member 5668. Thus, the compound motion assembly 5662 provides compound motion of the output interface 5722 relative to the input interface 5674 about both the first axis 5688 and the second axis 5690 using a single motor 5696, shown in FIG. 85. Therefore, the compound motion assembly 5662 requires only a single degree of freedom as a control input, which reduces the cognitive burden on the user while still providing a complex output movement.

Figure 87:
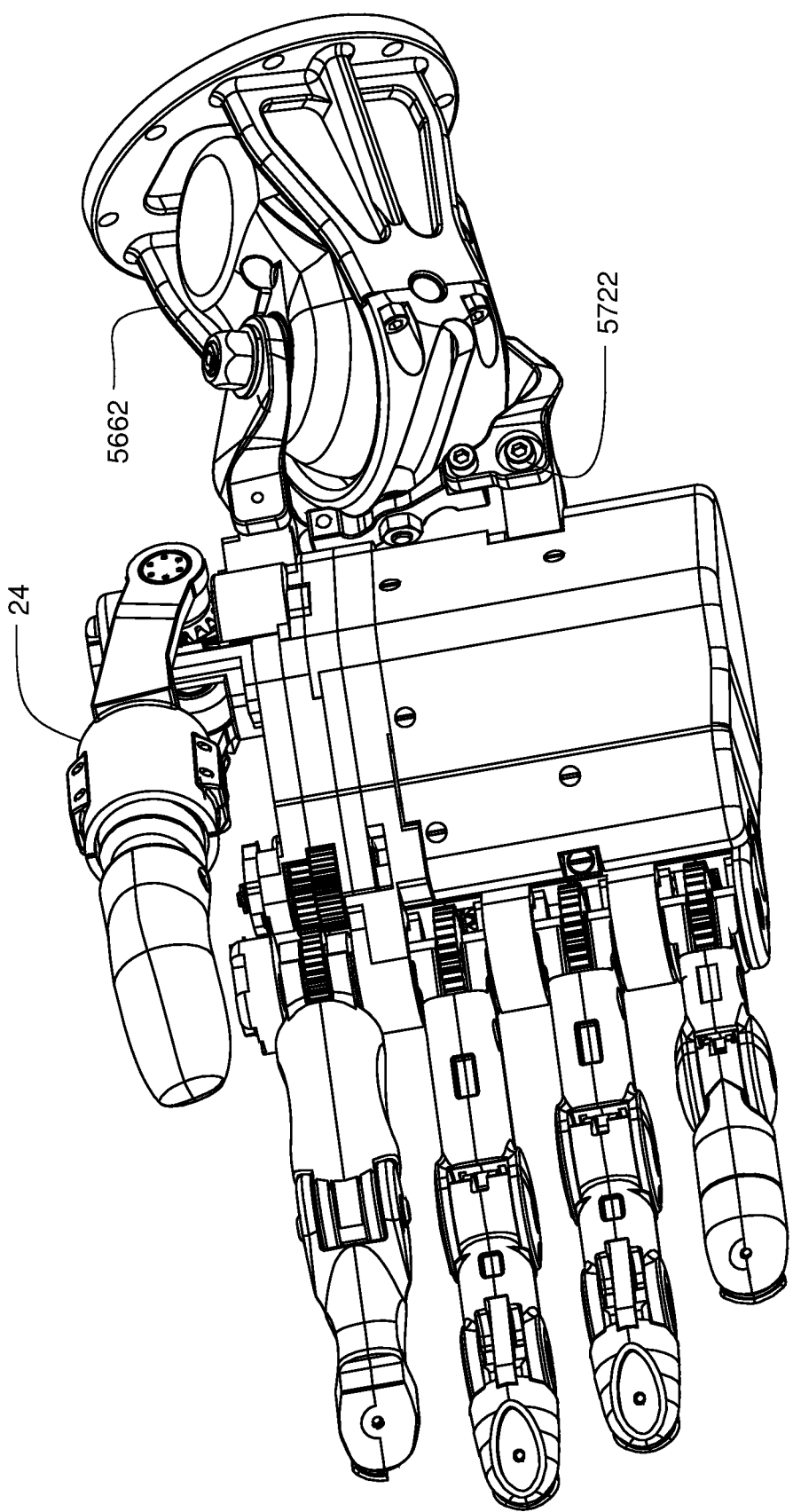
FIG. 87 is a side perspective view of a compound motion assembly of FIG. 81 having the hand assembly attached thereto.
Figure 88A:
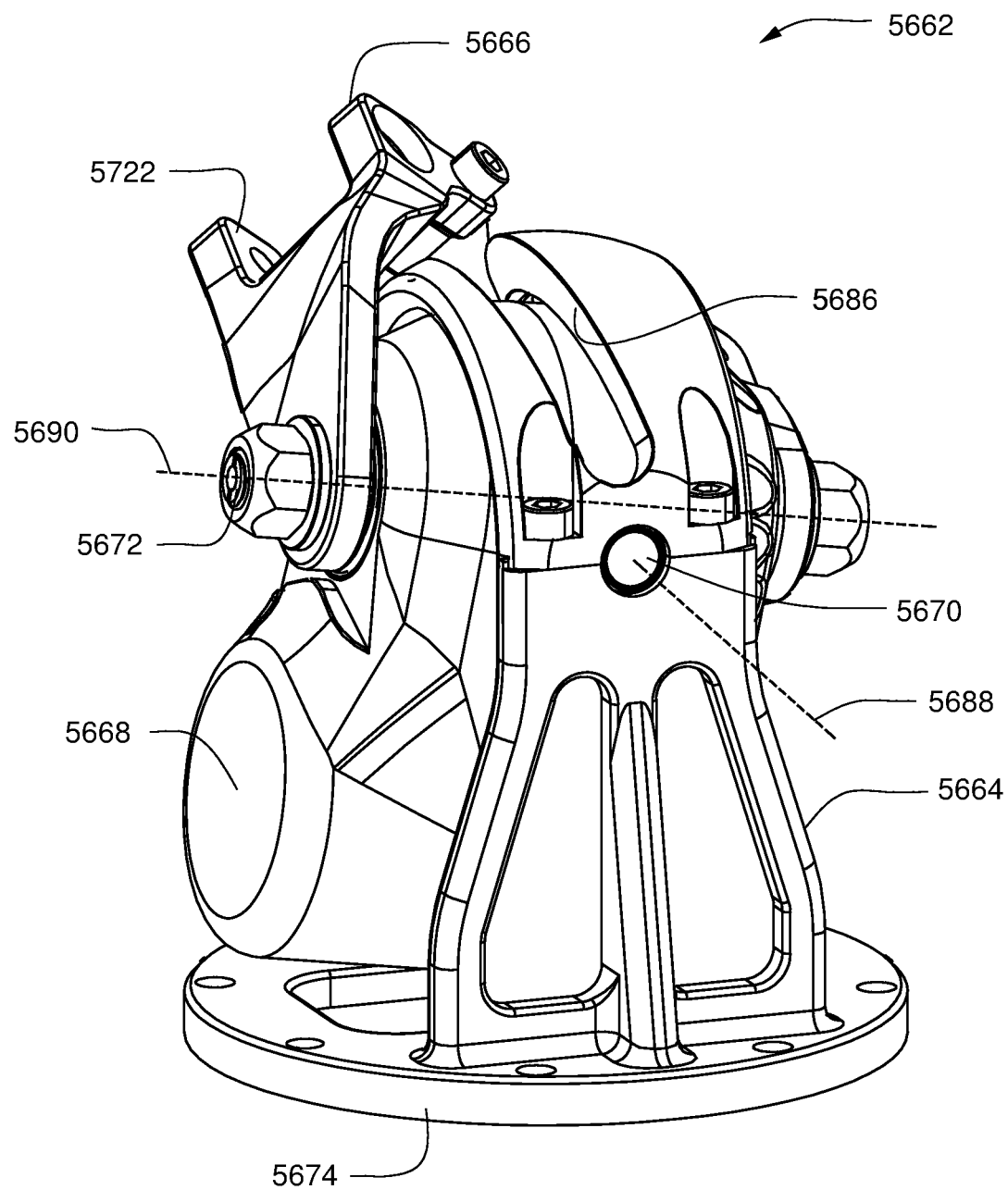
FIGS. 88A, 88B, 88C, 88D, 88E and 88F are side perspective views of the compound motion assembly of FIG. 81 at various positions along its full range of motion.
Figure 88B:
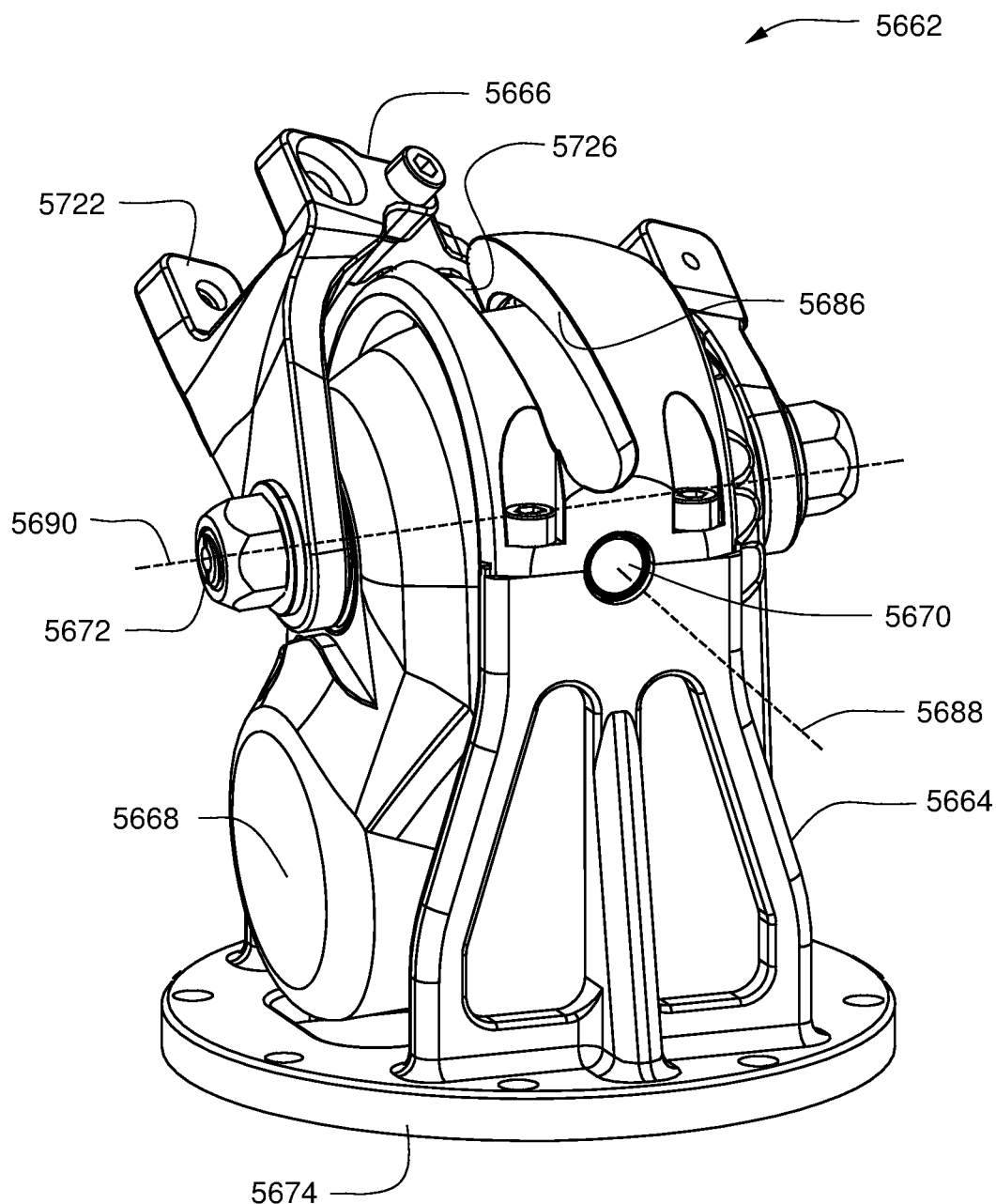
Figure 88C:
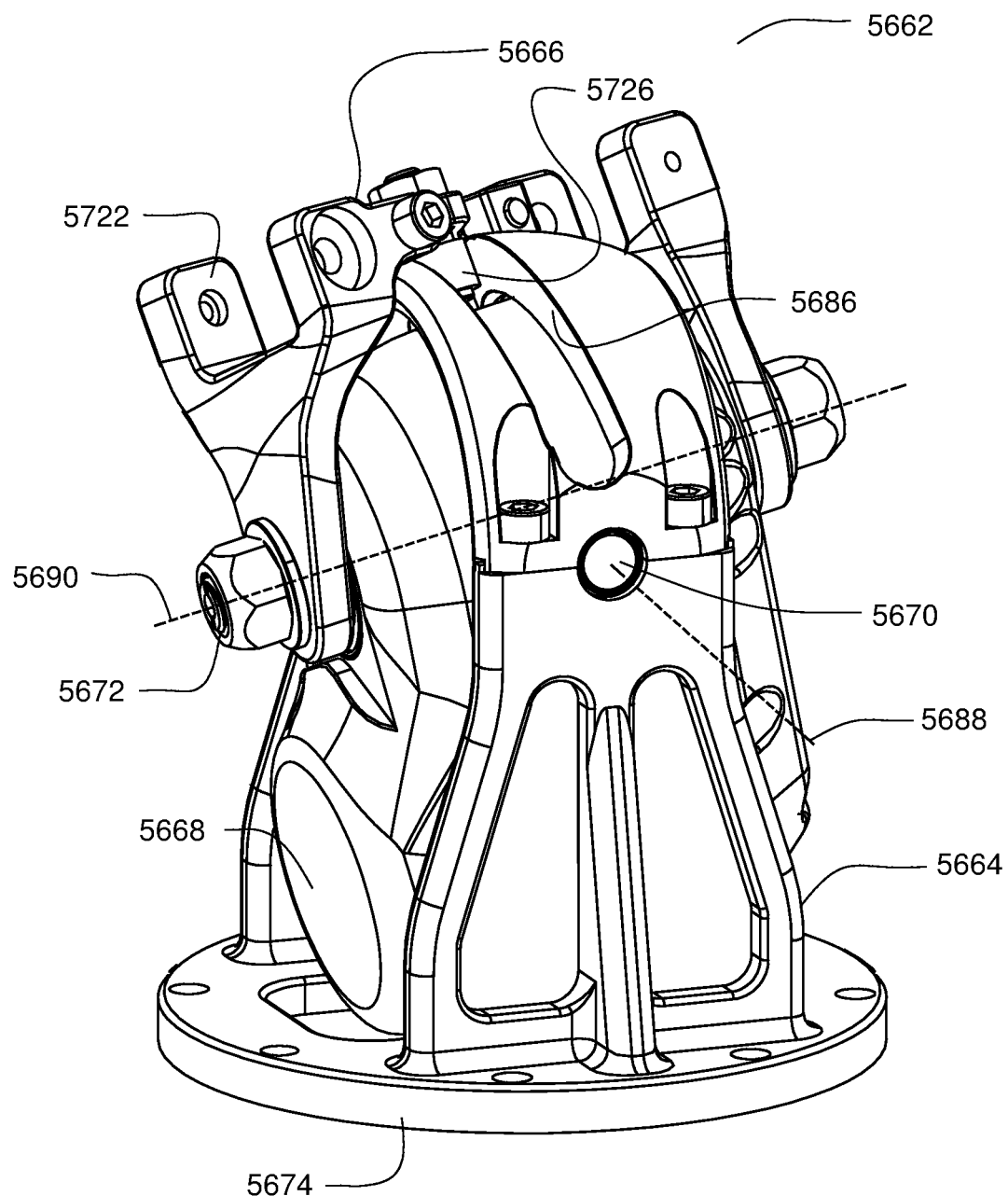
Figure 88D:
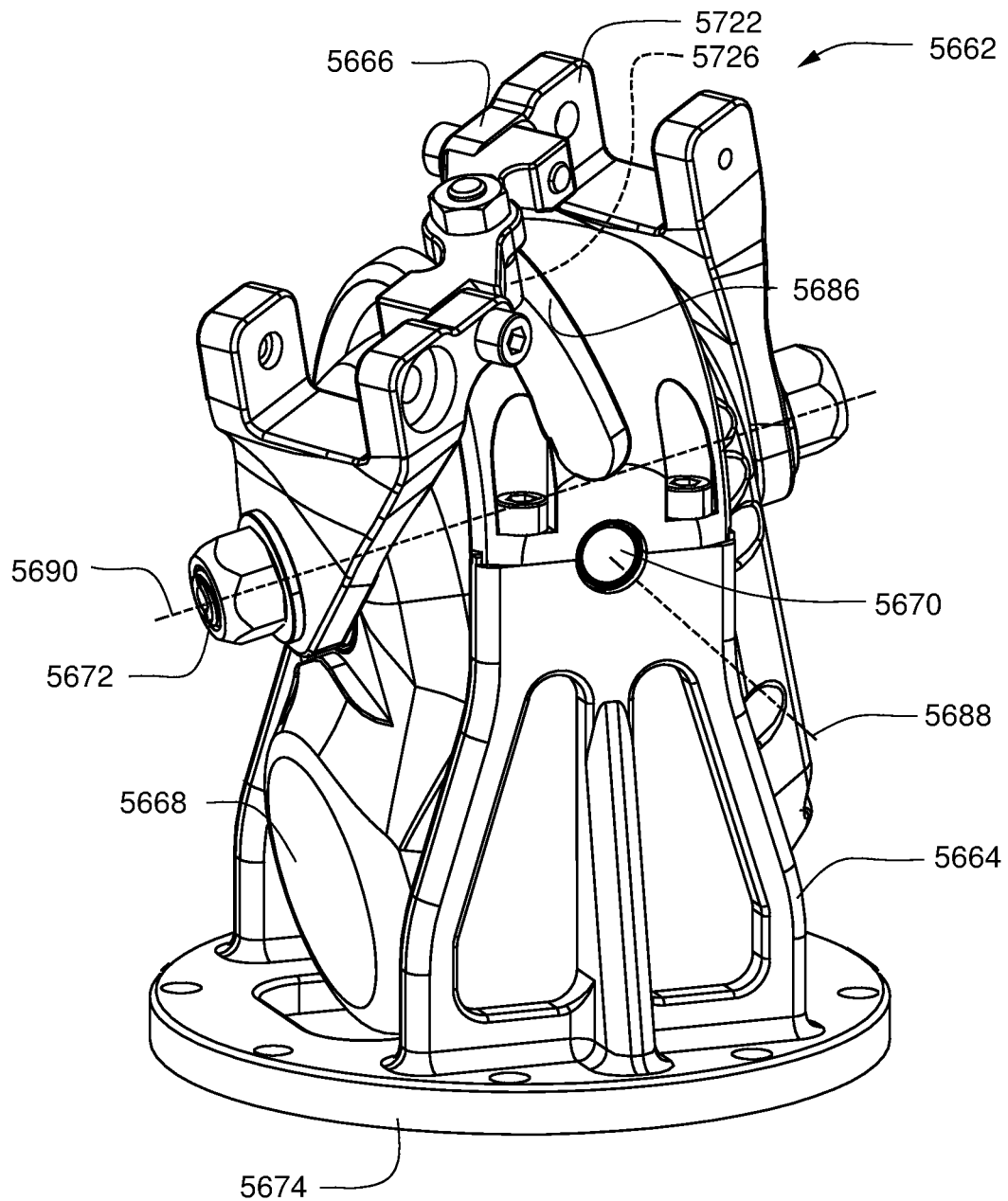
Figure 88E:
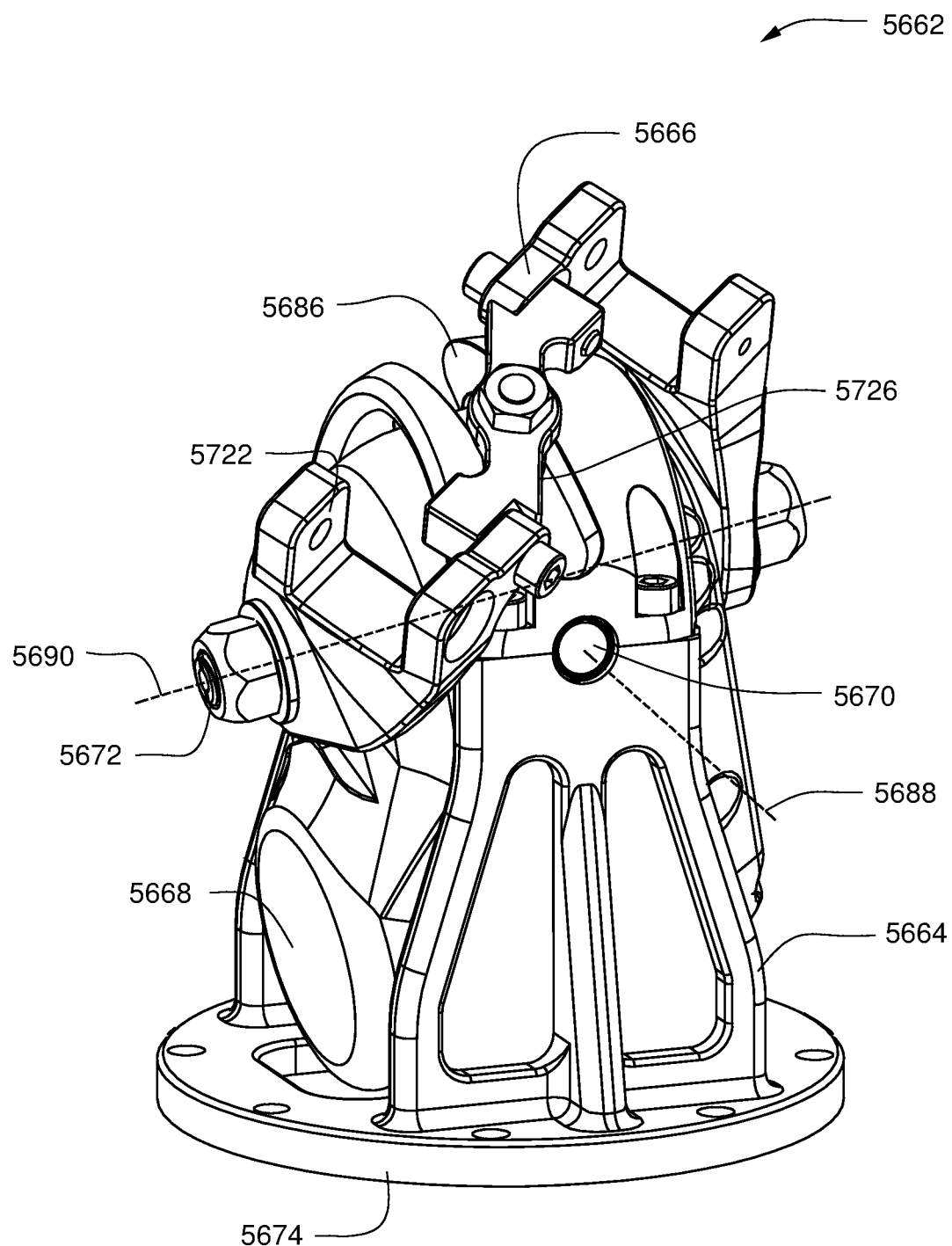
Figure 88F:
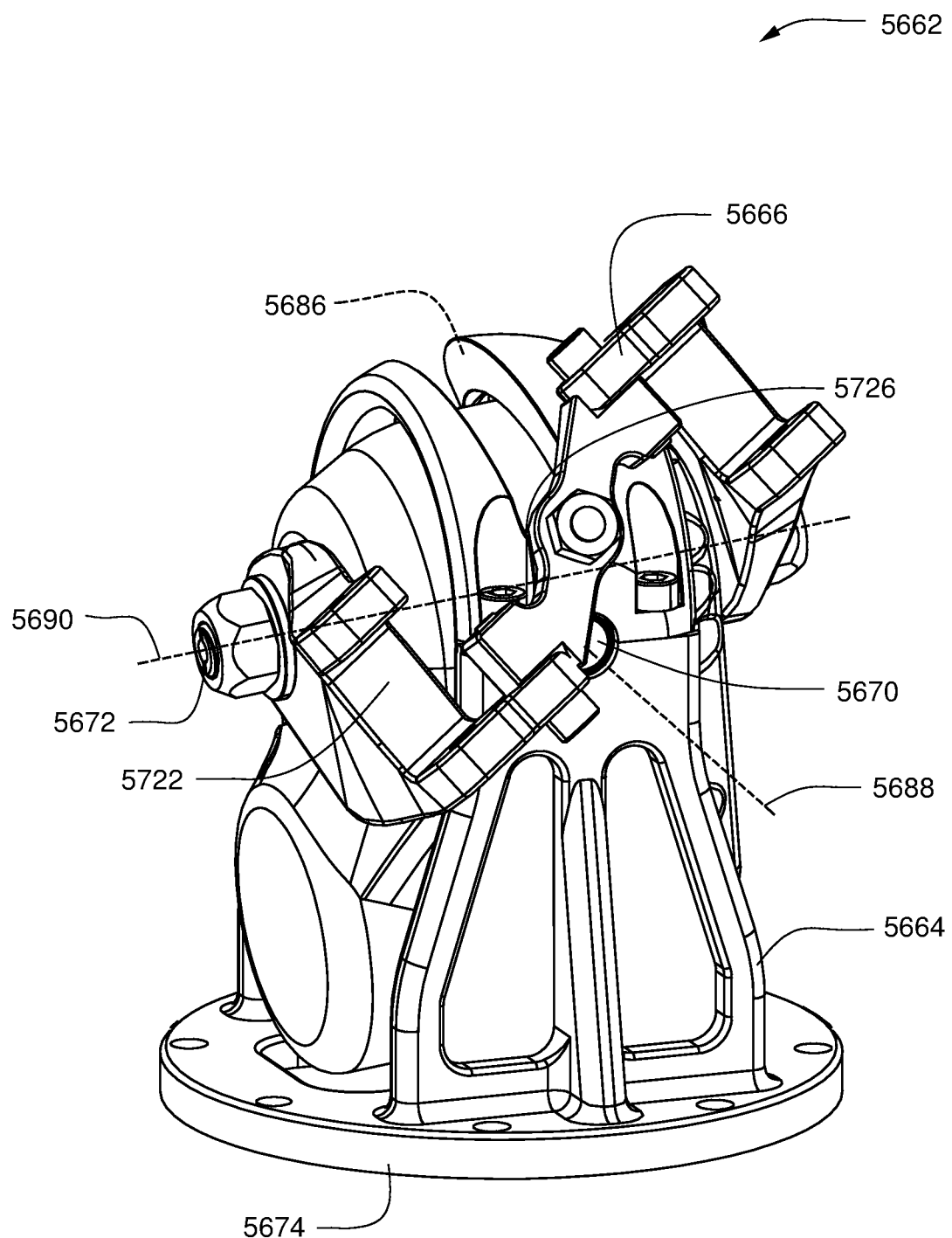
Figure 89:
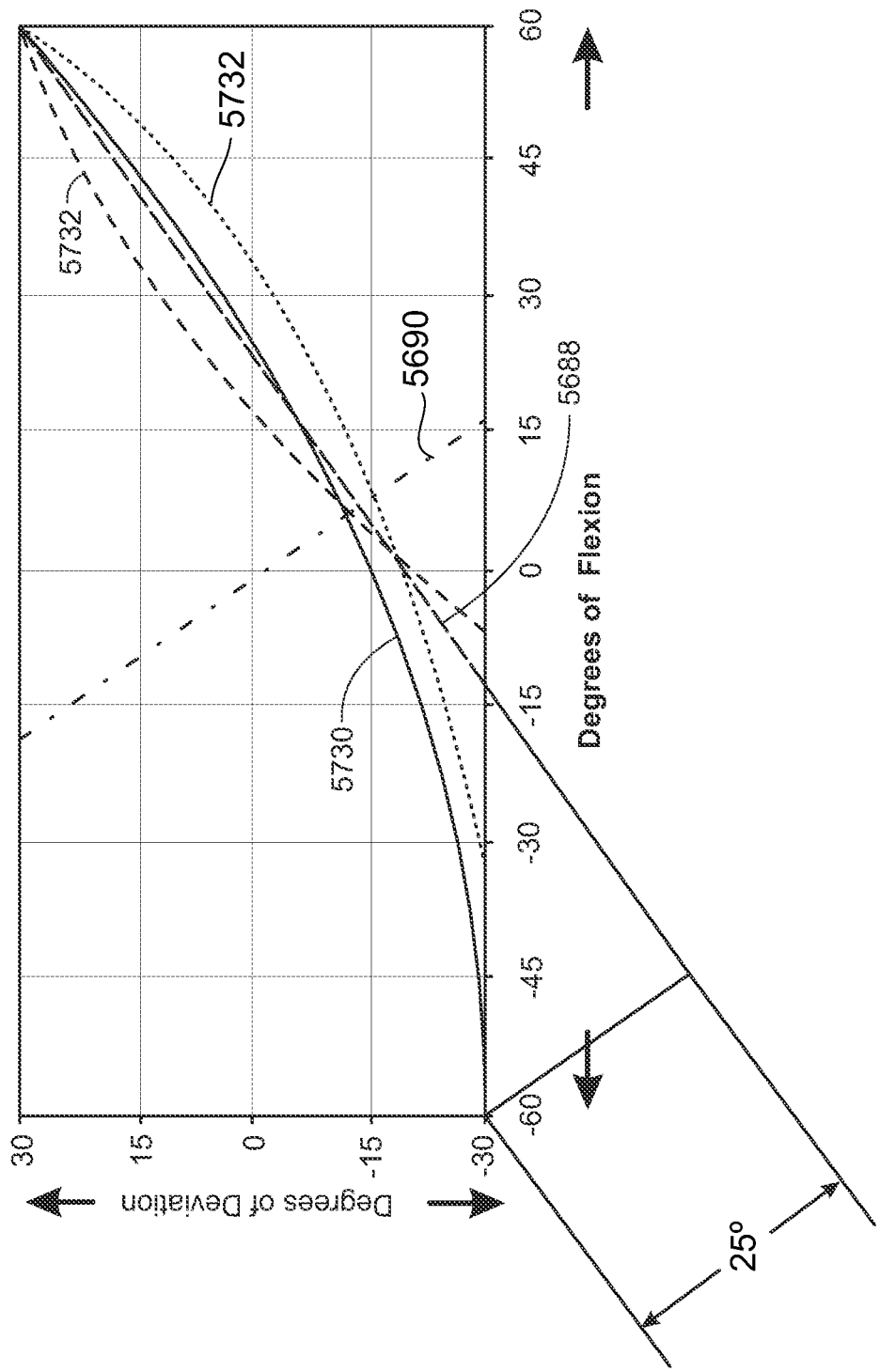
FIG. 89 is a line graph of a compound motion path of the compound motion assembly of FIG. 81.

As discussed above, the fixed path profile 5686 has a curvature that is selected to define the compound motion of the output member 5666 relative to the input member 5664. Referring to FIG. 89, the fixed path profile 5686, shown in FIG. 81, produces compound motion path 5730 having pivotal movement about both the first axis 5688 and the second axis 5690. It should be understood by those skilled in the art that the fixed path profile 5686 may be changed to produce alternative motion paths 5732, depending upon the desired movement of the output interface 5722, shown in FIG. 81. Thus, when the compound motion assembly 5662, shown in FIG. 87, is used with a prosthetic hand 24, shown in FIG. 87, the fixed path profile 5686 may be formed to provide the flexion-deviation movement path 4660, shown in FIG. 80, having all of the advantages discussed above in connection therewith. Alternatively, the fixed path profile 5686 may instead be formed to provide the hand assembly 24, shown in FIG. 87, with an alternative movement path 5732 having another advantageous path of movement for different user needs.

Referring back to FIG. 81, as discussed above, the path member 5678 is preferably removably attached to the support posts 5676. This advantageously allows the path member 5678 to be easily removed from the compound motion assembly 5662 and replaced if damaged or if an alternative motion path 5732, shown in FIG. 89, is desired for the output interface 5722. Thus, the compound motion assembly 5662 may advantageously be reprogrammed for different uses or different users by the swapping of a single part. Additionally, when implemented as a prosthetic wrist, as shown in FIG. 87, the compound motion assembly 5662 may be switched from a right handed to left handed prosthetic wrist, and vice versa, by changing only the path member 5678 and the output arms 5720, each of which is advantageously removably attached to the compound motion assembly for easy removal and installation.

Figure 90:
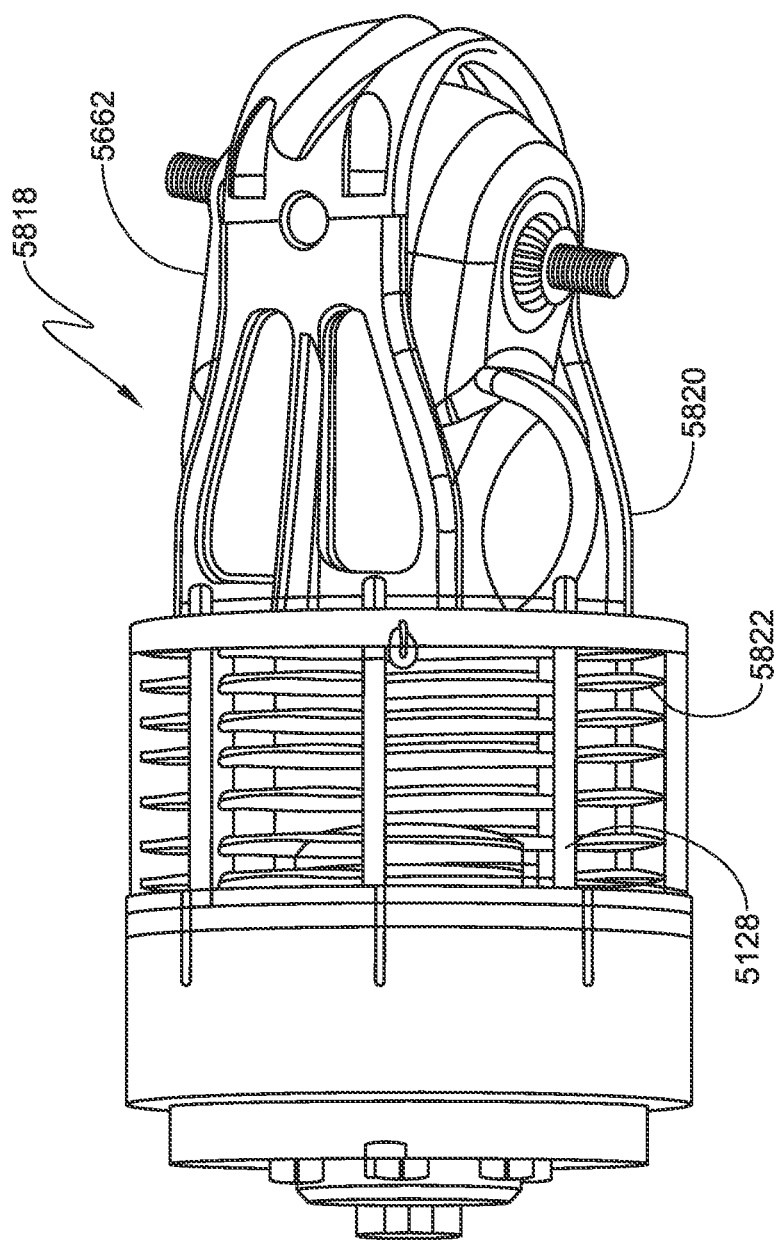
FIG. 90 is a side perspective view of an embodiment of an antenna according to the present invention.

Referring to FIG. 90, in some embodiments, the compound motion assembly 5662 and any metal structure secured thereto, such as hand assembly 24, shown in FIG. 87, may be incorporated into a first antenna 5818 for communication between the arm control module (ACM) stack 5128 and an external device such as a control unit for the prosthetic arm apparatus 10, shown in FIG. 1. The compound motion assembly 5662 forms a radiating element 5820 of the first antenna 5818 and a first printed circuitboard 5822 of the ACM stack 5128 connected to the radiating element 5820 provides the remainder of the antenna 5818.

Figure 91:
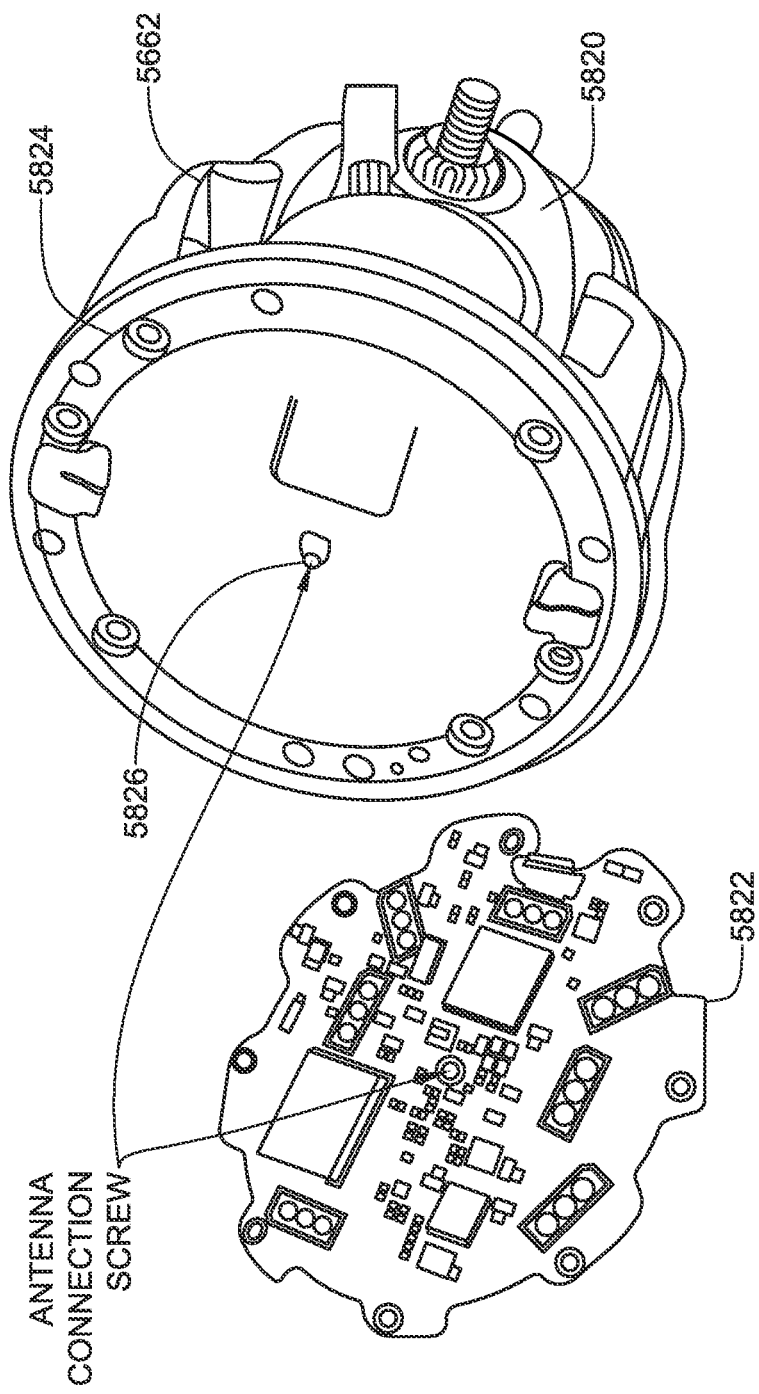
FIG. 91 is a partially exploded view of the antenna of FIG. 90.

Referring to FIG. 91, the compound motion assembly 5662 includes a grounding disc 5824 at the interface with the ACM stack 5128, shown in FIG. 90, that electrically isolates the radiating element 5820 from the first printed circuitboard 5822. A screw connection 5826 passes through the grounding disc 5824 to allow the printed circuitboard 5822 to be secured thereto with a screw (not shown). The screw connection 5826 advantageously facilitates both a mechanical connection between the printed circuitboard 5822 and the radiating element 5820 as well as an electrical connection between the radiating element 5820 and the antenna matching network circuit on the printed circuitboard 5822.

Figure 92:
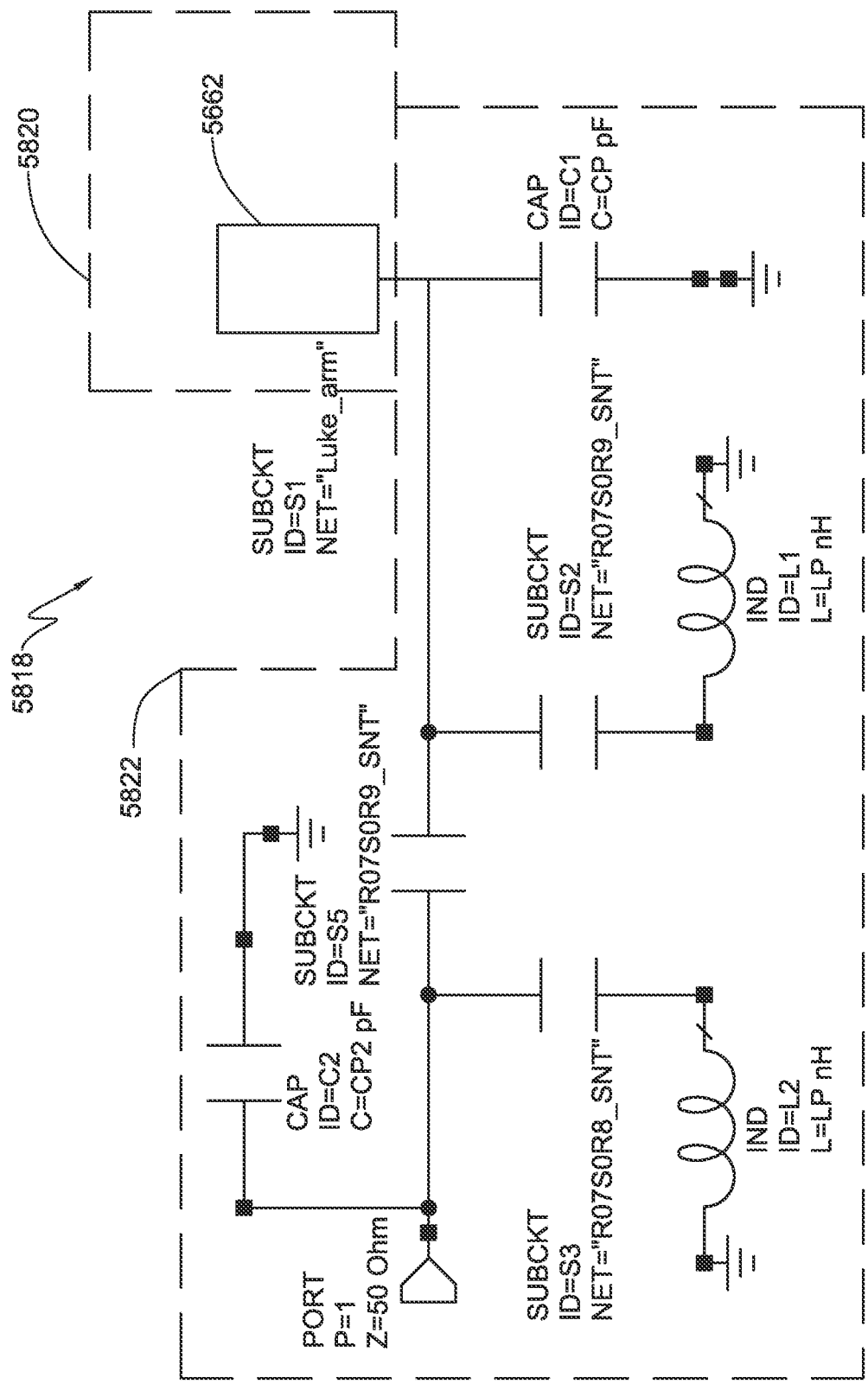
FIG. 92 is a schematic view of the antenna matching network of FIG. 90.

Thus, referring to FIG. 92, the compound motion assembly 5662, as well as any metal structure secured thereto, provides the radiating element 5820 for the first antenna 5818, while the rest of the electrical components of the first antenna 5818 may be housed on the printed circuitboard 5822. In some embodiments, the impedance of the compound motion assembly 5662, as well any metal structure secured thereto, is matched to that of the transceiver of the printed circuitboard 5822 to provide for efficient energy transfer. By providing the entire compound motion assembly 5662, and any metal structure attached thereto, as the radiating element 5820, with its impedance matched to that of the transceiver, the first antenna 5818 necessarily provides a better and more robust antenna than substantially any antenna that could be housed within the wrist structure itself. Therefore, the first antenna 5818 may advantageously be implemented as the primary communication channel for the prosthetic arm apparatus 10, shown in FIG. 1, transferring critical commands, such as commands relating to prosthetic movement, to and from the ACM stack 5128, shown in FIG. 90. Additionally, due to the size of the radiating element 5820, the signaling to and from the first antenna 5818 is less susceptible to multi-path interference, which often presents a significant problem for short-range communications within buildings due to signal reflections and the like.

Although multi-path interference is not a significant problem for the first antenna 5818 due to the size of the radiating element 5820, it may, in some embodiments, be a problem for short-range communications within buildings. In particular, typical short-range communication frequencies, for example, approximately 2.5 GHz, do not typically pass through human torsos. Additionally, signal reflection within a building may result in signals that are the same, except 180 degrees out of phase, being received by an antenna, which causes the signals randomly and periodically to completely cancel.

Figure 93:
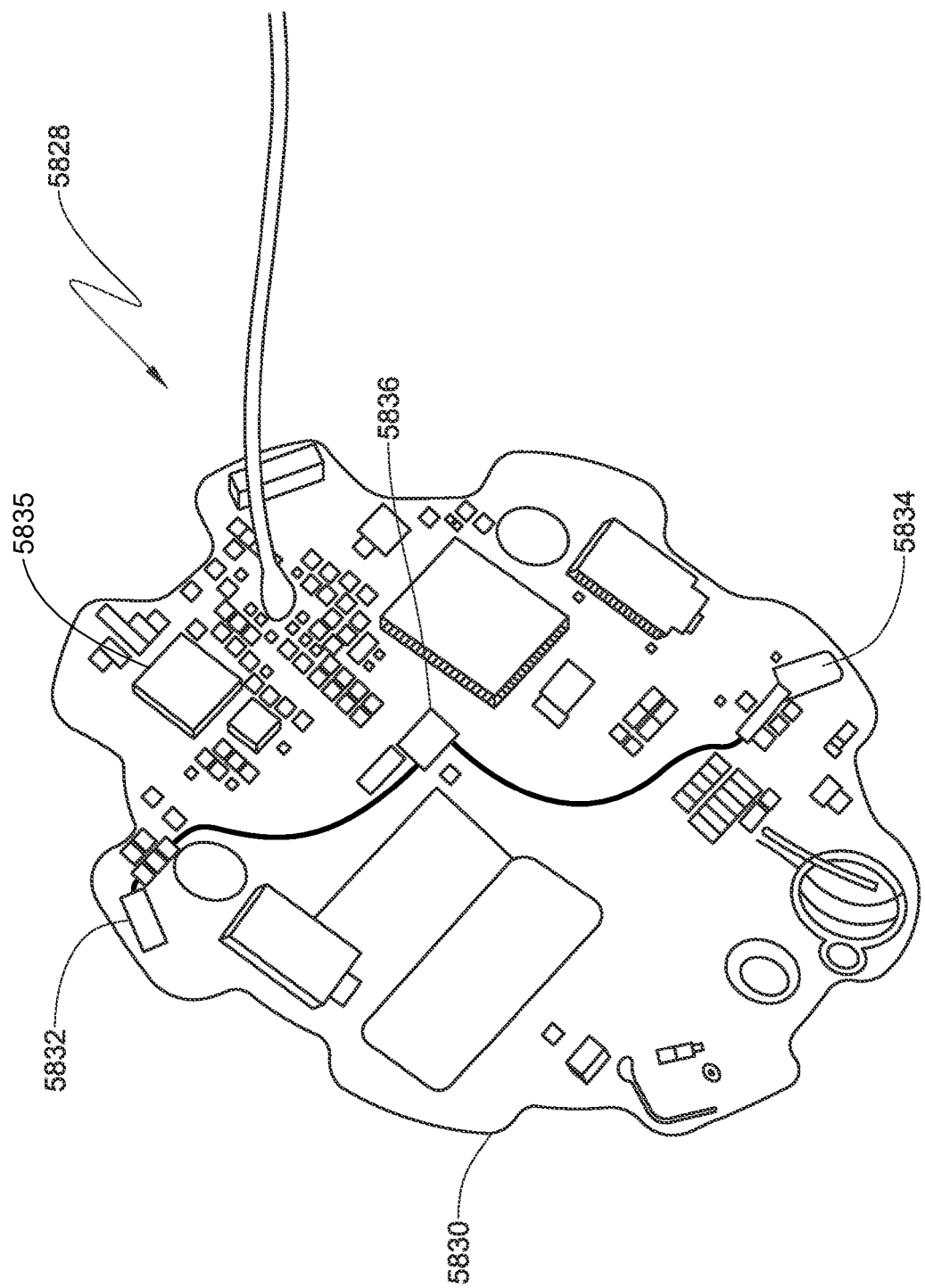
FIG. 93 is a top perspective view of an embodiment of another antenna according to the present invention.
Figure 94:
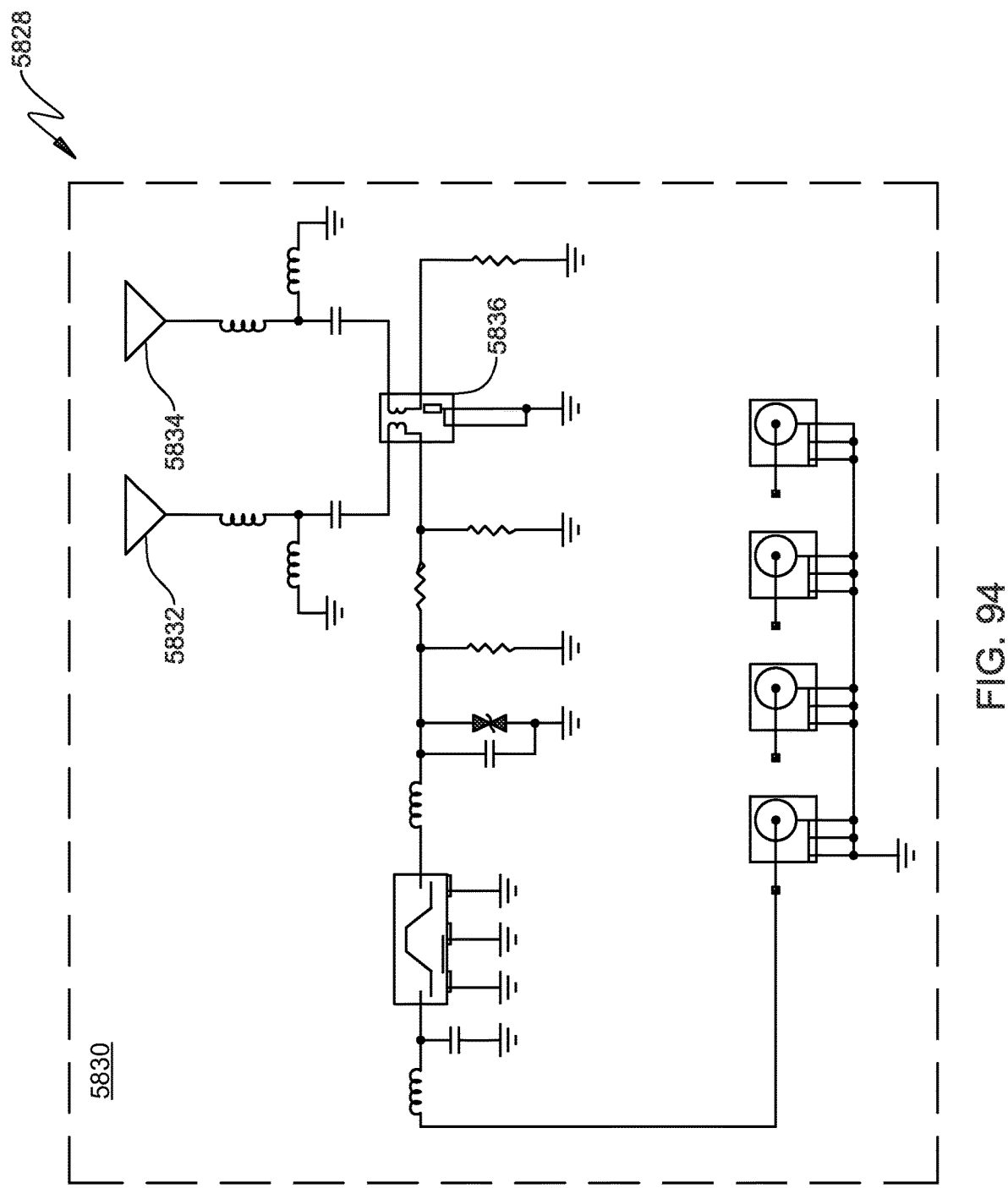
FIG. 94 is a schematic view of the antenna branching network of FIG. 93.

Accordingly, referring to FIGS. 93 and 94, a second antenna 5828 for overcoming the transmission issues associated with in-building interference may be formed entirely on a second printed circuitboard 5830 of the ACM stack 5128, shown in FIG. 90. The second antenna 5828 includes a first chip antenna 5832 and a second chip antenna 5834 mounted on the printed circuitboard 5830 at an angle of approximately 90 degrees relative to one another. The first chip antenna 5832 and the second chip antenna 5834 are connected to a transceiver 5835, shown in FIG. 93, of the second antenna 5828 through a combiner 5836 that passively combines signals received by the first and second chip antennas 5832 and 5834 by taking only the stronger of the two signals. In some embodiments, the combiner 5836 may be a 90 degree phase combiner, while in other embodiments the combiner may include some other phase angle. Additionally, although the first and second chip antennas 5832 and 5834 have been described as being offset approximately 90 degrees relative to one another, one skilled in the art should understand that the first and second chip antennas 5832 and 5834 may be offset at other angles to suit some other need while still achieving substantially the same benefit as that achieved with the 90 degree offset.

The offset angle between the first chip antenna 5832 and the second chip antenna 5834 advantageously allows the second antenna 5828 to mitigate multi-path interference by capturing signals in different phase angles. Thus, the second antenna 5834 may advantageously provide the prosthetic arm apparatus 10, shown in FIG. 1, with a secondary antenna for less critical signals where some interference is acceptable. For example, the second antenna 5828 may be used for calibration of the prosthetic arm apparatus 10, shown in FIG. 1, via a personal computer or for downloading data logs from the prosthetic arm apparatus 10, shown in FIG. 1, to the personal computer. Thus, while some embodiments of the present invention may implement only the first antenna 5818, shown in FIG. 90, or the second antenna 5828, other embodiments may implement both the first and second antennas 5818 and 5828 to cooperate and provide a more robust communication system.

Although described herein in the context of a prosthetic arm and/or prosthetic hand, it should be understood that the antennas described herein may be used for communication in various other devices and are not necessarily limited to use in a prosthetic arm/prosthetic hand.

Figure 95:
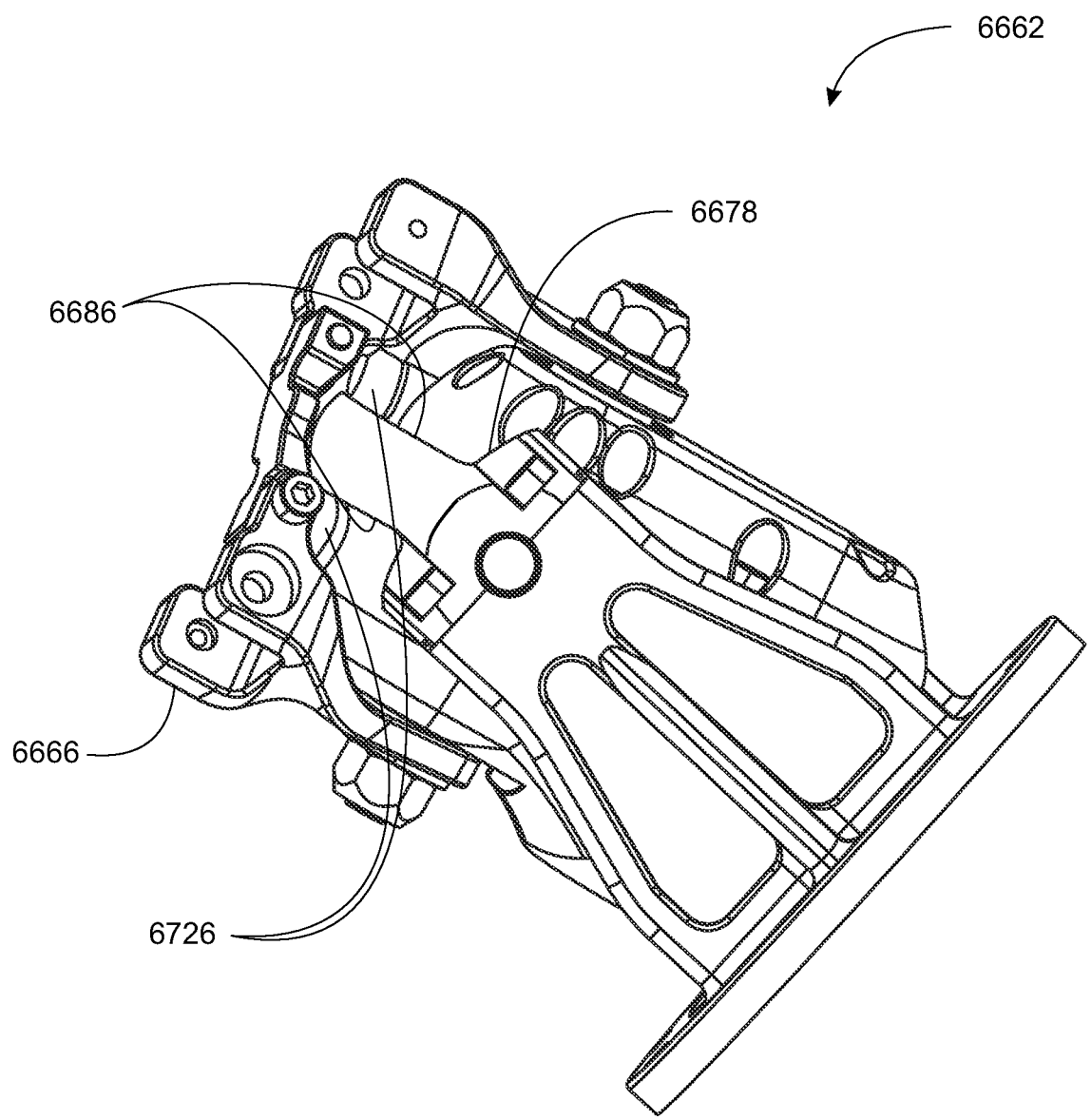
FIG. 95 is a side perspective view of another embodiment of a compound motion assembly according to the present invention.

Referring to FIG. 95, in some embodiments, compound motion assembly 6662 may include a path member 6678 having the fixed path profile 6686 formed on each peripheral edge thereof. In this embodiment, the output member 6666 includes two extensions 6726, each extension 6726 engaging one of the fixed path profiles 6686. This embodiment operates in substantially the same manner as the embodiments discussed above. However, this embodiment may advantageously provide for a more compact compound motion assembly 6662.

Referring back to FIG. 81, although described in connection with the detailed embodiments herein, it should be understood by those skilled in the art that the compound motion assembly 5662 may advantageously be implemented in various industrial and manufacturing environments, or the like. Thus, the compound motion assembly may provide equipment and/or machinery having complex compound motion paths 5730, shown in FIG. 89, controlled through simplified single degree of freedom inputs. In these embodiments, the compound motion assembly 5662 may be scaled up or down in size to meet specific or desired requirements. Additionally, path members 5678 may be swapped in and out to alter the compound motion path 5730, shown in FIG. 89. The input interface 5674 may advantageously be secured to a floor, a table or similar workstation to provide a fixed frame of reference from which the output interface 5722 is actuated. Additionally, the output interface 5722 may advantageously be adapted to accommodate various industrial or manufacturing tools thereon.

Figure 96:
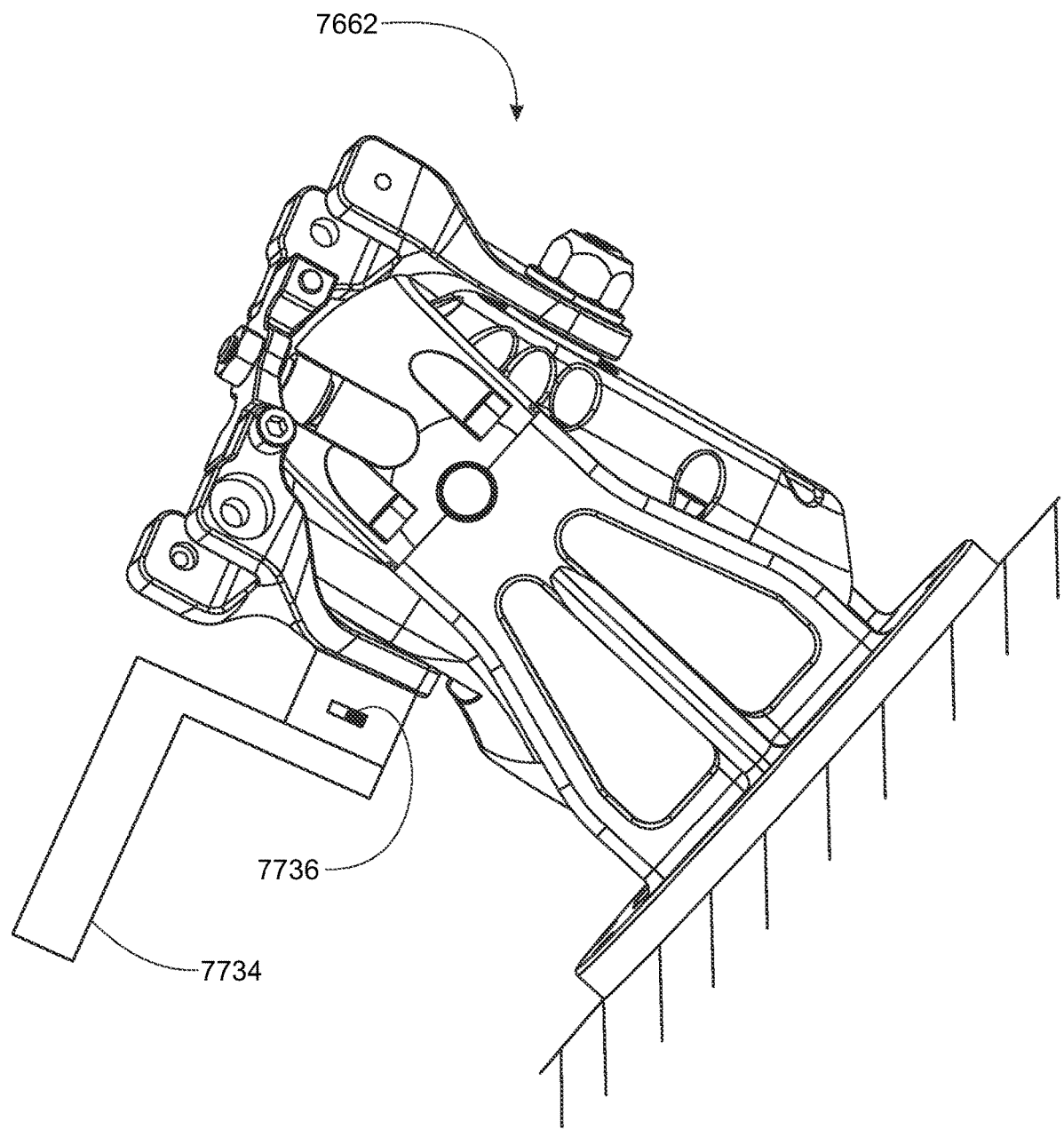
FIG. 96 is a side perspective view of another embodiment of a compound motion assembly according to the present invention.

Still referring to FIG. 81, although the compound motion assembly 5662 has been described as having a drive arrangement 5694, shown in FIG. 85, for actuating the compound motion assembly 5662, some embodiments of the present invention may not be powered, thereby simplifying the compound motion assembly 5662 by eliminating the drive arrangement 5694, shown in FIG. 85. For example, FIG. 96 shows an embodiment of a non-powered compound motion assembly 7662. The compound motion assembly 7662 may be moved by hand and locked in a desired position through the use of a brake 7736, or the like. Additionally, some non-powered embodiments of the compound motion assembly 7662 may include a handle 7734 to provide for easier manual actuation of the compound motion assembly 7662.

Figure 57B:
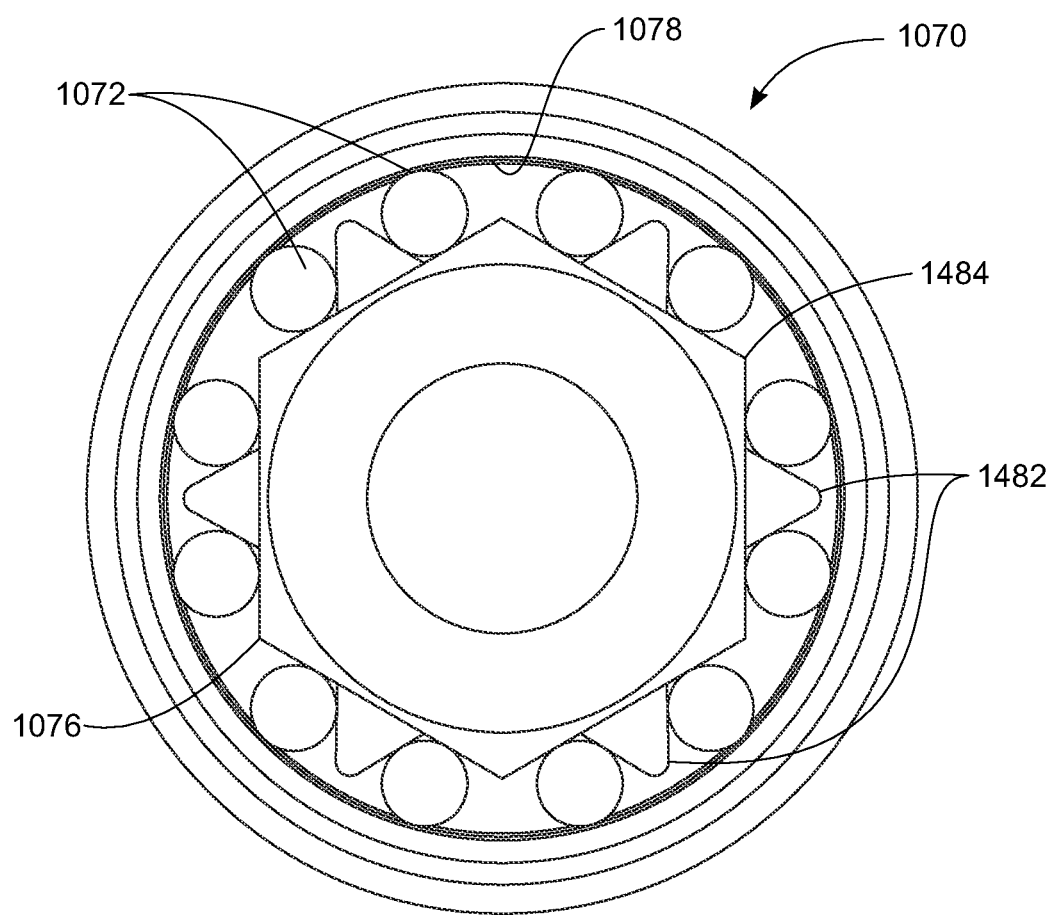
FIG. 57B is a cross-sectional view of another embodiment of the non-backdriving clutch of FIG. 12.

Referring to FIG. 57A and FIG. 57B, in various embodiments, the non-backdriving clutch 1070 may replace spacers of the input cage 1074 with springs 1482 between the rollers 1072. The springs 1482 push the rollers 1072 apart and into contact with both the race 1078 and the output polygon 1484, which may be an output hex 1076. Thus, when a backdriving torque (not shown) is applied to the output hex 1076 to friction lock the rollers 1072 between the output hex 1076 and the bearing race 1078, the rollers 1072 are already contacting both the race 1078 and the output hex 1076, thereby substantially eliminating backlash, i.e. a slight rotation of the output polygon 1076, when the backdriving torque (not shown) is applied. Thus, the non-backdrivable clutch 1070 imparts a frictional lock, which additional backdriving torque (not shown) through the output hex 1076 will not overcome. Additionally, as discussed above in connection with FIG. 12, in various embodiments, the non-backdriving clutch 1070 may unlock itself through the application of an input load through the input cage 1074. Variations of this embodiment may include, but are not limited to, additional or fewer springs 1482, additional or fewer rollers 1072 or a differently shaped race 1078. For example, in various embodiments, the relative position of the output hex 1076 and the race 1078 may be shifted, i.e., rather than the hollow, circular race 1078 with the output polygon 1484 inside, in various embodiments, the clutch may include an outer hollow output polygon surrounding a circular race. Additionally, although shown as a coil spring, it should be understood by those skilled in the art that the springs 1482 may be formed in various configurations and/or from a variety of metal or elastomeric materials to provide the force for separating the rollers 1072. In addition, the motor may be used to provide additional inertia to reduce back driving of the system.

Figure 57C:
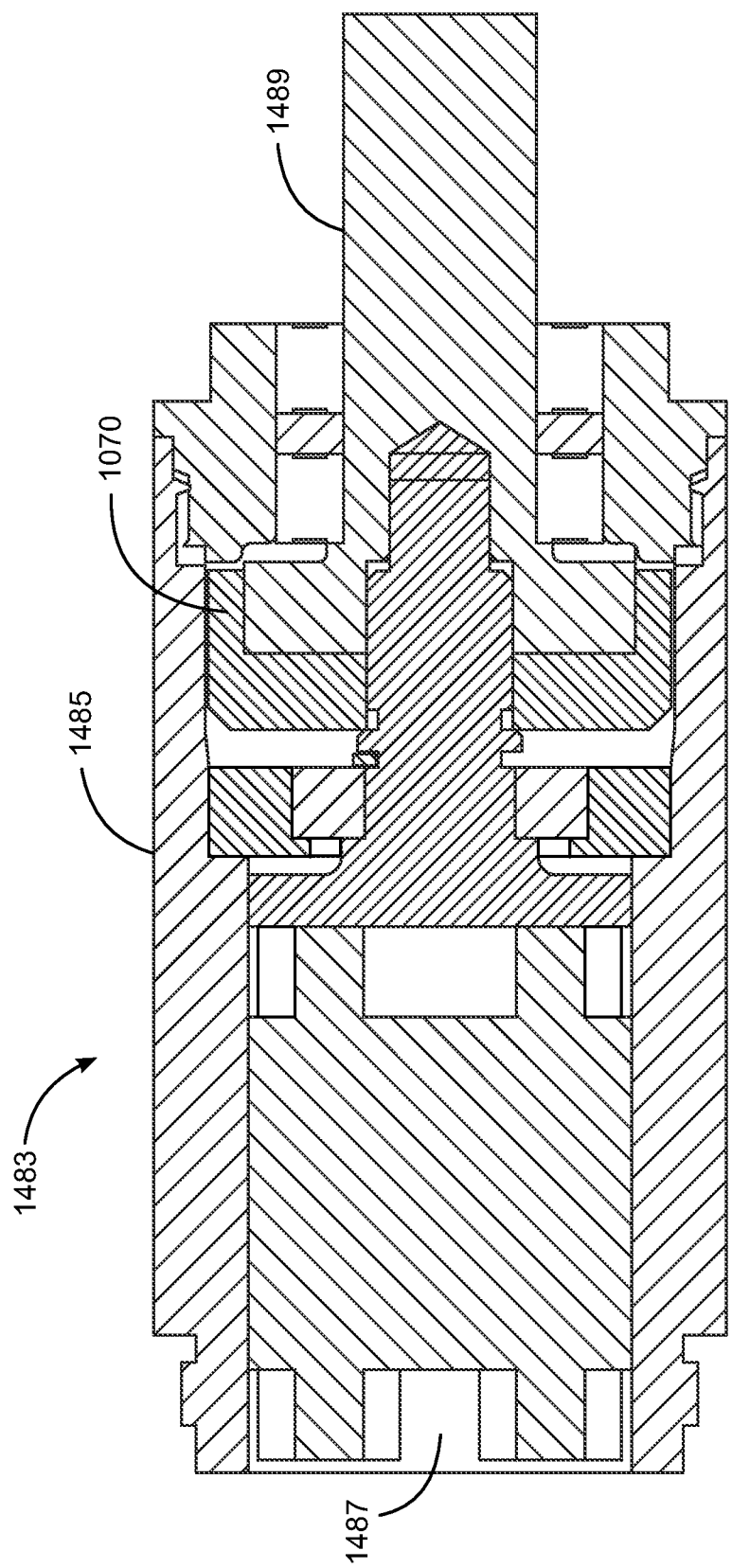
FIG. 57C is a cross-sectional view of a combination gearbox including the non-backdriving clutch of FIG. 57B.

Referring to FIG. 57C, in some embodiments, the non-backdriving clutch 1070 may be integrated in combination with a gearbox 1483 within a single gearbox housing 1485. In this embodiment, the gearbox 1483 may include an input 1487 for engaging and being driven by a motor (not shown) and an output 1489 that transmits torque from the motor (not shown) to the associated prosthetic joint or segment. For example, the combination gearbox 1483 may be used for the two thumb drives 232, the index drive 234 and the MRP drive 236, all shown in FIGS. 31-34, so that these drives may be assembled and disassembled as a single unit. This advantageously allows sensitive clutch components to be isolated and protected within a single housing 1485. Additionally, this allows the gearbox 1485 to build separately with the clutch 1070 and gearbox 1483 therein and later assembled into the hand assembly 2024, shown in FIG. 58A, as will be discussed below.

Figure 58A:
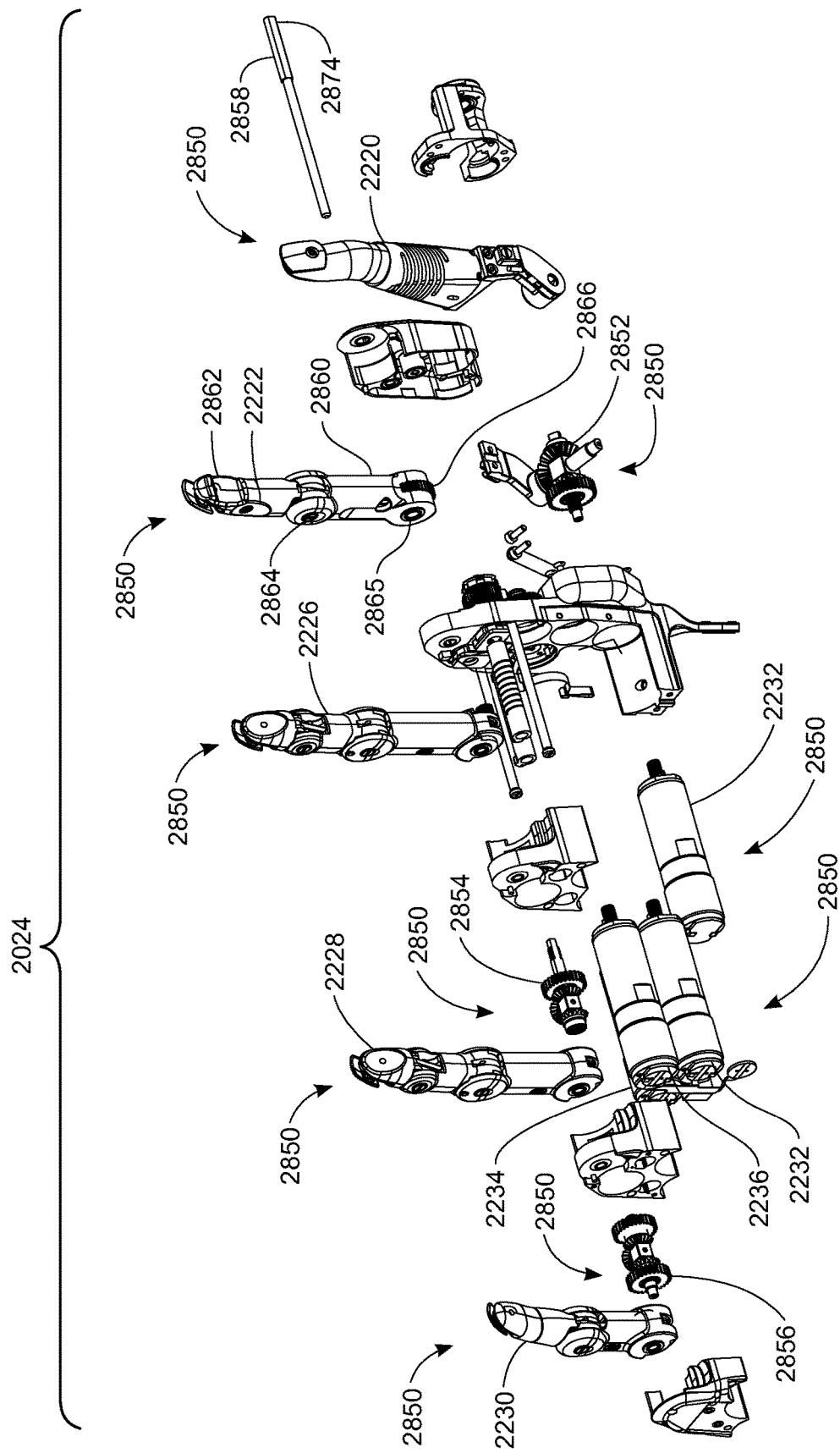
FIG. 58A is an exploded perspective view of an embodiment of the hand assembly according to the present invention.

Referring to FIG. 58A, in some embodiments, the hand assembly 2024 may include a plurality of self-contained subassemblies 2850 to advantageously make assembly and/or disassembly of the hand assembly 2024 easier. The self-contained subassemblies 2850 may be built in parallel and then quickly assembled into the full hand assembly 2024. The self-contained subassemblies 2850 may include, for example, the thumb drives 2232, the index drive 2236 and the MRP drive 2234, each of which may include the integrated gearbox 1483 and clutch 1070, shown in FIG. 57C. The self-contained subassemblies 2850 may also include a first MRP differential 2854 and a second MRP differential 2856 that may be fully assembled as complete units and easily dropped into the hand assembly 2024. The self-contained subassemblies 2850 may also include the thumb assembly 2220, the thumb differential 2852 as well as each of the index finger 2222, middle finger 2226, ring finger 2228 and pinky finger 2230. This advantageously allows the four finger subassemblies to be assembled as complete units and then assembled into the hand assembly 2024 and retained therein using a single pin 2858. Thus, the plurality of self-contained subassemblies 2850 may advantageously make assembly and/or disassembly of the hand assembly 2024 easier and may reduce build time, since each self-contained subassembly 2850 may be completed separately and simultaneously.

Still referring to FIG. 58A, in some embodiments, the index finger structure 2222 may include a base portion 2860 and a tip portion 2862, which are connected in a pivotal connection at a knuckle joint 2864. The base portion 2860 connects to the hand assembly 2024 through a pin hole 2865 and includes a gear segment 2866 fixedly connected at its lower end, which interfaces with the index drive 2234 to allow for controlled movement of the base portion 2860 about the pin 2858.

Figure 58B:
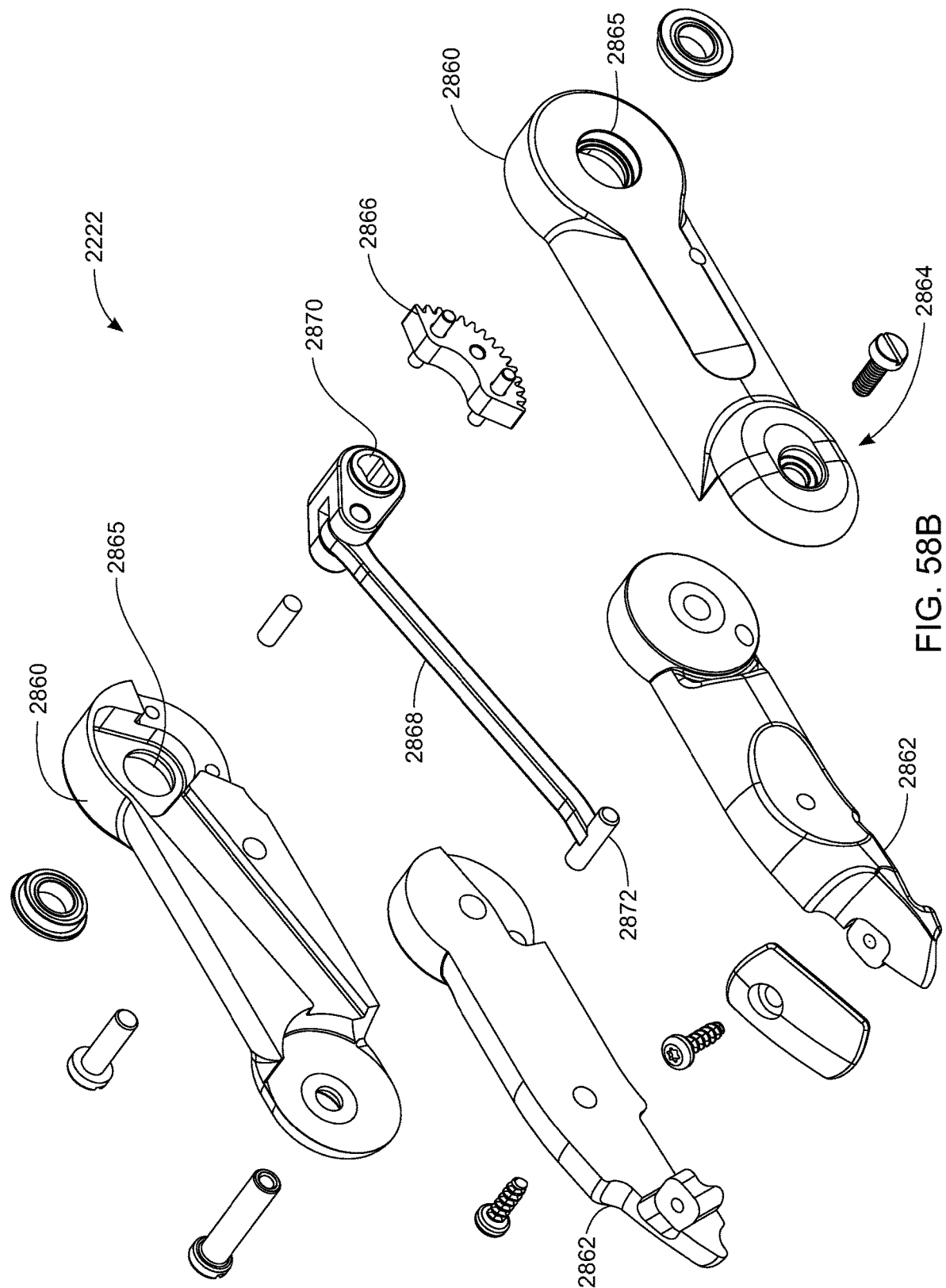
FIG. 58B is an exploded perspective view of an embodiment of an index finger structure of FIG. 58A.

Referring to FIG. 58B, within the index finger structure 2222 is disposed a two-part linkage element 2868 that includes a non-circular pin hole 2870 at its lower end and pivot bar 2872 at its distal end. The pivot bar 2872 connects to the tip portion 2862 at an offset location from the knuckle joint 2864. The non-circular pin hole 2870 is disposed adjacent to the pin hole 2865 and allows the pin 2858 to pass therethough when the index finger structure 2222 is assembled to the hand assembly 2024, with a corresponding non-circular portion 2874, shown in FIG. 58A, of the pin 2858 engaging the non-circular pin hole 2870. In operation, when actuated, the index drive 2234 drives the base portion 2860 of the index finger structure 2222 through the gear segment 2866. As the base portion 2860 moves, the two-part linkage 2868 remains grounded due to contact between the non-circular pin hole 2870 with the non-circular portion 2874 of the pin 2858. This, in turn, causes the pivot bar 2872 to move the tip portion 2862 relative to the base portion 2860, thereby achieving the movement of the index structure 2222 that is kinematically deterministic. Since the grounding of the two-part linkage 2868 is achieved through insertion of the pin 2858, it may advantageously be accomplished at essentially any point during assembly of the hand assembly 2024. Additionally, it also advantageously allows the index structure 2222 to be replaced without requiring disassembly of the hand assembly 2024 or a substantial part thereof.

Referring to FIG. 59, an embodiment for output load sensing through a drive 1486 having a worm gear 1488, such as the shoulder abduction drive 3428 of FIG. 44, is shown. Including one or more worm gears 1488 in the drive 1486 is beneficial because the worm gear 1488 may itself prevent backdriving. The worm gear 1488 may be arranged on a splined shaft 1490 between a first spring 1492 and a second spring 1494. The splined shaft includes a plurality of splines 1496 arranged axially around the surface of the splined shaft 1490 and a shaft input 1498 portion, which may be rotated directly by a motor (not shown) or through a gear train or the like. The worm gear 1494 is tubular and has an interior surface 1500 designed to slidably interface with the splines 1496 of the splined shaft 1490 such that the worm gear 1488 may slide axially along the surface of the splined shaft 1490. The worm gear 1488 meshes with an output gear 1502 such that when the splined shaft 1490 is caused to rotate through its shaft input portion 1498, the splined shaft 1490 rotatably drives the worm gear 1488 through the splines 1496 which, in turn, drives the output gear 1502. When a load (not shown) is applied to the drive through the output gear 1502, for example, if the user is lifting an object, the load will generate a torque T at the output gear 1502. Although the torque T will not cause the worm gear 1488 to rotate, the torque T may cause the worm gear 1488 to displace axially along the splined shaft 1490 compressing one of the first spring 1492 or the second spring 1494, depending upon the direction of displacement. Thus, by designing the drive system 1486 with the first spring 1492 and the second spring 1494 of known spring constants, the compliance, i.e. the displacement of the worm gear 1488, may be measured to estimate the output load (not shown). This drive system 1486 for output load sensing is particularly beneficial since the compliance is still present or active while the worm gear 1488 is not being rotated, but is instead acting as a non-backdriving element.

The prevention of backdriving with the various systems discussed above is beneficial because it allows the user to maintain a position of the prosthetic arm 10, shown in FIG. 1, while under a load (not shown). However, referring to FIGS. 60A and 60B, in some embodiments, it may be desirable to provide the various arm segments with break-away mechanisms 2504 that will separate the drive output from the drive input to prevent damage to the drive system if the load becomes too large. The break-away mechanism 2504 may include an input shaft 2506, an output shaft 2508 and two break-away spacers 2510 that are held in contact with the input shaft 2506 and output shaft 2508 by a compression member 2512. The input shaft 2506 and the output shaft 2508 each include a shaft body 2514 and a torque transmission tab 2516 extending axially outward from the shaft body 2514 between the break-away spacers 2510. The compression element member 2512 surrounds the break-away spacers 2510 and sandwiches the torque transmission tabs 2516 therebetween. The compression member 2512 may be, for example, a snap ring, a round metal ring, an o-ring, multiple o-rings, a coil spring, or the like. The compression member 2512 applies a preset compressive force to the breakaway spacers 2510.

In operation, the input shaft 2506 of the break-away mechanism 2504 is rotated by a motor (not shown) or the like to generate a desired movement of the prosthetic arm 10, shown in FIG. 1. Thus, the torque transmission tab 2516 of the input shaft 2506 rotates and transmits the rotation through the break-away spacers 2510 to the torque transmission tab 2516 of the output shaft 2508 as long as the torque required to cause rotation of the torque transmission tab 2516 of the output shaft 2508 is not large enough to overcome the preset compressive force provided by the compression member 2512. If the torque is large enough to overcome the preset compressive force, the torque transmission tab 2516 will push the break-away spacers 2510 apart and the torque transmission tab 2516 will rotate between the break-away spacers 2510 without transmitting torque therethrough. Thus, the break-away mechanism 2504 may prevent torque above a preset level from being transmitted through the drive system, where it can damage the drive system components. Accordingly, the break-away mechanism 2504 may limit the amount of torque applied to sensitive parts of the various drive systems of the prosthetic arm 10, shown in FIG. 1, and may, therefore, impart a longer lifespan on the prosthetic arm.

Figure 61A:
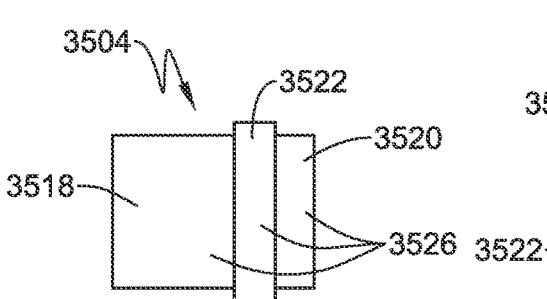
FIGS. 61A, 61B, 62A, 62B, 63A and 63B are various views of another embodiment of a breakaway mechanism according to the present invention.

Referring to FIG. 61A, another embodiment of a break-away mechanism 3504 includes an input ring 3518 and an output ring 3520 connected by a detent ring 3522. The breakaway mechanism 3504 may be connected between two prosthetic arm segments, for example, the input ring 3518 may be connected to the shoulder unit 1416, shown in FIG. 42A, and the output ring 3520 may be connected to the humeral rotator 16, shown in FIG. 1. Referring to FIGS. 62B and 62B, in some embodiments, the input ring 3518, output ring 3520 and the detent ring 3522 each includes an alignment marker 3524 on its outer surface 3526 to indicate proper positioning of the breakaway mechanism 3504.

Figure 61B:
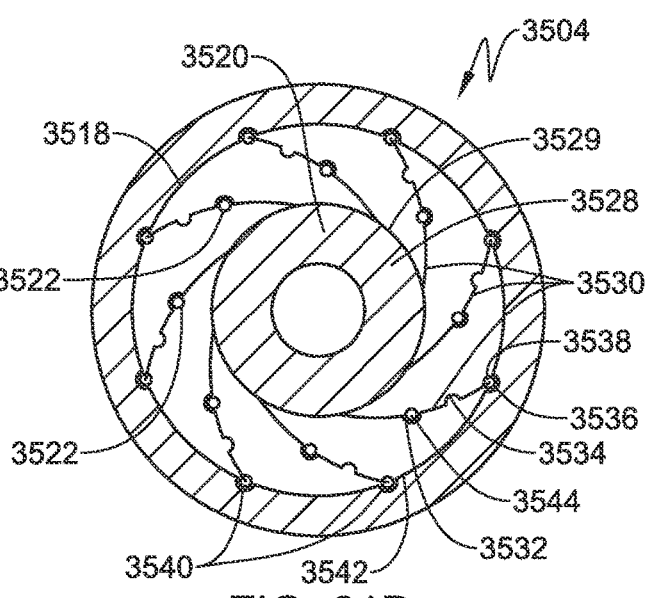

Referring to FIG. 61B, the output ring 3520 includes a central hub 3528 having an outer surface 3529 with a plurality of spring fingers 3530 radiating therefrom. Each spring finger 3530 has a first detent 3532 and a second detent 3534 along its length and a pin 3536 at its distal end 3538. The input ring 3518 includes a plurality of detents 3540 around the circumference of its inner surface 3542, within which the pins 3536 of the spring fingers 3530 may engage, as will be discussed in greater detail below. The detent ring 3522 includes a plurality of detent pins 3544 located partway between the inner surface 3542 of the input ring 3518 and the outer surface 3529 of the output ring 3520. The detent pins 3544 engage the first detents 3532 of the spring fingers 3530 during normal operation of the breakaway mechanism 3504, i.e. when torque is being transmitted through the breakaway mechanism 3504.

Figure 62A:
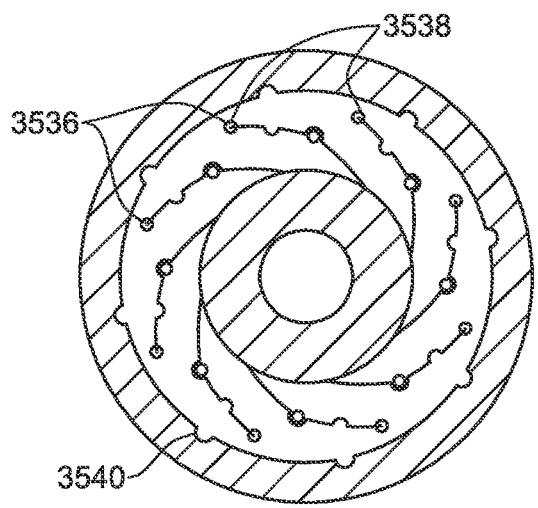
Figure 62B:
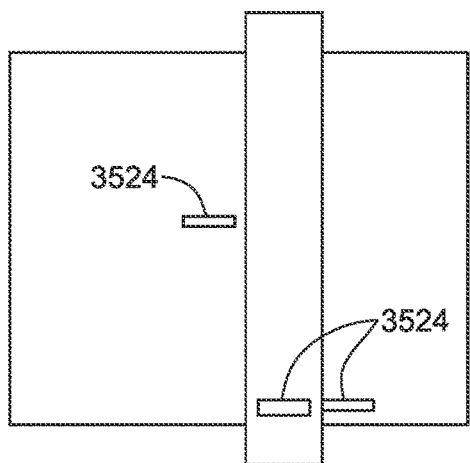

However, referring to FIG. 62A, if an overtorque situation occurs, the pins 3536 at the distal ends 3538 of the spring fingers 3530 will pop out of the ring detents 3540 so that the torque will not be transmitted back to the input ring 3518. Additionally, referring to FIG. 62B, the overtorque situation will also cause the alignment markers 3524 to move out of alignment. The user may then realign the alignment markers 3524 to transmit torque through the breakaway mechanism 3504.

Figure 63A:
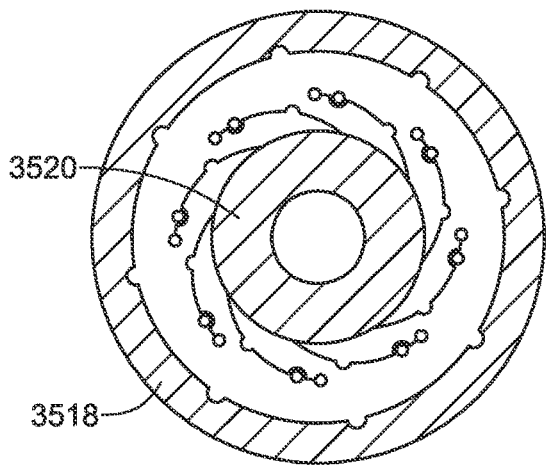
Figure 63B:
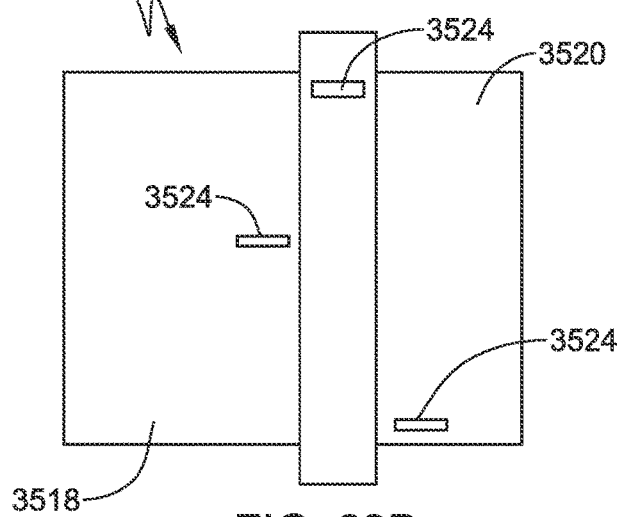

Referring to FIG. 63A, the user may also intentionally disengage the torque transmission by moving the alignment marker 3524 on the detent ring 3522 up to engage the breakaway mechanism 3504 in freeswing. As seen in FIG. 63B, this configuration entirely disengages the spring fingers 3530 from the input ring 3518, thereby allowing the output ring 3520 to rotate freely without driving the upstream components through the input ring 3518. Thus, this embodiment of the breakaway mechanism 3504 is advantageous because it also allows for the user to engage freeswing of the prosthetic arm 10, shown in FIG. 1.

These break-away mechanisms discussed above are beneficial because they prevent damage to the prosthetic arm apparatus 10 and increase user safety under high loading situations. Additionally, the break-away mechanisms are advantageous in that once the break-away mechanisms break under high loading, they may be reset by the user without the need to see a prosthetic technician.

Figure 64:
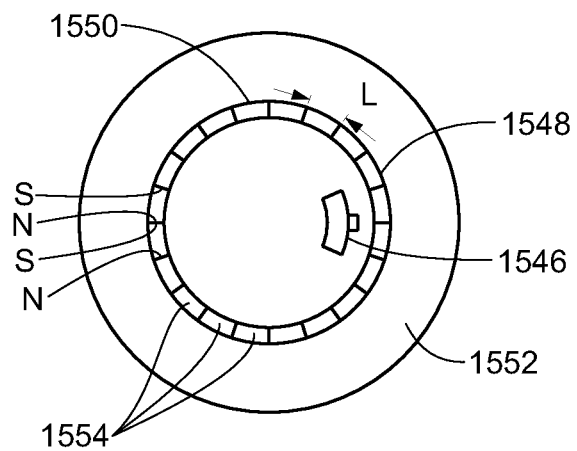
FIG. 64 is a front view of a magnetic sensor according to some embodiments of the present invention.

As discussed above, various embodiments of the prosthetic arm 10, shown in FIG. 1, include feedback mechanisms for compliance and position sensing, such as potentiometer 48, shown in FIG. 10. Referring now to FIG. 64, in some embodiments, the prosthetic arm 10, shown in FIG. 1, may include other feedback mechanisms, for example, a magnetic position sensor 1546. In these embodiments, at least one magnetic strip 1548 may be attached about the circumference of an inner surface 1550 of a rotatable drive component 1552. The magnetic strip 1548 includes a plurality of magnets 1554 of known length L1 arranged in series, each having a north pole N and a south pole S. Thus, the magnetic strip 1548 generates a magnetic field having a repeating pattern of alternating north poles N and south poles S. The magnetic position sensor 1546 is arranged to detect this magnetic field generated by the magnetic strip 1548. In operation, the rotatable drive component 1552 rotates, which causes the magnetic strip 1548 to rotate, thereby moving the portion of the magnetic strip 1548 being detected by the magnetic position sensor 1546. The magnetic position sensor 1546 detects this change in the magnetic field as the magnetic strip 1548 rotates from each north pole N to each south pole S and vice versa. Since the length L1 of each magnet 1554 is known, the detected changes in the magnetic field between each north pole N and/or each south pole S may be converted into the distance of rotational movement of the rotatable drive component 1552. Thus, the change in position of the rotatable drive component 1552 may be detected. The magnetic position sensor 1546 is also advantageous because it does not contact the rotating drive component 1552 and, therefore, will not experience contact wear due to the rotation of the rotatable drive component 1552.

Figure 65:
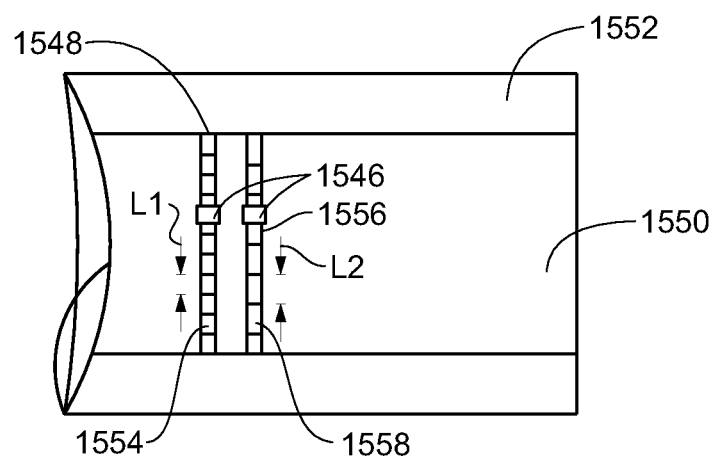
FIG. 65 is a side cross-sectional view of another embodiment of a magnetic sensor according to the present invention.

Referring to FIG. 65, in some embodiments, two magnetic position sensors 1546 may be used to detect the magnetic fields generated by the first magnetic strip 1548 and a second magnetic strip 1556 arranged next to each other around the circumference of the inner surface 1550 of a rotatable drive component 1552. A length L2 of each magnet 1558 of the second magnetic strip 1556 is, in some embodiments, different than the length L1 of the magnets of the first magnetic strip 1548. This difference in length allows for the magnetic position sensors 1546 to sense unique combinations of magnetic field values from the first magnetic strip 1548 and the second magnetic strip 1556 over the circumference of the inner surface 1550. Each unique magnetic field value may correspond to a position of the drive component 1552 and, therefore, absolute position of the drive component 1552 may be detected by the two magnetic position sensors 1546.

Figure 66:
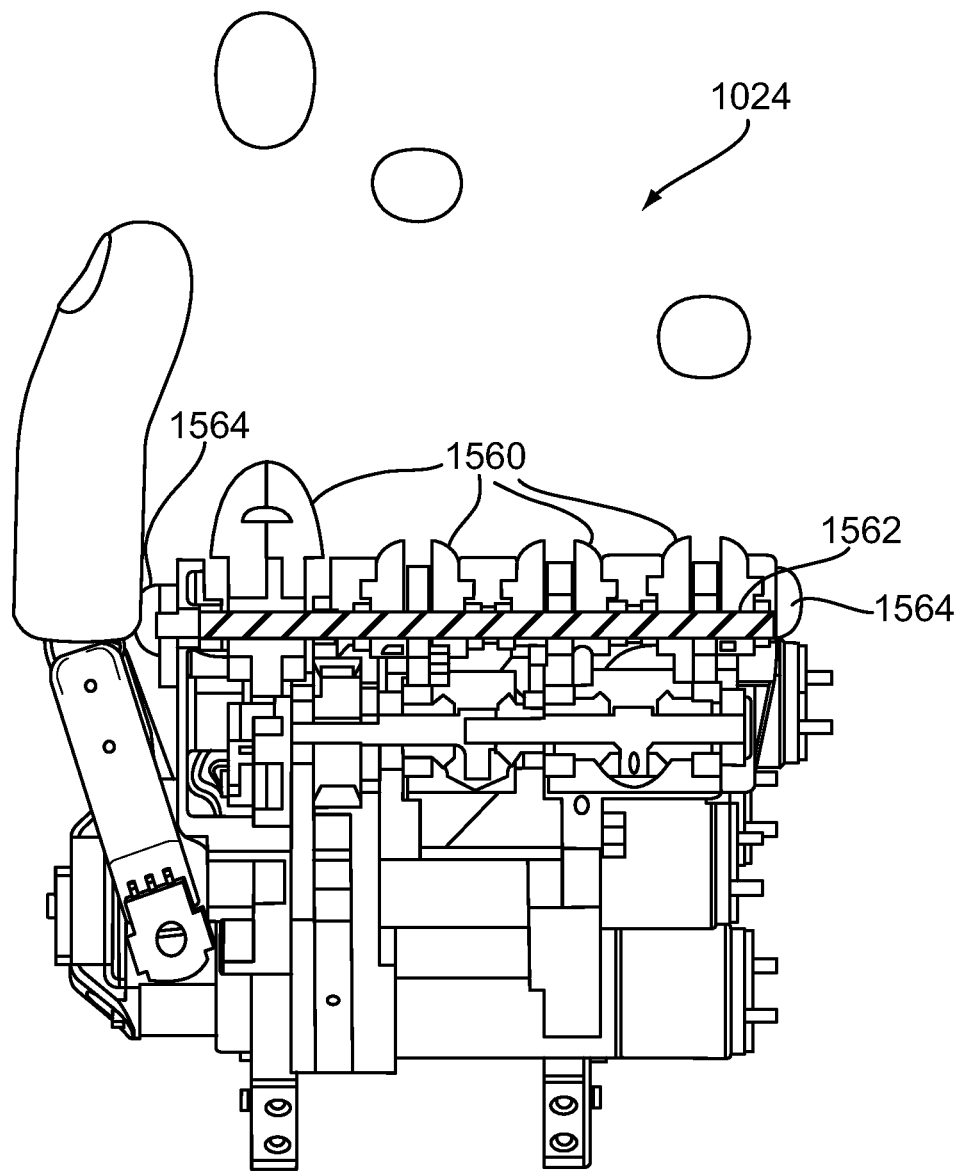
FIG. 66 is a cross-sectional view of a hand assembly according to an embodiment of the present invention.

In practice, the hand assembly 24, shown in FIG. 1, and particularly, the fingers of the hand assembly 24, i.e. the thumb structure 220, index finger structure 222, middle finger 226, ring finger 228 and pinky finger 230, all shown in FIG. 3, come into contact with objects frequently and, therefore, may be susceptible to wear and damage. Thus, referring to FIG. 66, it may be desirable for the prosthetic hand assembly 1024 to include removable fingers 1560. In this embodiment of the prosthetic hand assembly 1024, the removable fingers 1560 may be removed to allow for easier replacement of damaged fingers 1560 and also, to allow for easily customizable or tailored finger lengths for different user.

Each removable finger 1560 is driven in substantially the same manner as the fingers of the previously discussed embodiments. However, the removable fingers 1560 pivot about a common finger shaft 1562, rather than the individual pivot axles discussed in connection with FIG. 33. In some embodiments, end caps 1564 cover each end of the common finger shaft 1562 to prevent dirt or other contaminants from getting into the gear trains of the hand assembly 1024 and also to ensure that the common finger shaft 1562 does not become axially displaced unintentionally. In operation, either end cap 1564 may be removed from the hand assembly 1024 and the common finger shaft 1562 may be extracted to free the removable fingers 1560. Each finger 1560 may then be removed and replaced individually, as required.

As discussed above, the fingers 1560 of the hand assembly 1024 come into contact with objects frequently and are, therefore, susceptible to wear. Thus, referring to FIG. 67, some embodiments of the present invention may include a cosmesis 1566 for covering the hand assembly 1024 to reduce wear of the hand assembly 1024 and the fingers 1560, in particular. The cosmesis 1566 may be formed from silicone or a similar material, such as a urethane, to improve the grip capabilities of the hand assembly 1024 to assist with the various grasping and pinch functions of the hand, thereby, providing additional functionality.

Figure 68A:
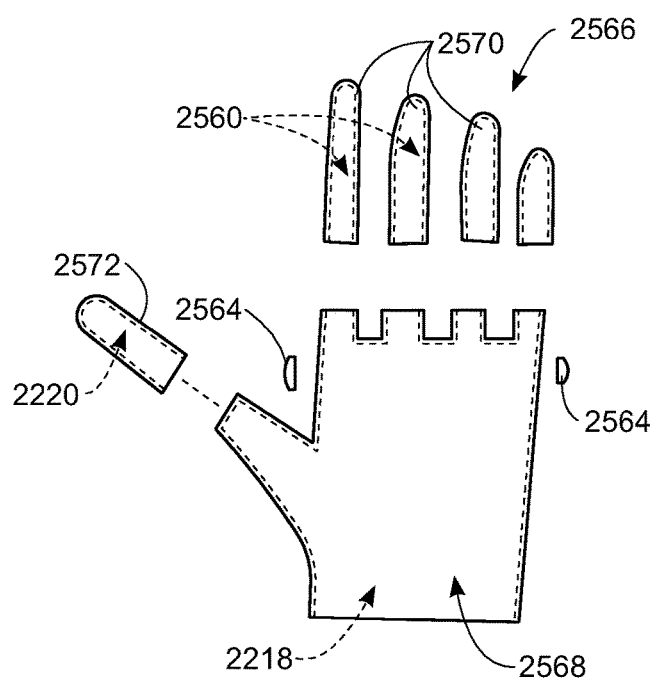
FIG. 68A is a front view of an embodiment of the cosmesis of FIG. 67 with removable finger portions.

In use, the cosmesis 1566 may wear more quickly around the fingers 1560 and the thumb structure 1220. Therefore, in some embodiments the cosmesis 1566 may separate into two or more sections to allow high wear areas to be replaced more frequently than low wear areas. For instance, referring to FIG. 68A, in some embodiments, the cosmesis 2566 includes a separate palm section 2568 covering the hand support 2218, finger sections 2570 covering each finger 2560 and a thumb section 2572 covering the thumb structure 2220. Thus, the finger sections 2570 and thumb section 2572 may each be replaced separately from the palm section 2568. Although shown as having separate finger sections 2570 and thumb section 2572, in various embodiments, the cosmesis 2566 may also include only two sections, for example, the finger sections 2570 and the thumb section 2572 may be combined into one section and the hand support 2218 may be covered by the separate palm section 2568.

Figure 40:
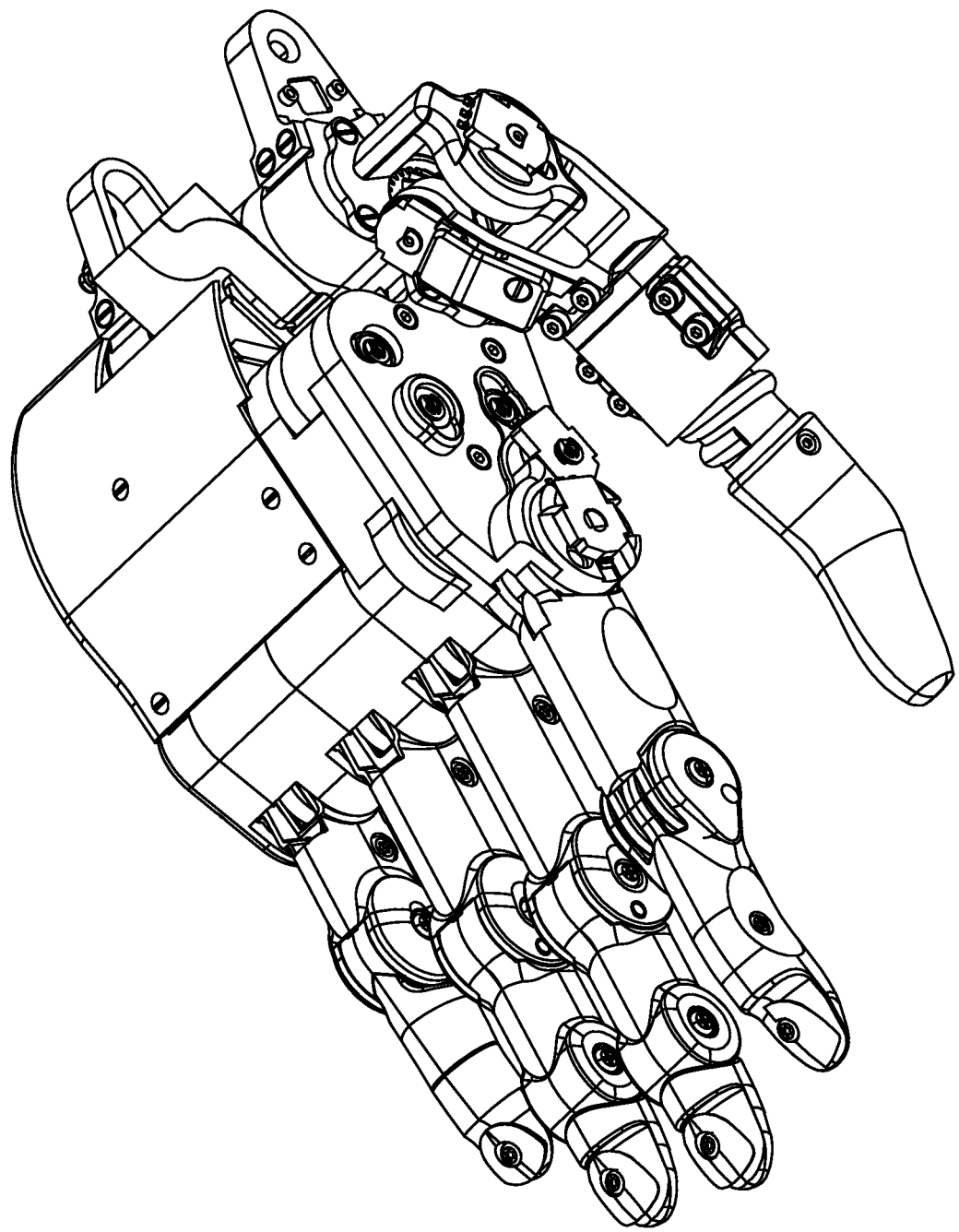
FIG. 40 is a perspective view of another embodiment of the hand.
Figure 68B:
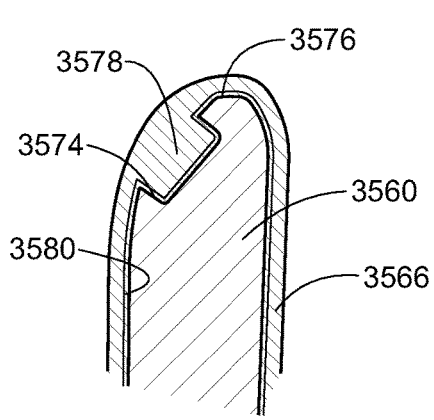
FIG. 68B is a cross-sectional view of an embodiment of a finger structure cosmesis of FIG. 68A.

Referring to FIG. 68B, in some embodiments of the present invention, the fingers 3560 may be provided with geometric features 3574, such as slots, in their outer surfaces 3576 that may accept corresponding geometric interlocks 3578 provided on the inner surface 3580 of the cosmesis 3566. This interlocking geometry may resist shear loads on the cosmesis 3566, thereby preventing the cosmesis 3566 from slipping off of the fingers 3560. Additionally, with respect to the hand cosmesis, fine pinch and other functions may require a structural backing at the tips of the fingers 3560 and thumb structure 3220. Therefore, in some embodiments, the geometric features 3574 of the fingers 3560 and thumb structure 3220 may each include a fingernail apparatus 579, shown in FIG. 40. The fingernail apparatus 579, shown in FIG. 40, interacts with the finger and thumb structure cosmesis 3566 to anchor the cosmesis 3566 of the fingers 3560 and thumb structure 3220, thereby mitigating and/or preventing the cosmesis 3566 from rolling over on the tips of the fingers 3560 and thumb structure 3220.

Figure 69:
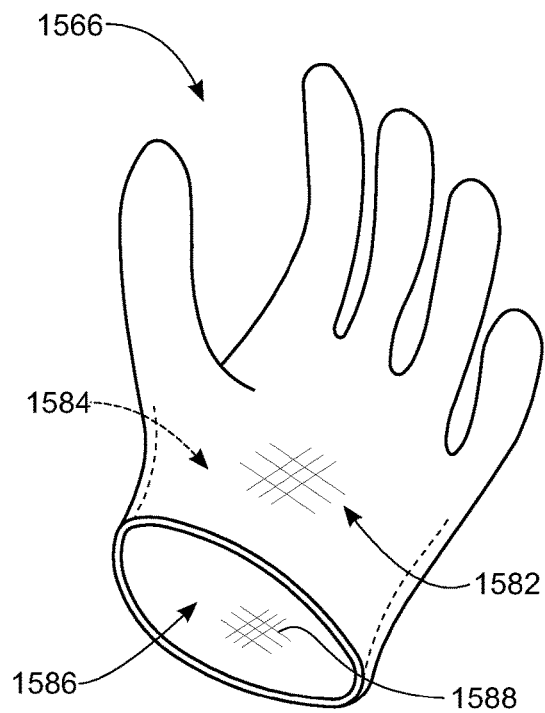
FIG. 69 is a perspective view of another embodiment of the cosmesis of FIG. 67.

Referring to FIG. 69, the palm section 1568 of the cosmesis 1566 may also be formed to resist slippage due to shear loads. For instance, a palm side 1582 of the cosmesis 1566 may be formed with a tacky inner surface 1584. In some embodiments, the material of the cosmesis 1566 itself will provide the tacky inner surface 1584, for example, silicone or a urethane material may be naturally tacky. In other embodiments, a tacky surface coating may be applied to the cosmesis to form the tacky inner surface 1584. Thus, as objects being held are pressed against the palm side 1582 of the cosmesis 1566, the tacky inner surface 1584 is pressed against the hand support 218, shown in FIG. 29, thereby resisting slippage. In some embodiments, a back side 1586 of the cosmesis 1566 is formed with a slippery inner surface 1588 to facilitate installation and removal of the cosmesis 1566. For example, the slippery inner surface 1588 may be formed by applying a surface modifying coating to the cosmesis, or applying a surface texture to the cosmesis 1566. For example, to install the cosmesis 1566 onto the hand support 218, shown in FIG. 29, the cosmesis 1566 may be pulled down and away from the palm so that the slippery inner surface 1588 of the back side 1586 slides along the hand support 218, while the tacky inner surface 1584 of the palm side 1582 is pulled away from the hand support 218. Thus, the cosmesis 1566 may be easily slid onto the hand support 218. To remove the cosmesis 1566, the palm side 1582 may again be pulled away from the hand support 218 while the cosmesis 1566 is pulled toward the fingers 1560, thereby allowing the cosmesis 1566 to slide easily off the hand support 218.

Figure 70:
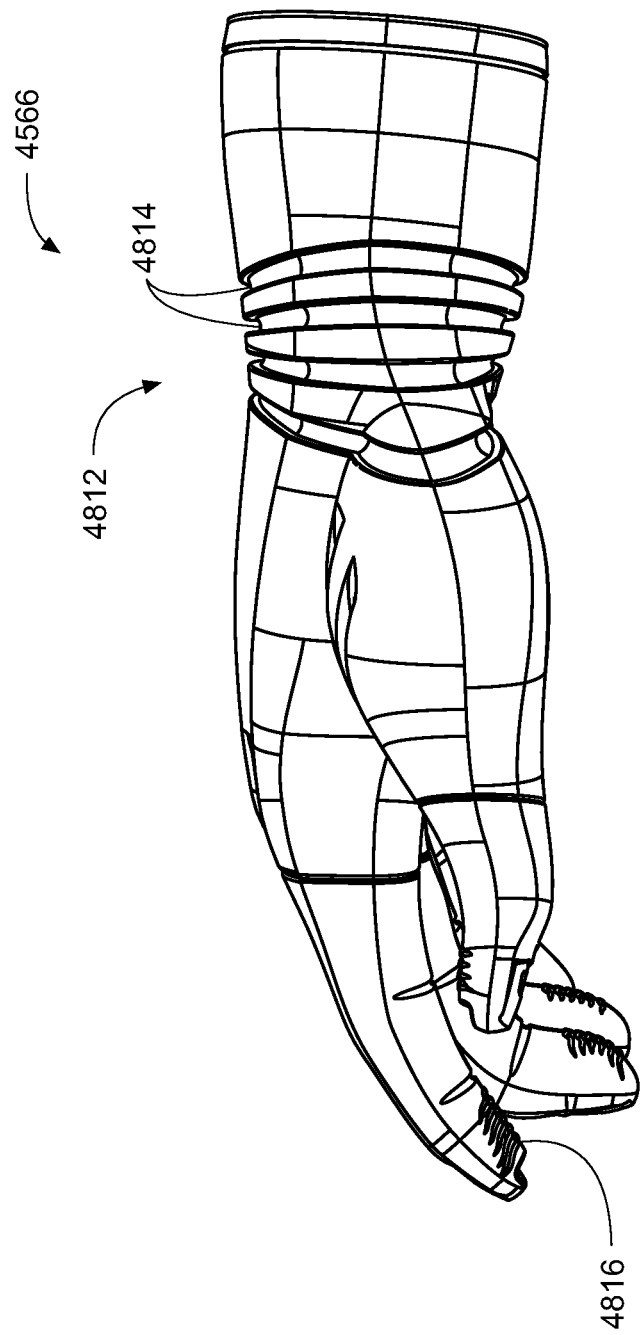
FIG. 70 is a side perspective view of another embodiment of a cosmesis according to the present invention.

Referring to FIG. 70, in some embodiments, the cosmesis 4566 may include corrugations 4812 having grooves 4814 wherein a thickness of the material forming the cosmesis 4566 is substantially less than the thickness of material of the rest of the cosmesis 4566. The corrugations 4812 and grooves 4814 may advantageously be positioned in locations where the prosthetic arm apparatus 10, shown in FIG. 1, moves and flexes to allow the cosmesis 4566 to flex along with the arm movement without bunching, wrinkling, tearing or the like. Additionally, although the corrugations 4812 are shown only in a wrist area for simplicity, it should be understood by those skilled in the art that the corrugations 4812 may be positioned in other locations where substantial movement is anticipated such as the fingers. In some embodiments, the cosmesis 4566 may also include raised ridges 4816 having a material thickness that is greater than substantially the rest of the cosmesis 4566 to provide improved grip in desired regions such as at the fingertips of the cosmesis 4566.

Figure 71:
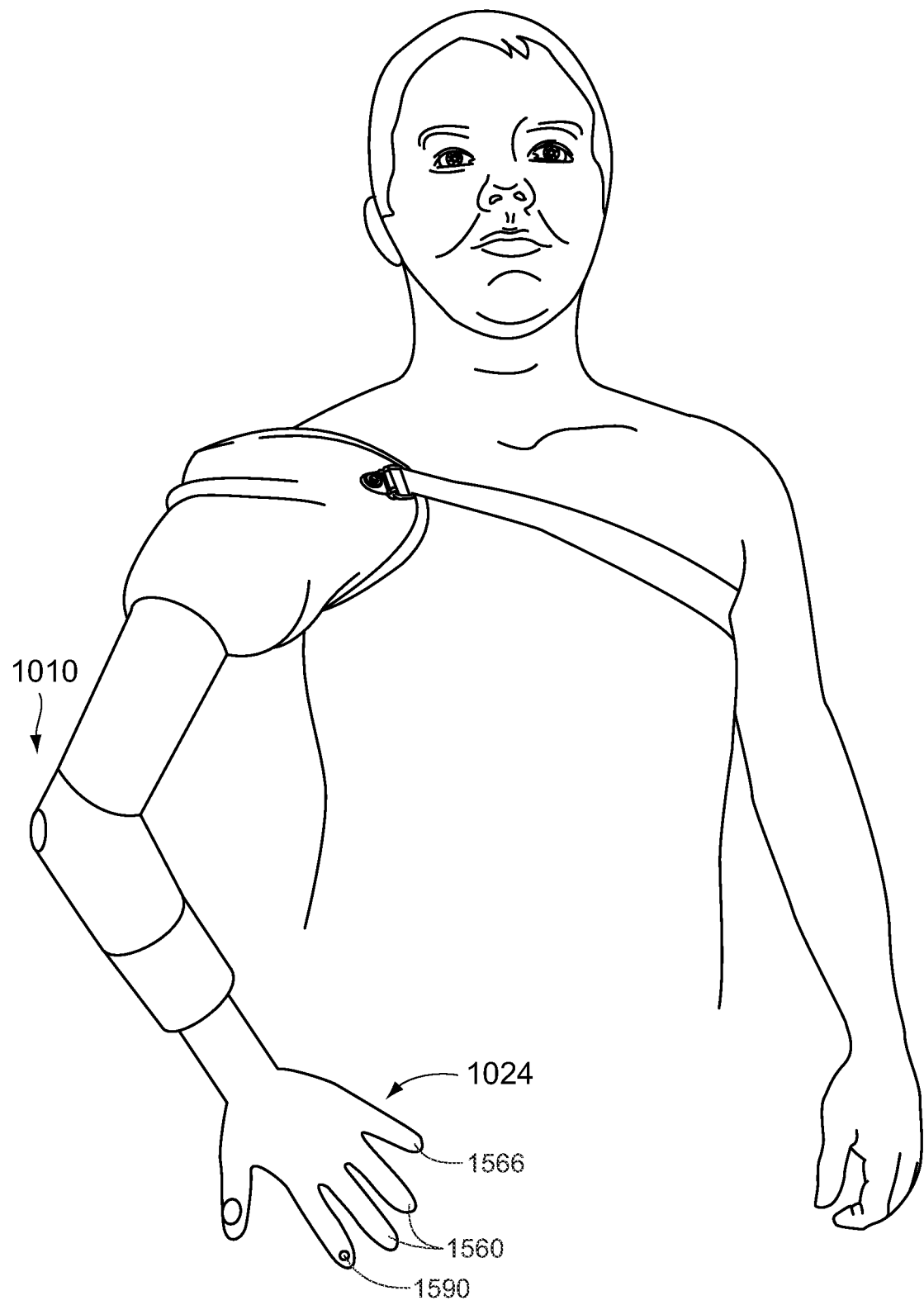
FIG. 71 is a perspective view of a prosthetic arm apparatus having a temperature sensor according to an embodiment of the present invention.

Referring to FIG. 71, in some embodiments, the fingers 1560 may include one or more additional functions. For example, one or more fingers 1560 may include a thermal sensor 1590 disposed thereon to determine the temperature of an object (not shown) brought into contact with the finger 1560. The signal from the sensor 1590 may be transmitted to a controller (not shown) for the prosthetic arm 1010 and displayed to the user as will be discussed in greater detail below. In some embodiments, temperature detection may be provided by forming the cosmesis 1566, or a portion thereof, from a temperature sensitive polymer, such as a polymer with a thermochromic color changing additive therein or thermochromic liquid crystal that allows a variety of colors to be shown as temperature changes, which will change color depending upon the temperature of the cosmesis 1566. For example, the cosmesis 1566 may change from one color to another if a present temperature is exceeded. This temperature sensing functionality may be used to determine the temperature of an object (not shown) in the hand 1024 and to warn the user of a high temperature or low temperature condition to mitigate the threat of burns or other harm.

Figure 72A:
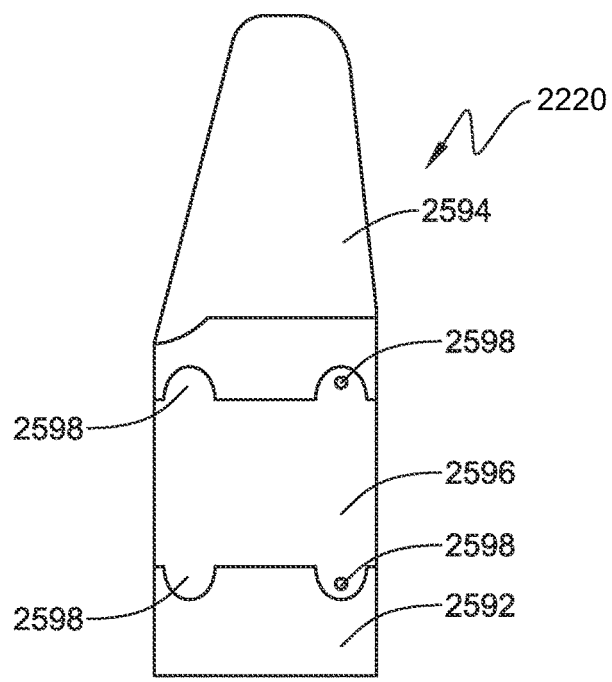
FIG. 72A is a side view of a thumb structure according to an embodiment of the present invention.

Referring to FIG. 72A, another embodiment of the thumb structure 2220 is shown for providing thumb compliance detection. The thumb structure includes a thumb base 2592 and a thumb tip 2594, which are each substantially rigid and are joined together by an elastomeric spring 2596. In some embodiments, the interface between the thumb tip 2594 and the elastomeric spring 2596 includes one or more alignment features 2598 to ensure proper alignment of the thumb tip 2594 with the elastomeric spring 2596. Similarly, the interface between the thumb base 2592 and the elastomeric spring 2596 also includes one or more alignment features 2598 to ensure proper alignment of the thumb base 2592 and the elastomeric spring 2596.

Figures 72B, 72C:
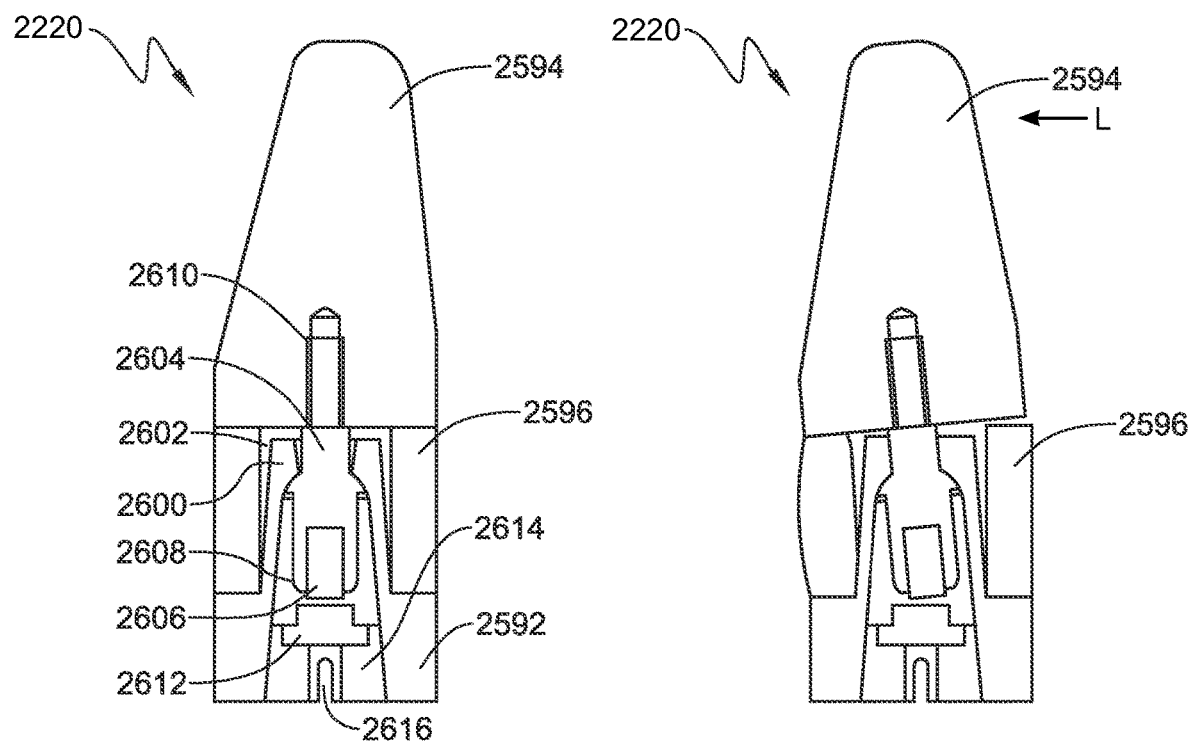
FIG. 72B is a side cross-sectional view of the thumb structure of FIG. 72A.
FIG. 72C is a side cross-sectional view of the thumb structure of FIG. 72A under a load.

Referring to FIG. 72B, within the thumb structure 2220, the thumb base 2592 includes a pivotal interface tube 2600 extending upward into a central bore 2602 of the elastomeric spring 2596. A pivot shaft 2604, having a magnet 2606 disposed at its lower end 2608, is arranged with the pivotal interface tube 2600 and extends upwardly therefrom into a central bore 2610 in the thumb tip 2594 of substantially the same diameter as the pivot shaft 2604. Below the pivot shaft 2604 within the thumb base 2592 is arranged a Hall effect sensor 2612 on a sensor bracket 2614. The sensor bracket 2614 includes a wire channel 2616 to facilitate wiring the Hall effect sensor 2612 to the prosthetic control circuits (not shown). Referring to FIG. 72C, in operation, when a load L is applied to the thumb tip 2594 the elastomeric spring 2596 compresses on the side of the thumb structure 2220 opposite the applied load L, allowing the thumb tip 2594 to tilt. The tilt of the thumb tip 2594 causes a corresponding tilt of the pivot shaft 2604 within the pivotal interface tube 2600, thereby displacing the magnet 2606 disposed on the lower end 2608 of the pivot shaft 2604. The Hall effect sensor 2612 detects this displacement of the magnet 2606, which can be correlated to the applied load L on the thumb tip 2594. By detecting the various loads on the thumb structure 2220, the user may ensure that objects are not gripped so hard that they could break and that the thumb is not subjected to loads that could cause failure of the thumb structure 2220.

Figure 73:
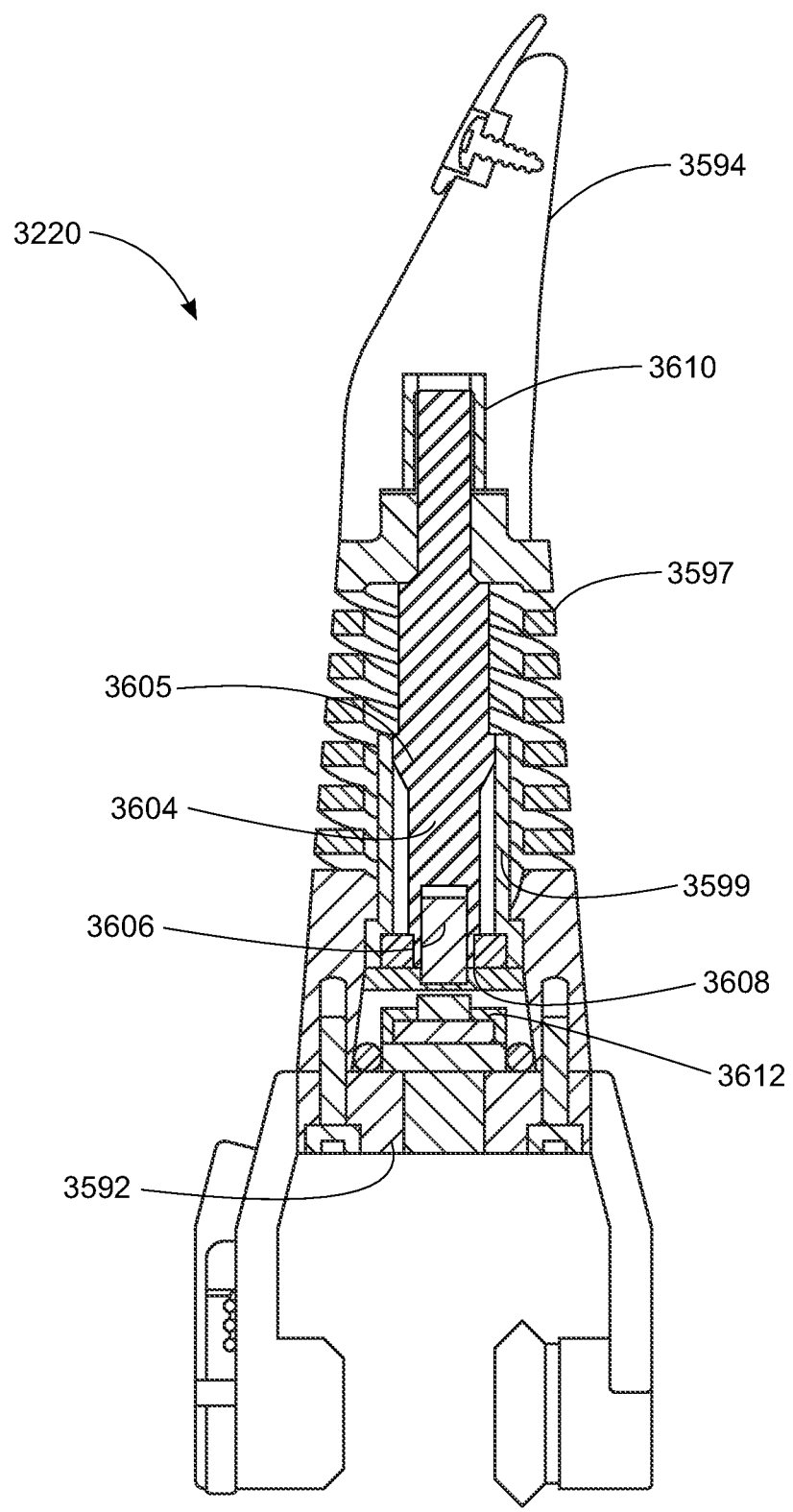
FIG. 73 is a side cross-sectional view of a thumb structure according to another embodiment of the present invention.

Referring to FIG. 73, wherein like numerals represent like elements, another embodiment of the thumb structure 3222 is shown for providing thumb compliance detection. In this embodiment, a helical spring 3597 replaces the elastomeric spring 2596, shown in FIG. 72B, between the thumb base 3592 and the thumb tip 3594. Additionally, a collar 3599 is disposed between the helical spring 3597 and the pivot shaft 3604 with a small clearance between a ball 3605 of the pivot shaft and the collar 3599. As with the previous embodiments, the pivot shaft 3604 has magnet 3606 disposed at its lower end 3608 and extends upwardly therefrom into a central bore 3610 in the thumb tip 3594 and is secured therein. Below the pivot shaft 3604 within the thumb base 3592 is arranged sensor 3612 for detecting movement of the magnet 3606. In operation, when a load L is applied to the thumb tip 3594, the ball 3605 contacts the collar 3599 and the helical spring 3597 compresses on the side of the thumb structure 3222 opposite the applied load L, allowing the thumb tip 3594 to tilt about the center of the ball 3605. The tilt of the thumb tip 3594 causes a corresponding tilt of the pivot shaft 3604, thereby displacing the magnet 3606 disposed on the lower end 3608 of the pivot shaft 3604. The sensor 3612 detects this displacement of the magnet 3606, which can be correlated to the applied load L on the thumb tip 3594. By detecting the various loads on the thumb structure 3222, the user may advantageously ensure that objects are not gripped so hard that they could break and that the thumb is not subjected to loads that could cause failure of the thumb structure 3222.

Figure 74:
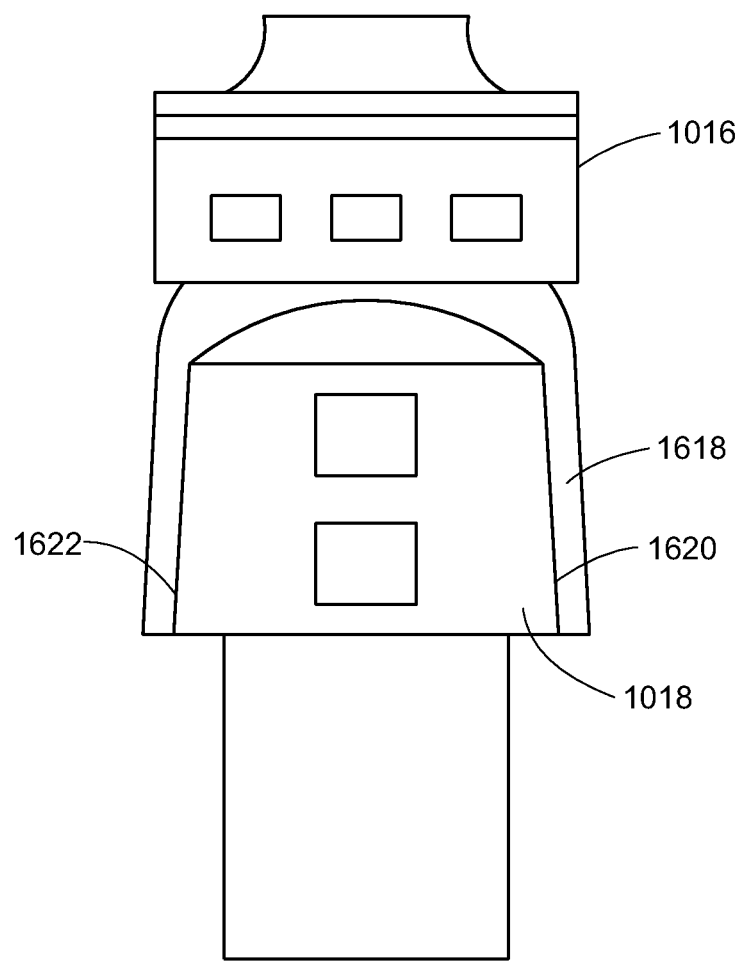
FIG. 74 is a top view of a humeral rotator and an elbow flexion assembly according to another embodiment of the present invention.

Referring to FIG. 74, in some embodiments, the humeral rotator 1016 may include a yolk 1618, rather than the cantilever mounting interface shown in FIG. 16, for interfacing with the elbow flexion assembly 1018. The yolk 1618, interfaces with a first side 1620 and a second side 1622 of the elbow flexion assembly 1018 to provide increased strength to the interface when compared to the cantilever mounting interface shown in FIG. 16, which only interfaces with one side of the elbow flexion assembly 1018.

Figure 75A:
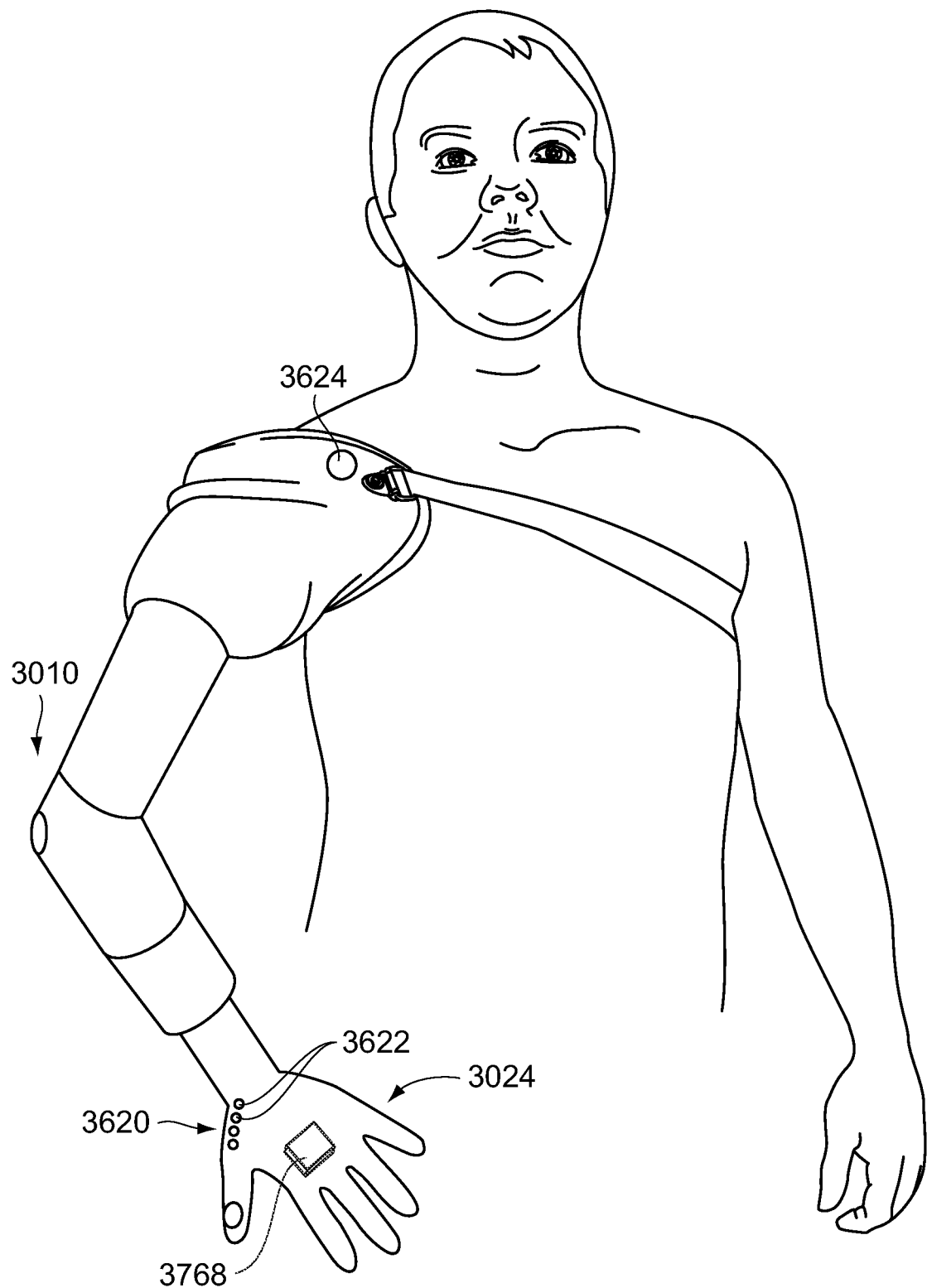
FIG. 75A is a perspective view of a prosthetic arm apparatus having safety features according to an embodiment of the present invention.
Figure 75B:
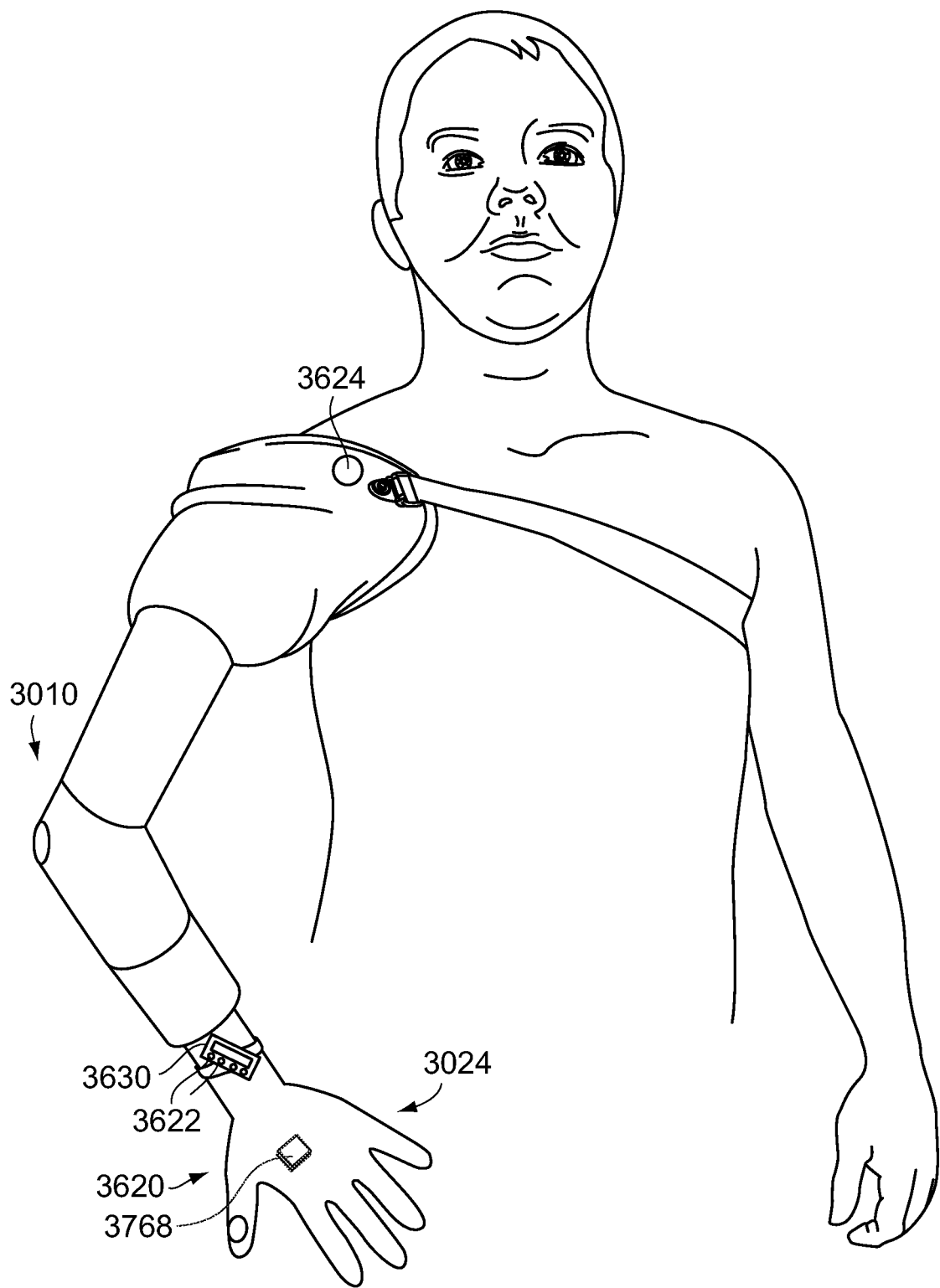
FIG. 75B is a perspective view of a prosthetic arm apparatus having safety features according to an embodiment of the present invention.

Referring to FIG. 75A, in some embodiments of the present invention, the prosthetic arm 3010 may be provided with a status indicator 3620. In some embodiments the status indicator 3620 may include, but is not limited to, one or more LEDs 3622 arranged on the hand assembly 3024. However, in other embodiments, the one or more LEDs 3622 may be located in various locations. The one or more LEDs 3622 may be configured to communicate a variety of information to the user, including, but not limited to, one or more of the following, battery power level, an operational mode of the prosthetic device, faults, alarms, alerts, messages, and/or the like. Additionally, although shown as one or more LEDs 3622 the status indicator 3620 may, in other embodiments, include a digital display and/or user interface, which may be arranged on the prosthetic device 3010, built into the prosthetic device 3010 and/or may be a separate display unit (for example, as shown in FIG. 75B as 3630), and in some embodiments, may be a unit worn similarly to a wrist watch or bracelet as shown in FIG. 75B as 3630. However, in other embodiments, the unit 3630 may be a portable unit that may be worn or carried near the user, for example, but not limited to, clipped on clothing, belt and/or attached to the user, and/or carried in a pocket either in the user's clothing and/or in a separate bag and/or pack. In some embodiments, the unit 3630 may be a PDA (personal data assistant), smart phone or other electronic device configured to communicate with the prosthetic device 3010 by way of a wireless communications protocol, including, but not limited to, RF and Bluetooth®.

Thus, in some embodiments, it may be desirable to include both a separate display unit and one or more LEDs 3622, where, for example, but not limited to, the one or more LEDs 3622 may be used to display one or more critical piece of information to the user, while the separate display unit, 3630 may provide a greater variety of information in more detail.

Figure 75C:
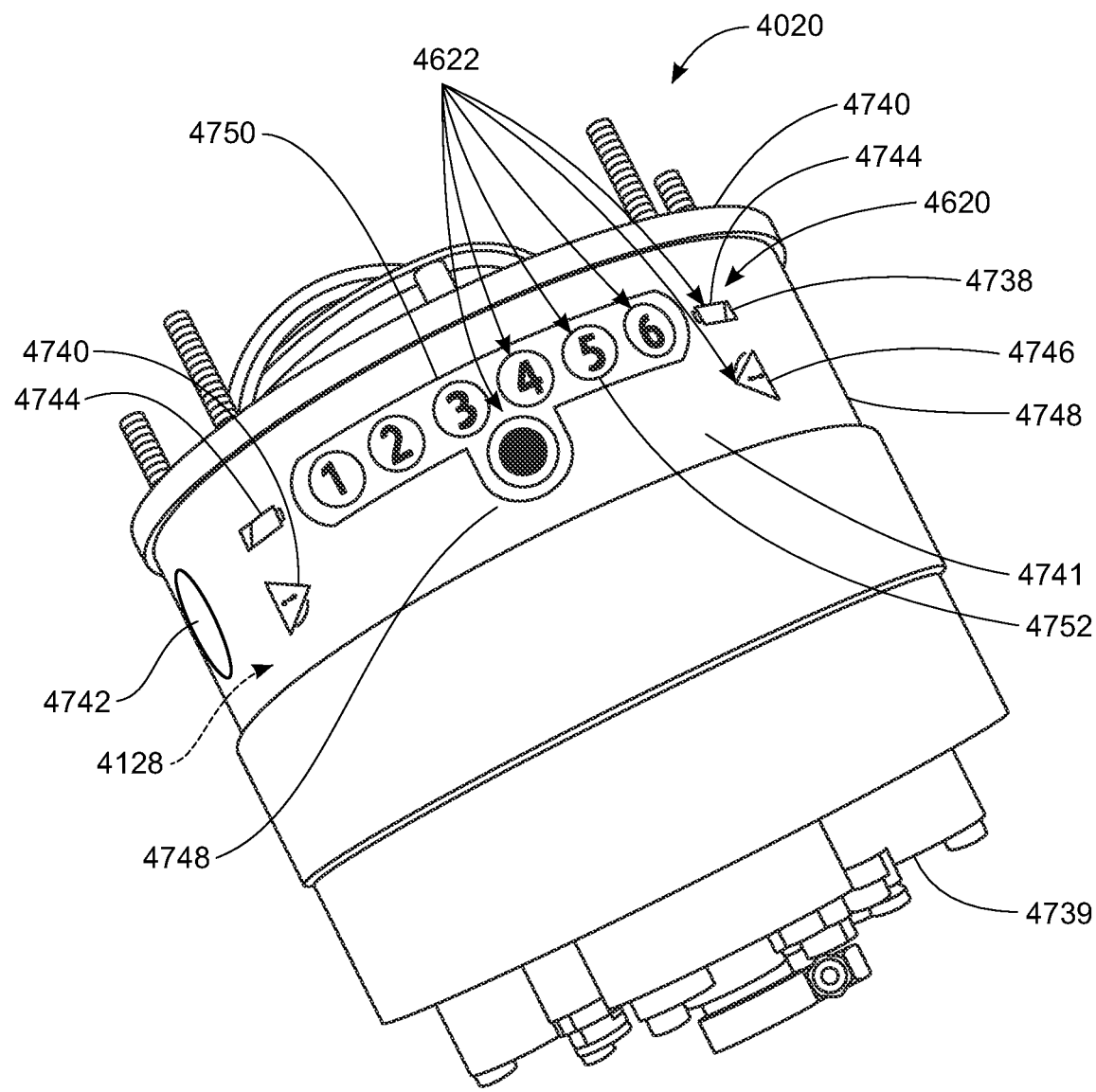
FIG. 75C is a perspective view of the wrist rotator according to an embodiment of the present invention.

Referring to FIG. 75C, an embodiment of the wrist rotator 4020 having the ACM stack 4128 housed therein is shown. The wrist rotator 4020 includes a housing 4738 having an input interface 4739, such as the elbow interface 170, shown in FIG. 23, and an output interface 4740, such as the wrist flexion assembly interface 172, shown in FIG. 23, at either end thereof. The housing also includes a user interface 4741 formed therein and in communication with the ACM stack 4128. The ACM stack 4128 controls operation of each segment of the prosthetic arm apparatus 10, shown in FIG. 1, including the wrist rotator 4020 and, therefore, integrating the ACM stack 4128 into the wrist rotator 4020 may be advantageous since the wrist rotator 4020 is likely to be present in prosthetic arms for essentially all types of amputees, whereas other segments may not be present, such as in a prosthetic arm apparatus for a transradial amputee.

The user interface 4741 may include the status indicator 4620 for communicating status information of the prosthetic arm apparatus 10, shown in FIG. 1, from the ACM stack 4128 to the user. The user interface 4741 may also include one or more user inputs 4742, such as buttons, switches, dials or the like for changing and/or customizing the status information that is conveyed from the ACM stack 4128 through the status indicator 4620.

The status indicator 4620 may include one or more LEDs 4622 configured to communicate the status information from the ACM stack 4128 to the user through illumination of the LEDs 4622. For instance, specific information may be communicated to the user through simple illumination, flashing patterns, color patterns and/or various combinations thereof. The LEDs 4622 may include a battery alert 4744 for alerting the user of a low power condition. Similarly, the LEDs 4622 may include a system alert 4746 for alerting the user of a system fault condition. The LEDs may include a mode indicator 4748, for example, to indicate whether the prosthetic arm apparatus 10, shown in FIG. 1, is in mode for controlling arm movement or a mode for controlling hand movement. Additionally, the LEDs 4622 may include an array 4750 of LEDs 4622 for providing specific information to the user on the current operational mode of the prosthetic device. For instance, when in a hand control mode, each LED 4622 in the array 4750 may represent a different sub control mode of the prosthetic device 10, shown in FIG. 1, such as different grip movements. In some embodiments, LEDs 4622 may be arranged at multiple locations around the circumference of the wrist rotator 4020 so that at least some of the LEDs 4622 remain visible to the user as the prosthetic arm 10, shown in FIG. 1, moves during operation.

Preferably, the user interface 4741 is formed from a rubberized material to allow actuation of the one or more user inputs 4742 therethrough and to prevent contaminants such as dirt, dust, water and the like from contacting and damaging the wrist rotator 4020. Additionally, the rubberized material preferably includes one or more translucent portions 4752 in the region of the status indicator 4620 for allowing light from the LEDs 4622 to pass therethrough and may also include one or more symbols printed on the translucent portions 4752 for conveying status information to the user.

Figure 75D:
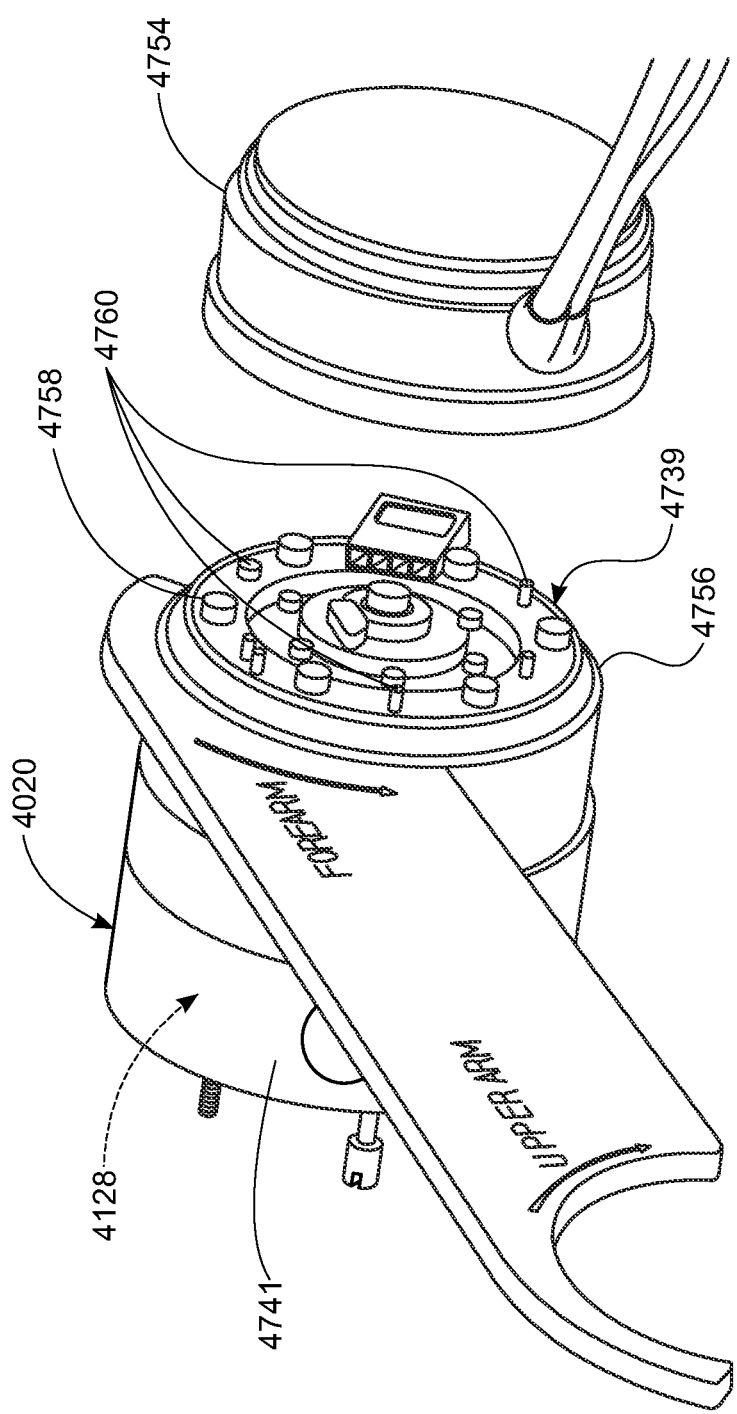
FIG. 75D is a side perspective view of the wrist rotator and a transradial mount according to an embodiment of the present invention.
Figure 75E:
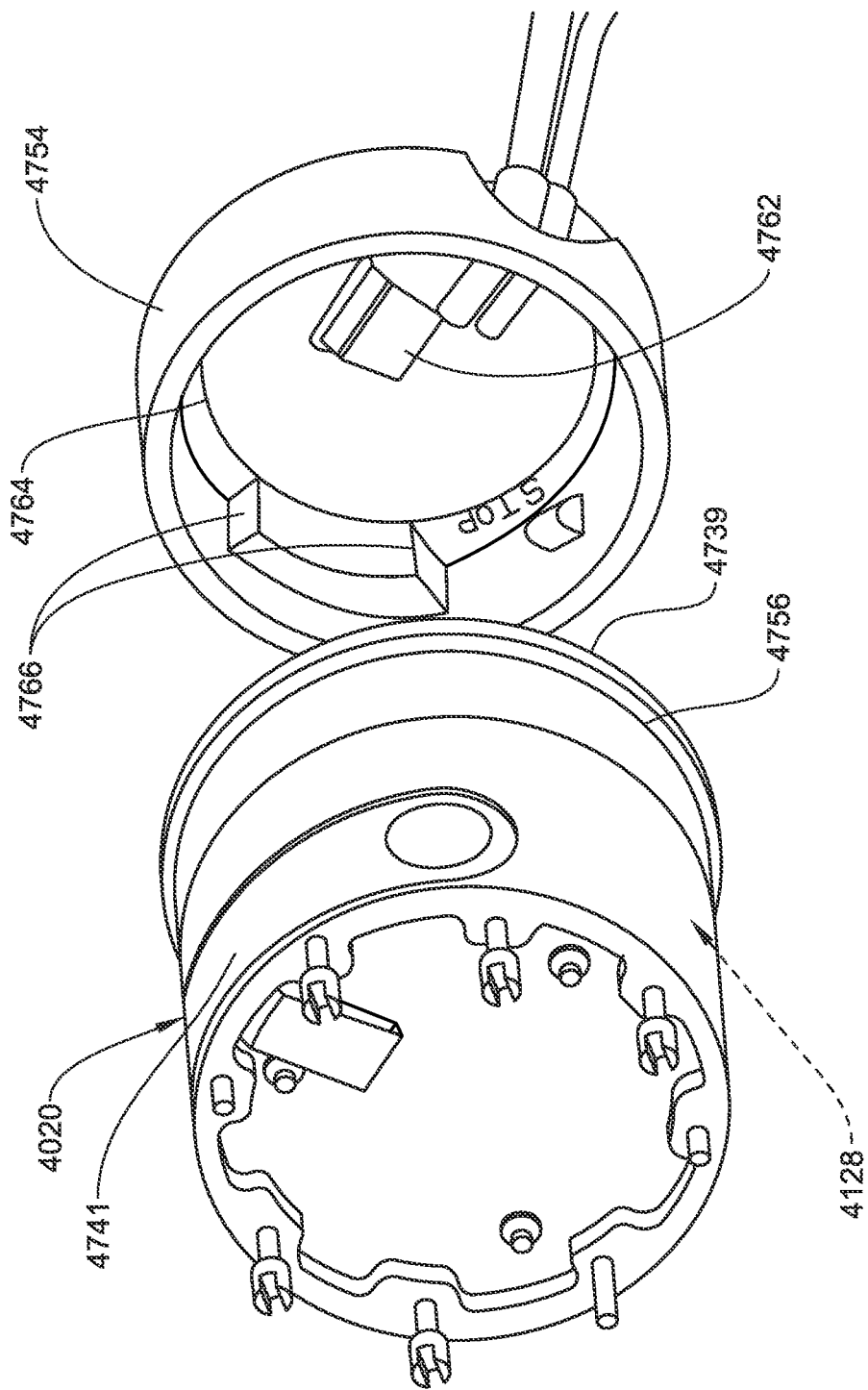
FIG. 75E is a front perspective view of the wrist rotator and a transradial mount of FIG. 75D.

Referring to FIGS. 75D and 75E, as discussed above, the wrist rotator 4020 having the ACM stack 4128 and the user interface 4741 is preferably a modular unit that may connect either to a transradial mount 4754 for a transradial amputee or the elbow flexion assembly 18, shown in FIG. 1, for a transhumeral or shoulder disarticulated amputees. To facilitate the connection, the input interface 4739 includes a captive spanner screw 4756 having male threads, an alignment pin 4758 and one or more torque transmission pins 4760. The transradial mount 4754 (or the elbow flexion assembly 18, shown in FIG. 1) includes female threads for engaging the male threads of the captive spanner screw 4756, a left hand alignment hole 4762, a right hand alignment hole 4764 and one or more torque transmission holes 4766.

To assemble the wrist rotator 4020 to the transradial mount 4754 or the elbow flexion assembly 18, shown in FIG. 1, power and communication wiring connections are first made between the parts. Then, the alignment pin 4758 of the wrist rotator 4020 is registered in either the left hand alignment hole 4762 or the right hand alignment hole 4764 of the transradial mount 4754 (or the elbow flexion assembly 18, shown in FIG. 1), depending upon whether the prosthetic arm apparatus 10, shown in FIG. 1, is to be a left-handed or right-handed prosthesis, respectively. A spanner wrench may then be used to engage the spanner screw 4756 and thread the male threads of the spanner screw 4756 into the female threads of the transradial mount 4754 (or the elbow flexion assembly 18, shown in FIG. 1). As the male threads engage the female threads, the torque transmission pins 4760 engage the torque transmission holes 4766 until the spanner screw 4756 is fully seated. This connection advantageously provides a universal interface between the wrist rotator 4020 and either the transradial mount 4754 or the elbow flexion assembly 18, shown in FIG. 1. The connection is also advantageously universal for both left-handed and right-handed prosthetic devices. For example, the using the right hand alignment hole 4764 provides for a desired range of motion for a right-handed prosthetic device, such as two hundred seventy degrees (270°). Using the left hand alignment hole 4762 provides a range of motion for a left-handed prosthetic device that is the mirror opposite of the range of motion for the right-handed prosthetic device, for example two hundred seventy degrees (270°) in the opposite direction of rotation. Additionally, when using either the left hand alignment hole 4762 or the right hand alignment hole 4764 in the connection, the user interface 4741 is advantageously maintained in the view of the user.

Referring back to FIGS. 75A and 75B, in some embodiments of the present invention, the prosthetic arm 3010 may be provided with an emergency switch 3624 which may turn off power to the system and thus engage the various brakes and/or clutches in the prosthetic arm 3010. In some embodiments, the emergency switch 3624 is a chin switch that the user may activate with their chin.

In some embodiments, another safety mechanism of the prosthetic arm 3010 may include an auto release mechanism 3768 for manually opening a grip of the prosthetic hand 3024. The auto release mechanism 3768 may be a button, switch or the like located on the back of the prosthetic hand 3024, which, when actuated, causes the prosthetic hand 3024 to open. Preferably, the auto release mechanism 3768 is located under the cosmesis 1566, shown in FIG. 67, and actuated therethrough, to prevent contaminants such as dirt, dust, water and the like from contacting and damaging the auto release mechanism 3768. The auto release mechanism 3768 is electrically coupled to a power source (not shown) of the prosthetic arm 3010, such as a battery, and to motor control circuits, such as the hand control module circuit boards 192, shown in FIG. 25, that control actuation of the motors within the prosthetic hand 3024, such as the two thumb drives 232, the index drive 234 and the MRP drive 236, all shown in FIGS. 31-34. Preferably, the auto release mechanism 3768 is connected to the motor control circuits for the two thumb drives 232, the index drive 234 and the MRP drive 236, all shown in FIGS. 31-34, in parallel to provide redundancy to the auto release mechanism 3768 so that even if one circuit fails, the others will still cause the associated prosthetic fingers to open. In some embodiments, additional redundancy may be provided to the auto release mechanism 3768 by connecting the auto release mechanism 3768 to the motor control circuit boards 192 through at least two switches, with only one switch being required to cause the prosthetic hand 3024 to open.

In operation, the user may depress the auto release mechanism 3768, which, in turn, actuates the switch or switches on the hand control module circuit boards 192. Actuation of the switch or switches causes power to be supplied from the power source (not shown) to the two thumb drives 232, the index drive 234 and the MRP drive 236, all shown in FIGS. 31-34, through the hand control module circuit boards 192, which causes the prosthetic hand 3024 to open. The speed at which the prosthetic hand 3024 opens may be tuned within the hand control module circuit boards 192 and is preferably less than approximately five (5) seconds. In some embodiments, the speed at which the prosthetic hand 3024 opens may even more preferably be set to less than approximately three (3) seconds. Thus, the user may advantageously actuate the auto release mechanism 3768 to release the grip of the prosthetic hand 3024 if it is closed and/or becomes stuck in hazardous and/or harmful situations; for example, if the grip becomes stuck around a car door handle, a bus handle, while shaking a child's hand or any other similar situation.

Although the auto release mechanism 3768 has been described as being electrically coupled to the power source (not shown) of the prosthetic arm 3010 and to the hand control module circuit boards 192, in other embodiments, the auto release mechanism 3768 may include a separate power source (not shown) and/or separate motor control circuits (not shown) located within the prosthetic hand 3024 to provide additional redundancy. Additionally, in other embodiments, the auto release mechanism 3768 may be a mechanical system rather than an electrical system, for example, the auto release mechanism 3768 may be a crank or the like for manually opening the prosthetic hand 3024.

The prosthetic arm apparatus of the present invention has a variety of benefits over conventional prosthetic devices, such as the modularity of each segment of the prosthetic arm apparatus as discussed above, which allows the formation of customized prosthetic devices for different users. In particular, each segment of the prosthetic arm apparatus 10 contains all of the actuators for that segment so that it may be removed as a separate unit. For instance, the hand assembly includes all of the finger actuators therein, allowing it to be connected and/or removed as a separate unit. Additionally, various degrees of freedom of the hand assembly are particularly beneficial because they allow the formation of various grasps or grips.

Although the invention has been described in the context of a prosthetic arm, an apparatus according to the elements of this invention could be used in other robotic tools, such as those used in manufacturing and/or teleoperations, where an operator is not connected directly to the controlled device. For example the prosthetic arm apparatus may be used for teleoperation in hazardous environments and/or hazardous activities, for the detonation of explosive devices or the like. In these environments, the prosthetic arm apparatus may provide a more intuitive interface for the user since the user will already be familiar with the natural movements of the arm, which may make control translation of the prosthetic arm apparatus easier.

Figure 97:
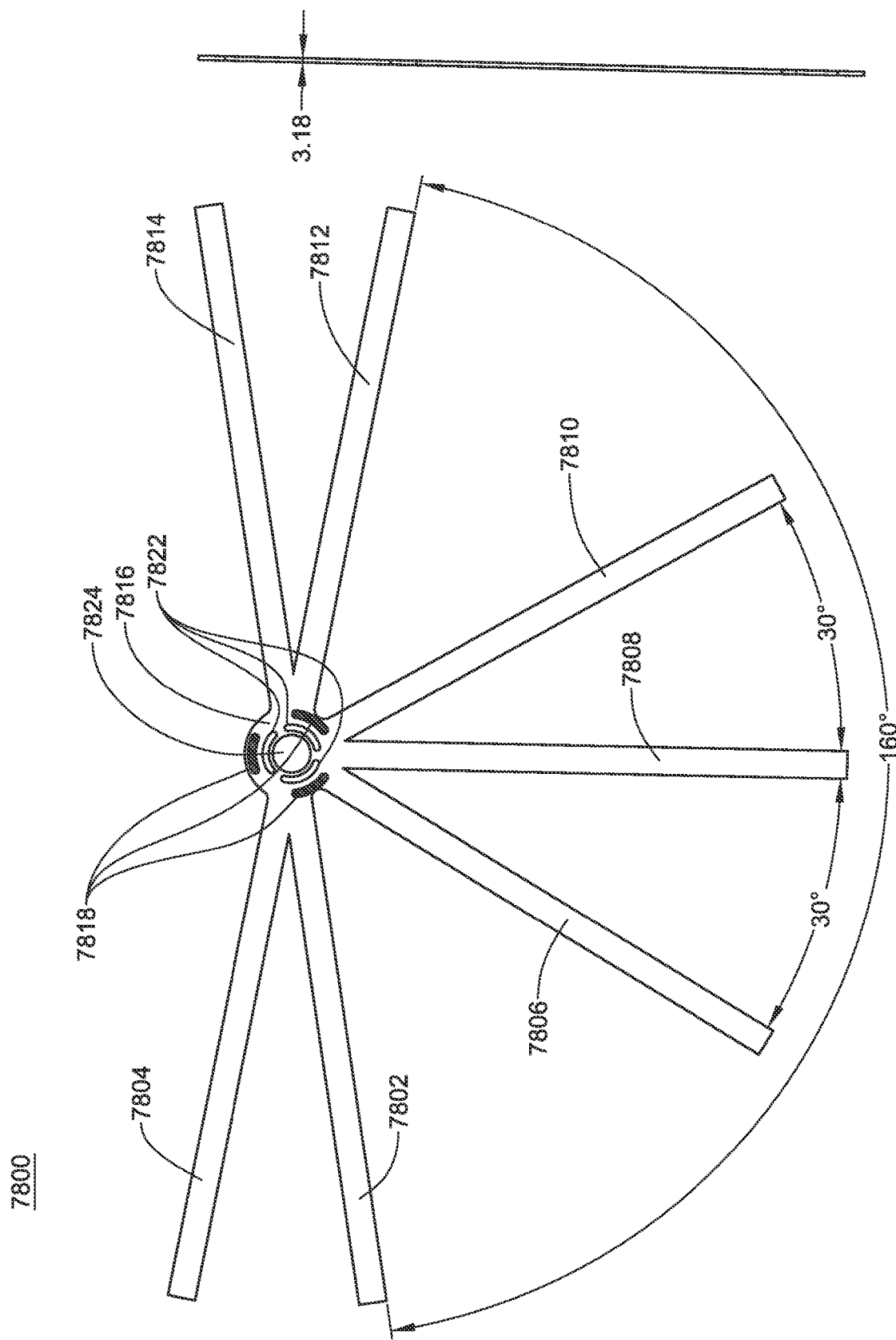
FIG. 97 is a top view of one embodiment of a socket preparation device/frame.

Referring now also to FIG. 97, in some embodiments, a portion of the prosthetic arm attaches to a socket or other device to attach the prosthesis to a user. In some embodiments, the socket may be made using a multistep procedure including, but not limited to, casting and/or creating the socket which may include attaching a device that connects the socket to the prosthesis. In some embodiments, it may be desirable to use a method of casting/creating the socket that allows for flexibility and or options in the size and shape of the socket. This may be desirable for many reasons, including, but not limited to, fitting the socket to the user such that the socket is comfortable and conforms with the user's body.

Referring still to FIG. 97, in some embodiments, a frame 7800 or socket preparation device (which may herein be referred to as a frame) as shown, may be used in creating the socket. The frame 7800 may include a plurality of legs 7802, 7804, 7806, 7808, 7810, 7812, 7814 or protrusions, e.g., seven (7), to provide for flexibility in creating the socket. In some embodiments, the number of legs may be seven (7), in other embodiments, the number of legs may be more than 7 and in some embodiments, the number of legs may be less than seven. In practice, a prosthetist, or other, may choose the appropriate legs 7802, 7804, 7806, 7808, 7810, 7812, 7814 for the fit desired and may bend the chosen legs e.g., one or more of 7802, 7804, 7806, 7808, 7810, 7812, 7814, to an appropriate shape and mount the legs 7802, 7804, 7806, 7808, 7810, 7812, 7814 to a socket. Following, the prosthetist, or other, may remove (e.g., cut off) any unnecessary/unused legs. Thus, in some embodiments, the frame allows for a custom fit to the user. In some embodiments, the frame may be made from aluminum or another material that provides for the desired result, for example, in some embodiments, the material may be selected based on the weight to strength ratio as well as its ability to bend without cracking or breaking. In some embodiments, the frame may be made from 5052 aluminum, however, in other embodiments, different grades of aluminum and/or different materials (e.g. metals, plastics, composites, etc) may be used.

Figure 98C:
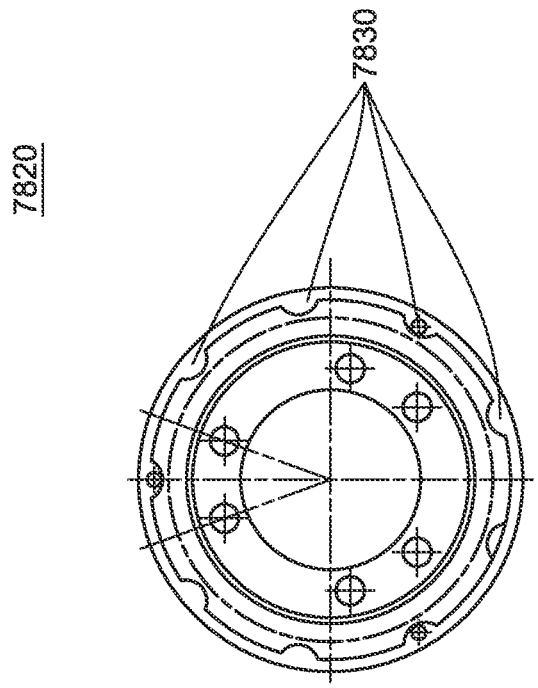
FIGS. 98A, 98B and 98C are various views of one embodiment of a prosthetic mounting device.
Figure 98B:
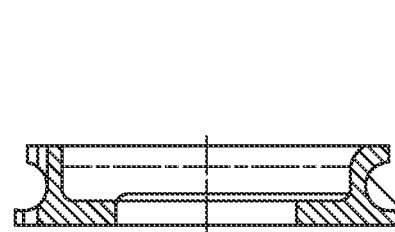
Figure 98A:
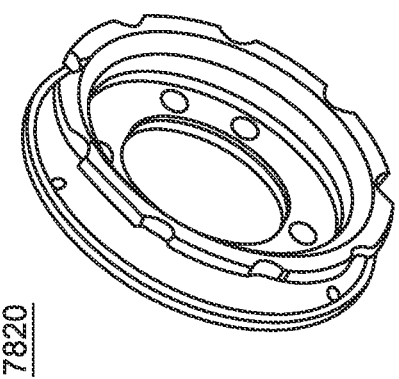

Still referring to FIG. 97, the frame 7800 includes a center portion 7816 at which each leg 7802, 7804, 7806, 7808, 7810, 7812, 7814 attaches. The center portion 7816 is the portion that will attach to a prosthetic mounting device (not shown, shown in FIGS. 98A-98C).

Referring now also to FIGS. 98A-98C and 99A-99D, the prosthetic mounting device 7820 may be attached to the frame. The frame center portion 7816 includes a series of holes 7818 on the outside and a series (3 in the embodiment shown) of openings 7822 on the inside and a large opening 7822 in the center. In some embodiments, the numbers of holes and/or openings may be greater than or less than the numbers shown on the figures. These openings 7818, 7822, and holes 7818 on the frame 7800 correspond to openings and holes on the prosthetic mounting device. As shown in FIGS. 99A-99D, the prosthetic mounting device 7820 attaches to the frame 7800 and to the shoulder portion 7826 of the prosthesis. The arrangements of both the holes and openings on the frame and the holes and openings on the prosthetic mounting device may be beneficial for various reasons, including, but not limited to, the ability to orientate the frame with respect to the prosthetic mounting device and the prosthesis which may provide greater flexibility for custom fitting the socket. In some embodiments, rotation of the frame with respect to the prosthetic mounting device provides+/−10 degree increments of rotation. In other embodiments, the spacing of the various holes and openings may vary and/or the number and/or the location of holes and openings may vary to provide various degrees of increments.

Referring now again to FIG. 98B, the some embodiments of the prosthetic mounting device 7820 are designed to be bonded into the socket. In various embodiments, there is a groove 7828 and anti-rotation features 7830 to connect, e.g. securely connect, to the socket. Using the frame 7800 to position the prosthetic mounting device 7820 in the appropriate location prior to creating the final socket, the prosthetic mounting device may be beneficial for many reasons, including, but not limited to, providing orientation for the socket.

In some embodiments, screws on the outside of the prosthetic mounting device function as pins to prevent rotation while bolts hold/secure the prosthetic mounting device to the prosthesis.

Figure 99C:
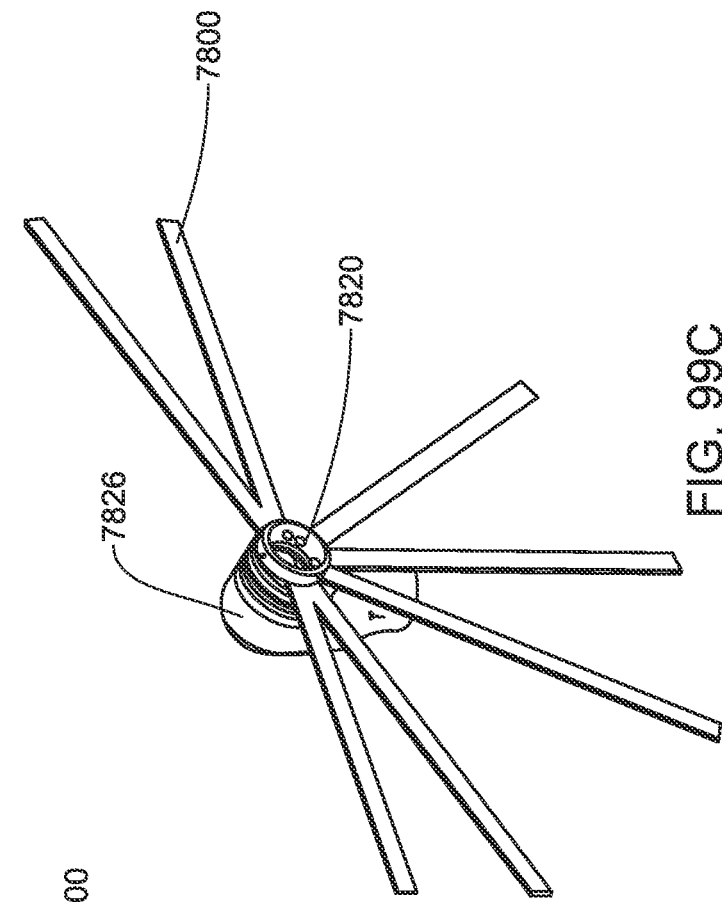
FIGS. 99A, 99B, 99C and 99D show various views of the socket preparation device together with a prosthetic mounting device, according to one embodiment.
Figure 99D:
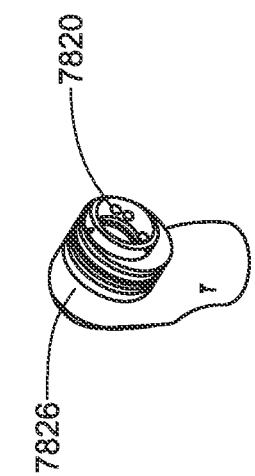
Figure 99A:
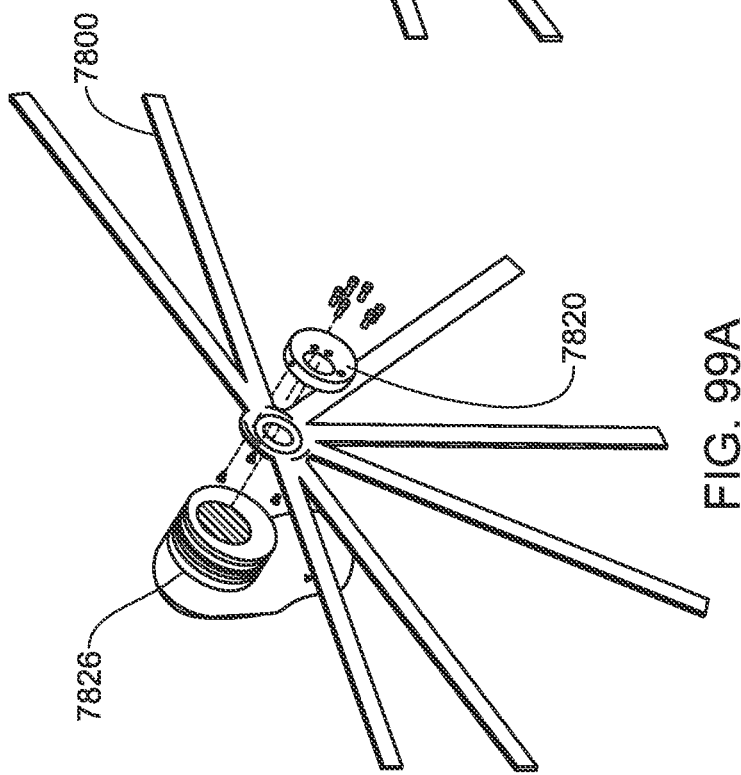
Figure 99B:
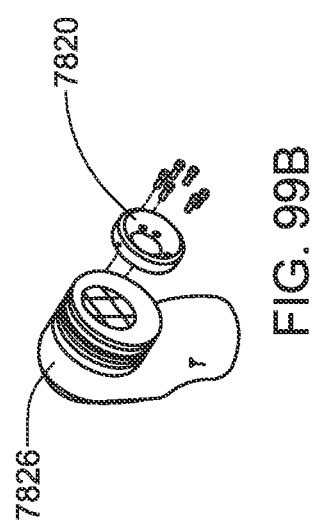
Figure 100A:
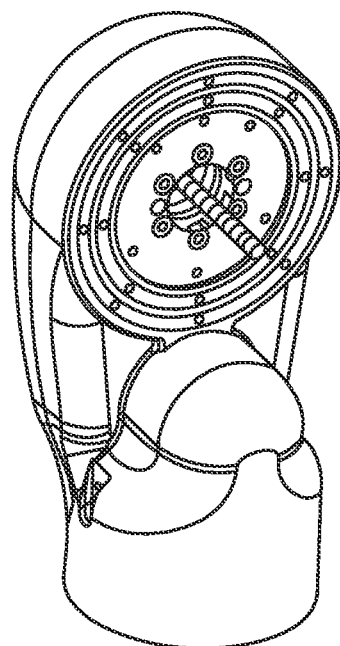
FIGS. 100A, 100B, 100C, 100D, 100E and 100F are various views of a shoulder flexor-abductor according to one embodiment.
Figure 100B:
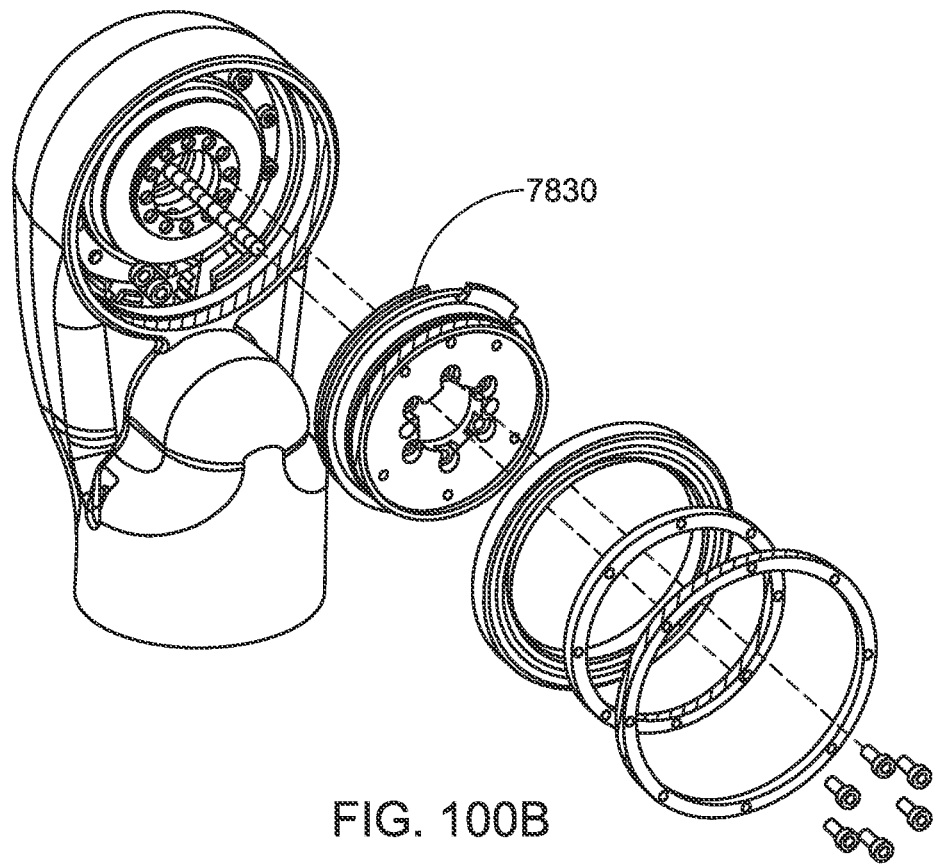
Figure 100C:
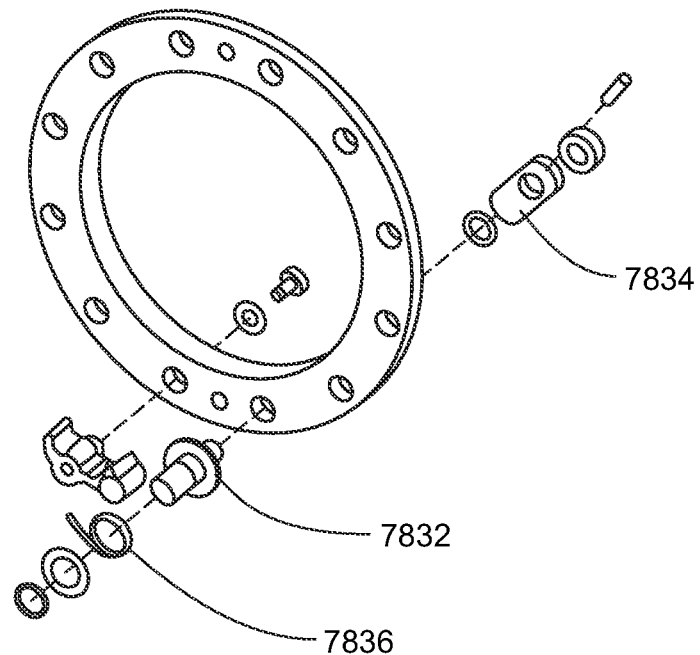
Figure 100D:
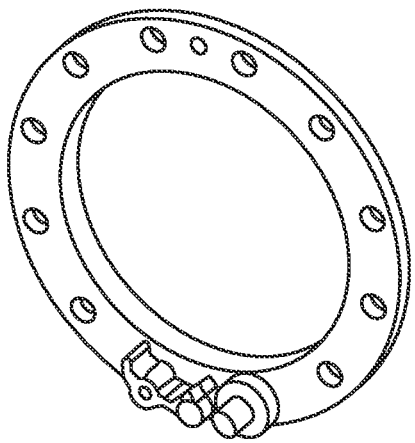
Figure 100E:
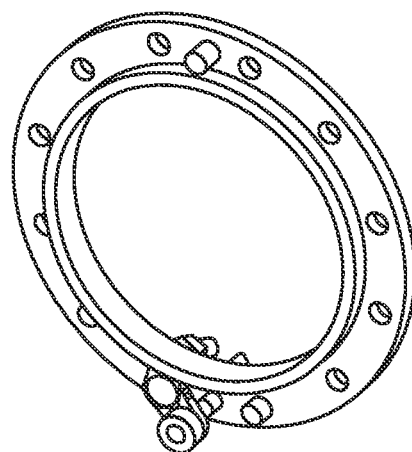
Figure 100F:
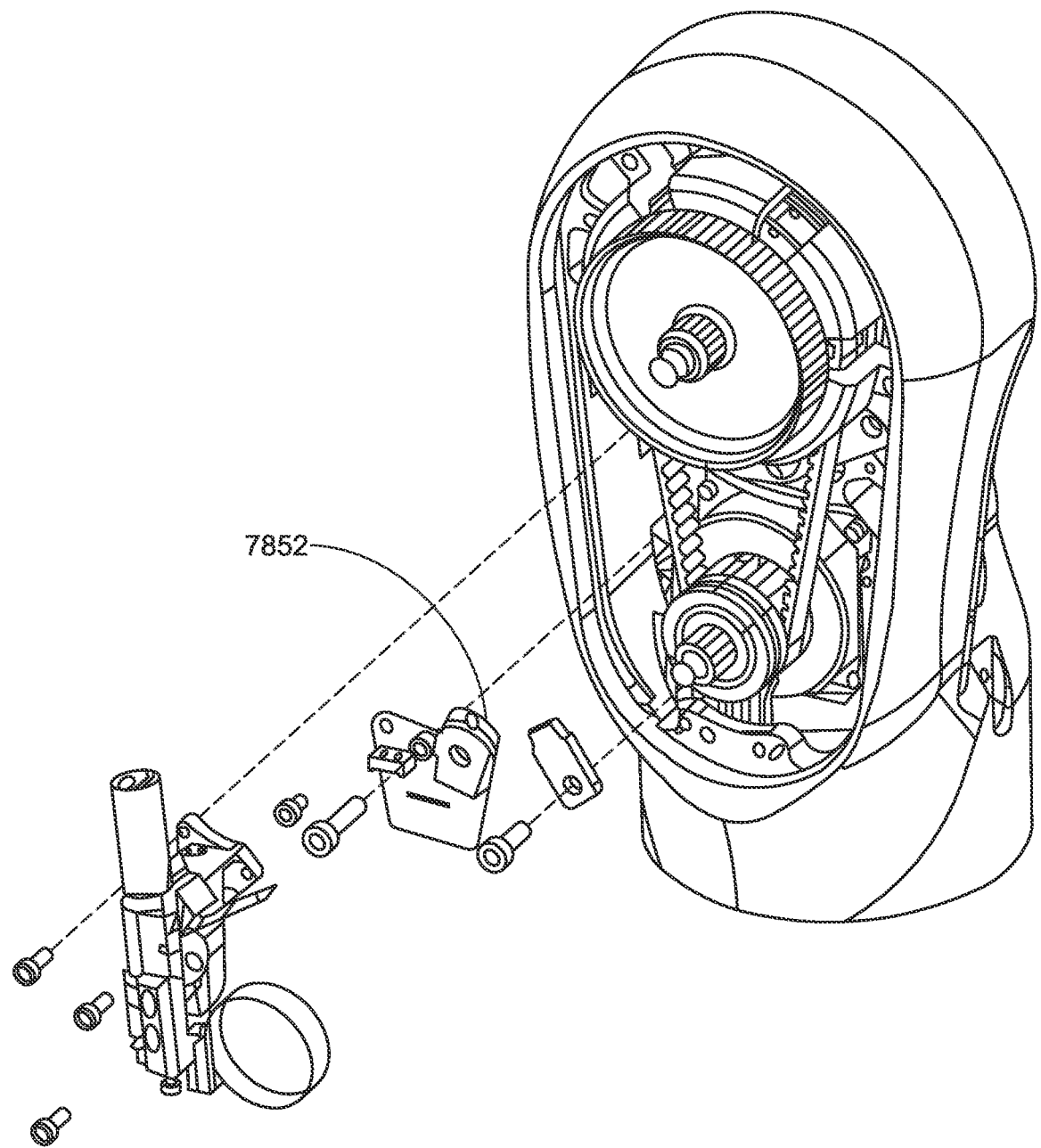
Figure 101A:
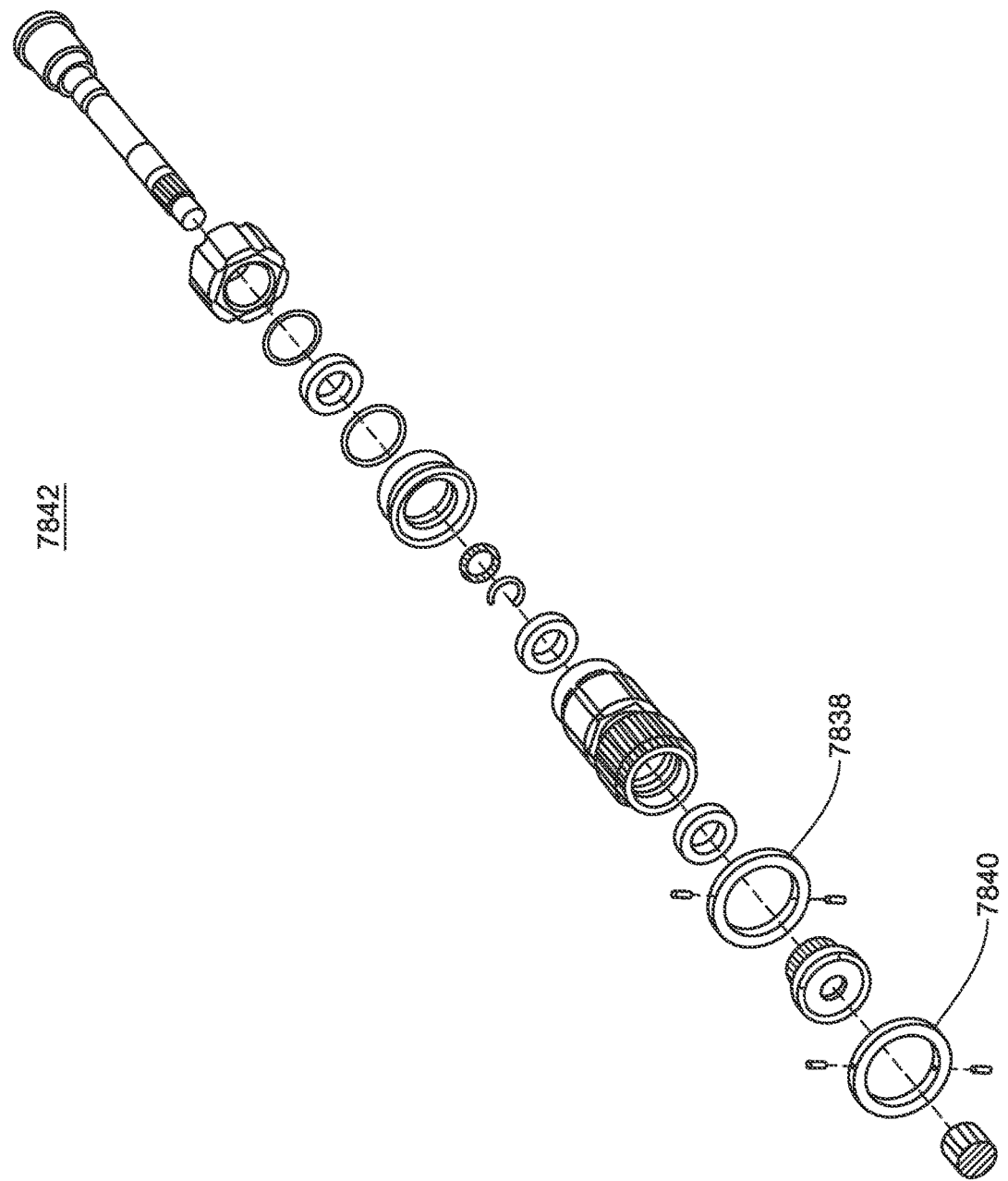
Figure 101D:
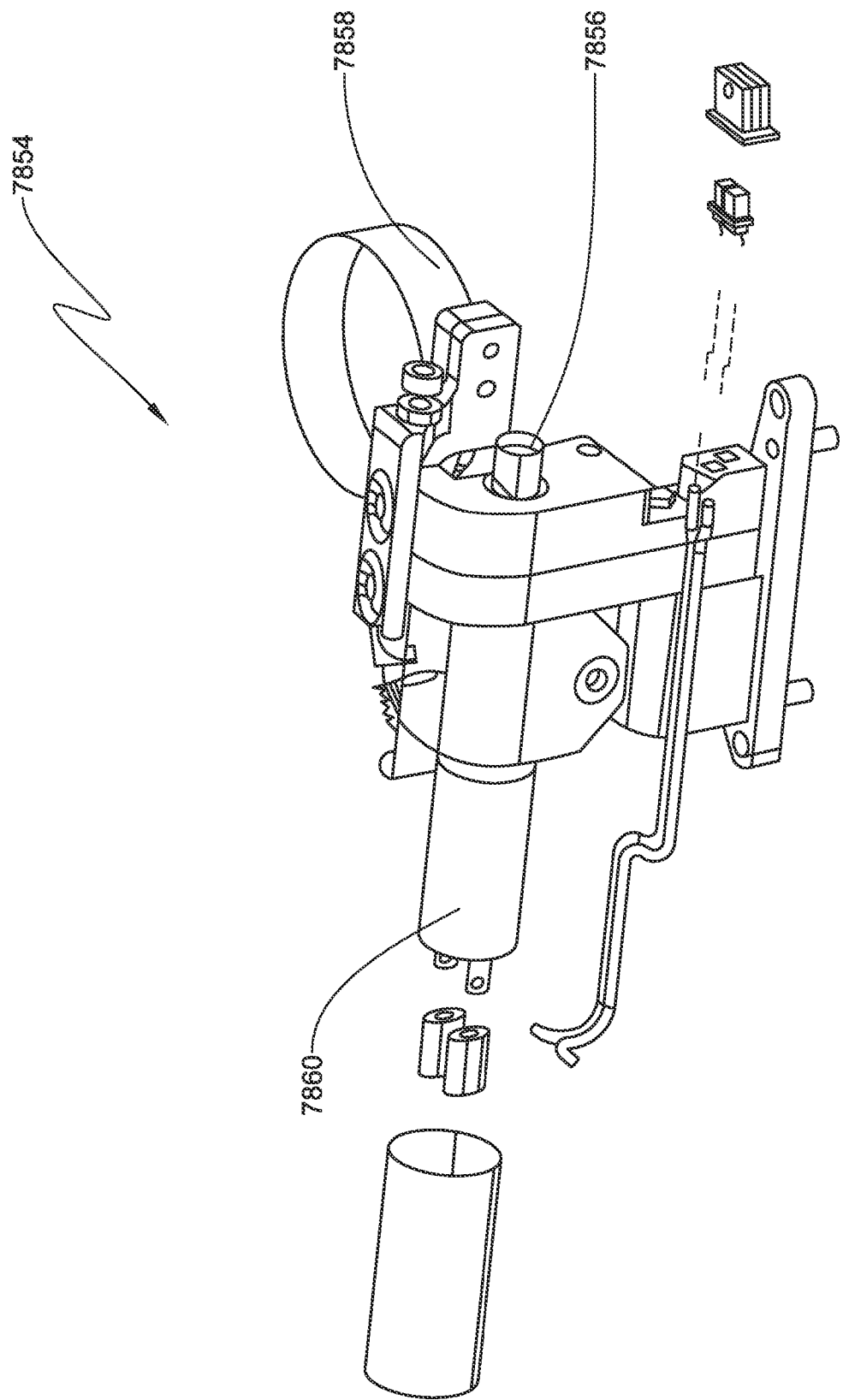
Figure 102B:
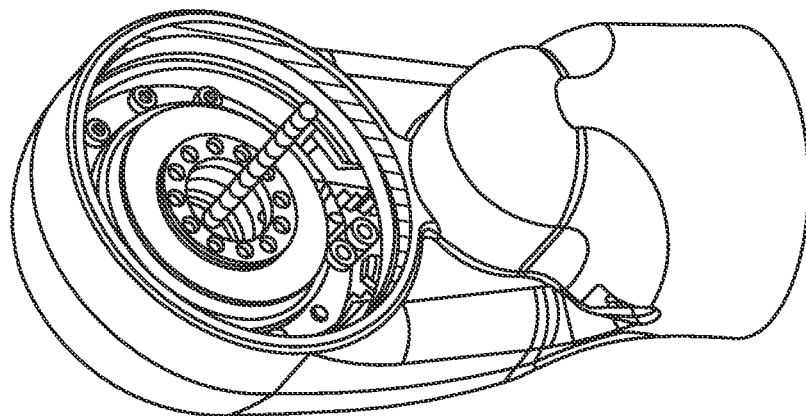
Figure 102A:
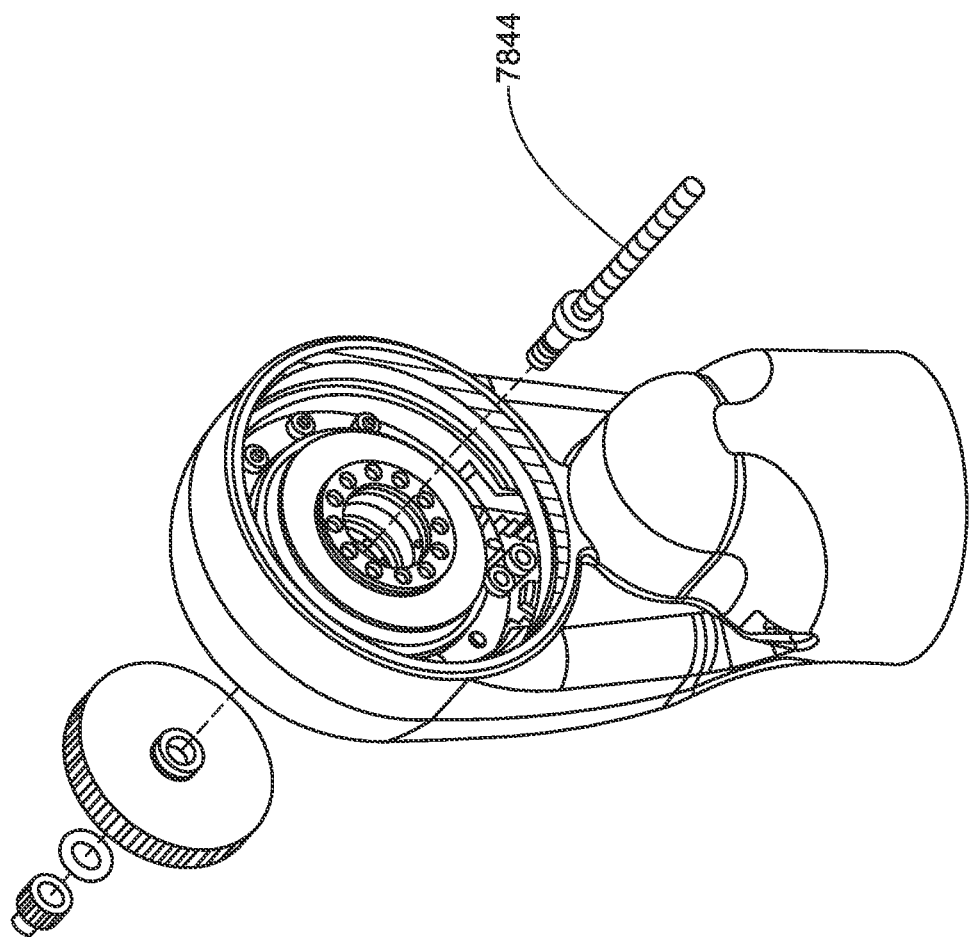
Figure 102C:
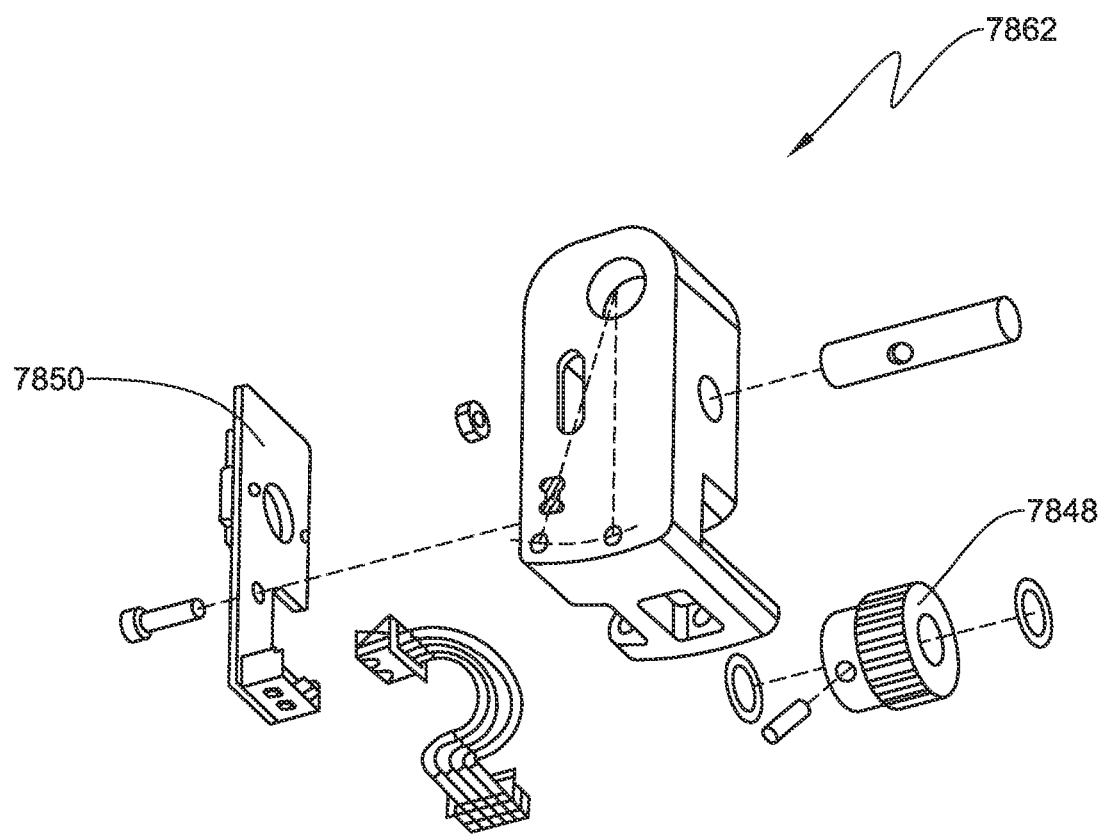
Figure 102D:
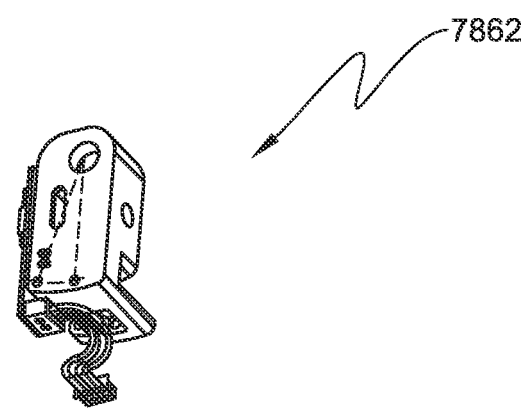
Figure 102E:
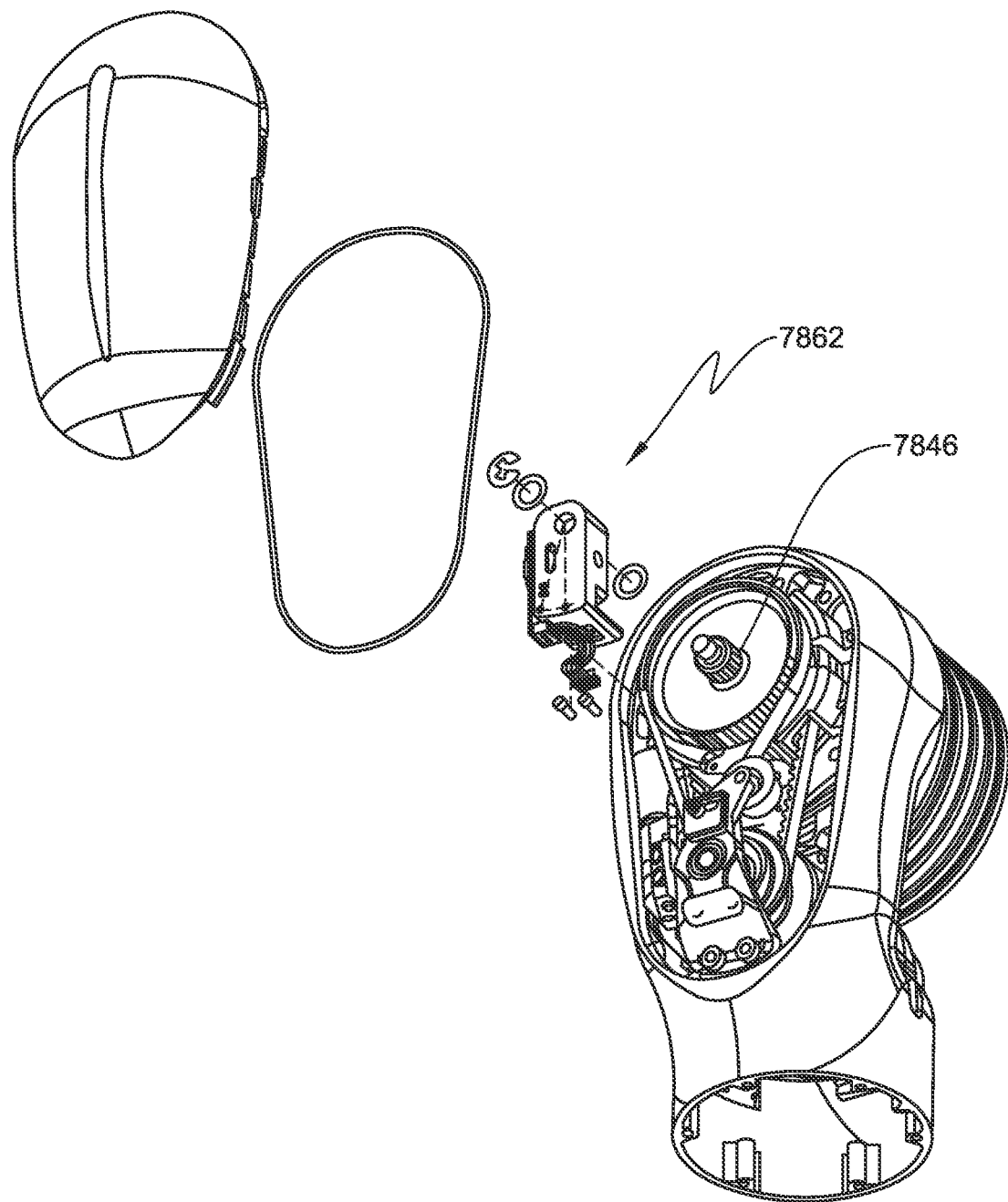

In some embodiments, once the prosthetic mounting device is attached to the prosthesis, for example, as shown in FIG. 99D, the prosthesis may be removed and the prosthetist may build up the socket. Finally, in some embodiments, the frame may be removed.

There are many advantages to the frame 7800 embodiments. These include, but are not limited to, one or more of the following. The frame 7800 may be used to ensure the proper location of the prosthetic mounting device so that the socket may be registered. Also, the frame allows a prosthetist to position the mounting device, and tweak/adjust the prosthetic mounting device position, until the prosthesis is in the desired anatomical position with respect to the intended user.

Referring now to FIGS. 100A-100F various views of a shoulder flexor-abductor are shown. In some embodiments, the shoulder may include a feedback flexor position sensor 7852 which may include a spiral surface 7830 that ensures that for any position of the flexor, there will be a different radius, which may be determined. Thus, in some embodiments, the shoulder may include a potentiometer, which may, in some embodiments, be similar to the potentiometers described above. A turning shaft 7832 is connected to a potentiometer using a turning arm 7834 and a preload spring 7836 keeps the turning arm 7834 preloaded in one direction. As the turning shaft 7832 spins with movement of the shoulder the flexor moves the spiral 7830 and the radius changes. During rotation, the resistance of the potentiometer is changed which may be correlated with a position.

Referring also to FIGS. 101A-101D, in some embodiments, the shoulder may also include a braking mechanism 7854, which, in some embodiments, may be a band brake including a brake band 7858, which stops both the flexor brake rotor 7838 and abductor brake rotor 7840. In some embodiments, the braking mechanism 7854 includes a band brake that is opened and closed by the brake motor 7860 and in some embodiments, a potentiometer 7856 may be used to determine whether the braking mechanism 7854 is engaged or disengaged by measuring the brake shaft angle. An adjustment block may be used to properly position the brake band 7858 so the correct tension is achieved when the braking mechanism 7854 is engaged and in some embodiments, the potentiometer 7856 may be used for brake motor 7860 control to engage and disengage the braking mechanism 7854 which may be desirable for many reasons, including, but not limited to, avoiding wearing out the rotors. In some embodiments, a current threshold (read by motor drive electronics) may be determined when a proper tension is achieved in the brake band 7858.

In some embodiments, the system may engage the braking mechanism 7854 of the shoulder and other joints with brakes in the system, when the system determines that the motors do not need to turn, thus, in some embodiments, the braking mechanism 7854 may be engaged to preserve the battery.

The shoulder brake may be closed or open and does not require power to maintain the state (whether open or closed). Thus, the brake only requires power to change the state from engaged to disengaged, and vice-versa.

Referring now to FIGS. 102A-102E, another embodiment of the abductor potentiometer sensor system 7862 is shown. The abductor roller screw 7844 shaft turns, which drives a nut, which opens the linkages which pivots the shoulder about the abductor pivot pin. The position of the abductor roller screw 7844 is determined using the abductor potentiometer sensor 7850. On the abductor roller screw shaft 7844 is a worm gear 7846. The worm gear 7846 mates with a worm wheel 7848. The worm wheel 7848 is mounted to the abductor potentiometer sensor 7850. In some embodiments this arrangement may be desirable/beneficial for many reasons, including, but not limited to, in some embodiments, the abductor roller screw 7844 may experience multiple rotations to a single rotation of the output shaft, for example, in some embodiments, the abductor roller screw 7844 may experience 16 rotations to a single rotation of the output shaft, however, in various other embodiments, the number of rotations may be greater than or less than 16. Thus, in these embodiments, reading the position of the abductor roller screw 7844 directly may not yield the necessary information. Therefore, in various embodiments, the rotations of the abductor roller screw 78434 are geared down, i.e., the multiple rotations (e.g. 16 rotations) are geared down by a factor (e.g., 20 to 1). The gear down factor is determined in some embodiments by the gears used in the system through the various embodiments. Thus, the gear down reads the rotation as less than 1 rotation, e.g. ⅘ h of a rotation or (288 degrees), however, in various other embodiments; this gear down factor may vary. Thus, the abductor potentiometer sensor 7850 may, in some embodiments, only measure less than a full rotation. Therefore, the abductor potentiometer sensor 7850 is reading a position intermediate within the power train; therefore, it is geared it down. There are many advantages to this system, including, but not limited to, the sensor measurement may occur on the same side as the electronics. Therefore, elimination and/or minimizing the number of wire wires over the moving joint.

Figure 103A:
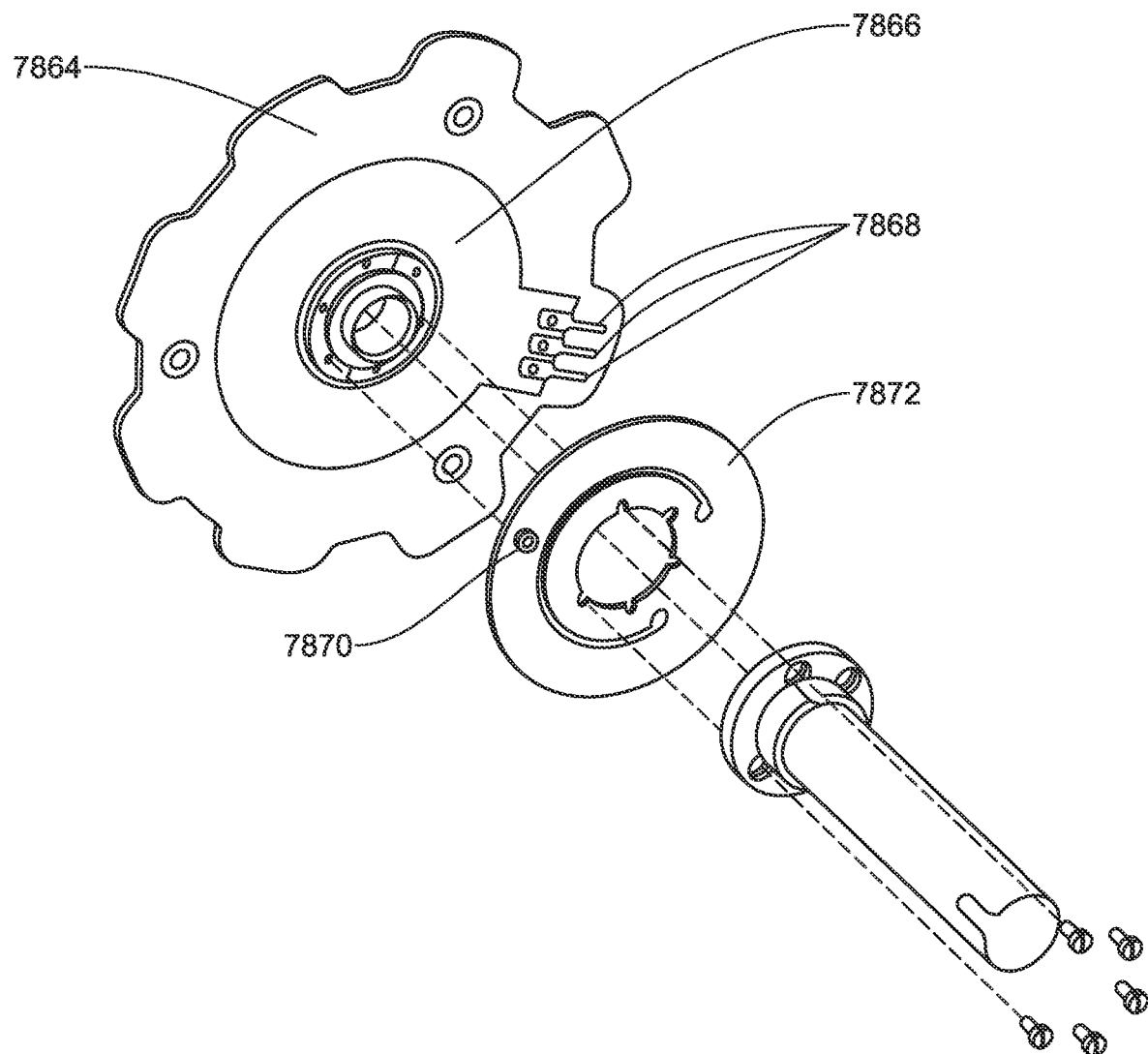
Figure 103C:
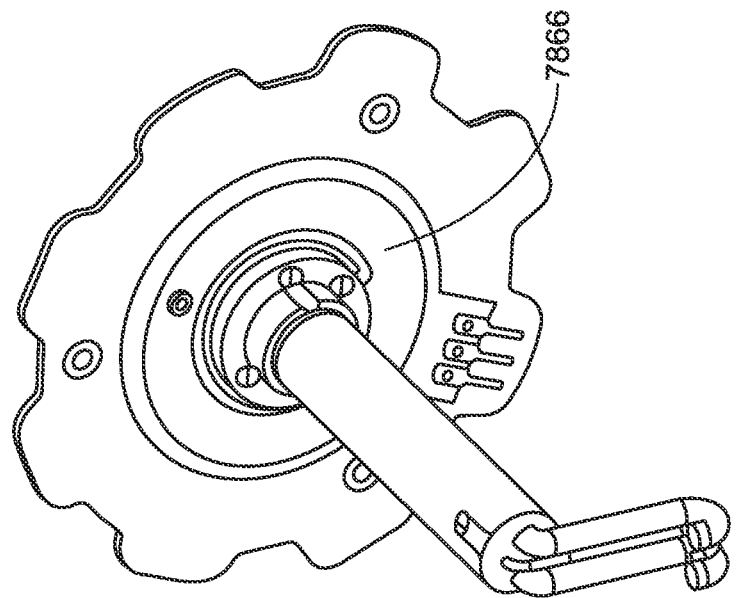
Figure 103B:
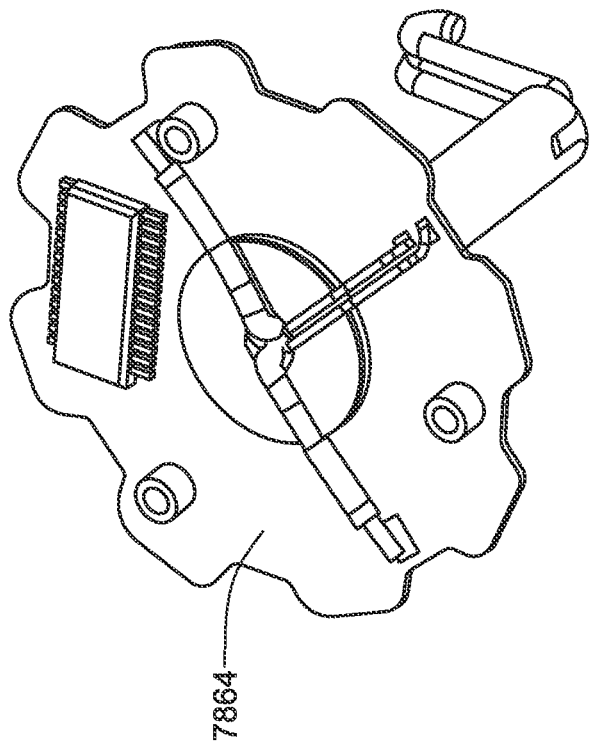

Referring now to FIGS. 103A-103C, various views of the wrist are shown, including views including one embodiment of a wrist rotator sensor. The wrist rotator sensor uses a potentiometer 7866 (which, in some embodiments, is a variable resistance potentiometer) and as a plunger is moved around the resistance is changed. In some embodiments, the wrist rotator sensor is integrated directly onto the circuit board 7864 which may be desirable for many reasons, including but not limited to, that the wrist rotator sensor is a single unit and may be "dropped into" the wrist rotator. In some embodiments, the design of the wrist rotator sensor includes alignment portions/features 7868 which may be desirable for many reasons, including, but not limited to, in manufacture, where, in some embodiments, the wrist rotator sensor may not be able to be assembled into the wrist unless aligned properly.

Figure 104A:
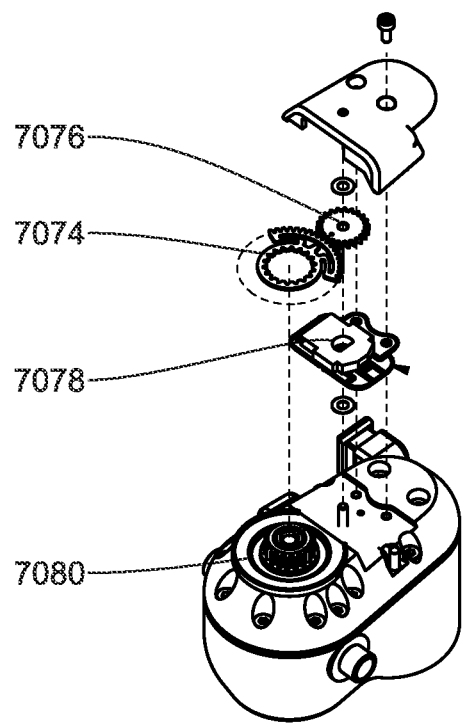
Figure 104B:
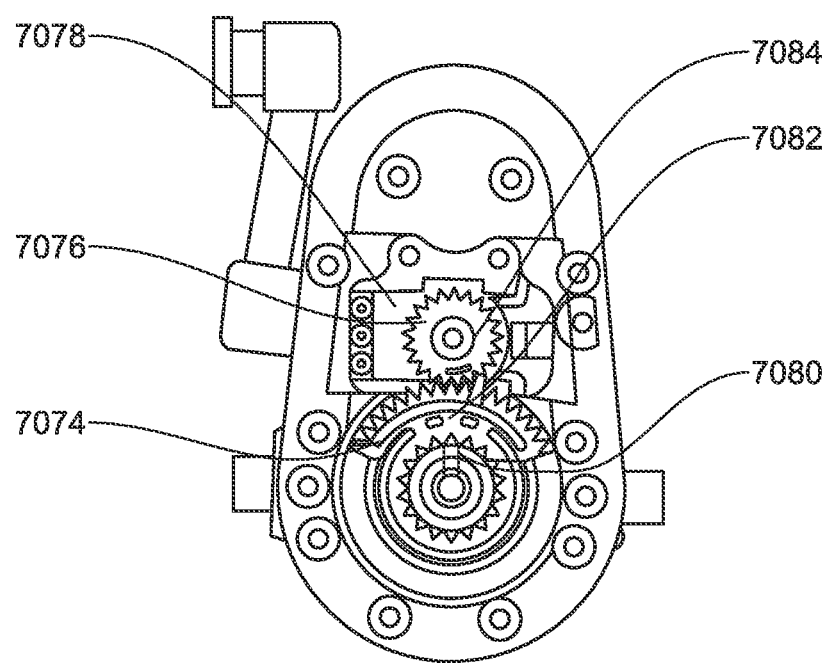

Also, in some embodiment, the wrist rotator sensor includes where the plunger 7870 is integrated into the sensor assembly and the plunger flexor spring 7872 pushes the plunger onto the sensor Referring now also to FIGS. 104A-104B, in some embodiments, the wrist also includes an external position sensor/potentiometer for the wrist flexion joint. In some embodiments, the external position sensor includes gears, including a sector gear 7074, a potentiometer gear 7076, which, including a potentiometer 7078, provide variable resistance based on position. In some embodiments, the external position sensor also includes alignment features on the output shaft 7080, sector gear 7082 and potentiometer gear 7084 to ensure the arrangement/alignment is correct. This sensor may be desirable for many reasons, including, but not limited to, that the positioning of the wrist is smooth, reliable and accurate, and consistent and less sensitive to temperature. This sensor may also be desirable for its ability to maintain/hold a position. The sensor may also be desirable for it requires a small amount of power (only when resistance reading) and therefore may improve battery life. In various embodiments, the sensor is a passive sensor i.e., the sensor does not require being powered up for use. The sensor is a resisting element.

In various embodiments, a system and method for battery charging is included. In various embodiments, a system may include at least one internal battery, and at least one external battery. However, in some embodiments, the system may include at least one external battery but no internal battery. In still other embodiments, the various embodiments of the system may include one or more external batteries. In various embodiments, the internal battery is located inside a device, which, in some embodiments, may include a prosthetic device. The at least one internal battery, in some embodiments, may not be readily accessible and/or directly accessible by a user. For example, in some embodiments, the at least one internal battery may be located in the device such that the battery housing is waterproof and/or protected from the outer environment and therefore, not accessible unless a plate and/or a battery cap and or other is first removed. In various embodiments, the at least one internal battery may be a rechargeable battery and therefore, in some embodiments, it may be desirable to recharge the battery from an external source rather than removing the not-readily-available internal battery to recharge the internal battery. In some embodiments, where the at least one internal battery may be readily accessible, it may be desirable to recharge the internal battery from at least one external source. In some embodiments, the at least one external source may include, but is not limited to, one or more of the following: at least one external battery and/or at least one AC adapter. In some embodiments, the at least one AC adapter may be a medical grade AC adapter, for example, a 60 watt XP Power AC adapter, model number AFM60, made by XP Power Limited, Singapore. In some embodiments, the AC adapter may be 24 VDC. However, in various embodiments, a different AC adapter or other adapter or outside charging device may be used. In some embodiments, the at least one AC adapter may be connected to the device to charge the at least one internal battery by connection to a charging port. In some embodiments where the device is a prosthetic arm device, the charging port may be located anywhere on the device, including but not limited to, on the forearm.

In some embodiments, the internal battery may be a 4S1P lithium-ion rechargeable 18650 cells battery for a nominal voltage of 14.8 VDC having 2 amp hours of capacity. However, in various other embodiments, the internal battery may be a larger or smaller voltage with more or less capacity. In some embodiments, the at least one internal battery may include a SMBus gas gauge IC and protection circuitry.

In some embodiments, the system may include no external batteries. However, in some embodiments, the system may include at least one external battery. In some embodiments, the at least one external battery may be used to power a device, for example, but not limited to, a prosthetic device. In some embodiments, the at least one external battery may be used to recharge an internal battery in a device. For example, in some embodiments, the at least one external battery may be used to recharge a non-removable internal battery in a device. In some embodiments, the at least one external battery may be a 4S2P lithium-ion rechargeable 18650 cells battery for a nominal voltage of 14.8 VDC and 5 amp hours of capacity. In some embodiments, the at least one external battery may include a SMBus gas gauge IC and protection circuitry. In some embodiments, the system may include one external battery and in some embodiments, the system may include two or more external batteries. In some embodiments, the at least one external battery may be worn by a user by attaching the external battery to a holster, a belt holster, a pack or other apparatus to secure the external battery to the user. In some embodiments, the external battery is connected to a device, for example, but not limited to, a prosthetic device, by an electric connector, for example, a cable.

In some embodiments where at least one external battery is used, a power button may be located on the holster or other holder of the external battery. In an exemplary embodiment, the holster may be configured to include a pushbutton holster (e.g., in some embodiments, this embodiment may be used when there is no internal battery) or a non-pushbutton holster (e.g., in some embodiments, this embodiment may be used when there is at least one internal battery). In some embodiments where both at least one internal battery and at least one external battery are included in the system, the internal battery includes an internal battery interface. In these embodiments, software is common to both the internal battery interface and the holster and configuration jumpers on the board may be read by the software to determine the type of board.

In various embodiments, the system may include a device, including, but not limited to, a medical device, e.g., a prosthetic device or prosthetic arm; at least one internal battery and at least one external battery. In some embodiment of this embodiment, the system may include at least two external batteries. In some embodiments, all the batteries may include built-in circuits for measuring state-of-charge and protection against faults. In some embodiments, one or more batteries may include built-in circuits for measuring state-of-charge and protection against faults. In some embodiments, similar to other "smart" batteries, the batteries may communicate this information to the system using the System Management Bus (SMBus) hardware/software protocol. In some embodiments, the at least one or at least two external batteries are charged by an external battery charger.

Figure 105:
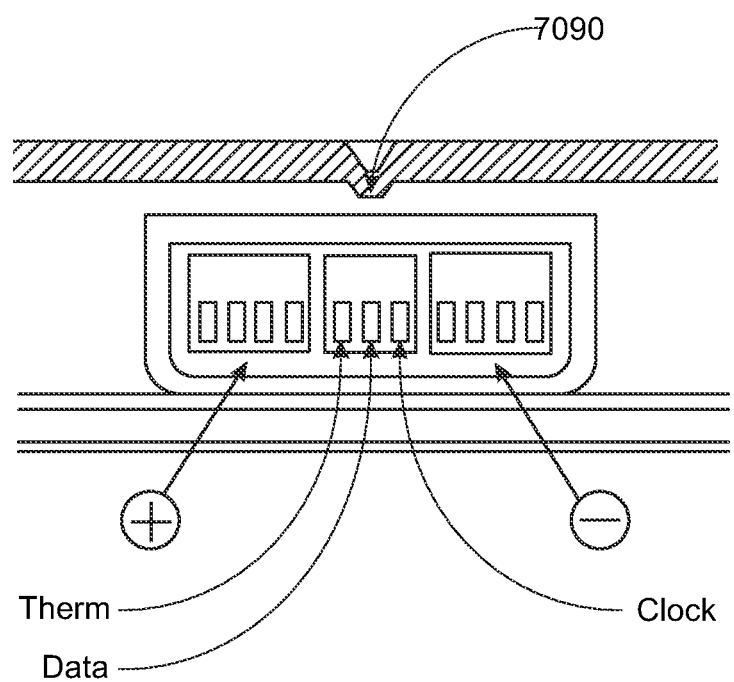

In some embodiments, as discussed above, a holster may be included wherein the holster accepts and secures the external battery. Referring now also to FIG. 105, one embodiments of a battery interface, view into holster or charger, is shown. In various embodiments, when one external battery is mounted in the holster, spring contacts in the holster mate to metal pads on the external battery, which interfaces the battery to the device's, e.g., prosthetic arm's, power and communication busses. The external battery charger duplicates the holster's interface to the battery for both supplying charge power and for SMBus communication.

Figure 107:
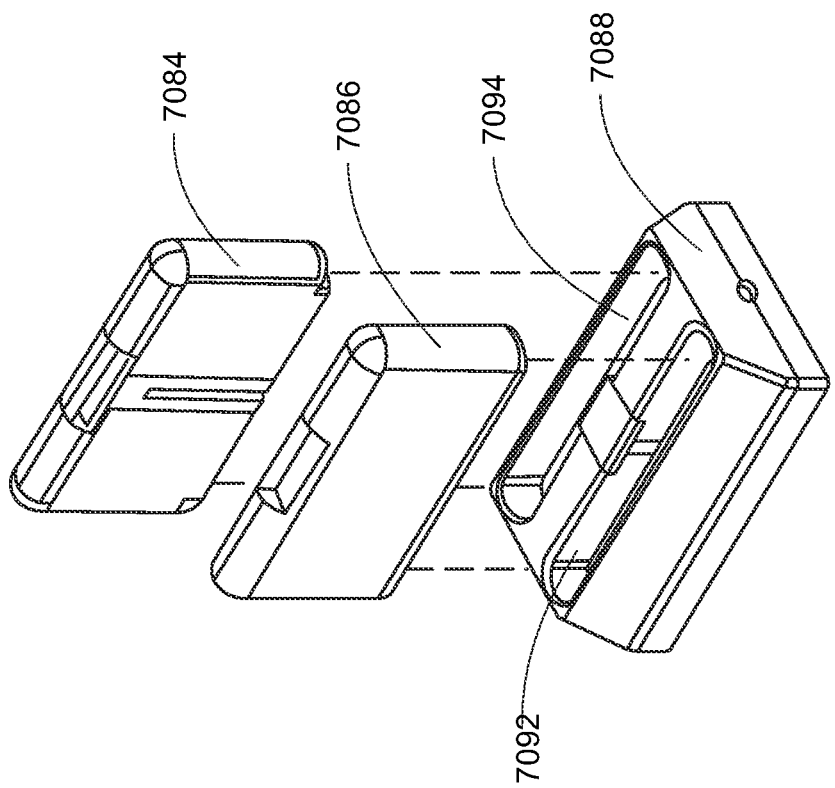
Figure 106:
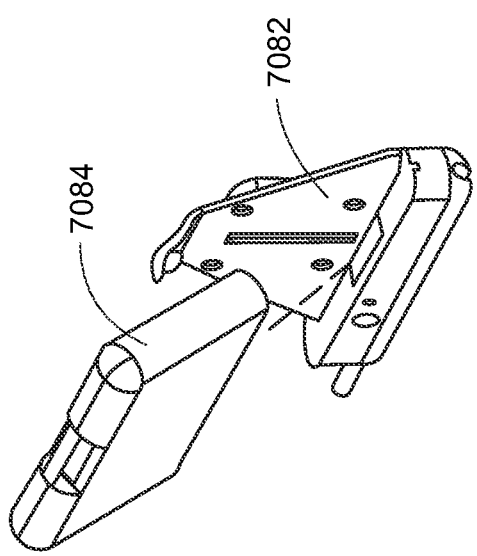

Referring also to FIG. 106, one embodiment of a holster 7082 and an external battery 7084 is shown. Referring also to FIG. 107, in some embodiments, a charger 7088 may accommodate one or more external batteries 7084, 7086. In the embodiment shown in FIG. 107, the charger 7088 accommodates two external batteries 7084, 7086.

In some embodiments, the external battery charger 7088 may be designed to charge up to two external batteries 7084, 7086 simultaneously. In some embodiments, for ease of use, the external batteries 7084, 7086 may be loaded vertically—like a toaster—relying on the battery's weight, in some embodiments, to create sufficient force to connect with the electrical contacts. In some embodiments, the external batteries 7084, 7086 may include a keying feature 7090, i.e., they may be keyed, to prevent being inserted backwards. In some embodiments, each charger bay 7092, 7094 may have a dedicated charge circuit; both of which, in some embodiments, may be overseen by a microcontroller with custom software.

In some embodiments, bulk power may be supplied to the battery charger 7088 by an off-the-shelf medical-grade power supply that produces 24 VDC. In some embodiments, this power may be the AC adapter described above, i.e., the same power supply that may be used to provide charge power to the device.

In some embodiments, the external battery charger 7088 is a Level 3 charger by the definitions of the Smart Battery System specification. Thus, the charger's 7088 microcontroller acts as the SMBus master, and queries each battery for its desired charging current and terminal charging voltage. The microcontroller forwards this information to the charge circuits. The microcontroller may provide the full requested charge power, or limit one or both batteries to avoid exceeding the rating of the power supply. Through the SMBus interface, the charger 7088 may also be able to query the external batteries' 7084, 7086 status and use this information to determine if a fault has occurred.

The interactions among the external batteries 7084, 7086, the charge circuits, and the microcontroller are complex. In general, the software and hardware are architected to disable power to the charging circuits by default. In some embodiments, only when a number of predetermined conditions are met (for example, but not limited to, one or more of the following: charge voltage in acceptable range, battery is present and communicating, battery reports no faults, requested charge current in acceptable range, etc.) will charge power be applied.

Figure 108:
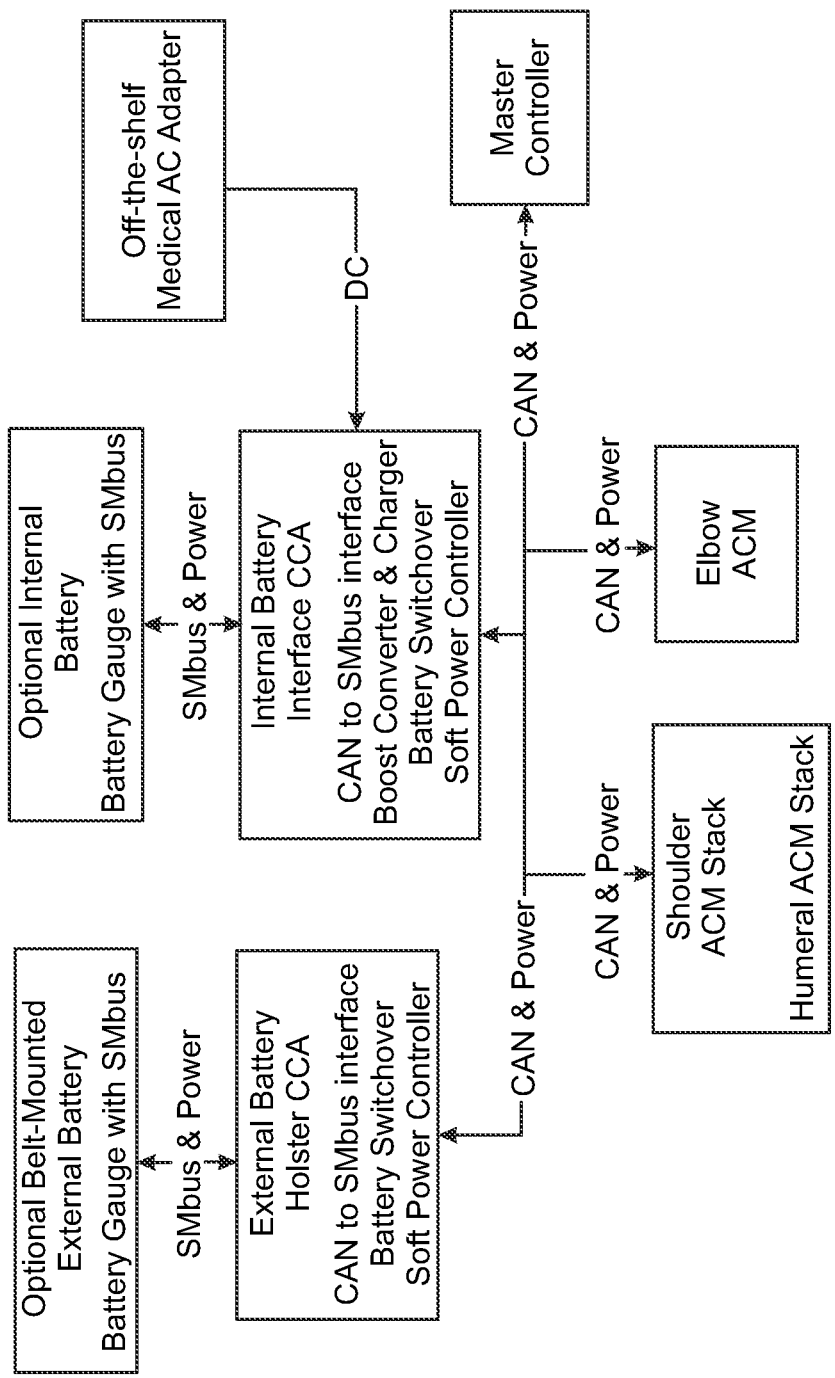

Referring now also to FIG. 108, a system block diagram of one embodiment of the battery system for a device is shown. As discussed above, in some embodiments, various embodiments of the battery system may be used with a prosthetic device, including, but not limited to, a prosthetic arm. However, in various embodiments, the various embodiments of the battery system may be used with any device requiring power. For purposes of illustration only, some embodiments of the system are described with reference to a prosthetic arm. However, this is for descriptive purposes only and it should be understood that the system is not limited to use with a prosthetic arm. In various other embodiments, the components described below with reference to a prosthetic arm, e.g., "shoulder ACM stack", may be different where the system is used in conjunction with a device other than a prosthetic arm device.

Figure 109:
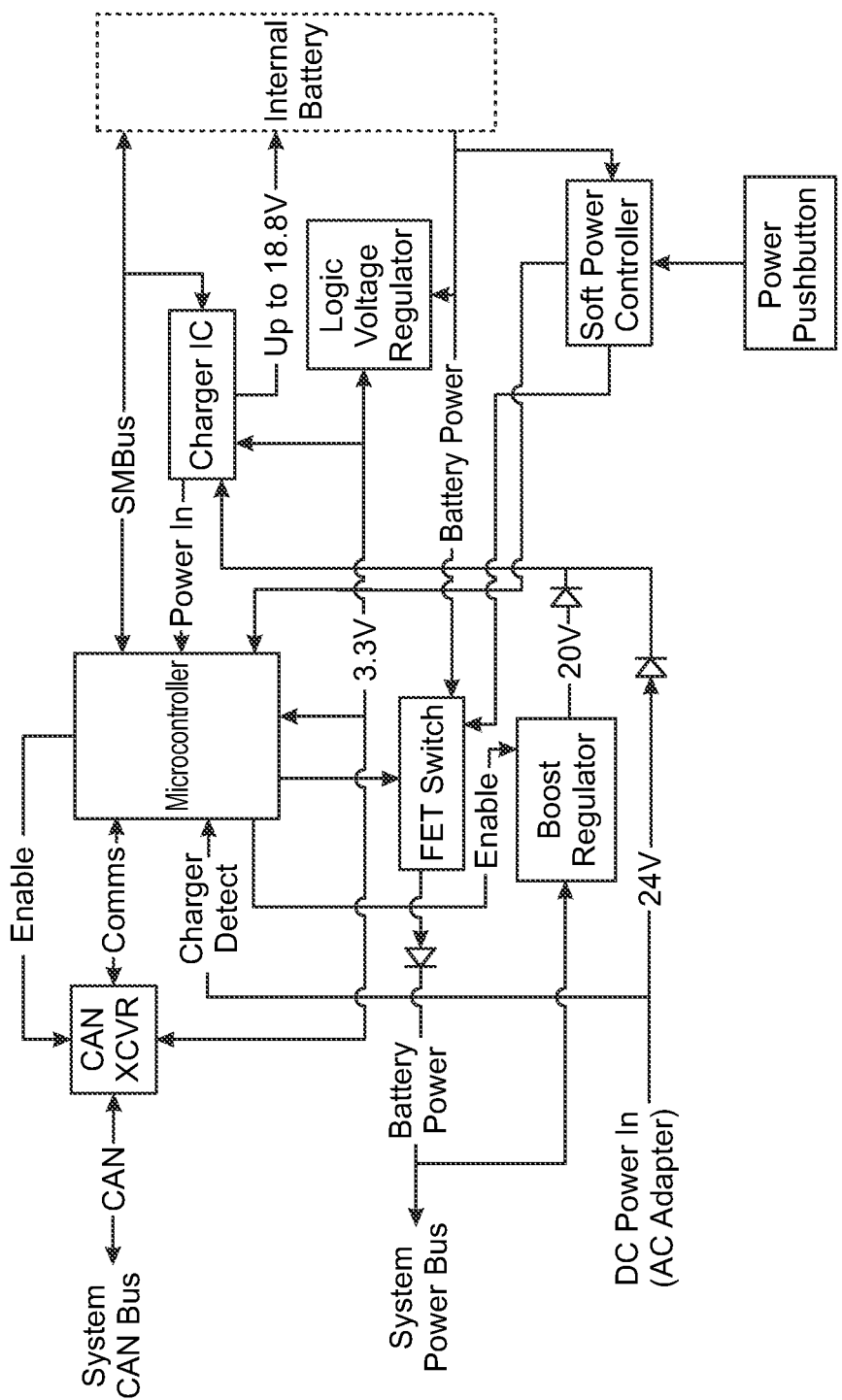
Figure 110:
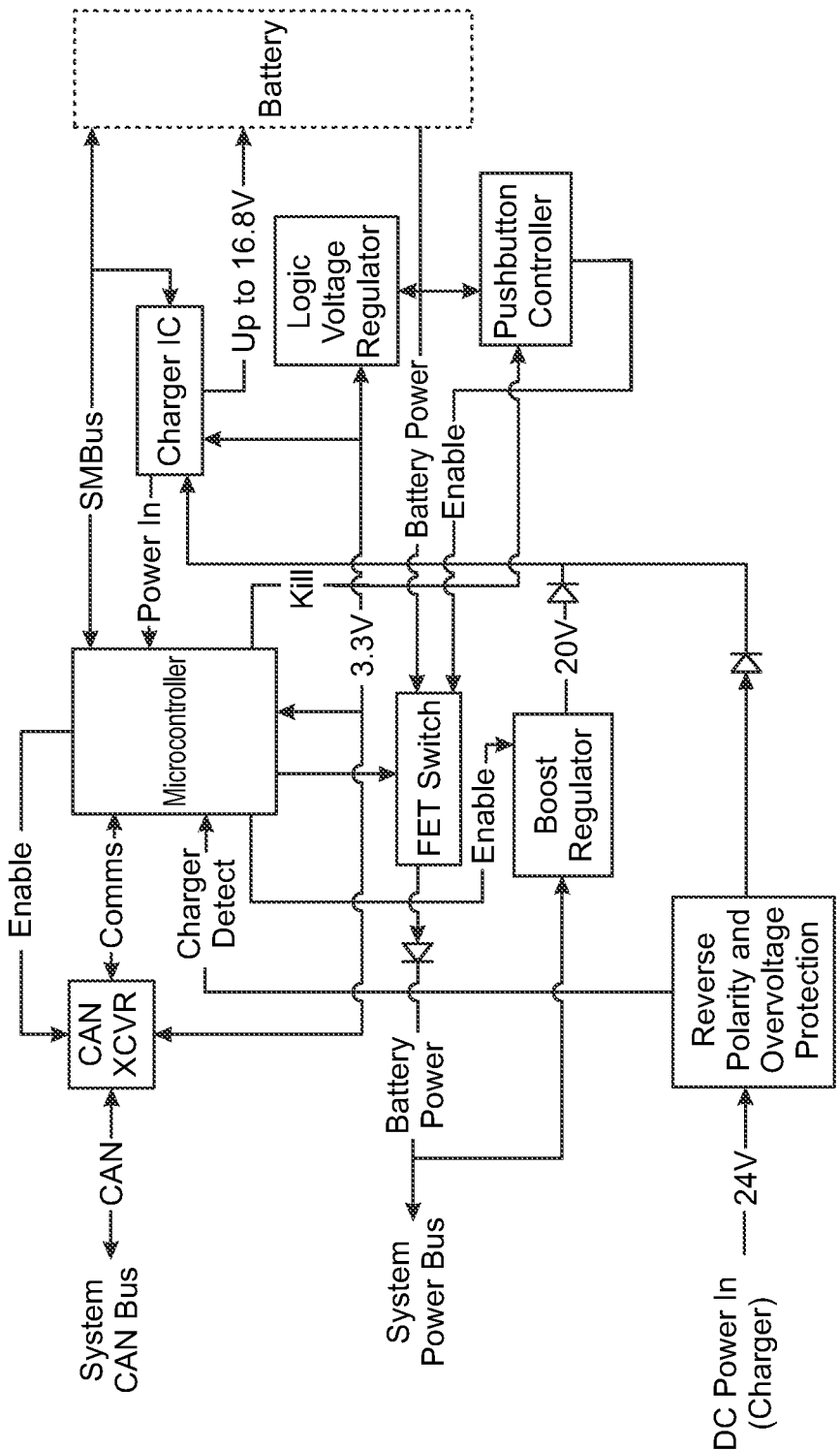

Referring now also to FIG. 109 and FIG. 110, diagrams of two embodiments of the internal battery interface are shown. In some embodiments, where the system includes an internal battery and at least one external battery, the internal battery connects to a custom circuit board called the internal battery interface. This board contains a microcontroller that talks e.g. on a CAN bus as a slave, to a master controller. The board also has a charging circuit for the internal battery. The charging circuit is powered, in some embodiments, from either an external 24 VDC power source (like from an AC adapter) or from the system power bus (getting power from the external battery). Because in some embodiments the 24 VDC AC adapter interface connector may be a common barrel connector, to reduce and/or eliminate the possibility that a user might connect the wrong voltage AC adapter and to protect against the wrong voltage or polarity AC adapter from affecting the internal battery interface electronics, in some embodiments, circuitry may be incorporated into the internal battery interface board to tolerate a range of AC adapter input voltages, for example, including, but not limited to, a range from −36 VDC to +36 VDC. In various other embodiments, this range may be different. In some embodiments, the voltage range may be determined by conducting a search of commonly available AC adapters with similar output connectors.

In some embodiments, the internal battery interface circuitry may include a soft power interface controller. In some embodiments, this controller monitors the power on/off button, and helps to control system power. In some embodiments, the microcontroller also participates in this functionality; however the soft power controller may, in some embodiments, independently shut off the system power if the microcontroller fails to respond to power off requests.

Figure 111:
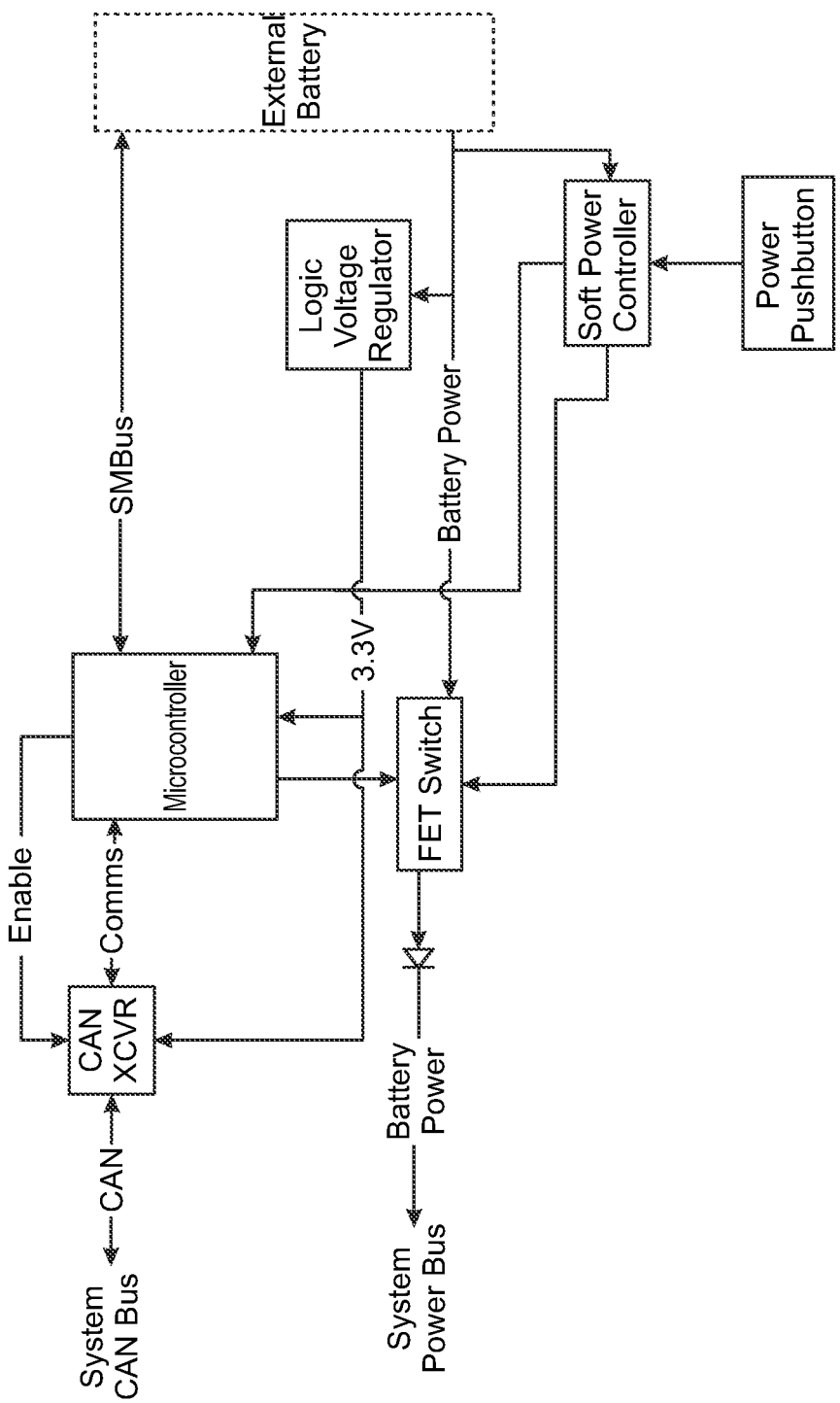
Figure 112:
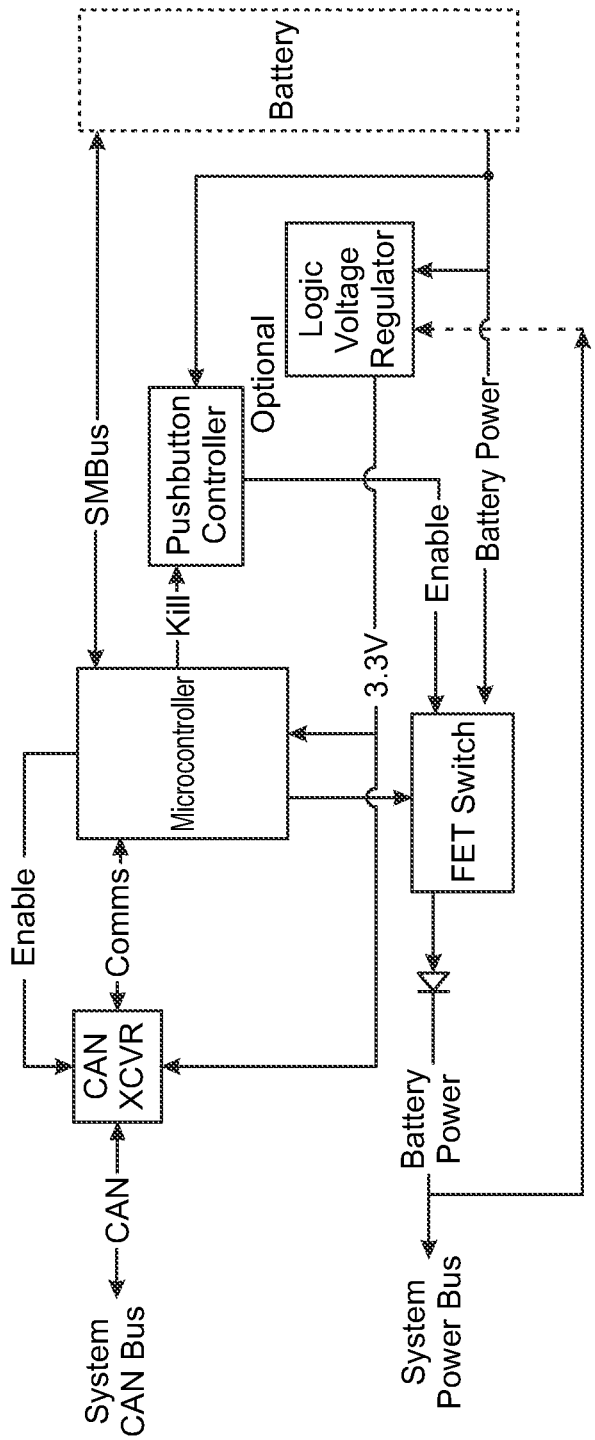
Figure 113:
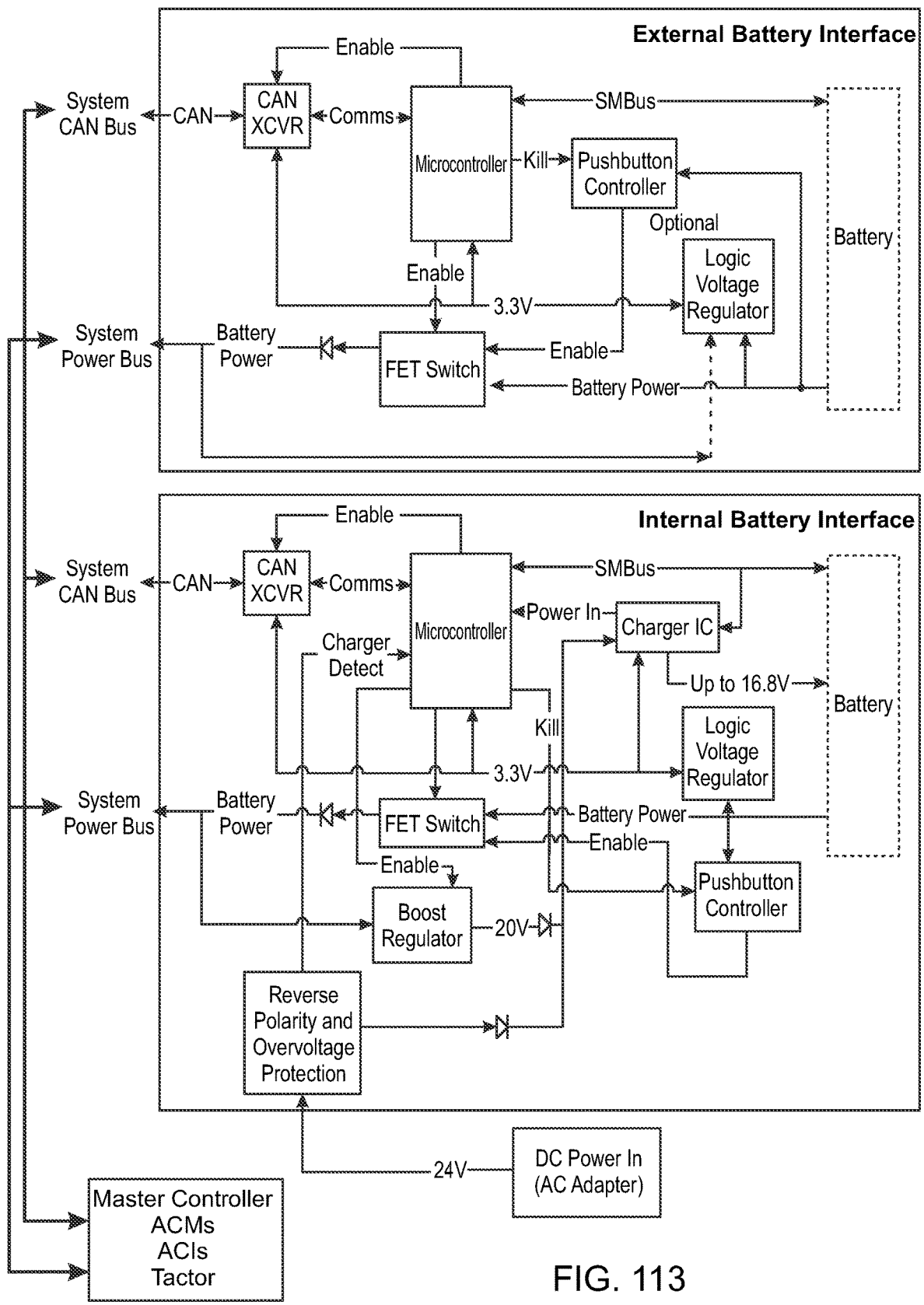

Referring now also to FIG. 111 and FIG. 112, diagrams of two embodiments of the external battery interface with a holster are shown.

In some embodiments, the external battery connects to another custom circuit board in the external battery holster, which is described in more detail below. In some embodiments, the schematic for the external battery holster board may be similar to the schematic of the internal battery interface board. In some embodiments, the schematic for the external battery holster board may be different from the internal battery interface board. In some embodiments, the external battery holster contains a microcontroller that talks, e.g. on a CAN bus as a slave, to the master controller, and it talks to the internal battery over a SMBus.

In some embodiments, the external battery interface circuitry includes a soft power interface controller. In some embodiments, this controller monitors the power on/off button, and helps to control system power. As with the internal battery interface board, in some embodiments, the microcontroller may also play a part in this functionality, however the soft power controller may independently shut off the system power should the microcontroller fail to respond to one or more power off requests. In some embodiments, the soft power controller in the holster 7082 is only installed when there is a pushbutton in the holster 7082.

Referring now also to FIG. 111, a system schematic of one embodiment of the system is shown. In this embodiment, the system includes an internal battery and at least one external battery. Again, referring to a prosthetic arm for illustration purposes, inside the prosthetic forearm, in some embodiments, an internal battery circuit board is located next to the internal battery. The internal battery circuit board includes a microcontroller that communicates with the internal battery including communications related to the charge of the internal battery. In addition, in some embodiments, the microcontroller communicates with the prosthetic arm systems communication bus (CAN Bus) which communicates with the master controller. The master controller, therefore, in various embodiments, receives information about the battery, which may include, but is not limited to, the amount of charge in the battery. The master controller can make decisions regarding when to charge the internal battery and also, when to switch between the external battery and the internal battery for powering the device, e.g., the prosthetic arm. The external battery also has an interface board with a microcontroller that communicates to the external battery and the arm system's communications bus (CAN bus), which communicates with the master controller. In some embodiments, a cable connects the external battery to the arm/device system. The power from the external battery may also power the arm/device.

In some embodiments, the internal battery circuit board includes a smart charger circuit that may either accept input power from the AC adapter or from the arm system power bus, thus charging the internal battery from the external battery. In some embodiments, the power from the power bus (which comes from the external battery) is boosted to a higher voltage for input to the smart charger.

The following are various methods that may be applied by the system to determine where to take power from, e.g., which battery to take power from, to power the device. These are not limiting factors and additional/alternative factors may be used in various embodiments. In some embodiments, one or more of the following are not used.

In some embodiments, whenever there is an external battery connected to the system, the master controller decides that the external battery powers the bus and therefore, disconnects the internal battery from the power bus.

In some embodiments, when the external battery remaining capacity goes below a preset/predetermined/preprogrammed threshold, the master controller may automatically command the internal battery to switch to power the bus.

In some embodiments, alerts and warnings may be displayed to the user (for example, using a user interface on the device) if the installed battery, i.e., the combined remaining capacity of all installed batteries, is below a preset/predetermined/preprogrammed threshold. Thus, in various embodiments, to determine the combined capacity/total capacity of all installed batteries, the total capacity of all internal batteries, and any external battery connected to the system, is used.

In some embodiments, where there is an internal battery and the device system first powers on, the system may always be initially powered by the internal battery until the master controller determines how many batteries are connected, for example, whether there is an external battery present.

In some embodiments, once the device power is turned on, the main computer/master controller determines whether there is an external battery present. If there is an external battery present, but if it is not connected, the master controller will allow the internal battery to power the bus.

However, in some embodiments, once the master controller determines that there is an external battery present, the master controller determines if the external battery has enough capacity, i.e., the external battery capacity exceeds a predetermine/preset/preprogrammed threshold, and if so, connects the external battery to the power bus and disconnects the internal battery from the power bus.

In some embodiments, the interface board near the internal battery may monitor the status of that internal battery to determine whether the internal battery needs to be charged, i.e., whether the capacity of the internal battery is less than a preset/preprogrammed/predetermined threshold. When an external battery is present and has greater than a preset/predetermined/preprogrammed threshold of remaining capacity, then, in some embodiments, the interface board may begin charging the internal battery using the external battery.

In some embodiments, connecting the AC adapter to the device takes priority over charging the internal battery from the external battery. This may be beneficial for many reasons, including, but not limited to, preserving the power that is in the external battery.

In some embodiments, the external battery, which, in some embodiments is also rechargeable, may be required to be removed/disconnected from the device and/or from the holster to be charged. Thus, in some embodiments, the external batteries will not recharge if connected to the device/arm.

As described above, some embodiments of the system include an external battery holster 7082. In these embodiments, the external battery holster 7082 may include contacts that allow the external battery 7084 to be unclipped from the holster 7082. In some embodiments, the holster 7082 may have a microcontroller, in some embodiments having a microcontroller, when the external battery 7084 is taken off the holster 7082 or is not connected to the holster 7082, the device/system may determine that the holster 7082 is still connected but that the external battery 7084 is no longer connected to the holster 7082. In some embodiments, where the device previously determined that two batteries, an internal and an external, are connected, the device can determine that the external battery 7084 has been disconnected. In some embodiments, when the external battery 7084 is disconnected from the holster 7082 the device/arm may automatically switch over to use the internal battery to power the device/arm. In some embodiments, the system may determine that the external battery 7084 is disconnected by monitoring the falling voltage.

In some embodiments, when the system first turns on, the circuit in the interface circuit closes and powers the bus. Then the master controller sees the external battery 7084 and turns the holster 7082 on and the interface circuit off and then the external battery 7084 powers the bus.

In some embodiments, when the external battery 7084 is disconnected from the holster 7082, the external battery 7084 may reach a preset/predetermined/preprogrammed hot swap "threshold voltage" and the system may then turn on the internal battery interface circuit and turn off the holster 7082/external battery interface circuit.

Next, in some embodiments, if a new, for example, charged external battery is inserted into the holster 7082, the holster 7082 interface knows that an external battery has been connected to the system, and, in some embodiments, the master computer then turns the holster 7082/external interface circuit on and the internal battery interface circuit off.

Thus, in some embodiments, the system includes a method and system for "hot swapping" a battery/power source that is powering a device. In some embodiments, for example, having a device including at least one internal battery and two external batteries, where the device is powered by the external battery and the system determines that the external battery becomes disconnected, the system may continue regular operation by turning the external interface circuit off and the internal interface circuit on, thereby continuously powering the device. Then, when, for example, the external battery is connected again to the system/device, the system recognizes that the external battery is again connected and turns the internal interface circuit off and the external interface circuit on, thereby the device is powered again by the external battery.

In some embodiments, this method may be used to "hot swap" a first external battery for a second external battery. In some embodiments these may be beneficial for changing external batteries when one external battery's charge has depleted and a second external battery is more charged than the first. For example, in some embodiments, where the first external battery has been powering the device for a threshold period of time which may be close to the maximum use, a user may hot swap the first external battery for a second external battery which may be, in some embodiments, fully charged. This may be beneficial for continuously powering the device without interruption.

In some embodiments, for example, in embodiments where the system is used with a medical device, for example, a prosthetic device, which may include a prosthetic arm, the system allows for functionality of the device/arm using an internal battery, which may be supplemented by an external battery. Therefore, for example, where a user may be dressing/undressing, using the internal battery during this time allows for arm functionality without being tethered to an external battery by a cable. The tethering and/or cable may make tasks, for example, dressing/undressing, more difficult. However, this system allows for use of an external battery, which may have longer use per charge, and also, for a hot swap of the external battery. The system also includes the ability to recharge the internal battery using the external battery which provides for a system of assuring the user that the internal battery will be charged when next needed, for example, if morning tasks depleted the internal battery charge by 75%, once connected to the external battery, for example, during the daytime hours, the internal battery will be recharged to 100% from the external battery. Then, for evening tasks, for example, which may include those tasks that are more convenient to accomplish without a tether to an external battery, the internal battery will be available/charged. This system is advantageous for many reasons, including, but not limited to, providing ease of recharging the internal battery, continuous use of the device even while swapping power sources, and allowing for use of the device/arm for tasks where being tethered or having cables may inhibit/make difficult one's ability to complete the desired tasks efficiently and/or with ease. In various embodiments, the AC adapter may be used, for example, overnight, to charge the internal battery while the charger may be used to charge the one or more external batteries.

In various embodiments, the user interface on the device may indicate to the user the charge status of the one or more batteries, i.e., internal and/or external battery, connected to the device/arm. For example, in some embodiments, the wrist display may indicate the total amount of remaining capacity which is calculated based on the total batteries connected to the system, e.g., in some embodiments, 1 battery or 2 batteries. Therefore, in these embodiments, if 2 batteries are connected to the system, the battery indicator adds the total capacity of both batteries and determines the remaining capacity. Thus, for example, if no external battery was connected to the device, and the internal battery is 100% charged, the user interface may indicate that the charge is 100%. However, if an external battery is then connected to the system, and it is not itself 100% charged, the user interface battery indicator may indicate less than 100%, taking into consideration the amount of charge remaining on both batteries. Thus, this may be advantageous for many reasons, including, but not limited to, the system reporting an accurate remaining capacity to the user taking into consideration all the batteries connected to the device.

Although this system has been described with respect to prosthetic devices, in some embodiments, the system may be used in any device including, but not limited to, those devices where the internal rechargeable battery is not user replaceable or where the internal rechargeable battery is difficult to replace and/or remove to recharge. In some embodiments, the system may be used on any device that is a portable continuous duty system where it is desirable that the device continuously be powered on to perform one or more tasks. In some embodiments, the system may be used with a medical device.

In various embodiments, the hot swap described above may be used once an external battery is disconnected and an AC adapter is connected. Thus, once the system determines that the external battery is disconnected, the system switches to using the internal battery. Following, once the AC adapter is connected to the device, the system switches to using the AC adapter to charge the internal battery. Also, vice-versa, where the AC adapter is currently connected and is then disconnected and an external battery is connected, the internal battery will be charged from the external battery.

The system may be used in many devices including, but not limited to, infusion pumps, monitoring device and other device having a high duty cycle. The various embodiments of the systems includes one or more power sources, which may include one or more, but not limited to, the following: AC adapter, rechargeable battery internal to the device, rechargeable battery external to the device, and where one of these power sources is powering the device, another of these power sources may be connected to the device and henceforth power the device. Additionally, one or more of the power sources may recharge one or more of the other power sources, for example, an external battery may recharge an internal battery and/or an AC adapter may recharge an internal battery. In some embodiments, while the device is currently in use and powered by an external device, the external device may also provide charge to an internal battery to recharge the internal battery.

Thus, in some embodiments of the system, the external battery not only runs the device, but also, recharges the internal battery at the same time, and can swap out the external battery for with a second external battery when the first external battery's charge is depleted. All of these may be accomplished while the device is fully powered in a continuous, uninterrupted manner.

In various embodiments, the system may be advantageously used in devices where it may be beneficial for the device not to be plugged in, and/or not to be tethered, for example, but not limited to, laptops and/or surgical devices.

In some embodiments the system may be advantageous in devices where removing the internal battery may interrupt the ongoing use of the device and/or trigger a start up process which would interrupt the performance of a device.

In some embodiments, the system may include methods for hot swapping two or more batteries that may be user accessible. For example, the system may include a first battery and a second battery. The first battery may be 100% charged and the second battery may be 50% charged, or in various embodiments, the first battery may be more charged than the second. The first battery may charge the second battery while the first battery powers a device. Thus, in some embodiments, a first battery may serve as a charger battery and a second battery may serve as a charged battery. In some embodiments, once the first battery/charger battery is depleted of its charge to a preset/threshold/predetermined/preprogrammed level, the second battery/charged battery may be swapped out automatically such that the second battery/charged battery is now running the device and first battery/charger battery is being recharged by the second battery. Thus, the first battery and the second battery swap tasks. Thus, in some embodiments, this method provides that one battery is always more charged than a second battery and therefore, the device may be continuously powered without interruption and/or without restarting and/or starting up processes.

In some embodiments, the various hot swap methods may include methods for increasing the life of the battery by not exceeding a preset/predetermined minimum charge, e.g., 50%. In some embodiments, the system may favor maintaining the internal battery at a charge as high as possible.

Figure 114A:
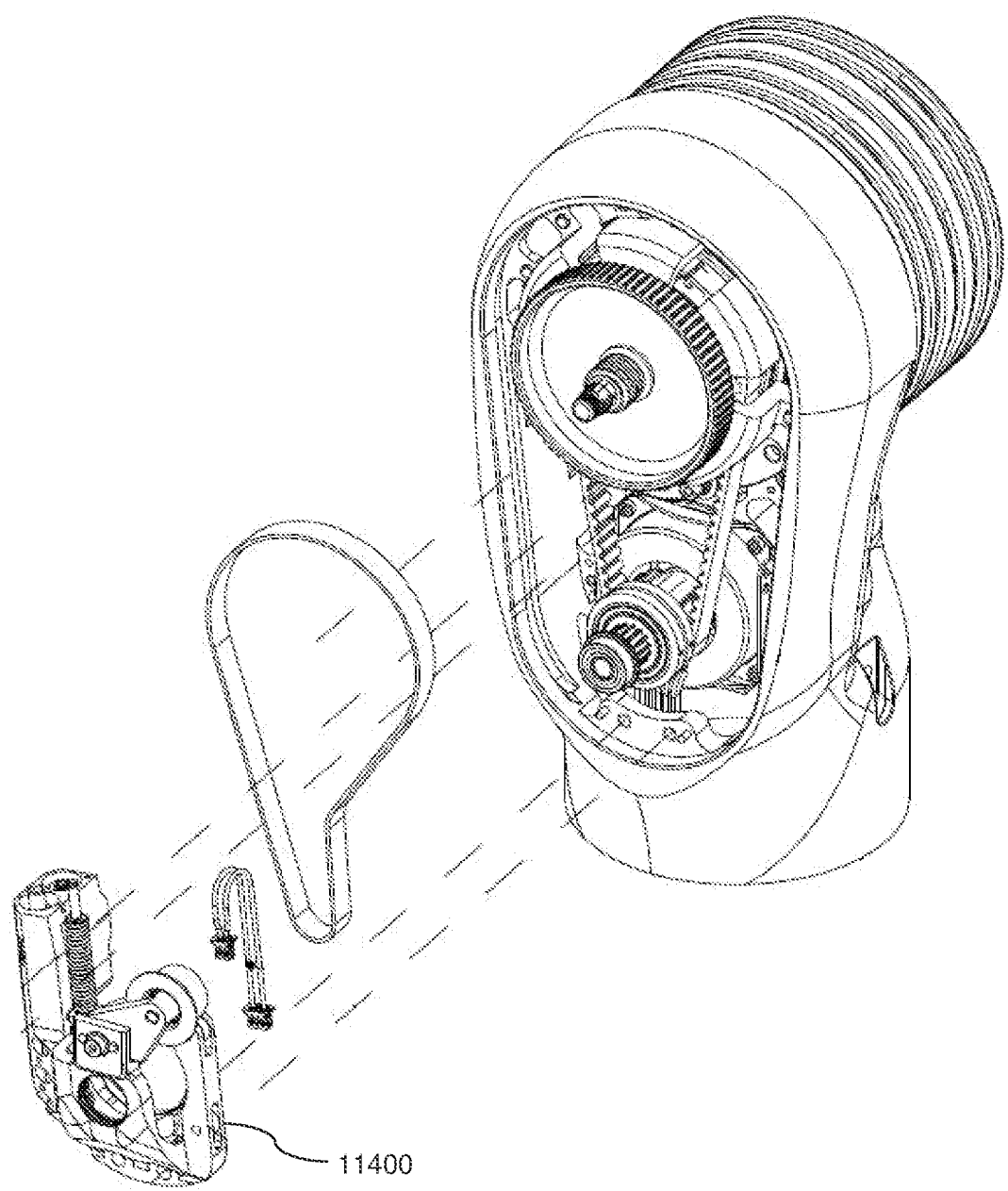
Figure 114B:
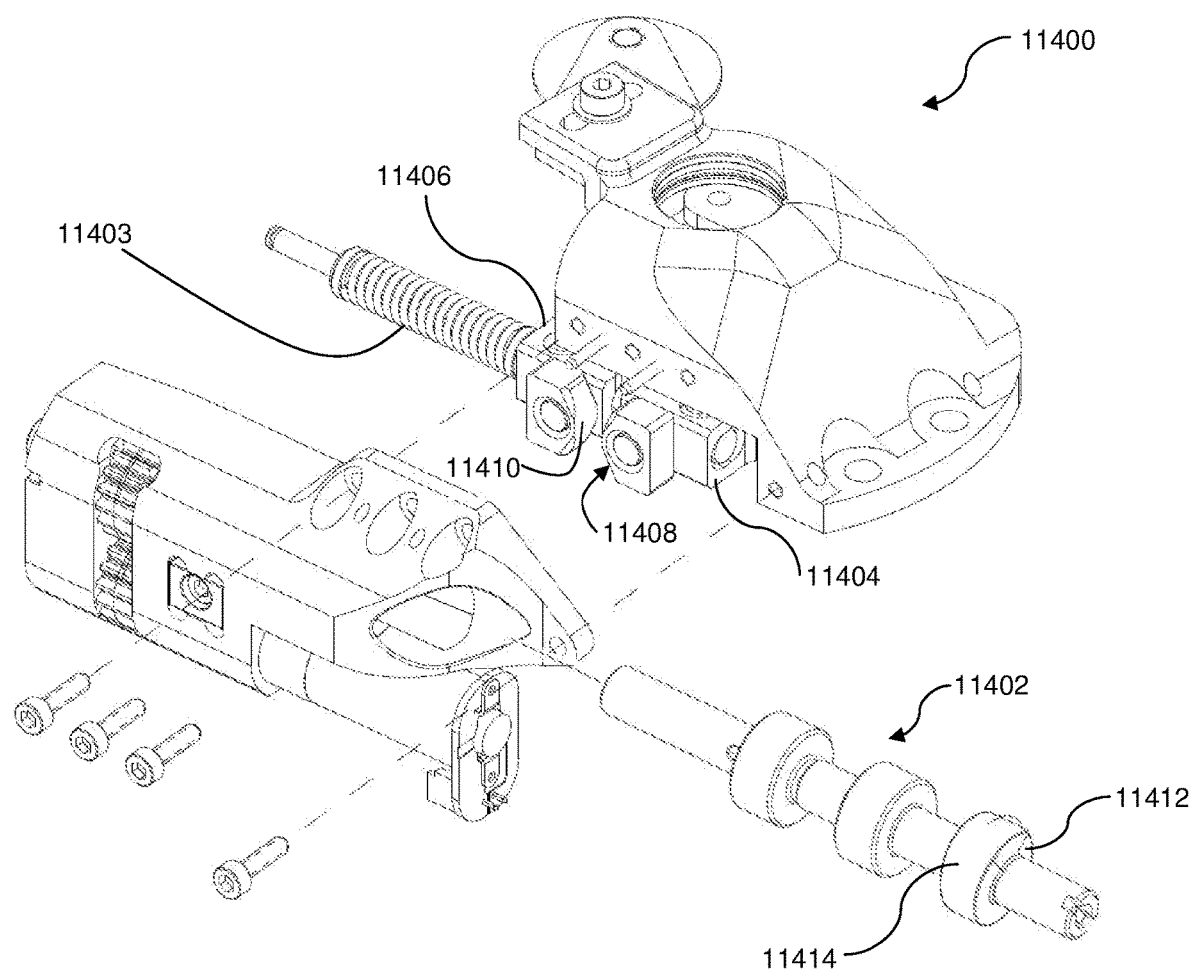
Figure 114C:
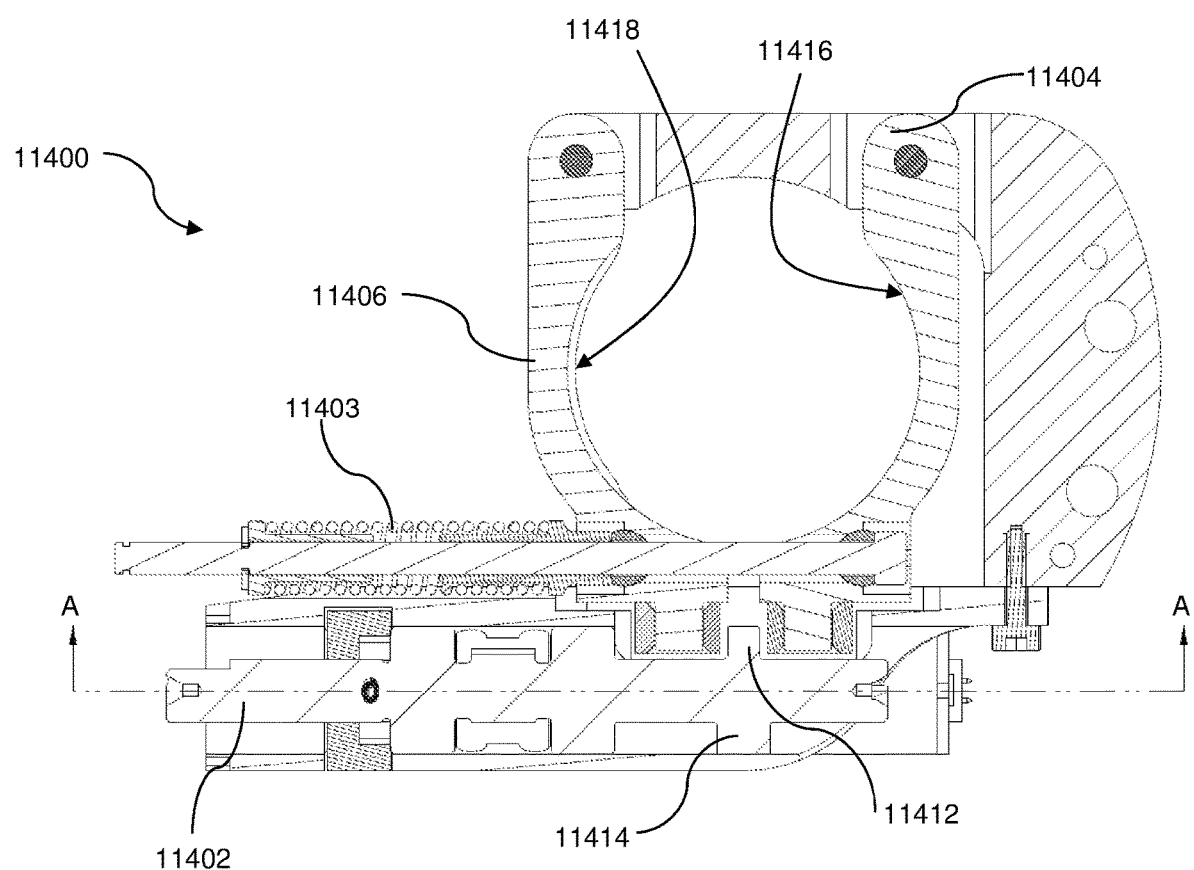
Figure 114D:
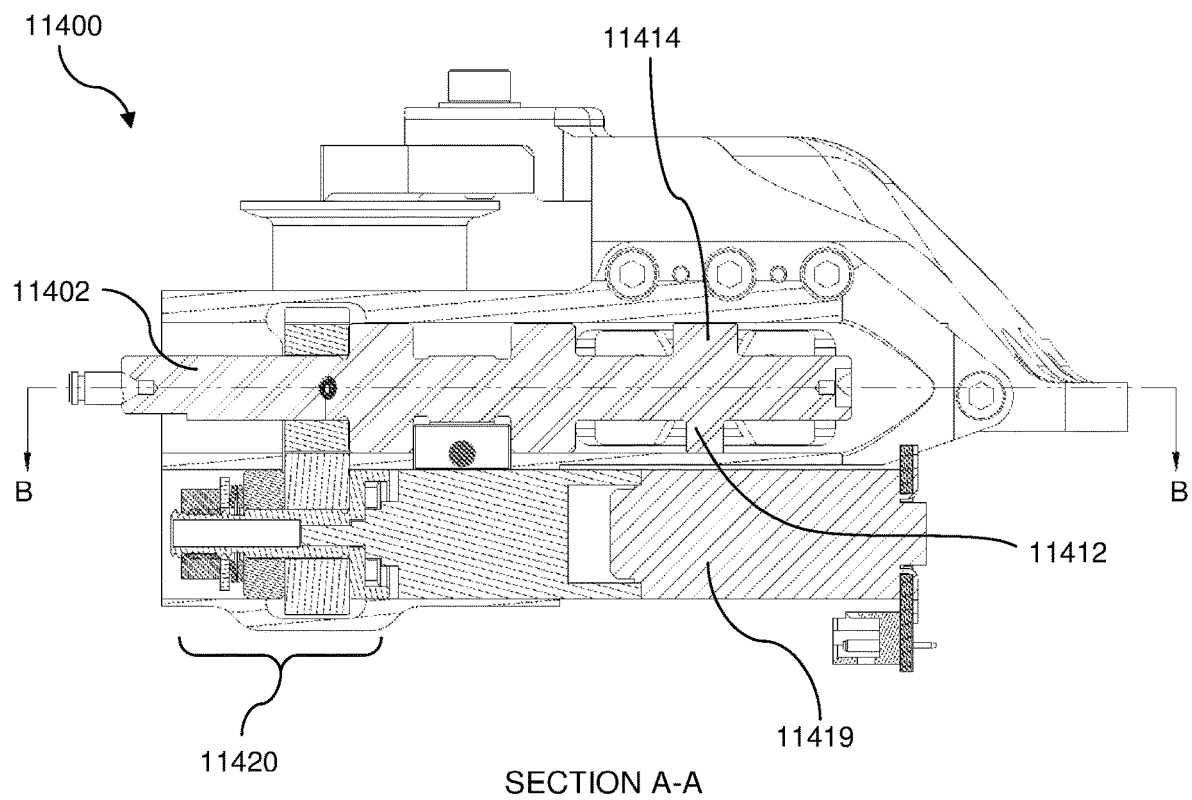

Referring now to FIGS. 114A-114F, in some embodiments the shoulder may include a braking apparatus or system, which, in some embodiments, may be a caliper braking apparatus or system 11400. In some embodiments, the braking apparatus or system may be used in other applications, other than the shoulder of a prosthetic arm. FIGS. 114B-114D are views of embodiments of a caliper braking system, including a cam rod 11402 for actuating the calipers of the caliper braking system 11400. The cam rod 11402 may include cam surface disposed towards one end of the cam rod 11402. The cam surface may include a first actuation portion 11412 and a second actuation portion 11414, the second actuation portion 11414 being substantially wider than the first actuation portion 11412. In some embodiments, the cam surface may gradually increase in width around the circumference of the cam rod. Starting with the first actuation portion 11412, the cam surface profile may increase in width around the cam rod circumference and end with the second actuation portion 11414. In some embodiments, the cam rod 11402 may be actuated by a motor 11419. Further, in some embodiments, the cam rod 11402 may be actuated by the motor 11419 by way of a clutch assembly 11420 as seen in FIG. 114D. The clutch assembly 11420 may transfer the rotational power from the motor to the cam rod and further may avoid malfunctions and failures of the caliper braking system 11400 by absorbing unwanted axial forces exerted through the motor.

The calipers of the braking system, in some embodiments, may include a first caliper 11406, and a second caliper 11404. The first caliper 11406 may further include a first cam actuation surface 11410. Similarly, the second caliper 11404 may further include a second cam actuation surface 11408. The first cam actuation surface 11410 and the second cam actuation surface 11408 may be configured to engage the cam surface of the cam rod 11402 such that, as the cam rod 11402 is actuated, the first and second cam actuation surfaces may transition from being in contact with the first actuation portion 11412 of the cam surface to being in contact with the thicker, second actuation portion 11414 of the cam surface. As the second actuation portion 11414 comes into contact with the first and second cam actuation surfaces, it will move the first and second cam actuation surfaces, and thus the first and second calipers, substantially away from each other, as seen in FIG. 114E.

In some embodiments, the caliper braking system 11400 may include a bias member 11403, as seen in FIGS. 114B and 114C. The bias member 11403 may be engaged with the first caliper 11406 and the second caliper 11404 such that the bias member encourages the first and second calipers towards each other. Thus, as the cam rod 11402 is actuated, and the second actuation portion 11414 of the cam surface comes into contact with the first and second cam actuation surfaces of the first and second calipers, respectively, the first and second calipers will move substantially away from each other, against the encouragement of the bias member 11403.

Figure 114E:
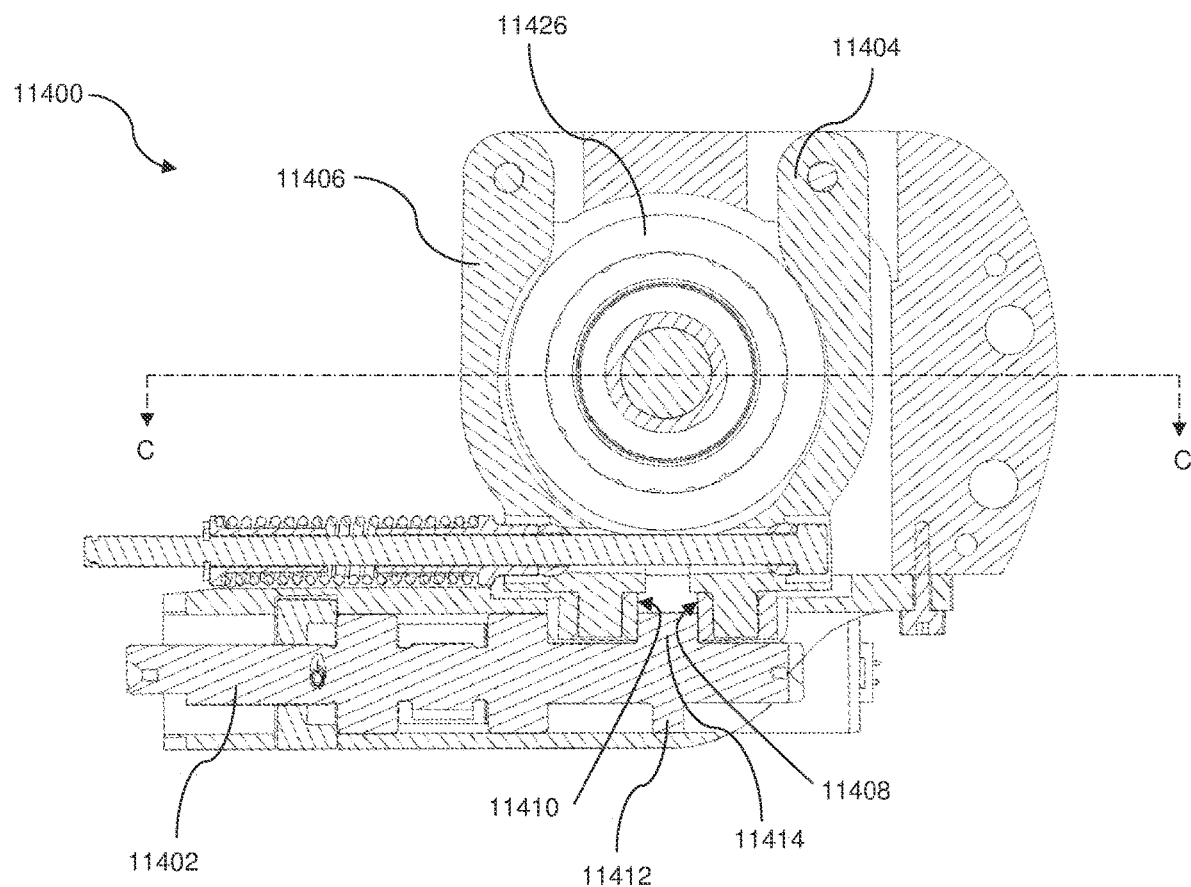
Figure 114F:
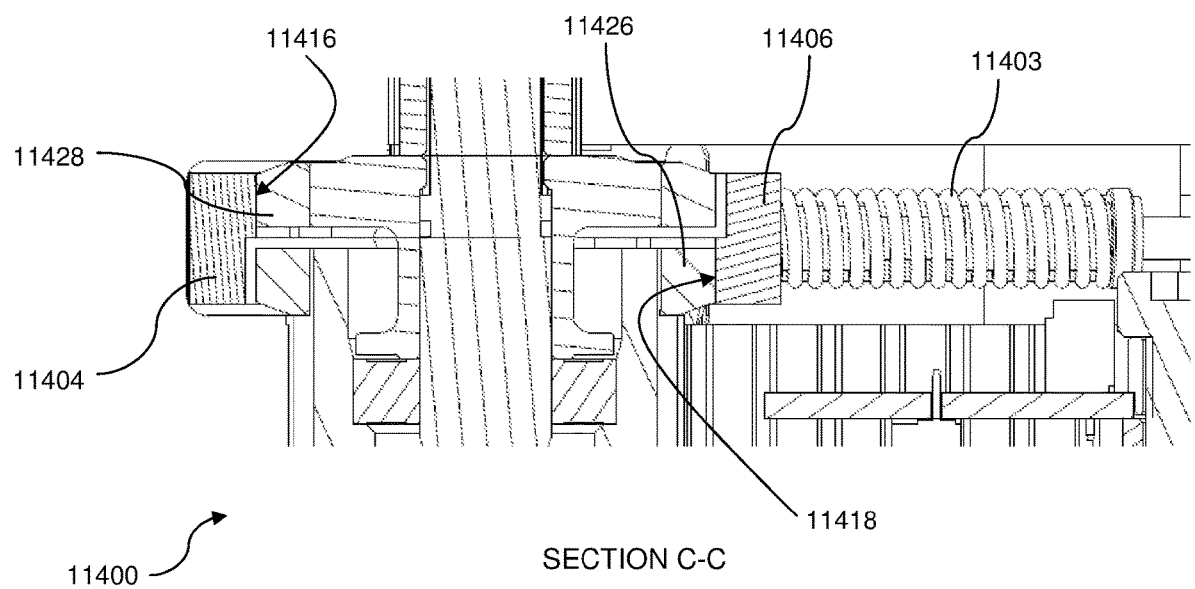

Referring now to FIGS. 114E and 114F, in some embodiments, the first and second calipers may be configured to engage a first and second brake rotor, respectively. The first and second brake rotor may be concentrically aligned to each other such that they have a concentric center of rotation to each other. The first and second brake rotors may also be adjacently disposed. The first caliper 11406 may have a first engagement portion 11418 that is configured to engage with the first brake rotor 11426. Similarly, the second caliper 11404 may have a second engagement portion 11416 that is configured to engage with the second brake rotor 11428. In the resting state of the calipers, the bias member 11403 encourages the calipers in a direction substantially towards each other so the first engagement portion and the second engagement portion engage with the first and second brake rotors, respectively, such that brake rotors are prevented from freely rotating due to circumferential friction on each rotor by the respective engagement portion. When the cam rod 11402 is actuated, the first and second calipers move substantially away from each other, as mentioned above. This action causes the first engagement portion and the second engagement portion to disengage from the first and second brake rotors, respectively, as seen in FIG. 114E, thereby allowing the brake rotors to move freely.

In some embodiments, the first and second calipers and their respective first and second rotor engagement portions may be configured such that the first caliper 11406 will only engage the first brake rotor 11426, and the second caliper 11404 will only engage the second brake rotor 11428. In other words, the first and second brake rotors may be oriented concentrically to each other, yet they each will be engaged by their respective caliper separately, as seen in FIG. 114F. This configuration will allow the first and second brake rotor to differ in diameter and still be able to effectively engage with their respective first and second calipers.

Referring now to FIGS. 115A-B, in some embodiments the hand may include an index pivot assembly or system 11500. The index pivot assembly 11500 may include an index base assembly 11502, an index member assembly 11504, a threaded pivot shaft 11506, and a pivot retention assembly 11508 which, in some embodiments, may be retained in the index base assembly 11502 by at least one fastening member 11514. In some embodiments, the at least one fastening member 11514 is a screw. Further, the index member assembly 11504 may include a pivot ground element 11516 that is rotatably disposed within the index member assembly 11504 such that the index member assembly 11504 is free to rotate relative to the pivot ground element 11516. In some embodiments, one or more bushings 11520 may be disposed in between the index member assembly 11504 and the pivot ground element 11516 in order to facilitate rotational movement and to reduce the amount of wear between the index member assembly 11504 and the pivot ground element 11516.

The index member assembly 11504 may be pivotably attached to the index base assembly 11502 by inserting the threaded pivot shaft 11506 into the index base assembly 11502 and through the pivot ground element 11516 and having the pivot ground element 11516 fixed in the index base assembly 11502 by the pivot retention assembly 11508. The pivot ground element 11516 may be fixed in the index base assembly 11502 such that the pivot ground element 11516 cannot rotate relative to the index base assembly 11502, while maintaining the rotational freedom of movement of the index member assembly 11504 relative to the pivot ground element 11516, and thus, the index base assembly 11502.

The pivot retention assembly 11508 may, in some embodiments, include a retention base 11510 and a plurality of compression members 11512. The pivot retention assembly 11508 may be engaged with the threaded pivot shaft 11506 such that when the threaded pivot shaft 11506 is tightened, the pivot retention assembly 11508 exerts radially compressive force on the pivot ground element 11516 so that the pivot ground element 11516 is fixed in the index base assembly 11502 and cannot rotate relative to the index base assembly 11502. In some embodiments, the threaded pivot shaft 11506 is threaded into the pivot retention assembly 11508 and the pivot retention assembly 11508 exerts the radially compressive force on the pivot ground element 11516 when the threaded pivot shaft 11506 is tightened. In some embodiments, the threaded pivot shaft 11506 is threaded into the retention base 11510 to accomplish exerting the radially compressive force on the pivot ground element 11516. In some embodiments the compression members 11512 may be wedge shaped and interface with the retention base 11510, the pivot ground element 11516, and a plurality of inclined surfaces 11518 in the index base assembly 11502. Upon tightening the threaded pivot shaft 11506, the retention base 11510 may urge the wedge-shaped compression members 11512 along the inclined surfaces 11518 such that the inclined surfaces 11518 move the compression members 11512 in a direction towards the pivot ground element 11516 so that the compression members 11512 exert a radially compressive force on the pivot ground element 11516. In some embodiments, there may be two wedge-shaped compression members 11512, and the inclined surfaces 11518 may be facing each other, such that they urge the two compression members substantially towards one another so that they exert a radially compressive force on two respective points of contact on the pivot ground element 11516 that are substantially opposite from one another.

Referring now to FIGS. 116A-B, in some embodiments, the hand may include a compliance assembly 11600. The compliance assembly 11600 may include an index finger structure 11614 being driven through an index sun shaft 11602, a set of index planets 11604, an index planet carrier 11606, and an index ring gear 11608.

The interior teeth of the index ring gear 11608 may operatively engage each planet of the index planet set 11604, the rotation of the index planet set 11604 rotating the index planet carrier 11606. The index finger structure 11614 may be driven by the exterior teeth of the index planet carrier 11606, which is driven by the rotation of the index planet set 11604 due to the operative engagement of each planet of the index planet set 11604 with the interior teeth of the index ring gear 11608.

The rotation of the index planet carrier 11606 may be slower than that of the index ring gear 11608 due to a gear reduction function carried out by the rotation of the index planet set 11604. Torque may be transmitted from the index finger structure 11614 through the index planet carrier 11606 and index ring gear 11608 to the index sun shaft 11602 when there is a load on the index finger structure 11614. The index planet carrier 11606 may be axially supported by way of an index pin 11612 and an index pin bushing 11610, the pin 11612 being radially supported by the bushing 11610. The index pin 11612 may be coaxial with the index sun shaft 11602, and the index pin 11612 may reduce the amount of unwanted bending forces experienced by the index sun shaft 11602 from the index planet carrier 11606 by acting independently of the index sun shaft 11602.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. Index pivot system for a prosthetic hand comprising:
   an index base assembly;
   a pivot ground element configured to be fixed relative to said index base assembly and rotate relative to an index member assembly;
   a pivot shaft configured to fix said index base assembly and said pivot ground element;
   a retention base configured to be fixed relative to said pivot shaft; and
   a fastening member configured to fix said retention base relative to said index base assembly.

2. Index pivot system of claim 1 wherein said pivot shaft is configured to be threadingly fixed relative to said index base assembly.

3. Index pivot system of claim 1 wherein said retention base configured to be threadingly fixed relative to said pivot shaft.

4. Index pivot system of claim 1 further comprising a compression member configured to compress said pivot ground element against said index base assembly.

5. Index pivot system of claim 4 wherein said compression member and either or both of said pivot shaft and said index base assembly are configured to cooperatively compress said pivot ground element.

6. Index pivot system of claim 4 wherein said index base assembly has a first inclined surface and/or said compression member has a second inclined surface, configured to cooperatively compress said pivot ground element.

* * * * *